United States Patent
Golkowski et al.

(10) Patent No.: US 11,344,643 B2
(45) Date of Patent: May 31, 2022

(54) DEVICES, SYSTEMS, AND METHODS FOR STERILIZATION, DISINFECTION, SANITIZATION AND DECONTAMINATION

(71) Applicant: Sterifre Medical, Inc., Kirkland, WA (US)

(72) Inventors: Czeslaw Golkowski, Ithaca, NY (US); Rick Shea, Seattle, WA (US); Jonathan W. Greene, Ithaca, NY (US); Mark Golkowski, Ithaca, NY (US); Danwei Ye, Cleveland, OH (US); Robert Allen, Cleveland, OH (US); Ben Parker, Cleveland, OH (US); Sergey Makarov, Cleveland, OH (US); Jason R. Ertel, Cleveland, OH (US)

(73) Assignee: Sterifre Medical, Inc., Kirkland, WA (US)

( * ) Notice: Subject to any disclaimer, the term of this patent is extended or adjusted under 35 U.S.C. 154(b) by 284 days.

(21) Appl. No.: 16/758,779

(22) PCT Filed: Oct. 24, 2018

(86) PCT No.: PCT/US2018/057404
§ 371 (c)(1),
(2) Date: Apr. 23, 2020

(87) PCT Pub. No.: WO2019/084203
PCT Pub. Date: May 2, 2019

(65) Prior Publication Data
US 2021/0023250 A1    Jan. 28, 2021

Related U.S. Application Data

(60) Provisional application No. 62/727,344, filed on Sep. 5, 2018, provisional application No. 62/599,649, filed
(Continued)

(51) Int. Cl.
*A61L 2/00*    (2006.01)
*A61L 9/00*    (2006.01)
(Continued)

(52) U.S. Cl.
CPC .............. *A61L 2/202* (2013.01); *A61L 2/0094* (2013.01); *A61L 2/208* (2013.01); *A61L 2/24* (2013.01);
(Continued)

(58) Field of Classification Search
CPC ..... A61L 2/00; A61L 2/16; A61L 2/20; A61L 2/202; A61L 2/208; A61L 2202/24
(Continued)

(56) References Cited

U.S. PATENT DOCUMENTS

| 4,863,688 A | 9/1989 | Schmidt et al. |
| 4,992,247 A | 2/1991 | Foti |

(Continued)

FOREIGN PATENT DOCUMENTS

| CA | 2735739 | 1/2011 |
| CA | 2767726 | 4/2011 |

(Continued)

OTHER PUBLICATIONS

Advance Sterilization Products, Amendment Sterrad ® 50 Sterilizer K981625, dated Jan. 5, 1999 in 6 pages.
(Continued)

*Primary Examiner* — Monzer R Chorbaji
(74) *Attorney, Agent, or Firm* — Knobbe Martens Olson and Bear, LLP

(57) ABSTRACT

A sterilization, disinfection, sanitization, or decontamination system having a chamber defining a region, and a generator for creating a free radical effluent with reactive oxygen, nitrogen, and other species and/or a vaporizer. A closed loop circulating system without a free-radical destroyer is pro-
(Continued)

vided for supplying the mixture of free radicals from the generator mixed with the hydrogen peroxide solution in the form of the effluent to the chamber. The system is used in sterilizing, disinfecting, sanitizing, or decontaminating items in the chamber or room and, with a wound chamber, in treating wounds on a body. The wound chamber may be designed to maintain separation from wounds being treated. Various embodiments can control moisture to reduce or avoid unwanted condensation. Some embodiments can be incorporated into an appliance having a closed space, such as a washing machine. Some embodiments may include a residual coating device that deposits a bactericidal coating on sterilized items.

23 Claims, 94 Drawing Sheets

Related U.S. Application Data on Dec. 15, 2017, provisional application No. 62/577,130, filed on Oct. 25, 2017.

(51) Int. Cl.
*A61L 2/20* (2006.01)
*A61L 2/24* (2006.01)
*H01J 37/32* (2006.01)

(52) U.S. Cl.
CPC ..... *H01J 37/32348* (2013.01); *A61L 2202/11* (2013.01); *A61L 2202/122* (2013.01); *A61L 2202/13* (2013.01); *A61L 2202/14* (2013.01); *A61L 2202/15* (2013.01); *A61L 2202/24* (2013.01); *A61L 2202/25* (2013.01)

(58) Field of Classification Search
USPC .................................................. 422/1, 28, 32
See application file for complete search history.

(56) References Cited

U.S. PATENT DOCUMENTS

| | | | |
|---|---|---|---|
| 5,087,418 A | 2/1992 | Jacob | |
| 5,173,258 A | 12/1992 | Childers | |
| 5,209,411 A | 5/1993 | Dineley et al. | |
| 5,445,792 A | 8/1995 | Rickloff et al. | |
| 5,508,009 A | 4/1996 | Rickloff et al. | |
| 5,534,221 A | 7/1996 | Hillebrenner et al. | |
| 5,578,280 A | 11/1996 | Kazi et al. | |
| 5,779,973 A | 7/1998 | Edwards et al. | |
| 5,792,435 A | 8/1998 | Mueller et al. | |
| 6,073,627 A | 6/2000 | Sunnen | |
| 6,077,480 A | 6/2000 | Edwards et al. | |
| 6,113,851 A | 9/2000 | Phygen | |
| 6,156,267 A | 12/2000 | Pai et al. | |
| 6,187,266 B1 | 2/2001 | Lin et al. | |
| 6,329,628 B1 | 12/2001 | Kuo et al. | |
| 7,091,441 B1 | 8/2006 | Kuo | |
| 7,186,374 B2 | 3/2007 | Zelina et al. | |
| 7,621,985 B1 | 11/2009 | Kuo | |
| 7,777,151 B2 | 8/2010 | Kuo | |
| 7,803,315 B2 | 9/2010 | McDonnell et al. | |
| 7,880,887 B2 | 2/2011 | Olson et al. | |
| 8,115,135 B2 | 2/2012 | Kuo | |
| D656,622 S | 3/2012 | Gasser et al. | |
| 8,153,078 B2 | 4/2012 | Bacik et al. | |
| 8,221,679 B2 | 7/2012 | Golkowski | |
| 8,444,919 B2 | 5/2013 | Erickson | |
| 8,551,399 B2 | 10/2013 | Shannon et al. | |
| 8,591,807 B2 | 11/2013 | Berentsveig et al. | |
| 8,591,808 B2 | 11/2013 | Berentsveig et al. | |
| 8,636,951 B2 | 1/2014 | Shannon et al. | |
| 8,658,089 B2 | 2/2014 | Berentsveig et al. | |
| 8,668,882 B2 | 3/2014 | Berentsveig | |
| 8,758,681 B2 | 6/2014 | Golkowski | |
| 8,927,896 B2 | 1/2015 | Kuo | |
| 8,974,737 B2 | 3/2015 | Erickson | |
| 8,977,115 B2 | 3/2015 | Penman, Jr. | |
| 8,992,829 B2 | 3/2015 | Shannon et al. | |
| 9,010,574 B2 | 4/2015 | Gasser et al. | |
| 9,027,385 B2 | 5/2015 | Hingley et al. | |
| 9,050,385 B2 | 6/2015 | Weinberger et al. | |
| 9,138,005 B2 | 9/2015 | Berentsveig et al. | |
| 9,192,164 B2 | 11/2015 | Berentsveig et al. | |
| 9,226,495 B2 | 1/2016 | Berentsveig et al. | |
| 9,241,491 B2 | 1/2016 | Berentsveig et al. | |
| 9,333,275 B2 | 5/2016 | Berentsveig | |
| 9,849,204 B2 | 12/2017 | Taggart | |
| RE47,582 E | 8/2019 | Golkowski | |
| 2002/0068028 A1 | 6/2002 | Hight, III | |
| 2005/0063882 A1* | 3/2005 | Centanni | G01N 29/036 422/292 |
| 2005/0129571 A1* | 6/2005 | Centanni | A61L 2/202 422/62 |
| 2005/0260097 A1 | 11/2005 | Williams et al. | |
| 2006/0027539 A1 | 2/2006 | Golkowski | |
| 2007/0221582 A1 | 9/2007 | Holland et al. | |
| 2007/0274858 A1 | 11/2007 | Childers et al. | |
| 2008/0014113 A1 | 1/2008 | Centanni | |
| 2008/0267819 A1 | 10/2008 | Bacik et al. | |
| 2011/0027125 A1* | 2/2011 | Golkowski | A61L 11/00 422/186.21 |
| 2012/0277662 A1 | 11/2012 | Golkowski | |
| 2014/0105783 A1 | 4/2014 | Levsen et al. | |
| 2017/0304476 A1 | 10/2017 | Taggart et al. | |
| 2019/0314535 A1 | 10/2019 | Golkowski et al. | |

FOREIGN PATENT DOCUMENTS

| | | |
|---|---|---|
| EP | 0298694 | 1/1989 |
| EP | 0774263 | 5/1997 |
| EP | 0906125 | 4/2004 |
| EP | 1557181 | 7/2005 |
| EP | 2525838 | 7/2011 |
| GB | 2371986 | 8/2002 |
| JP | 4088347 | 3/1992 |
| JP | 2002-360672 | 12/2002 |
| JP | 2006-205085 | 8/2006 |
| JP | 2014-023596 | 2/2014 |
| KR | 10-0782040 | 12/2007 |
| WO | WO 1988/004939 | 7/1988 |
| WO | WO 1991/005573 | 5/1991 |
| WO | WO 1997/047331 | 12/1997 |
| WO | WO 2009/005252 | 1/2009 |
| WO | WO2011/003179 | 1/2011 |
| WO | WO2011/085466 | 7/2011 |
| WO | WO 2011/149188 | 12/2011 |
| WO | WO 2014/123280 | 8/2014 |
| WO | WO 2016/064288 | 4/2016 |
| WO | WO 2017/218832 | 12/2017 |
| WO | WO 2019/084203 | 5/2019 |

OTHER PUBLICATIONS

Attri et al. "Generation mechanism of hydroxyl radical species and its lifetime prediction during the plasma-initiated ultraviolet (UV) photolysis." Scientific Reports 5, Article No. 9332 (2015).
Ellie. The first ever digital UV sterlizing pod available at https://www.indiegogo.com/projects/ellie-the-first-ever-digital-uv-sterlizing-pod-baby-technology--2, retrieved from internet Apr. 6, 2017.
International Search Report and Written For PCT Application No. PCT/US18/57404, dated Jan. 11, 2019 in 13 pages.
International Search Report and Written Opinion for PCT Application No. PCT/US2017/037762, dated Nov. 20, 2017 in 21 pages.
Plasmapp, Fast Low-Temerature Sterilization, downloaded from www.plasmapp.co.kr on Jul. 4, 2019 in 14 pages.
Sadowitz, Benjamin et al., A Novel Non-Thermal Plasma/Free radical Sterilization System for Burn Wound Disinfection, Burn Poster EAST 2013 Compatibility Mode, University of Colorado

(56) References Cited

OTHER PUBLICATIONS

Denver, Anschutz Medical Campus, College of Engineering and Applied Science in 1 page.

* cited by examiner

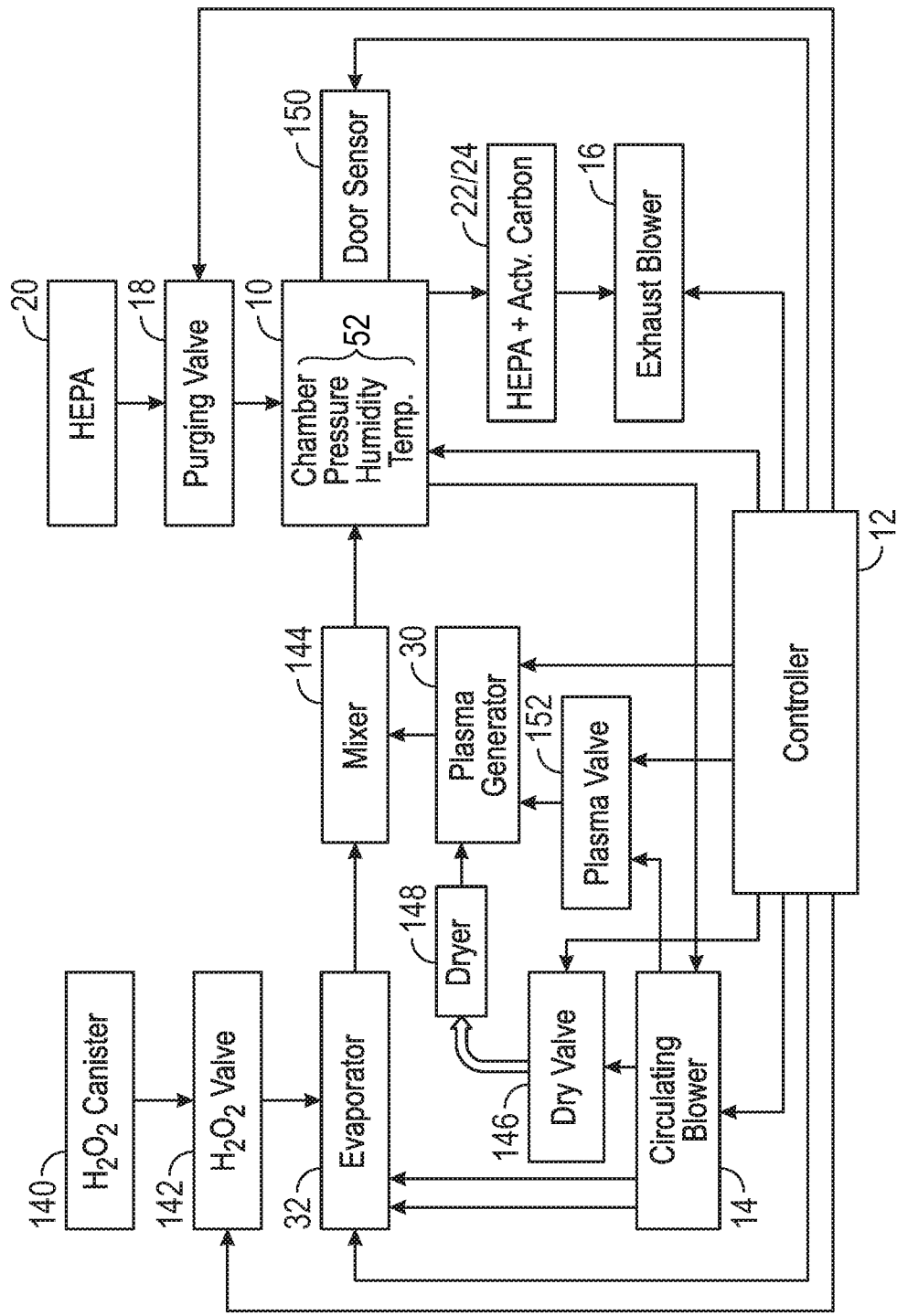

DEVICES, SYSTEMS, AND METHODS FOR STERILIZATION, DISINFECTION, SANITIZATION AND DECONTAMINATION

BACKGROUND

Technical Field

Several embodiments of the present disclosure relate generally to the art of generating atmospheres having sterilizing, disinfecting, sanitizing, decontaminating, and/or therapeutic aspects, and more particularly to sterilization, disinfection, sanitization, and/or decontamination of therapeutic devices, as well as related systems and methods.

Description of the Related Art

Sterilization, disinfection, sanitization, and decontamination methods are used in a broad range of applications. A variety of methods are used, including steam, chemicals, fumigants, radiation, among others. Drawbacks to these methods exist, and are addressed by the devices, systems and methods disclosed herein.

SUMMARY

As disclosed herein, a variety of items or surfaces may require processing in order to reduce the bioburden and decrease risk of infections. For example, critical items (such as surgical instruments, which contact sterile tissue), semi-critical items (such as endoscopes, which contact mucous membranes), and noncritical items (such as stethoscopes, which contact only intact skin) require various types of treatment, for example sterilization, high-level disinfection, and low-level disinfection, respectively. The present disclosure provides for various systems, devices and methods for disinfecting/sanitizing various items (e.g., medical devices or electronics) and surfaces (e.g., workspaces, patient rooms, organic material, including but not limited to patient wounds).

Various systems, devices, and methods are provided for herein in order to accomplish disinfection of one or more items, surfaces etc. Additionally, in several embodiments the systems, devices and methods are configured to allow low or high level disinfection. In still additional embodiments, the systems, devices and methods are configured to allow sterilization.

For example, provided for herein in several embodiments, is a system for high-level disinfection of at least one item, comprising a first unit comprising a disinfectant generator, a second unit comprising a chamber for containing an item or items to be disinfected and configured for at least temporarily fluidic communication with the first unit and at least one conduit in fluidic communication with the first unit and the second unit, wherein the conduit is configured to convey the disinfecting effluent from the first unit to the second unit. In several embodiments, the disinfectant generator is configured to generate a disinfecting effluent capable of destruction of vegetative microorganisms, mycobacterium, small or non-lipid viruses, medium or lipid viruses, fungal spores, and bacterial spores on the at least one item.

In several embodiments, the disinfectant generator comprises a free radical generator. Depending on the embodiment, the free radical generator generates one or more types of free radical, such as ozone, superoxide, singlet oxygen, peroxide, hydroxyl radicals, nitric oxide, hydrogen peroxide, nitrous oxide, nitrogen dioxide, or peroxynitrite. In several embodiments, the free radical generator is configured to generate more than one type of free radical. In several embodiments, multiple free radical generators are included in the system, either of different free radical generating capacities, or capable of operating together to generate more than one type of free radical. In several embodiments, the free radical generator also comprises a reservoir of disinfectant media. In several embodiments, the reservoir is in fluid communication with a vaporizer unit, wherein the vaporizer unit is configured to generate a vapor of the disinfectant media. Some embodiments involve generation of a mist of disinfectant media. In several embodiments, the free radical generator comprises a gas distribution unit, wherein the gas distribution unit is in fluidic communication with the free radical generator and the reservoir of disinfectant media. In several embodiments, the gas distribution unit conveys a gas (e.g., recycled effluent or atmospheric gas) from at least one outlet of the gas distribution unit to an inlet of the free radical generator and to the reservoir of disinfectant media or the vaporizer unit.

In several embodiments, the chamber of the second unit comprises a sealed and enclosed area in which the item or items to be disinfected may be placed. In several embodiments, the chamber comprises a first portion and a second portion configured to reversibly and interact with one another to form a sealed and enclosed area. In several embodiments, there is provided an insert configured to be placed within the sealed and enclosed area (be it a unitary or multipart chamber), the insert configured to contain the at least one item to be disinfected. There is also, in several embodiments, at least one seal on the chamber that is configured to allow entry of the disinfecting effluent into the sealed and enclosed area. Some embodiments also employ that seal to allow an egress of disinfecting effluent. In several embodiments, the at least one seal is configured to maintain the sealed and enclosed area as sealed upon cessation of the temporarily fluidic communication with the first unit. Thus, in such embodiment, the chamber acts as a self-contained environment and transport/storage unit for the item(s).

In several embodiments, the system further comprises a controller unit, wherein the controller unit is configured to control the activation of the first unit and the conveyance of the disinfecting effluent from the first unit to the second unit.

In several embodiments, the disinfectant generator comprises a vaporizer that is configured to generate a vapor or mist of the disinfectant media. In some embodiments, the disinfectant media is atomized or otherwise suspended in a gaseous medium to be conveyed to the chamber. In several embodiments, the disinfectant media may be in a powder format (e.g., analogous to powder coating). In several embodiments, the vaporizer comprises a wicking material disposed within the disinfectant media and positioned to have at least a portion of the gas distributed by the gas distribution unit across or through the wicking material. In such embodiments, the flow of gas across or through the wick facilitates the formation of the vapor or mist of disinfectant media. In several embodiments, the vaporizer comprises a bubbler configuration wherein at least a portion of the gas from the gas distribution unit it bubbled into the disinfectant media to generate the vapor. Depending on the embodiment, the disinfectant media comprises a liquid and the vaporizer comprises a float sensor configured to regulate the level of the disinfectant media.

In several embodiments, the gas distribution unit comprises at a first and a second conduit, wherein the first conduit is in fluid communication with the free radical generator and wherein the second conduit is in fluid communication with the vaporizer unit.

In several embodiments, the system includes at least one conduit exiting the free radical generator and at least one conduit exiting the vaporizer unit, wherein the conduit from the free radical generator and the conduit from the vaporizer unit enter the second unit comprising the chamber. In several embodiments, the conduit from the free radical generator and the conduit from the vaporizer unit are integrated into a single conduit that enters the second unit comprising the chamber (e.g., they are joint at a point prior to entering the chamber). In alternative embodiments, the chamber receives a separate inflow of free radicals and vaporized disinfectant media, which are mixed together in the chamber based on gas flow patterns within the chamber. In several embodiments, the chamber further comprises at least one conduit exiting the chamber, wherein the at least one conduit is fluidically connected with the disinfectant generator. In several such embodiments, the at least one conduit fluidically connected with the disinfectant generator recycles disinfectant effluent from the chamber back to the disinfectant generator. In such embodiments, there is potential for recycling disinfectant effluent that may still be "live"—in other words has the ability to continue to disinfect/sterilize an item. This leads to higher efficiency, in several embodiments, as the plasma generator and vaporizer can be adjusted in a tailored fashion to prevent generation of excess free radicals and/or disinfectant/sterilant.

In several embodiments, the second unit further comprises an additional conduit that fluidically connects an interior of the chamber with an exterior environment. In several embodiments, the additional conduit comprises one or more of a filter, a free radical destroyer and a blower.

In several embodiments, the first portion of the second unit comprises an inlet and an outlet configured to receive into the chamber and allow to exit the chamber the disinfectant effluent generated by the disinfectant generator.

In several embodiments, the system is configured to operate in an open-loop mode, wherein the system is configured to allow atmospheric gas to enter the chamber. In several embodiments, the system is further configured to operate in a closed-loop mode following the open-loop mode, wherein the closed loop mode restricts gas flow into and out of the chamber to gas comprising the disinfectant effluent generated by the disinfectant generator.

In several embodiments where the chamber is formed from multiple parts (e.g., a first and a second, though additional multi-part chambers are provided for as well), the first part and the second part of the second unit are at least partially joined with one another. In several embodiments, the insert of the second unit is configured to receive and contain the at least one item based at least in part on a dimension or shape of the at least one item.

Depending on the embodiment, a variety of different items or surfaces can be treated (e.g., sterilized or disinfected). For example, in several embodiments the at least one item to be disinfected comprises an internal lumen and the second unit and the insert are configured to convey disinfectant effluent through the internal lumen. In several embodiments, the second unit is configured to convey disinfectant effluent around an exterior surface of the at least one item. In still additional embodiments, the second unit is configured to allow disinfection of a plurality of items, each of the plurality of items comprising an internal lumen. In several embodiments, the second unit is configured to store the at least one item until a subsequent use of the at least one item. Such embodiments, may involve second units that are configured to stack or nest with at least one additional second unit. In several embodiments, the second unit is substantially rigid, while in other embodiments, the second unit is flexible. In several embodiments, the insert is configured to contain a plurality of items of particular shapes and sizes, and wherein the insert is configured with a specific receiving area for each of the plurality of items.

In several embodiments, the system includes an additional conduit fluidically communicating with an exterior environment and an interior of the chamber. In several embodiments, that additional conduit further comprises one or more of a valve to control gas flow from the environment to the interior of the chamber, a filter, and a heater element. In such embodiments, the conduit can be used to allow a pre-treatment gas into the chamber, e.g., to dry and heat the chamber prior to initiating a sterilization or disinfection cycle.

In several embodiments, the free radical generator is a cold plasma generator that generates ozone. In several embodiments, the reservoir of disinfectant media comprises a liquid or solid source of hydrogen peroxide.

Several embodiments provided for herein are particularly advantages for treating a variety of types of items or surfaces, as in several embodiments, the system operates at a pressure not significantly different from an ambient environmental pressure. In some embodiments, the system operates at a pressure between about 600 mm Hg and 800 mm Hg. In several embodiments, the system operates at or around an ambient temperature, for example in several embodiments, the system operates at a temperature ranging from about 15 degrees Celsius to about 50 degrees Celsius. In some embodiments, the system operates at a humidity within an interior of the chamber of between about 20% and 90% relative humidity. Such embodiments advantageously allow for the optional use of the system to achieve high-level disinfection (or sterilization) of electronic devices. In some embodiments, the system further comprises at least one desiccant depot configured to assist in maintaining the humidity.

In several embodiments, the system allows for high-level disinfection to be achieved in a cycle time of between about 120 seconds to about 10 minutes. In some embodiments, sterilization can be achieved in times ranging from about 5 to about 20 minutes.

There are also provided for herein various methods for disinfecting (or sterilizing) at least one item, comprising placing the at least one item in the insert of a system disclosed herein and activating the system to expose the at least one item to the disinfectant effluent for an amount of time sufficient to achieve high-level disinfection of the at least one item.

In several embodiments, a method for disinfecting at least one item comprises placing the at least one item an insert configured to contain the at least one item, placing the insert in a chamber that forms a sealed and enclosed area around in the insert and the at least one item, activating a disinfectant generator, wherein the disinfectant generator comprises a free radical generator and a reservoir of disinfectant media in fluid communication with a vaporizer unit.

In several embodiments, the disinfectant generator is configured to generate a disinfecting effluent capable of destruction of vegetative microorganisms, mycobacterium, small or non-lipid viruses, medium or lipid viruses, fungal spores, and bacterial spores on the at least one item. In several embodiments, the activation of the disinfectant generator causes disinfecting effluent to enter the chamber and disinfect the at least one item. Similar methods are employed, in several embodiments, to sterilize an item (or items) and/or a surface or wound.

In several embodiments, the activation of the system also activates a gas distribution unit that conveys the disinfecting effluent to move from the disinfectant generator to the chamber. In several embodiments, activation of the system first results in the system operating in an open-loop mode where the chamber is open to receive atmospheric gases followed by a closed-loop mode where the chamber is open to receive only disinfecting effluent. In such embodiments, the open-loop mode is configured to heat and dry the chamber and the at least one item within the chamber. In some embodiments, the open-loop mode is configured to dry the chamber by heat and/or dry air and the at least one item within the chamber. In some embodiments the closed loop includes a desiccator in the loop that is configured to dry (at least partially) the chamber and the at least one item within the chamber. Not all embodiments employ the open loop configuration; some embodiments operate only on a closed-loop method. In several embodiments, the methods employ disinfecting effluent comprising vaporized hydrogen peroxide and free radicals. In some embodiments, the interior of the chamber does not experience a pressure significantly different from an ambient environmental pressure. In several embodiments, the interior of the chamber is heated or cooled to a temperature ranging from about 15 degrees Celsius to about 50 degrees Celsius. This can include, for example, temperature ranging from about 15° C. to about 20° C., about 20° C. to about 25° C., about 25° C. to about 30° C., about 30° C. to about 35° C., about 35° C. to about 40° C., about 40° C. to about 45° C., or about 45° C. to about 50° C. In several embodiments, the interior of the chamber is maintained at a humidity of between about 20% and 90% relative humidity. In some embodiments, for the disinfection cycle, the interior of the chamber must have sufficient % relative humidity to start the cycle. This can include a minimum of between about 0% relative humidity to about 60% relative humidity, about 10% to about 60% relative humidity, about 20% to about 60% relative humidity, about 30% to about 60%, about 40% to about 60% relative humidity, about 50% to about 60% relative humidity, or any ranges in between such as about 0% to about 5% relative humidity, about 5% to about 10% relative humidity, about 10% to about 15% relative humidity, about 15% to about 20% relative humidity, about 20% to about 25% relative humidity, about 25% to about 30% relative humidity, about 30% to about 35% relative humidity, about 35% to about 40% relative humidity, about 40% to about 45% relative humidity, about 45% to about 50% relative humidity, about 50% to about 55% relative humidity, and about 55% to about 60% relative humidity. In some examples, the interior of the chamber can have a maximum of about 75% relative humidity. In some examples, the interior of the chamber can have a maximum of about 95% non-condensing relative humidity. In several embodiments, the methods allow for high-level disinfection to be achieved in a cycle time of between about 120 seconds to about 10 minutes. As discussed above, in several embodiments, the methods disclosed herein allow for sterilization to be achieved in cycle times ranging from about 5 to about 20 minutes. In some examples, the cycle times can range from between 0 seconds to about 20 seconds, about 20 seconds to about 40 seconds, about 40 seconds to about 1 minute, about 1 minute to about 1 minute 20 seconds, about 1 minute 20 seconds to about 1 minutes 40 seconds, about 1 minute 40 seconds to about 2 minutes, about 2 minutes to about 2 minutes 20 seconds, about 2 minutes 20 seconds to about 2 minutes 40 seconds, about 2 minutes 40 seconds to about 3 minutes, about 3 minutes to about 3 minutes 20 seconds, about 3 minutes 20 seconds to about 3 minutes 40 seconds, about 3 minutes 40 seconds to about 4 minutes, about 4 minutes to about 4 minutes 20 seconds, about 4 minutes 20 seconds to about 4 minutes 40 seconds, about 4 minutes 40 seconds to about 5 minutes.

There is also provided for herein a system for treating at least one item, whether organic or inorganic, or surface, comprising a first unit comprising a disinfectant generator, wherein the disinfectant generator comprises a free radical generator, wherein the free radical generator generates free radicals, a vaporizer unit in fluidic communication with a reservoir of disinfectant media, wherein the vaporizer unit is configured to generate a vapor of the disinfectant media, a gas distribution unit, wherein a gas from at least one outlet of the gas distribution unit to an inlet of the free radical generator and to the reservoir of disinfectant media or the vaporizer unit, wherein the disinfectant generator is configured to generate an effluent capable low-level disinfection, high-level disinfection or sanitization of the at least one item, a second unit comprising a chamber for containing an item or items to be treated, wherein the chamber is configured to form a sealed and enclosed area which can receive the at least one item, and at least one conduit in fluidic communication with the first unit and the second unit, wherein the conduit is configured to convey the disinfecting effluent from the first unit to the second unit.

Depending on the embodiment, the system can be configured for high-level or low-level disinfection of the at least one item. Alternatively, the system can be configured for sanitization or sterilization of the at least one item. In some embodiments, the system is configured for treatment of a plurality of items, each of the plurality of items having an internal lumen. In several embodiments, the system further comprises an insert configured to be placed within the sealed and enclosed area, the insert configured to contain the at least one item to be treated. In several embodiments, the system is configured for treatment of an organic surface. In some such embodiments, the organic surface is a food item. In several embodiments, the organic surface is a wound (e.g., an open wound). In several embodiments, the chamber is flexible, optionally customizable, and configured to enclose the wound.

Further provided for herein is a sterilization, disinfection, sanitization, or decontamination system comprising a sterilant source that generates sterilant, a chamber configured to contain an item to be sterilized, disinfected, sanitized, or decontaminated and to receive the sterilant from the sterilant source, a flow generator configured to circulate the sterilant from the sterilant source to the chamber in a closed-loop such that the sterilant sterilizes, disinfects, sanitizes, or decontaminates the item in the chamber; and a residual coating source that generates a bactericidal coating, wherein the flow generator is configured to circulate the bactericidal from the residual coating source to the chamber in a closed-loop such that the bactericidal coating is deposited on the item in the chamber.

In several embodiments, the bactericidal coating comprises silver. In several embodiments, the bactericidal coating comprises copper. In some embodiments, combinations of copper and silver are used. In several embodiments, the bactericidal coating comprises a sacrificial layer. In several embodiments, the system is configured to deposit the bactericidal coating on the item in the chamber after the flow generator circulates the sterilant.

In several embodiments, the sterilant source comprises a plasma generator configured to generate free radicals and wherein the sterilant comprises the free radicals. Depending on the embodiment, the sterilant source is optionally places within the chamber, while in some embodiments, the sterilant source is outside the chamber.

In several embodiments, the sterilant source comprises an evaporator configured to receive hydrogen peroxide and generate hydrogen peroxide vapor or microdroplets and wherein the sterilant comprises the hydrogen peroxide vapor or microdroplets.

In some embodiments, the system is configured to deliver sterilant to a wound on a subject, wherein the wound is at least partially surrounded by a drape or patch that creates a dead space between the drape or patch and the wound, wherein the sterilant flows through the dead space. In some such embodiments, the sterilant is delivered at a negative pressure. In several embodiments, the sterilant comprises reactive oxygen and/or nitrogen species (RONS) and vaporized hydrogen peroxide (VHP).

Additionally provided for herein, in several embodiments, is a sterilization, disinfection, sanitization, or decontamination system comprising an evaporator configured to receive a level of liquid agent at a first location, generate a vapor from the liquid agent, and release the vapor at a second location, a chamber configured to contain an item to be sterilized, disinfected, sanitized, or decontaminated and to receive the vapor from the evaporator; and a flow generator configured to circulate the vapor from the chamber to the evaporator in a closed-loop such that the vapor sterilizes, disinfects, sanitizes, or decontaminates the item in the chamber, wherein the evaporator comprises a wicking material disposed between the first location and the second location, the wicking material configured to absorb and encourage evaporation of the liquid agent, and wherein based at least in part on the level of the liquid agent, the evaporator is configured to achieve a condensation level at or below a threshold level at the second location.

In several embodiments, the threshold level is at or below a saturation level of the vapor such that there is substantially no condensation at the second location. In several embodiments, the relative humidity is optionally monitored and actively controlled during the sterilization cycle. In several embodiments, the system also includes a measuring device configured to measure the level of liquid agent, wherein based at least in part on the measured level, the evaporator is configured to adjust the level of liquid agent at the first location. For example, in one embodiment, the measuring device is a switch float.

In several embodiments, the evaporator further comprises a vibration element configured to create a mist of the liquid agent at or near the first location. In some such embodiments, the vibration element comprises a piezoelectric vibration element. In several embodiments, the evaporator is configured to generate the vapor at or near ambient temperature. In such embodiments, the ambient temperature is approximately room temperature and/or environmental humidity in the location of the system. In several embodiments, the evaporator further comprises a drain operable to drain the liquid agent from the evaporator.

In several embodiments, the system can also include a plasma generator configured to generate free radicals to be mixed with the vapor to sterilize, disinfect, sanitize, or decontaminate the item.

Still additional embodiments provide for a sterilization, disinfection, sanitization, or decontamination system comprising a vapor generator configured to generate vapor, a chamber configured to contain an item to be sterilized, disinfected, sanitized, or decontaminated and to receive the vapor from the vapor generator, a flow generator configured to circulate the vapor from the chamber to the vapor generator in a closed-loop such that the vapor sterilizes, disinfects, sanitizes, or decontaminates the item in the chamber, an air input coupled with the chamber and configured to allow dry air into the chamber, an exhaust coupled with the chamber and configured to remove existing air from the chamber, a sensor disposed in the chamber and configured to sense a level of at least one of humidity, pressure, and temperature within the chamber; and a controller in data communication with the sensor and configured to receive the sensed level from the sensor, wherein based at least in part on a difference between the sensed level within the chamber and external the chamber, the controller is configured transmit instructions either to the exhaust to remove at least a portion of the existing air from the chamber or to the air input to allow dry air into the chamber such that a condensation level in the chamber is at or below a threshold level.

In several embodiments, the threshold level is such that there is substantially no condensation in the chamber. In several embodiments, after the exhaust removes at least a portion of the existing air from the chamber, the air input in response allows dry air into the chamber. In several embodiments, the air input allows dry air into the chamber, the exhaust in response removes at least a portion of the existing air from the chamber. In some embodiments, the system also includes a sensor configured to sense whether the chamber is open, wherein the controller is further configured to execute instructions in order to, in response to determining with the sensor that the chamber is open, transmit instructions to the vapor generator to shut down and to the exhaust to remove the existing air from the chamber. In several embodiments, the vapor generator comprises an evaporator or a plasma generator.

Still additional systems are provided for herein, such as a sterilization, disinfection, sanitization, or decontamination system, comprising an effluent generator configured to generate effluent, wherein the effluent generator comprises a plasma generator, a chamber configured to contain an item to be sterilized, disinfected, sanitized, or decontaminated, the chamber comprising an input configured to receive the effluent from the effluent generator, a flow generator configured to circulate the effluent from the chamber to the effluent generator in a closed-loop, and a dryer disposed in a path of the closed-loop between the flow generator and the plasma generator. In several embodiments, the system includes a sensor disposed in the chamber and configured to sense a level of at least one of humidity, pressure, and temperature within the chamber and a controller in data communication with the sensor and configured to receive the sensed level from the sensor. In several embodiments, based at least in part on a difference between the sensed level within the chamber and external the chamber, the controller is configured transmit instructions to the dryer to dry at least a portion of the effluent entering the plasma generator such that a condensation level at the input of the chamber is at or below a threshold level.

In several embodiments, the threshold level is set at a level such that there is substantially no condensation in the chamber. In several embodiments, the path of the closed-loop between the flow generator and the plasma generator comprises a first branch and a second branch, wherein the dryer is disposed in the first branch and comprises a dry valve such that when the dry valve is opened, at least a portion of the effluent enters the dryer. In several embodiments, the system also includes a plasma valve in the second branch such that when the plasma valve is closed, the plasma valve blocks the effluent from entering the plasma generator through the second branch. In one embodiment, the effluent generator comprises an evaporator.

Also provided for herein is a chamber for sterilizing, disinfecting, sanitizing, or decontaminating one or more wounds on a patient, the chamber comprising an intake port configured to receive gaseous effluent from a effluent generator, an exhaust configured to return the gaseous effluent in the chamber to the effluent generator. an inflatable structure configured to be inflated by the gaseous effluent such that the inflatable structure does not come into contact with the one or more wounds on the patient and such that the gaseous effluent can circulate within the inflatable structure, and a sealing device that substantially seals the inflatable structure to the patient and thereby substantially containing the gaseous effluent within the inflatable structure. In several embodiments, the chamber includes an access port that enables a user to access the one or more wounds while the chamber is fitted to the patient. In several embodiments, the sealing device comprises a cuff and wherein the inflatable structure is configured to fit over at least a portion of the patient's arm or leg. In several embodiments, the cuff comprises latex.

There is additionally provided for a sterilization, disinfection, sanitization, or decontamination system for an appliance having a chamber with a closed space, the system comprising an effluent generator configured to generate effluent, wherein the effluent generator comprises at least one of: an evaporator and a plasma generator, a flow generator configured to circulate the effluent in a closed loop between the chamber and the effluent generator; and a Free Radical Destroyer (FRD) to remove free radicals from the effluent before it is discharged into the environment or into the room at the end of the cycle. In one embodiment, the plasma generator comprises an ozone generator. In one embodiment, the evaporator comprises a hydrogen peroxide evaporator. In one embodiment the appliance is a washing machine, dryer, microwave, dishwasher or other appliance with an enclosed chamber. In several embodiments, the system is used for room sterilization and wherein the system further comprises an effluent generator configured to generate effluent of varied humidity. In one embodiment, the effluent generator is placed in the room. In an alternative embodiment, the effluent generator is placed outside of the room and delivers the circulating sterilant to the room through input and output conduit.

The present disclosure provides various embodiments of devices, systems, and methods which can generate atmospheres having sterilizing, disinfecting, sanitizing, decontaminating, and/or therapeutic aspects. In several embodiments, the generated atmospheres undergo a relatively gentle process that is compatible with all materials (e.g., natural and manmade), live tissue, and electronics. In some embodiments, the generated atmospheres are produced with a "green" process, e.g., utilizing relatively low power consumption and producing non-toxic products and by-products. In some embodiments the sterilizing, disinfecting, sanitizing, decontaminating and/or therapeutic procedure is used as a singular therapy. In some embodiments the sterilizing, disinfecting, sanitizing, decontaminating and/or therapeutic procedure is used in conjunction with active and/or passive wound treatment modalities. These treatment modalities can include, but are not limited to, debridement, biological dressing(s), hydrogels, negative pressure wound therapy, and other treatment modalities. In some embodiments, one or more of these modalities are integrated with the sterilizing, disinfecting, sanitizing, decontaminating devices and/or therapeutic procedures as disclosed herein.

In several embodiments, a combination of reactive oxygen and/or nitrogen species (RONS) and vaporized hydrogen peroxide (VHP) provides significant and unexpected advantages over alternative technologies. In several embodiments, a RONS and VHP combination is eco-friendly because no harsh chemicals are used in the process and there are no residuals post processing from the sterilant. Another advantage of the RONS and VHP combination technology is flexible treatment coverage. For example, in wound healing, patches, boots, sleeves, arm cuffs (and the like) of various sizes can be used. This enables treatment to be administered to a range of areas, e.g., from small to whole body doses (in the case of treating burn victims). Furthermore, the treatment process is streamlined because sterilant circulates continuously across the wounded area without requiring provider supervision once a patch, boot, or arm cuff is applied. One embodiment of the RONS and VHP combination device is lightweight (e.g., 15 pounds or less) allowing it to be used for units that are portable (e.g., mounted on a pole or other mobile furniture). Additionally, some embodiments of the RONS and VHP combination technology have a reasonably low cost of goods that allow greater access and widespread use of the technology (e.g., a medical facility can employ multiple devices, which reduces risk of patient to patient (or provider) infection.

The present disclosure provides various embodiments of devices, systems and methods for sterilization, disinfection, sanitization, and/or decontamination of, for example, patient to patient, patient to caregiver, caregiver to patient, caregiver to caregiver, other personnel that are employed by or visit health care facilities, regulated and unregulated medical devices, medical equipment, heat and/or moisture sensitive devices or items, and in particular interior and/or exterior surfaces of small diameter or sensitive medical equipment. Some embodiments of the present disclosure relate to use in the veterinary field including devices, systems and methods for sterilization, disinfection, sanitization, and/or decontamination of, for example, a veterinarian treating an animal patient. As described above, in several embodiments, the variations in size of the device are advantageous in the veterinary space, given the wide range of animal sizes. In several embodiments, the devices and methods disclosed herein are useful for animal shelters, in order to limit spread of infection or disease for animals not having received normal veterinary care. Various embodiments may also be used outside healthcare facilities in a variety of industrial and consumer applications.

In several embodiments, there are provided systems and devices for delivering gaseous mixture of hydrogen peroxide vapor or microdroplets and cold plasma effluent (sterilant) under therapeutic parameters to reduce a targeted infection in a subject. Certain embodiments include devices and systems for delivering pressurized sterilant (or lower than atmospheric pressure or intermittent pressures) to reduce bioburden and promote healing in the wounds of a subject having one or more health conditions, including, but not limited to, skin and soft tissue infections (SSTIs), sepsis, localized infection, and/or osteomyelitis. Some embodiments disclosed herein relate to reducing pathogenic infections in soft tissue of a subject in order to promote wound healing in persistent or chronic wounds.

Several embodiments of the present disclosure provide a gaseous sterilant delivery device for delivering an ambient/pressurized/under-pressurized sterilant to a subject. In some embodiments, the device includes a source of sterilant functionally coupled to a subject interface unit, optionally a gas flow regulator that measures flow rate of the sterilant and optionally a gas pressure regulator that measures pressure of the sterilant as the sterilant is delivered through the subject interface unit to the subject, wherein the sterilant treats an infection in or on the subject.

In several such embodiments, the pressure of the sterilant delivered to the subject is from about 0.05 ATM to about 2.0 ATM, in particular about 0.15 ATM to about 1.0 ATM, and any values in between. In additional embodiments, the pressure ranges from about 0.05 ATM to about 0.10 ATM, about 0.10 ATM to about 0.15 ATM, about 0.15 ATM to about 0.20 ATM, about 0.20 ATM to about 0.25 ATM, about 0.25 ATM to about 0.50 ATM, about 0.50 ATM to about 0.75 ATM, about 0.75 ATM to about 1.0 ATM, about 1.0 ATM to about 1.5 ATM, about 1.5 ATM to about 1.75 ATM, about 1.75 ATM to about 2.0 ATM, and any pressure in between, including endpoints. In some other embodiments, the sterilant is delivered at ambient pressure.

In several embodiments, wherein the under-pressure of the sterilant delivered to the subject is from about −10 mmHg to about −300 mmHg, in particular about −10 mmHg to about −180 mmHg, and any values in between. For example, in some embodiments, the under-pressure ranges from about −10 mmHg to about −20 mmHg, −20 mmHg to about −30 mmHg, −30 mmHg to about −50 mmHg, −50 mmHg to about −70 mmHg, −70 mmHg to about −100 mmHg, −100 mmHg to about −120 mmHg, −120 mmHg to about −150 mmHg, −150 mmHg to about −180 mmHg, −180 mmHg to about −200 mmHg, −200 mmHg to about −250 mmHg, −250 mmHg to about −300 mmHg, and any pressure in between, including endpoints.

Several embodiments of the present disclosure also provide strict control of relative humidity (RH) delivered to the subject. RH of the circulating sterilant can vary during the sterilizing cycle according to the preprogrammed levels. Several embodiments disclosed herein include a relative humidity sensor.

In several embodiments, the humidity of the sterilant delivered to the subject in some parts of the cycle, especially during the beginning of the cycle, vary from about 20% to about 90%, and any values in between. In some embodiments, the humidity during the beginning of the cycle varies from about 20% to about 30%.

Several embodiments disclosed herein also include sterilization with UV light. In some embodiments the sterilization system further includes a UV light source in a chamber. In some embodiments, a UV light shelf is used to sterilize the bottom of an object placed directly on it.

Several embodiments disclosed herein also include one or more $N_2O$, NO, $NO_2$ sensors.

Several embodiments disclosed herein also include one or more oxygen and/or ozone, $H_2O_2$ sensors.

Several embodiments disclosed herein also include a gas flushing mechanism to reduce the incidence of or prevent a subject from being exposed to the sterilant when the subject interface unit is removed.

Several embodiments disclosed herein also include a subject interface unit that includes an attachment mechanism for maintaining a seal on the subject (or an area of a subject's appendage) while the sterilant gas is being delivered.

Several embodiments disclosed herein also include treating the infection in the subject that includes reducing bioburden in a wound located on the subject.

Several embodiments disclosed herein also include treating the infection in the subject by reducing one or more symptom(s) associated with the infection.

Several embodiments disclosed herein also include treating the subject by reducing the risk of developing an infection of one or more pathogenic organisms in the subject by pre-exposing them to the sterilant prior to onset of an infection at a wound site. In accordance with these embodiments, a subject can be treated with the sterilant upon presentation of a new wound.

Several embodiments disclosed herein also include treating infections that include an area of the subject's body infected by at least one pathogen selected from the group consisting of a bacterium, a virus, a fungus, a parasite, a protozoan, and an antibiotic resistant bacterium, or a combination thereof.

In several embodiments, the infection is a lesion, including, but not limited to, a surgical wound, a trauma wound, a burn, an abscess, an actinic keratosis, a keloid, a scar, skin cancer or a combination thereof.

The present disclosure also provides various embodiments of gaseous sterilization, disinfection, sanitization, and/or decontamination that can be carried out, optionally without a vacuum, at atmospheric pressure, and/or at room temperature. Some embodiments can also be carried out at slight negative pressure (e.g., as a safety precaution), slight positive pressure, and/or temperatures above or below room temperature.

The present disclosure also provides various embodiments of devices, systems, and methods for reducing or removing the build-up of mold, bacteria, bio film, and other pathogens which may arise in appliances such as dishwashers, dryers, and/or washing machines, particularly front loading washing machines and in a fruit and vegetable containment compartments of refrigerators.

The present disclosure also provides various embodiments of consumer product applications for sterilization, disinfection, sanitization, and/or decontamination. Examples of such use can include cosmetics (e.g., make up applicators), eyewear, dental products, toothbrushes, home use products for a medical condition (e.g., CPAP masks), infant care products, and pet care products. In general, the present disclosure applies to various industries that include but are not limited to, health care, sports medicine, veterinary care, dental care, agriculture, food processing, research, packaging, pharmaceuticals, home health, day care, senior care, private and public services, and military/emergency field care.

The present disclosure provides various embodiments of devices, systems, and methods for sterilization, disinfection, sanitization, and/or decontamination of food processing facilities and equipment. The provided disclosure can provide devices, system, and methods for those working with foods and in contact with potential bacteria (e.g., *Salmonella, E. coli*). Various embodiments involve the COP (clean out of place) step of food processing. The COP process involves cleaning, disinfecting, and decontaminating food processing equipment that has been disassembled for cleaning. Embodiments include, but are not limited to, the disinfecting and sanitizing of fittings, clamps, product handling utensils, tank vents, pump rotors, impellers, casings, and hoses. Various embodiments involve the CIP (clean in place) step of food processing. The CIP process involves cleaning the interior surfaces of food process equipment. Embodiments include, but are not limited to, the cleaning, disinfecting, and decontaminating tanks, pipes, and pumps. Various food processing embodiments involve cleaning, disinfecting, and decontaminating food contact surfaces including, but not limited to, fillers, mixers, conveyors, equipment, pipelines, tanks, vats, evaporators, and pasteurizers. Various food processing embodiments involve cleaning, disinfecting, and decontaminating non-food contact surfaces including, but not limited to, floors, walls, tables, chairs, benches, drains, troughs, and drip pans. In some embodiments the hard, non-porous, outside surface of airtight sealed packages containing food or other products are sanitized. The present disclosure provides various embodiments of devices, systems, and methods for use in sports medicine. In some non-limiting embodiments, the following items can be sterilized, disinfected, sanitized, or decontaminated: orthopedic fixtures, orthotics, ultrasound machines, and surgical implant parts.

Various advantageous embodiments of devices, systems, and methods described herein can be used without a vacuum, at constant atmospheric pressure (or slight negative or positive pressure), and/or at ambient temperature. In certain embodiments, a substantially continuous flow of sterilizing, disinfecting, sanitizing, and/or decontaminating vapor provided in a closed loop manner (optionally) without exhausting the vapor (e.g., a single cycle of continuous flow) can allow for relatively fast and efficient sterilization, disinfection, sanitization, and/or decontamination. In some embodiments, free radicals (e.g., reactive oxygen and nitrogen species—RONS) are generated using a plasma generator and/or a vaporizer to produce highly bactericidal yet non-toxic and/or gentle gaseous effluent. The effluent (e.g., reactive species and vaporized hydrogen peroxide) passes through a chamber, and then is recirculated in a closed loop system. In additional embodiments, the advantageous sterilizing, disinfecting, sanitizing, and/or decontaminating effects can be achieved in an open system. The chamber can be in the form of a movable chamber (e.g., a rotating tumbler) to sterilize, disinfect, sanitize, and/or decontaminate items like surgical masks or fabrics or medical waste, or in the form of a stationary chamber for more solid items. In several embodiments, the chamber can comprise a flexible bag or other compliant container that can encompass items of irregular shapes (or shapes that are otherwise less desirable for a dedicated type of chamber (e.g., a limb of an animal with a wound, a long catheter, etc.). In some embodiments, the chamber can comprise an entire room or a whole commercial or residential building. In some embodiments inside the chamber there is a container of custom size and shape based on the device or devices to be placed inside the container for sterilization, disinfection, sanitation, and/or decontamination. A blower may be provided inside the chamber to create turbulence. Various embodiments can be operated at room temperature so that heat sensitive materials (e.g., plastics, food, and/or live tissue) can be sterilized, disinfected, sanitized, and/or decontaminated. In several embodiments, a modest temperature increase is affected, but with temperatures remaining low enough to avoid damage to the items to be sterilized, disinfected, sanitized, and/or decontaminated. Furthermore, in some embodiments, the environment within the chamber (e.g., temperature) may be self-regulated or controlled (e.g., heated or cooled) to a condition different than the ambient conditions. In addition, the level of moisture within the chamber can be self-regulated (e.g., maintained at equilibrium) or controlled so that moisture sensitive items (e.g., electronics) can be sterilized, disinfected, sanitized, and/or decontaminated.

Various embodiments can also self-regulate and/or control moisture to reduce or avoid unwanted condensation. For example, a vaporizer or an evaporator may have a design configured to output vaporized hydrogen peroxide or other sterilizing, disinfecting, sanitizing, and/or decontaminating agent at or below the saturation level for the pressure in the chamber. By outputting the vaporized agent at such pressure levels, the evaporator can reduce or eliminate condensation of the agent at the output of the evaporator and thus also on the walls of the chamber and/or items in the chamber.

Additional devices, systems, and methods for self-regulating or controlling moisture to reduce or avoid condensation may include the regulated or controlled addition and removal of air and/or the use of a dryer in the closed-loop system to reduce the vapor saturation level of circulating effluent to desired levels.

For those embodiments used in conjunction with preheating and drying the items to be sterilized, disinfected, sanitized, and/or decontaminated, an input conduit equipped with a valve, heater and filter can supply fresh air to the system and an exhaust blower with an upstream filter and a free radical neutralizer can be used to remove moisture and active radicals from the system. The exhaust blower may be operated at a low speed mode during sterilization, disinfection, sanitization, and/or decontamination to create a negative-pressure condition in the chamber (e.g., approximately 1 to 2 cm of $H_2O$ lower than ambient pressure).

In several embodiments, a multi-output flow generator can be used to apportion flow in the closed loop, and also to provide multiple outlets to sterilize, disinfect, sanitize, and/or decontaminate multiple items or to feed multiple chambers. In several embodiments, tubing can be utilized to deliver sterilizing, disinfecting, sanitizing, and/or decontaminating vapor to lumens of medical and/or dental devices, particularly those with a small inner diameter and/or sensitive materials that would not be compliant with higher temperature, higher humidity, and/or pressure sterilization approaches.

Certain embodiments described herein can also be used with a wound chamber to aid healing by providing effluent to a wound. For example, a wound chamber may be used that maintains space around the patient's body and avoids/minimizes touching the wound. The wound chamber may include one or more rib structures, a multi-chamber design, or other features that provide structural support to maintain separation from the patient's wound. Therapeutic vapor may be contained within the wound chamber at a positive pressure, which may help maintain separation from the wound, or negative pressure, which may help prevent the vapor from escaping the chamber into the atmosphere. The wound chamber may include one or more access features such as ports, zippers, snaps, Velcro®, etc. that enable users of the chamber to access the wound. The wound chamber may be sealed to the patient using any suitable mechanisms, which may include a flexible cuff, tape, Velcro®, straps, or other mechanical implementations. The wound chamber may include and input line to deliver the vapor and an output line to enable recirculation of the vapor back through the effluent generator in a closed loop system. Additionally the chamber may include line connected to a vacuum pump. In some cases where it is beneficial for wound healing process to increase the pressure in the wound relative to the ambient pressure, additional line maybe connected to a pressure pump that would increase the pressure in the wound chamber. In general, it may be desirable to form the wound chamber out of biocompatible materials such as latex or suitable plastics. In some instances, a Tyvek® bag may be used.

The disclosure also presents a method of sterilizing, disinfecting, sanitizing, and/or decontaminating items using the above-described apparatus. The method includes placing the items in the chamber, pre-heating and drying them in an open-loop, disinfecting using a closed loop circulating system to supply bactericidal free radicals generated by an electric discharge with free radicals in antimicrobial liquid to the chamber, then flushing and drying the system in an open-loop.

Various embodiments can be self-contained allowing for portability and/or adaptation to relatively large scale commercial applications and/or to sterilize, disinfect, sanitize, and/or decontaminate facilities such as operating rooms, hospital rooms or entire buildings.

Some embodiments described herein can also be used for reducing or removing the build-up of mold, bacteria, biofilm, and other pathogens which may arise in appliances having closed spaces such as dishwashers, clothes dryers, and/or washing machines, particularly front loading washing machines and refrigerators.

In several embodiments, disclosed is a sterilization, disinfection, sanitization, or decontamination system, comprising a sterilant reservoir, an ozone generator, a vaporizer unit, a chamber, at least one flow generator, and a dryer. In some embodiments, the vaporizer unit is configured to be fluidly connected to the sterilant reservoir and the ozone generator. In some examples, the vaporizer unit is configured to mix a sterilant from the sterilant reservoir and ozone from the ozone generator. In some examples, the vaporizer unit is configured to generate an effluent of sterilant and ozone. In some embodiments, the chamber is configured to contain an item to be sterilized, disinfected, sanitized, or decontaminated. In some examples, the chamber comprises an input configured to receive the effluent from the vaporizer unit. In some embodiments, the at least one flow generator is configured to circulate the effluent from the chamber to the vaporizer unit. In some embodiments, the dryer is disposed between the flow generator and the vaporizer unit. In some embodiments, the system can include at least one valve configured to allow the dryer to be bypassed. In some embodiments, the system can include at least one valve configured to prevent any effluent from escaping the system.

In some embodiments, the sterilant reservoir comprises hydrogen peroxide that is converted to hydrogen peroxide vapor by the vaporizer unit. In some embodiments, the average level of hydrogen peroxide vapor is between about 250 PPM and 900 PPM. In some embodiments, the sensor is disposed in the chamber and configured to sense a level of at least one of humidity, pressure, and temperature within the chamber. In some embodiments, the vaporizer unit is a nebulizer. In some embodiments, the system further includes a mist catcher configured to collect mist from the nebulizer. In some embodiments, the mist catcher is downstream of the nebulizer. In some embodiments, the chamber is configured to withstand a negative pressure between 2 cm $H_2O$ to about 10 cm $H_2O$. In some embodiments, the system is configured to operate between a temperature between 20° C. to 25° C. In some embodiments, the average level of ozone generated by the ozone generator is between about 500 PPM and 1200 PPM. In some embodiments, the sterilization, disinfection, sanitization, or decontamination system is one of a desktop unit, a consumer unit, a wall mounted unit, a hand sterilization/disinfection unit, or a mobile unit. In some embodiments, the sterilant reservoir comprises a replaceable cartridge. In some embodiments, the system further comprises a sub-chamber configured to receive a sensitive portion of the item to be sterilized, disinfected, sanitized, or decontaminated. In some embodiments, the sub-chamber is configured to provide ultraviolet light to sterilize and/or disinfect the sensitive part.

In several embodiments, disclosed is a method for sterilizing or disinfecting at least one item. In some embodiments, the method can include placing the at least one item into a chamber configured to contain the at least one item. In some embodiments, the method can include activating a conditioning phase, wherein the conditioning phase comprises activating at least one flow generator to circulate air in a closed loop between the chamber and a dryer. In some embodiments, the method includes activating a sterilization or disinfection phase. In some embodiments, the sterilization or disinfection phase can include activating at least one valve to prevent the flow of air through the dryer. In some embodiments, the sterilization or disinfection phase can include activating at least one blower to circulate air through a vaporizer unit to generate an effluent, wherein the vaporizer unit is fluidly connected to at least one of an ozone generator and sterilant reservoir. In some embodiments, the sterilization or disinfection phase can include circulating effluent in a closed loop between the chamber and the vaporizer unit to prevent any effluent from escaping to an outside environment. In some embodiments, the method can include activating a purging phase. In some embodiments, the purging phase can include circulating air through at least one of the ozone generator and vaporizer unit. In some embodiments, the purging phase can include activating at least one valve to allow air flow through an inlet and outlet to remove effluent from the chamber and the at least one of the ozone generator and vaporizer unit.

In some embodiments, the method includes a vaporizer unit that is a nebulizer. In some embodiments, the nebulizer of the method is connected to a mist catcher, the mist catcher configured to collect mist from the nebulizer. In some embodiments, the method includes at least one of the inlet or outlet that includes a filter configured to convert effluent into water vapor and oxygen. In some embodiments, the vaporizer unit of the method is configured to mix fluid from the ozone generator and the sterilant reservoir, and the effluent comprises a mix of ozone and sterilant. In some embodiments, the sterilant reservoir of the method comprises hydrogen peroxide. In some embodiments, the average level of hydrogen peroxide of the method is between about 250 PPM and 900 PPM. In some embodiments, the vaporizer unit of the method is a nebulizer. In some embodiments, the chamber of the method is configured to withstand a negative pressure between 2 cm $H_2O$ to about 10 cm $H_2O$. In some embodiments, the system of the method is configured to operate between a temperature between 20° C. to 25° C. In some embodiments, the system of the method is configured to operate under a relative humidity between about 10% to about 85%. In some embodiments, the chamber of the method is configured to operate between 20° C. to 40° C. In some embodiments, the ozone generator of the method is at least one of a dielectric barrier discharge, a low pressure mercury ozone generator, and a $Xe_2$ excimer ozone generator. In some embodiments, the ozone generator of the method employs ultraviolet radiation. In some embodiments, the ultraviolet light of the method ranges between about 100 nm to about 280 nm. In some embodiments, the conditioning phase of the method is activated only if the initial percent relative humidity of the system is greater than 20% at the start of the conditioning phase. In some embodiments, the target conditioning cycle of the method is between about 60 seconds to about 120 seconds. In some embodiments, the sterilant reservoir of the method comprises a replaceable cartridge. In some embodiments, the method is configured to sterilize or disinfect a device including one or a plurality of lumens. In some embodiments, the effluent of the method is pushed through each of the one or a plurality of lumens. In some embodiments, the effluent of the method is pulled through each of the one or a plurality of lumens.

In several embodiments, disclosed is a sterilization, disinfection, sanitization, or decontamination system, comprising a sterilant, a nebulizer, a mist catcher, a bubble sensor, a chamber, at least one flow generator, a dryer, and at least one sensor. In some embodiments, the sterilant reservoir comprises hydrogen peroxide. In some embodiments, the nebulizer is configured to be fluidly connected to the sterilant reservoir and the ozone generator. In other embodiments, the nebulizer is configured to nebulize a sterilant from the sterilant reservoir and ozone from the ozone generator. In other embodiments, the system is configured to generate an effluent of sterilant and ozone. In other embodiments, the nebulizer provides an average level of hydrogen peroxide vapor between about 250 PPM and 900 PPM and an average level of ozone between about 500 PPM and 1200 PPM. In some embodiments, the mist catcher is configured to be fluidly connected downstream of the nebulizer, wherein the mist catcher is configured to collect mist from the nebulizer. In some embodiments, the bubble sensor is fluidly connected to the nebulizer, wherein the bubble sensor is configured to detect whether air is being delivered to the nebulizer from the sterilant reservoir. In some embodiments, the chamber configured to contain an item to be sterilized, disinfected, sanitized, or decontaminated, the chamber comprising an input configured to receive the effluent from the vaporizer unit, and wherein the chamber is configured to withstand a negative pressure between 2 cm $H_2O$ to about 10 cm $H_2O$. In some embodiments, the at least one flow generator configured to circulate the effluent from the chamber to the vaporizer unit. In some embodiments, the dryer is disposed between the flow generator and the vaporizer unit. In some embodiments the sensor is disposed in the chamber and configured to sense a level of at least one of humidity, pressure, and temperature within the chamber. In some embodiments, the system is configured to operate between a temperature between 20° C. to 25° C. and under a relative humidity between about 10% to about 85%. In some embodiments, the system includes at least one valve configured to allow the dryer to be bypassed. In some embodiments, the system includes at least one valve configured to prevent any effluent from escaping the system.

In other embodiments, the sterilization, disinfection, sanitization, or decontamination system further comprises an ozone generator. In other embodiments, the ozone generator is one of a low pressure mercury ozone generator and a $Xe_2$ excimer ozone generator.

In several embodiments, disclosed is a system for sterilizing, disinfecting, sanitizing, or decontaminating a device comprising at least one lumen. In some embodiments, the system includes a container, an input, and an output. In some embodiments, the container includes a retaining structure configured to retain the device comprising at least one lumen. In some embodiments, the input is located on a surface of the container. In other embodiments, the input is fluidly connected to an interior of the container. In other embodiments, the input includes a plurality of openings, wherein each of the plurality of openings is configured to be fluidly connected to a separate one of each one of the lumens at least one lumen. In other embodiments, the input is fluidly connected to an external effluent source and is configured to allow effluent to pass through the input and into an interior of the container. In some embodiments, the output is located on the surface of the container. In other embodiments, the output is fluidly connected to the interior of the container. In other embodiments, the effluent is configured to leave the system through the output.

In some embodiments, the system is configured to push effluent through the lumens of the device. In some embodiments, the container of the system comprises a flexible material disposed over a rigid frame. In some embodiments, the container of the system has a negative pressure of between 2 cm $H_2O$ to about 80 cm $H_2O$. In some embodiments, the inlet and outlet of the system are located on opposite surfaces of the container. In some embodiments, the plurality of openings of the input of the system is configured to provide different at least two different functions. In some embodiments, the retaining structure of the system is a hook. In some embodiments, the retaining structure of the system is configured to sterilize, disinfect, sanitize, or decontaminate a surface of the device in contact with the retaining structure.

BRIEF DESCRIPTION OF THE DRAWINGS

FIG. 1H shows a block diagram of an example embodiment using a dryer in a full bypass of the effluent supply to the plasma generator to prevent or reduce condensation in the chamber.

As illustrated in FIG. 33B, in some embodiments, the system for sterilizing/disinfecting hands can be wall mounted.

FIG. 38A shows the initial plumbing diagram of the system for sterilizing and/or disinfecting; FIG. 38B shows the plumbing diagram of the system during the conditioning phase; FIG. 38C shows the plumbing diagram of the system during the exposure phase; and FIG. 38D shows the plumbing diagram of the system during the purge phase.

DETAILED DESCRIPTION

General

Figure 1A:
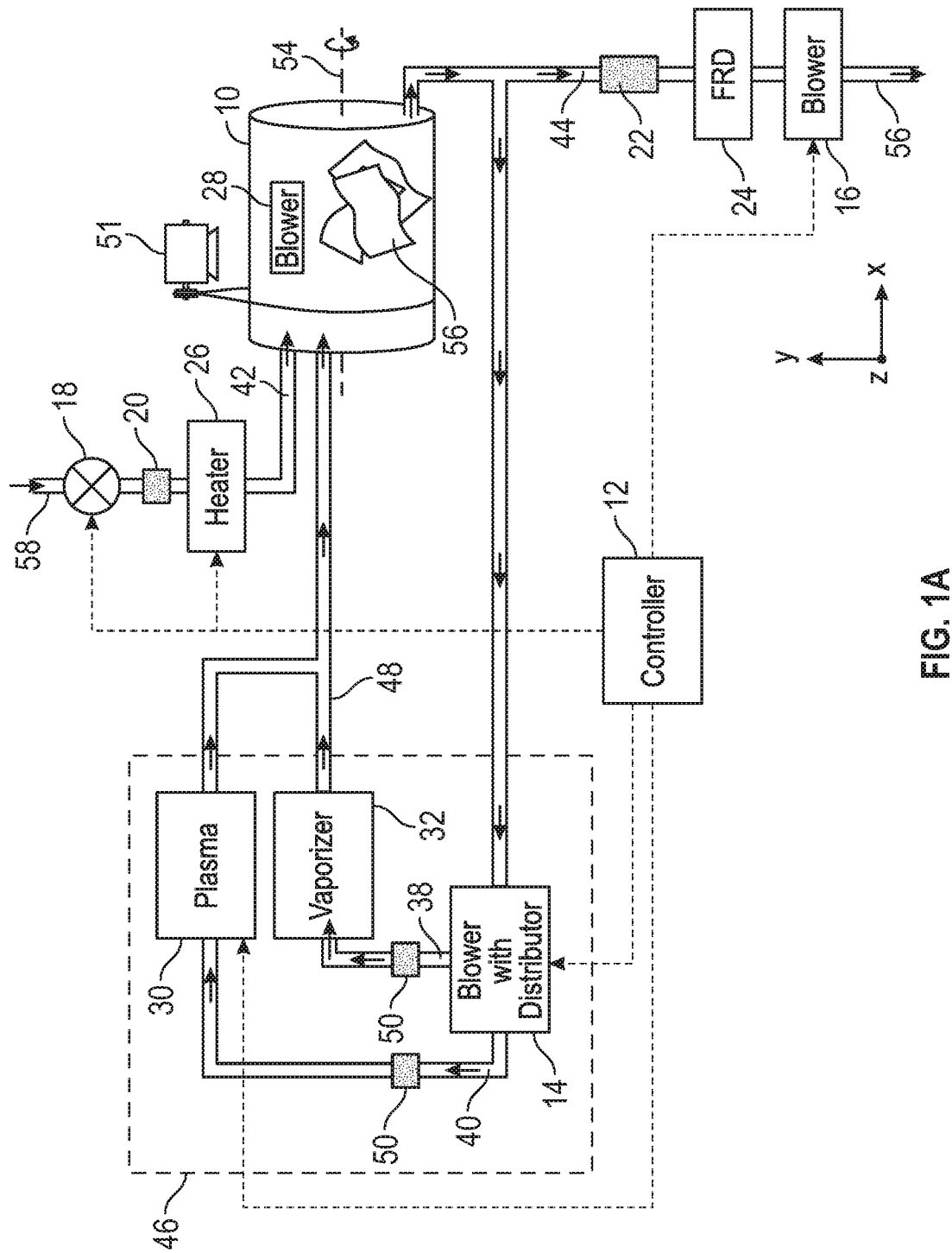
FIG. 1A shows a block diagram of a first embodiment of the disclosure with a tumbler-type chamber.

Sterilization, disinfection, sanitization, and decontamination methods are used in a broad range of applications, and have used an equally broad range of sterilization, disinfection, sanitization, and decontamination agents. The term "sterilization" generally refers to the inactivation of bio-contamination, especially on inanimate objects. The term "disinfection" generally refers to the inactivation of organisms considered pathogenic. Although the term "sterilization" may be used in describing certain embodiments herein, it would be appreciated that, unless otherwise indicated, such embodiments can also be used for disinfection (e.g., high-level disinfection, low-level disinfection, etc.), sanitization, and/or other types of decontamination, e.g., as provided with their regulatory definitions.

Sterilization is also important in the wound space. Existing wound therapy includes a standard procedure of care for treatment for chronic wounds, those that last longer than 30 days, that starts with physical debridement. This mechanical process, which involves resection of nonviable cells from abscessed tissues, ensures complete removal of bacterial biofilms that inhibit the healing process. Depending on the severity and longevity of the wound, patients may require antibiotic therapy, either through intravenous or oral applications. Beyond debridement and antibiotics, other treatments have been developed including Negative Pressure Wound Therapy (NPWT), Hyperbaric Oxygen Therapy (HOT), Biological Dressings (BD), and Hydrogels. Negative Pressure Wound Therapy, also known as vacuum assisted wound therapy, is a noninvasive wound closure system that uses controlled, localized sub-atmospheric (negative) pressure to promote healing. Pressure is maintained continuously or intermittently via a pump to a sterile, latex free polyurethane or polyvinyl alcohol foam dressing. Hyperbaric Oxygen Therapy, another active treatment, relies on patients sitting in a pressurized chamber of pure oxygen to increase their blood oxygen levels. Biological dressings, such as allogeneic bi-layers, are cultured from skin equivalents to create a living dressing to aid in chronic wound treatment. Hydrogels, such as Becaplermin, contain platelet derived growth factors that theoretically promote wound healing.

Pulsed or silent electric discharge in air or other gases produces non-thermal plasma. Non-thermal plasma processing involves producing plasma in which the majority of the electrical energy goes into the excitation of electrons. These plasmas are characterized by electrons with kinetic energies much higher than those of the ions or molecules. The electrons in these plasmas are short-lived under atmospheric pressure; instead they undergo collisions with the preponderant gas molecules. The electron impact on gas molecules causes dissociation and ionization of these molecules, which creates a mix of reactive species, in the form of free radicals, reactive oxygen and nitrogen species, ions, and secondary electrons. These reactive species cause unique and diverse chemical reactions to occur, even at relatively low temperatures. These chemical reactions are utilized in low temperature decontamination and sterilization technologies. While there are certain non-thermal plasma devices for wound treatment (or disinfection, sterilization, etc. of devices and objects), prior to the embodiments disclosed herein, all suffered from various therapeutic and practical limitations. First, all of these devices require interaction between the plasma and the wound (or object); that is, since the electric discharge takes place directly on the tissue, the treated tissue itself plays the role of an electrode. This makes the application of non-thermal plasma exquisitely sensitive to small movements or changes in geometry. This adds significant complexity to the treatment and requires the provider to have specialized training to maintain the proper tolerances. Other limitations include the inability to cover large surface areas in a short period of time and equipment that has a large environmental footprint and requires a high upfront cost. Additionally, current commercialized non-thermal plasma devices have a requirement for significant provider training and time to administer treatment including one on one provider to patient care.

As discussed in greater detail herein, vaporized hydrogen peroxide (VHP) can be used for sterilization. Certain methods of sterilization with VHP include open loop systems, in which the VHP is applied to the items to be sterilized and then exhausted, and closed loop systems, where sterilizing vapors are recirculated.

In closed loop systems, a carrier gas, such as air, is dried and heated prior to flowing past a vaporizer. A hydrogen peroxide aqueous solution is introduced into the vaporizer and which enables this solution to be vaporized. The resulting vapor is then combined with the carrier gas and introduced into a sterilization chamber of varying size, shape, and material. A blower exhausts the carrier gas from the sterilization chamber and recirculates the carrier gas to the vaporizer where additional VHP is added. Between the sterilization chamber and the vaporizer, the recirculating carrier gas passes through a catalytic destroyer (where any remaining VHP is eliminated from the carrier gas), a dryer, a filter and a heater.

United States Patent Application Publication No: US 2005/0129571 A1 by Centanni discloses a closed loop sterilization system. The purpose of using the closed loop is to prevent decrease of the free radical concentration in the circulating effluent. Centanni teaches that there should be a VHP (vapor hydrogen peroxide) destroyer employed in the loop. Centanni teaches that the ozone is mixed with the hydrogen peroxide vapor or microdroplets and the vapor or microdroplets are produced by injecting hydrogen peroxide water solution on a hot plate and thus evaporating it.

As discussed in greater detail herein the present application provides for various systems, devices, and related methods for sterilizing, disinfecting, sanitizing, and/or decontaminating a variety of items, ranging from surgical equipment or other medical devices to electronic equipment, as well as services, rooms, and other items including, but not limited to soft goods, foods, and related manufacturing equipment. A general overview will be provided, with additional detail related to each of the components of such systems and devices provided below. As mentioned above, the term "sterilization" shall be appreciated to not only encompass the removal of all or substantially all microorganisms and or other pathogens from an object or surface but shall also encompass (unless otherwise specified) disinfection, sanitizing, and decontamination.

In several embodiments, there is provided a system for sterilization that comprises a free radical generator, a vaporizer, and a chamber that encloses or otherwise contains items to be sterilized. In some embodiments, these components are directly connected to one another, e.g., are a unitary device. However, in several embodiments a variety of conduits connect the respective portions of the system together in a combination of one way, or two-way, fluidic connections between the various components.

In several embodiments, the system additionally comprises a controller element. The controller element serves to integrate and coordinate the function of the various components of the system for example cycle duration, amount of free radicals generated and introduced into the chamber and the like.

Several embodiments further comprise a flow distributor. In several embodiments, the flow distributor is fluidically connected with the free radical generator in the vaporizer. As discussed below, the free radical generator in the vaporizer can be positioned in parallel with respect to one another, or in series, with either the vaporizer or the free radical generator occupying the first position in the series, depending on the embodiment. In several embodiments, the flow distributor is fluidically connected with the free radical generator and/or the vaporizer by way of one or more conduits. Depending on the embodiment, one or both of the conduits can also comprise a filter element that functions to remove particulate matter and/or other materials from the gas being passed from the flow distributor to the free radical generator and/or vaporizer. Various embodiments employ different types of filters, such as charcoal filters, HEPA filters, and the like, as discussed in more detail below.

A fluidic connection is also provided, in several embodiments between the free radical generator into the vaporizer and the chamber. In other words, these conduits convey either independently or in a joined format, the effluent is generated from the free radical generator and/or vaporizer. In several embodiments a first conduit delivers the free radicals to the chamber and a second conduit delivers vaporized sterilant to the chamber. However, in other embodiments, two independent conduits meet at a junction point such that the flow of free radicals and vaporized sterilant are combined prior to, or concurrent with, entry into the chamber. In several embodiments either the controller and/or the flow distributor adjust the relative distribution of free radicals and vaporized sterilant that are combined and subsequently pass into the sterilization chamber. In some embodiments, the combination of the free radical generator, sterilant vaporizer, and flow distributor (as well as their respective fluidic conduit connections) are collectively referred to herein as the effluent generator.

In several embodiments an outlet conduit exits the sterilant chamber and provides a flow pathway for access sterilant to return to the flow distributor of the effluent generator. In several embodiments this allows recycling of unspent sterilant/free radicals and allows for a more efficient sterilization process as efficacious concentrations of sterilant can be reached within the chamber more quickly.

In some embodiments, the exit/recycling conduit leaving the sterilant chamber is bifurcated and provides an outflow pathway to the external environment. In several embodiments this conduit further comprises one or more of a filter element, a free radical destroyer, and/or on additional blower/exhaust fan. In several embodiments this additional bifurcated pathway functions when the system is operating in an open loop configuration, which is discussed in more detail below. In such embodiments remaining particulate matter that has exited the sterilant chamber, and optionally, the free radical destroyer eliminates any remaining free radicals that may have exited the chamber. The additional blower/exhaust fan serves to regulate the flow of gases along this additional bifurcated exit pathway. In some embodiments of an open loop operation, prior to the initiation of the sterilization cycle the sterilant chamber is purged and the gaseous contents of the chamber are exited to the environment through this additional bifurcated pathway, having been safely filtered with free radicals destroyed, such that the output to the environment is functionally inert.

In several embodiments, an additional environmental inlet pathway is provided that allows external environmental air to enter the system. In several embodiments this inlets has an independent entrance into the sterilization chamber. In several embodiments the inlet conduit comprises one or more of a valve (e.g., a purge valve), a filter elements, and a heater element. In some embodiments, this inlet pathway allows environmental air to be filtered, pass through the heater element, and enter the interior of the sterilization chamber, serving to warm, and dehumidifier a the interior of the sterilization chamber. In several embodiments this environmental air, after having heated and dried the interior of the sterilization chamber, exits to the environment, via the bifurcated outflow pathway briefly described above. Thereafter, in several embodiments the purge valve can be closed and the additional blower exhaust fan can be disengaged, thereby allowing sterilization system to operate in a closed loop fashion—in other words, free radicals and vaporized sterilant from the effluent generator enter the interior compartment of the sterilization chamber, exit the interior of the sterilization chamber and are recycled via conduit back to the effluent generator via the flow distributor, that is controlled by the controller element.

Figure 16:
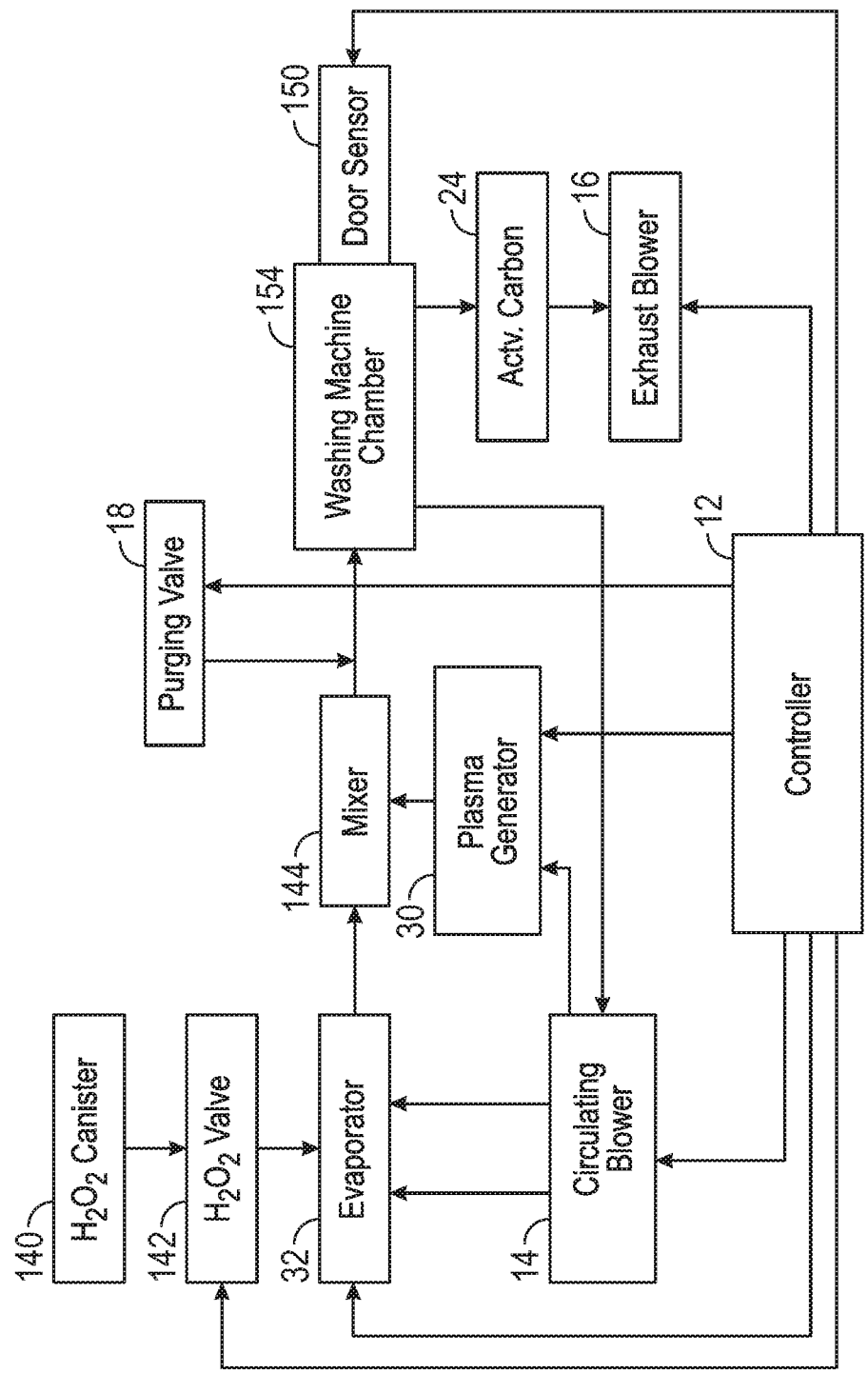
FIG. 16 shows a block diagram of an example embodiment incorporated into a washing machine.
Figure 17:
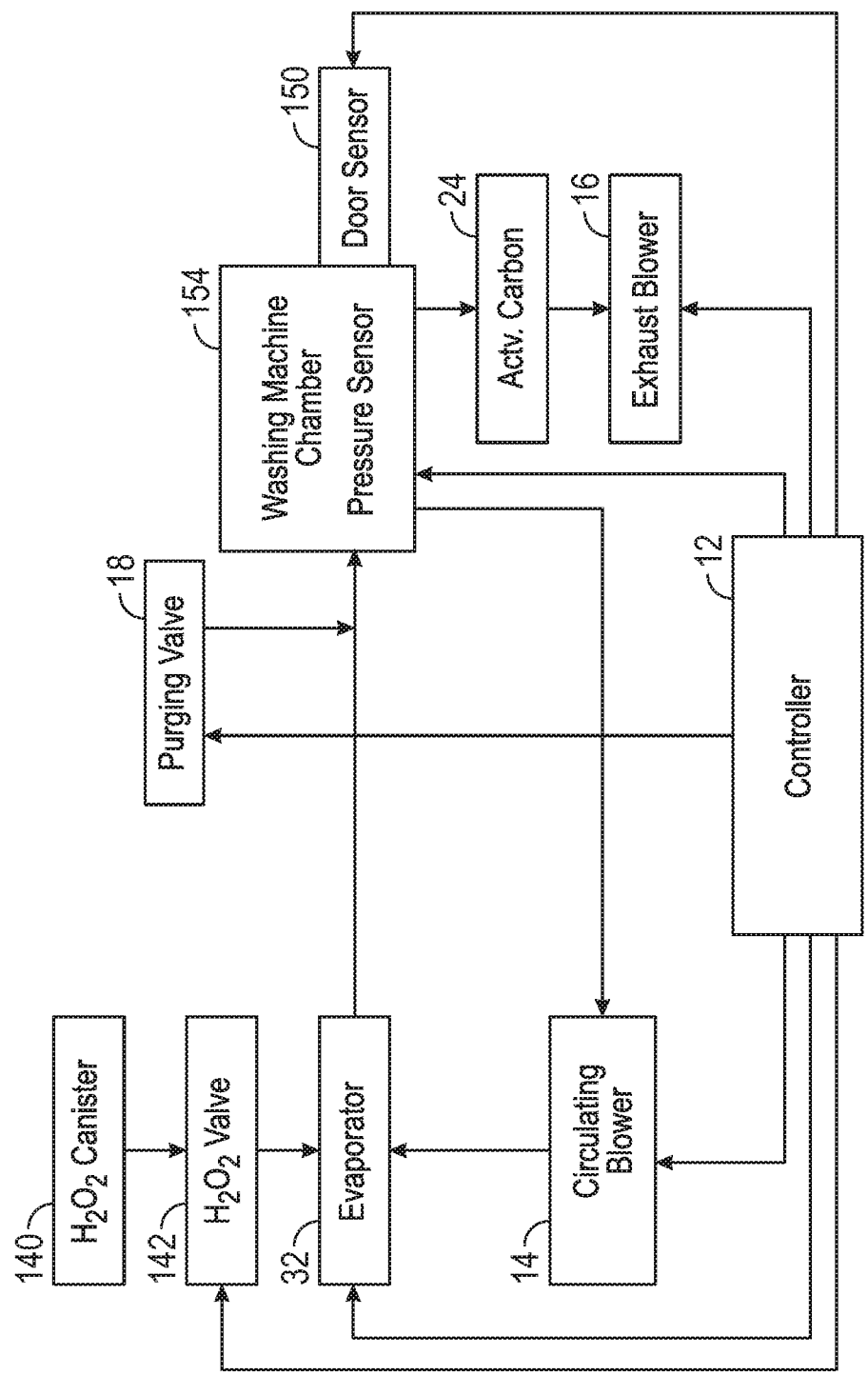
FIG. 17 shows a block diagram of another example embodiment incorporated into a washing machine.

FIGS. 1 through 2 and 4 through 7 show block diagrams of a sterilization system, illustrating various embodiments of the present disclosure that use a sterilization chamber. FIGS. 10 to 12 and 14 to 15 show additional embodiments using a wound chamber. FIGS. 16 to 18 show further embodiments incorporated into a washing machine, though it shall be appreciated that these embodiments are readily adaptable, based on the disclosure provided herein, to other appliance types. It shall also be appreciated that various embodiments described herein may apply to healthcare (e.g. acute care settings, point of care settings, and/or long term care setting), industrial, and/or consumer applications. Various embodiments described herein may also apply to an entire room or a commercial or residential building. Although the term "sterilize," "sterilant," "sterilization," etc. may be used in describing certain embodiments herein, it would be appreciated that such embodiments can also be used for disinfection, sanitization, and/or decontamination.

In the present application, it will be understood that those parts of the disclosure that are in common between the various figures are given the same reference number in each figure, and will not be separately discussed in the detailed description of each figure.

Broadly stated, in several embodiments, the sterilization systems disclosed herein utilize a combination of broad mixture of free radicals (e.g., reactive oxygen and nitrogen species) used in sterilizing and decontamination devices to sterilize items placed in the sterilization chamber, or over which the wound chamber is placed. Various embodiments can be self-contained, small, light-weight, and portable. In some instances, some embodiments can be battery operated or powered by hand. In other examples, some embodiments can be scaled to larger volume.

Sterilization Chambers

Depending on the embodiment, the sterilization chambers for use with the systems, devices, and methods disclosed herein can vary in their dimensions and other features. Regardless, in several embodiments, the sterilization chamber is configured to receive sterilant and the item to be sterilized. Depending on the embodiment, the sterilization chamber can be stationary or movable. Whether stationary or movable, chambers can optionally be encased in a housing that also includes one or more additional components of the sterilization system (e.g., plasma generator, controller, etc.). In several embodiments, the chamber comprises a tumbler-type chamber, which, in operation, is rotated around an axis. For example, in several embodiments, the chamber is rotated about a longitudinal axis, while in additional embodiments, it is rotated around a lateral axis or a vertical axis. In still additional embodiments, the chamber can be moved about more than one axis simultaneously. Likewise, in additional embodiments, the chamber may be movable, but need not rotate in any particular passion, for example the chamber may simply oscillate, vibrate, shake, or otherwise move in a pattern of predetermined or random motions such the contents inside the sterilization chamber are likewise moved.

It shall be appreciated from the disclosure herein, the dimensions of the sterilization chamber are readily adjustable for any particular application or method of sterilizing. For example, the size and shape of the chamber can be adjusted for such embodiments wherein small medical devices are sterilized, while in other embodiments the chamber (or chambers) can be scaled up in size in order to sterilize larger items, large quantities of items, or a plurality of items to be sterilized simultaneously. In some examples, the chamber may be a room to be decontaminated. Thus, the sterilization chamber provided for herein can be any geometric shape and can vary in dimension depending on the intended use of the sterilization system. With respect to dimensions, the sterilization chambers may have a volume ranging from about 10 L to about 10,000 L. For example, the sterilization chambers may have a volume of 10 L, 10.5 L, 11 L, 11.5 L, 12 L, 12.5 L, 13 L, 13.5 L, 14 L, 14.5 L, or 15 L. In some examples, the sterilization chamber may have a volume ranging from about 10 L to about 50 L, about 50 L to about 100 L, about 100 L to about 250 L, about 250 L to about 500 L, about 500 L to about 1000 L, about 1000 L to about 2500 L, about 2500 L to about 5000 L, about 5000 L to about 7500 L, about 7500 L to about 10,000 L, and any chamber volume in between those listed, including endpoints. In some embodiments, the sterilization chamber can have a chamber size with the dimensions of about 150-250 mm by about 250-350 mm by about 200-300 mm, for example, about 204 mm by about 310 mm by about 230 mm.

As shall be appreciated from the disclosure provided herein, in several embodiments the sterilization chamber is an existing enclosure separate from the sterilization system, and the sterilization system is attached to, or otherwise fluidically connected with, the existing separate enclosure such that the interior of the existing separate enclosure can be exposed sterilant, thereby allowing sterilization of all of the surfaces and/or objects present within the existing separate enclosure. For example, in several embodiments the sterilization chamber is in fact a hospital room (e.g., a patient room), a storage room for equipment, or another room or enclosure that contains objects or surfaces to be sterilized.

In other embodiments, the chamber can be custom shaped to fit objects of a particular size or shape. In several embodiments, the chamber is unitary with the remainder of the system, while in some embodiments, the chamber is a separate, modular piece of the system. In several embodiments, the chamber comprises a disposable unit. In some such embodiments, a disposable chamber can be single use, while some embodiments comprise a multi-use chamber. Optionally included in such multi-use formats are indicators for the life-cycle of the chamber, for example indicating a number of cycles remaining before replacement is recommended.

As discussed in more detail below, in several embodiments, the chamber further contains an internal container of custom size and shape based on the device or devices to be sterilized, disinfected, sanitized, and/or decontaminated inside the container. In several such embodiments, the chamber comprises one or more adaptor that is integrated or attached to the container and serves as a conduit to deliver sterilant to and/or from the container. In some embodiments, a self-sealing value or material is used to ensure the objects inside the container remain disinfected or sterilized. For example, in several embodiments, a self-sealing membrane that is configured to be punctured is used. In several embodiments, a duck bill valve is used, wherein the valve is predisposed to be in a closed position.

In several embodiments, the system optionally comprises a fixed chamber (e.g., integrated or otherwise operably connected with a controller unit and/or blower/distributor—in essence, a one piece or minimal piece type system). In several embodiments employing a fixed chamber, the conduit plumbing, discussed in more detail below, is directly into and out of the chamber. Advantageously, such a chamber size provides a significant degree of volume within the sterilization/disinfection chamber vis-à-vis the overall size of the system. Additionally, such an approach, in several embodiments, provides enhanced consistency of airflow within the chamber, thereby providing for highly consistent and efficacious sterilization/disinfection of a variety of different types and shapes of devices. In some embodiments, the sterilization chamber can circulate air, for example, between about 15 chamber exchanges/min to about 30 chamber exchanges/min, between about 5 chamber exchanges/min to about 50 chamber exchanges/min or any ranges in between such as about 5 chamber exchanges/min to about 10 chamber exchanges/min, about 10 chamber exchanges/min to about 15 chamber exchanges/min, about 15 chamber exchanges/min to about 20 chamber exchanges/min, about 20 chamber exchanges/min to about 25 chamber exchanges/min, about 25 chamber exchanges/min to about 30 chamber exchanges/min, about 30 chamber exchanges/min to about 35 chamber exchanges/min, about 35 chamber exchanges/min to about 40 chamber exchanges/min, about 40 chamber exchanges/min to about 45 chamber exchanges/min, and about 45 chamber exchanges/min to about 50 chamber exchanges/min. In some embodiments, air circulation can be over a hundred exchanges/min. In some examples, the fewer exchanges will result in longer time periods for sterilization. In some examples, the larger number of exchanges will shorten the sterilization time.

In additional embodiments, the chamber is optionally removable from the remainder of the system. While several embodiments of such an approach does require additional connectors between the removable chamber and the effluent generator, or other components of the system, a removable chamber approach advantageously allows for a very compact size of the system when not in use (e.g., the chamber can be removed, stored separately, folded or otherwise compacted/disassembled). Additionally, such an approach is advantageous because a plurality of chambers of different sizes can be provided for in a single system, thereby allowing a corresponding chamber size to be used with an item to be sterilized/disinfected of a certain size. Such an approach improves overall efficiency of sterilant/disinfectant use, so that an appropriate amount of sterilant/disinfectant is provided for a device of a given size.

In several embodiments, the systems provided for herein can be mounted or utilized in a variety of different formats. For example in several embodiments the system can be a countertop unit. Alternatively, an under-counter, under-cabinet, or wall mounted unit can be provided for, to enhance space savings and retain workable benchtop space in a given environment. In additional embodiments, the system can be a freestanding system, in several embodiments dimensioned to fit next to an existing countertop or cabinet. In several embodiments, such a freestanding system can be dimensioned to be relatively tall, relatively deep, and relatively narrow, thereby optimizing its ability and capacity for sterilization/disinfection while reducing its overall footprint. Depending on the embodiment, or the requirements of a given workspace, such an approach could utilize systems that are less than, equal to, or greater than a given countertop height. Systems provided for herein may also be height adjustable and/or portable (e.g. small enough to be moved from one site to another, or provided on a rolling cart or other mobile accessory). The systems disclosed herein, depending on the embodiment may be front loading, top loading, or loaded by any other approach (e.g., by sliding a container comprising items to be sterilized/disinfected into the sterilizing/disinfectant chamber). Additionally, depending on the embodiment, the systems provided for herein may be self-contained with respect to their conduit plumbing. However, in several embodiments the systems are hard-plumbed, such that the various conduits external to the system (e.g. output to the environment, air input, heater/dryer, and optionally sterilant/disinfectant source) are provided by a pre-existing infrastructure.

In several embodiments, a plurality of items are sterilized or disinfected simultaneously. While in some embodiments, this involves simply placing the plurality of items within the chamber, in additional embodiments, specialized apparatuses are used. For example, in several embodiments, there is provided a specialized apparatus for disinfecting or sterilizing the exterior of a plurality of devices while simultaneously disinfecting or sterilizing a lumen of each of the devices.

For example, in several embodiments, the sterilization/disinfection systems disclosed herein comprise an endoscope rack or manifold that sterilizes and disinfects endoscopes and similar devices, including other lumen containing devices. For example the endoscope rack can be used with scopes related to the following fields, gastroenterology, endoscopic ultrasound scopes, pulmonology, ENT (ear, nose, and throat), speech, and urology. Additionally, in some embodiments scopes with working channels such as for biopsy or suction can be used with the endoscope rack. Advantageously, in several embodiments, the endoscope unit (a term that encompasses units to sterilize/disinfect other lumen containing devices) allows the endoscopes or other devices to remain within the unit (either in a bulk section or in individual sections, and maintain sterility while inside the unit. In several embodiments, the unit may optionally further comprise an adapter configured to fluidically connect with a blower that conveys sterile or disinfected air into the working channel of the endoscope until it is dry. In several embodiments, the conveyed air is heated and/or dehumidified. In several embodiments the drying process ranges from about 5 to about 120 seconds, including about 5 to about 10 seconds, about 10 to about 20 second, about 20 to about 30 seconds, about 30 to about 60 seconds, about 60 to about 90 seconds, about 90 to about 120 second, and any time there between, including endpoints. In several embodiments, the systems disclosed herein comprise the dryer as a separate compartment from the chamber. However, in several embodiments, the chamber serves to store the devices during disinfection/sterilization and also during the drying process (if included). Moreover, the chamber may also serve as a storage area. In some embodiments, the endoscope or other device is placed within a separate compartment, optionally flexible, that creates a barrier between the device and the environment, such that the sterility/disinfected state will be maintained even after being removed from the chamber. Such embodiments advantageously allow the sterilized/disinfected devices to be stored and/or transported to a site of next use while maintaining the sterility/disinfected state.

In some embodiments, the chamber, including any sub-chambers or containers, are configured for continuous circulation of the effluent. In several embodiments, this includes continuous circulation through the lumen(s) of any lumen-containing devices.

The material that makes up the inner wall of the chamber can vary depending on the embodiment. In several embodiments, the chamber comprises a non-conductive, non-corrosive, or otherwise non-reactive material, such that the inner wall of the chamber does not react with the sterilant. Suitable materials include, but are not limited to, glass, plastics, polymers, metals, stainless steel (e.g., 304 or 316 stainless), ABS plastic, aluminum, bronze, carbon graphite, cast iron, ceramic (AL203), ceramic magnet, CPVC, EPDM, epoxy, Hastelloy-C®, Kel-F®, LDPE, natural rubber, NORYL®, nylon, polycarbonate, polypropylene, PPS (Ryton®), PTFE (Teflon®), PVC, PVDF (Kynar®), silicone, Titanium, Tygon®, Viton® or combinations thereof. Moreover, in several embodiments, the inner wall of the chamber may be made of a first material while other layers, including insulating or other layers may be other materials.

Effluent Generator

As discussed in greater detail below, several embodiments involve the use of a sterilant that is generated by an effluent generator. In several embodiments, the effluent generator is a sub-unit of a larger system that comprises at least one of a plasma generator (e.g., a free radical generator), a vaporizer (e.g., a unit that generates a vapor of a sterilant, such as hydrogen peroxide, a blower/distributor, and associated conduits to fluidically connect such components. In some embodiments, the effluent generator comprises all of those components, though in other embodiments only a portion of those are included in the effluent generator. In the latter embodiments, the other components may be housed elsewhere in the system or are integrated into the system externally (e.g., a system may be coupled to an existing blower at a site where sterilization/decontamination is to occur).

Plasma or Free Radical Generator

In several embodiments, the systems disclosed herein comprise a plasma or free radical supply unit. In several embodiments, a cold plasma generator such as a plasma electric free radical generator is used. In several embodiments, an ozone generator is used. In several embodiments, a dielectric barrier discharge system is used. The plasma free radical generator 30 can be any kind of dielectric barrier discharge device, electrical corona device, a glow discharge device, or a microwave generator. One non-limiting example of a device which can be used within the teachings of the disclosure is an ozone generator such as, for example, ozone generator cell SY-G20 manufactured by Longma Industrial Zone, Bao'an District, Shenzhen, 518108, P.R.C. In some embodiments, the ozone generator includes two plates, each of which is configured to provide approximately 600 ppm/min. In some embodiments, the ozone generator is a Dielectric Barrier Discharge ozone generator wherein the metal is not exposed. Depending on the embodiment, any other type of system that generates free radicals may be used, for example a system or device that produces sufficient energy to break bonds, such as covalent bonds, for example through hemolytic bond cleavage. Additional embodiments, employ free radical generators that operate via silent corona discharge UV light to split $O_2$ to create single oxygen atoms, which then interact with $O_2$ to form $O_3$ (ozone).

In some embodiments, the sterilant (e.g., ozone) concentration can be from about 350 ppm to about 1200 ppm or any ranges in between such as about 350 ppm to about 400 ppm, about 400 ppm to about 450 ppm, about 450 ppm to about 500 ppm, about 500 ppm to about 550 ppm, about 550 ppm to about 600 ppm, about 600 ppm to about 650 ppm, about 650 ppm to about 700 ppm, about 700 ppm to about 750 ppm, about 750 ppm to about 800 ppm, about 800 ppm to about 850 ppm, about 850 ppm to about 900 ppm, about 900 ppm, to about 950 ppm, about 950 ppm to about 1000 ppm, about 1000 ppm to about 1050 ppm, about 1050 ppm to about 1100 ppm, about 1100 ppm to about 1150 ppm, about 1150 ppm to about 1200 ppm. In some examples, ozone can be generated at a rate of 600 ppm/minute. At the end of the sterilization cycle, in some embodiments, the final ozone concentration before the chamber door is opened can be about 600 ppm.

Other embodiments employ ultraviolet (UV) radiation to split $O_2$ to create single oxygen atoms alternatively or in addition to non-thermal plasma methods for generating ozone, such as corona discharge. Gases comprising air or oxygen may be irradiated with UV light within the free-radical generator to generate ozone. Relatively shortwave UV radiation, such as low pressure UV radiation, less than approximately 254 nm, or vacuum ultraviolet (VUV) radiation, less than approximately 200 nm, may be preferred for the generation of ozone, as molecular oxygen strongly absorbs radiation within these wavelengths, particularly the VUV spectrum. UV lamps may be employed which are tuned to emit radiation within either or both of these spectra. In some embodiments, the wavelength of the UV light is between approximately 100 nm and 240 nm, 160 nm and 240 nm, or 180 nm and 200 nm. In some embodiments, the wavelength of the UV light used in the ozone generator is approximately 185 nm. Wavelengths of UV light between approximately 150 nm and 200 nm may be advantageous, particularly when used to irradiate air, because nitrogen is less prone to absorb radiation within this spectrum of wavelengths. Consequently, UV radiation within this spectrum may be less likely to produce reactive nitrogen species (e.g., nitrogen oxide, nitrous oxide, nitrogen dioxide, nitric acid). The elimination or reduction of reactive nitrogen species (RNS) within the effluent may result in improved material compatibility in certain applications. For example, electronic components comprising metal, such as copper, may be susceptible to detrimental nitric acid formation in the presence of reactive nitrogen species. These by-products may gradually corrode the sterilized materials or result in other detrimental material compatibility effects. The UV lamps used to generate ozone may comprise coatings (e.g., on the UV bulbs) or other types of filters which may narrow the spectral range of radiation to or around the wavelengths described herein.

Vaporizer

In several embodiments, a vaporizer is included in the effluent generator (other embodiments employ a stand-alone vaporizer). Depending on the embodiment, the vaporizer contains a liquid sterilizing agent, or a solid agent that is at least partially converted to a liquid during a sterilization cycle. In several embodiments, a liquid sterilizing agent such as hydrogen peroxide solution is used. The gas entering the vaporizer (e.g., either from an external source or recycled from the chamber), comes into contact with the solution, is vaporized (e.g., evaporation, boiling, sublimation, etc.) to produce an effluent comprising reactive oxygen species (e.g., bactericidal effluent). While certain embodiments are described with particular reference to hydrogen peroxide as the sterilizing/disinfecting agent, it will be appreciated that the system is also applicable to other solutions and/or pure liquids, such as peracetic acid, formalin solution, aldehydes such as formaldehyde, propriolactone, chlorine dioxide, and the like.

In several embodiments, the vaporizer comprises a "bubbler" or "aerator" or other "evaporator" element, in which the gas passes through a container of liquid to yield a vapor. In other embodiments, the vaporizer comprises plates or wicks that hold or are soaked with sterilant and over which the gas passes. In several embodiments, an electronic device or other motorized device (e.g., a shaker, vibration plate, or piezoelectric element) is used to assist in the vaporization of the sterilant/disinfectant. Various configurations of vaporizers can be employed, depending on the embodiment. FIGS. 1C-1E, described in more detail below, depict various embodiments of evaporator elements that are employed in certain embodiments of the vaporizer. For example, in several embodiments, the evaporator comprises a plurality of tubes with a wicking material disposed between the tubes. In several embodiments, a portion of the wick rests in a pool of sterilant/disinfectant. In several embodiments, there is a float element (optionally coupled to a sensor) that regulates the amount of sterilant/disinfectant in the pool at a given time. The sterilant/disinfectant is wicked up the wicking element and gas is passed across the wicking element or bubbled through the wicking element to yield evaporation, misting, and generally formation of a sterilant/disinfectant vapor. In several embodiments, the wicking material is baffled in order to enhance the surface area of the wick and increase the efficiency of sterilant/disinfectant vapor formation. In several embodiments, interwoven layers of wicking material are used, for example a first layer or layers in contact with the sterilant/disinfectant pool that are interwoven with a second layer or layer not in contact with the sterilant/disinfectant, wherein the interwoven section allows transfer of sterilant/disinfectant wicked into the first layer to the second layer. Depending on the embodiment, evaporation/vaporization can optionally occur passively (e.g., without heat) by the flow of air through the wet wicking material, though in several embodiments a heating source is used.

In several embodiments, the sterilant is provided in a quantity sufficient for a single sterilization/decontamination cycle. However, in several embodiments, a multi-run cartridge or container of sterilant is provided. In some embodiments, the sterilant (e.g., hydrogen peroxide) concentration (or the average concentration) can be from about 30% to about 60% concentration, e.g., about 30%, about 35%, about 40%, about 45%, about 50%, about 55%, or about 60% concentration. In some examples, the hydrogen peroxide vapor or microdroplets concentration can be from about 100 ppm to about 10,000 ppm or any ranges in between such as about 100 ppm to about 600 ppm, about 500 ppm to about 2500 ppm, about 1000 ppm to about 4000 ppm, about 1500 ppm to about 5000 ppm, about 2500 ppm to about 6000 ppm. At the end of the sterilization cycle, the final hydrogen peroxide vapor or microdroplets concentration can be about 600 ppm or less (e.g., about 550 ppm or less, about 525 ppm or less, about 500 ppm or less, about 475 ppm or less, about 450 ppm or less, about 425 ppm or less, or about 400 ppm or less) in some embodiments. In some examples, the hydrogen peroxide vapor or microdroplets concentration can range between 250 ppm to about 900 ppm or any ranges in between such as about 250 ppm to about 300 ppm, about 300 ppm to about 350 ppm, about 350 ppm to about 400 ppm, about 400 ppm to about 450 ppm, about 450 ppm to about 500 ppm, about 500 ppm to about 550 ppm, about 550 ppm to about 600 ppm, about 600 ppm to about 650 ppm, about 650 ppm to about 700 ppm, about 700 ppm to about 750 ppm, about 750 ppm to about 800 ppm, about 800 ppm to about 850 ppm, and about 850 ppm to about 900 ppm. In some embodiments, the peak level of sterilant (e.g., hydrogen peroxide) can be dependent on temperature range.

In some embodiments, the chamber temperature can range between about 20° Celsius to about 40° Celsius, this can include for example 20° Celsius, 21° Celsius, 22° Celsius, 23° Celsius, 24° Celsius, 25° Celsius, 26° Celsius, 27° Celsius, 28° Celsius, 29° Celsius, or 30° Celsius. In some embodiments the temperature can include ranges in between about 20° Celsius to about 22° Celsius, about 22° Celsius to about 24° Celsius, about 24° Celsius to about 26° Celsius, about 26° Celsius to about 28° Celsius, about 28° Celsius to about 30° Celsius, about 30° Celsius to about 32° Celsius, about 32° Celsius to about 34° Celsius, about 34° Celsius to about 36° Celsius, about 36° Celsius to about 38° Celsius, or about 38° Celsius to about 40° Celsius. In some examples, higher temperatures correspond to higher concentrations (e.g. ppm) of hydrogen peroxide. In several embodiments, the vaporizer is dried or otherwise treated upon exhaustion of the sterilant.

Blower

In several embodiments, a blower or air distribution unit is used to convey gases through the plasma generator and/or vaporizer. In several embodiments, this unit also provides sufficient motive force to push the sterilant/disinfectant effluent into the sterilization chamber. Depending on the embodiment, the blower/flow generator comprises a pump, such as a circulating pump, a positive displacement pump, or an air conveyor, a fan, or a blower optionally integrated with a flow distributor. In embodiments comprising a flow distributor, the distributor is configured to convey a desired percentage of air/sterilant to either the plasma generator or vaporizer (e.g., the blower can be a controllable-speed blower, though optionally in several embodiments, the blower is a single-speed blower). As discussed in more detail below, the ratio of air/sterilant conveyed to the plasma generator and vaporizer is variable, depending on the embodiment. In several embodiments, the variation in flow is fixed prior to a sterilization/decontamination cycle. In additional embodiments, the variation in flow is dynamic during a cycle, for example, adjusting the flow between the plasma generator and the vaporizer depending on the amount of free radicals or hydrogen peroxide vapor or microdroplets being recycled from the chamber.

In several embodiments, the blower with the flow distributor recycles effluent from the chamber (e.g., via one or more conduits) and distributes it into the plasma generator and/or vaporizer. In several embodiments, a filter (or filters) is used in-line between the blower and the plasma generator and/or vaporizer. Distribution can vary with each cycle, or within a cycle. For example, in several embodiments, effluent that is recycled is sent 30:70 to the plasma generator and vaporizer, respectively. Other proportions are used, in several embodiments, such as 10:90, 20:80, 40:60, 50:50, 60:40, 70:30, 80:20, 90:10 or any distribution there between. In several embodiments, the recycling advantageous allows for the optimized use of the sterilant/free radicals in the effluent, replacing or rejuvenating the required component only when needed. In several embodiments, sensors in the chamber, the conduit, the blower or other location are used to sense the amount of free radical and/or sterilant and report the amount or concentration to a controller module, which thereafter signals the blower/distributor to adjust flow accordingly. Moreover, in several embodiments, this approach allows the system to reach an optimal concentration of sterilant in a reduced amount of time, thereby decreasing cycle times.

Conduits for Gaseous Communication

Also provided for herein in several embodiments are a series of conduits that are configured to convey gases and/or sterilant/disinfectant between the various components of the sterilizing/disinfecting systems. For example, in several embodiments, there is at least one conduit within the effluent generator that carries gas (which may comprise recycled sterilant/disinfectant) from the blower/distributor to the plasma generator and/or the vaporizer. The number of conduits depends, at least in part in some embodiments, on the configuration of the components of the effluent generator. For example, a single conduit may be used in embodiments wherein the plasma generator and the vaporizer are in series. In other embodiments where the plasma generator and vaporizer are in parallel, multiple conduits may be used. Likewise, depending on the embodiment, the number of exiting the plasma generator and/or the vaporizer is dependent, at least in part, on whether these components are in series or in parallel.

As with the chamber materials described above, in several embodiments, the conduit(s) comprises a non-conductive, non-corrosive, or otherwise non-reactive material, such that the conduit(s) does not react with the sterilant/disinfectant. Suitable materials include, but are not limited to, glass, plastics, polymers, metals, stainless steel (e.g., 304 or 316 stainless), ABS plastic, aluminum, bronze, carbon graphite, cast iron, ceramic (AL203), ceramic magnet, CPVC, EPDM, epoxy, Hastelloy-C®, Kel-F®, LDPE, natural rubber, NORYL®, nylon, polycarbonate, polypropylene, PPS (Ryton®), PTFE (Teflon®), PVC, PVDF (Kynar®), silicone, Titanium, Tygon®, Viton® or combinations thereof.

In several embodiments, the conduit(s) comprise one or more filters that function to eliminate particulate or other matter from an incoming and/or recirculating gas stream within the sterilization/disinfection system. A variety of filter types can be used, depending on the embodiment. For example, in several embodiments, a HEPA filter is used. In some embodiments, ionic filters, carbon filters, UV filters, cellulose filters, silica based filters or the like are used, either alone or in combination.

In addition to conduit to conduct gases through the system components, several embodiments one or more valves are used to regulate flow through the system. For example, the sterilization/disinfection system may comprise one or more pressure valves that regulate flow into/out of the chamber (or other components of the system). Depending on the embodiment, valves that are open to the environment may also be present. For example, in one embodiment, a valve to the environment is configured to open and allow environmental air to pass into an optional heater and/or filter, and then pass into the chamber at the start of a sterilization/disinfection cycle, in order to pre-heat and/or dry the chamber. In additional embodiments, the system may also valve that regulates flow through a conduit that runs from the chamber to the external environment and serves to vent the chamber to the environment at the end of a sterilization/disinfection cycle. In several embodiments, the valve is preceded by one or more of a filter (e.g., a HEPA filter) and a free radical destroyer. In such embodiments, the exit conduit is configured to deactivate/destroy any remaining sterilant/disinfectant effluent prior to it exiting the system to the environment. In several embodiments, valves of the system are independent of a control system and self-regulating (e.g., operating based on a pressure, temperature or other type of threshold), while in other embodiments, the valve(s) are regulated by a controller unit.

Controller

In some embodiments there is a controller unit that interacts with and/or controls or regulates the operation of one or more of the plasma generator, the evaporator, the hydrogen peroxide cartridge, blowers/fans, valves (if any) as well as the electronics and control boards for the system. In some embodiments, the controller unit is dimensioned to be wall or counter mounted. In several embodiments, the controller is integral with, or contained within the effluent generator or the chamber. In some embodiments, the control unit receives information, either from a user or automatically (such as by an identifier on an object to be sterilized/ disinfected or a carrier for such object) that is used to determine an appropriate sterilization cycle (e.g., time, concentration of sterilant/disinfectant, pressure change, humidity control, etc.). As discussed in more detail below, the controller comprises one or more special-purpose computing devices that is hard-wired or programmed to regulate the operation of the sterilization/disinfection system.

Heater/Dryer

As discussed herein, in several embodiments, the sterilizing/disinfecting system includes at least one heater and/or dryer. By way of example, a dryer may be a desiccant dryer or a dehumidifier utilizing a refrigeration system. Depending on the embodiment, a heater may be used to preheat the conduits and/or the chamber in order to provide for a dry and warmed environment into which items to be sterilized/ disinfected are introduced (e.g., the chamber). In several embodiments, this approach reduces and/or eliminates condensation that could form in or on an item that is sterilized/ disinfected, which could provide a potential future source or site of contamination, for example during storage of the item until next use. See, for example FIGS. 1G and 1H that illustrate additional non-limiting examples of embodiments configured to help maintain desired vapor saturation levels to reduce or avoid undesired condensation. As discussed above, in several embodiments, the controller interacts with and regulates the dryer and/or heater to maintain desired humidity levels in the chamber and thereby avoid undesired condensation.

Sensors

As mentioned briefly above, in several embodiments, one or more sensors are used to monitor various aspects of the components and/or performance of the sterilization/disinfection systems. For example, sensors may be used to monitor and/or regulate the amount of sterilant/disinfectant that is moved into the chamber, the concentration of sterilant/disinfectant in the chamber at a given point (or points) in the cycle, control or regulate destruction/release of sterilant/disinfectant from the chamber to the atmosphere, control or regulate recycling of sterilant/disinfectant to the effluent generator, control or regulate distribution of gas flow (which may include recycled sterilant/disinfectant) between the plasma generator and the vaporizer, as well as a variety of other parameters, including but not limited to temperature, pressure, humidity, cycle duration, etc. It shall be appreciated that such sensors can be used in any component of the system individually, or can be used to monitor the system as a whole (e.g., providing a plurality of types of data to the controller, which integrates the data and adjusts the system as needed).

Accessories

Indicators

A variety of accessories are provided for herein that are operatively interactive with the sterilizing/disinfecting systems disclosed here. For example, quality control and/or regulatory compliance indicators (e.g., disposable after every cycle, semi-disposable for use after a number of cycles, or non-disposable) may be incorporated in many embodiments. Such indicators may include chemical indicators (e.g., those that visually confirm that the indicator (which is to be placed in the chamber or in a package or carrier for a device to be sterilized/disinfected) has been exposed to a selected degree (e.g., amount/concentration) of sterilant/disinfectant to achieve the desired effect. Biological indicators may also be used, such as a positive control strip or container that comprises a known quantity of a type of biological organism that is desirably eliminated by the sterilization/disinfection system. This indicator can demonstrate visually (or otherwise) that the biological organisms have been rendered inert or killed by the sterilization/disinfection process. The indicators can optionally be used directly in the chamber, affixed to an item to be sterilized/disinfected, or in a container or vessel that contains an item to be sterilized/disinfected. In several embodiments automated or electronic sensors are used. Thus, in several embodiments, such chemical and/or biological indicators have a quality control function that ensures that a given sterilization/disinfection cycle has run to a required degree of efficacy.

Residual Coating Apparatus

In several embodiments, there is also provided an additional apparatus, or component of the system, that comprises a residual coating deposition device, wherein such a device functions to deposit a residual coating on an item or items in the chamber. In several embodiments, the residual coating that is bactericidal and may optionally be sacrificial in nature (e.g., removable after potential contamination). In several embodiments, the residual coating material has bactericidal properties such as silver, copper, or a combination of bactericidal materials. In several embodiments, the residual coating is biocompatible with human subjects and is preferably used on items that come into contact with patients or other persons (e.g., surgical tools, endoscopes, dental products, infant care products, etc.). Prior to deposition the residual coating material may be in the form of a gas, a liquid, a solid agent that is converted into a liquid during the coating cycle, or other suitable material.

Item Containers

In several embodiments, as discussed in more detail herein, various custom containers are provided for. In several embodiments, the containers are custom sized for an item (or items) to be sterilized/disinfected. In several embodiments, the containers provide a customized insert or relief to house the item (items), for example to protect the item from impact or other forces that could damage the item. In some embodiments, the containers are hard shell or otherwise rigid. In additional embodiments, the containers are flexible and configured to conform to the general shape of the item. In still additional embodiments, the containers are flexible, but provided in a "sized to fit" format. In some embodiments, the containers are configured to be stackable, able to be hung, or otherwise configured for easy and compact storage. As discussed herein, in several embodiments, the containers are configured to allow the item to be stored within the container until its next use, thereby maintaining the sterile/disinfected item and surrounding environment. In several embodiments, the containers are configured to allow sterilization/disinfection of items comprising a lumen (or lumens). In several embodiments, the container is configured to provide a sterilant/disinfectant not only the exterior surfaces of the item, but also to internal lumens. In several embodiments, the containers comprises a dedicated inlet/outlet for sterilizing/disinfecting the external surfaces of the item, and a second (or more) dedicated inlet/outlet for sterilizing/disinfecting the internal, luminal surfaces of the item. In several embodiments, customized containers are particularly useful because they allow sterilization/disinfection of large (e.g. long) items that using other approaches would require the items to be stretched out to all or substantially all of their longitudinal lengths. In contrast, the custom containers provided for in several embodiments allow a large item to be sterilized/disinfected in a compact footprint, thereby reducing the surface area/volume of space required for a system to accomplish that sterilization, reducing waste (e.g. excessively large packaging) and facilitating storage of sterilized/disinfected items until their next use, even when storage space may be limited. In several embodiments, the container comprises an identifier that enables the user of the system to determine and initiate a sterilization/disinfection cycle that is optimal for the item to be sterilized/disinfected.

Organizational Units and System Carriers/Carts

In several embodiments, the systems and devices disclosed herein also optionally comprise one or more organizational unit in order is system carrier or cart. In several embodiments for example, the system further comprises one or more trays, drawers, or dividers that are configured to carry, house, or otherwise store various accessories routinely used with the system. For example in several embodiments the system may further comprise an organizational unit that houses a plurality of different types of sterilization/disinfection indicators, such as the indicator strips discussed above. In additional embodiments, the system may comprise one or more accessory units that are configured to assist in integrating the sterilization/disinfection system into the environment in which it is used. For example, considerations that may impact the ultimate footprint, and design of the a system for a given use include, but are not limited to the available space for the units in a certain environment, the available space for storage of consumables (such as hydrogen peroxide cartridges, sterilization/disinfection containers, and storage of sterilized/disinfected items). Workflow, either current or anticipated, is also a consideration in determining a configuration of the sterilization/disinfection system for a certain environment of use. Additionally, the safety of users and/or patients is an additional consideration. The systems, devices, and methods disclosed herein are amenable to use in a variety of settings, including point-of-care locations, acute care settings, long-term care settings, or other commercial environments (production or processing plants, large healthcare facilities, medical waste facilities and the like).

Implementation Parameters

As discussed in more detail below, the systems, devices, and methods disclosed herein enable the user to disinfect (either high-level or low level disinfection, depending on the device) and/or sterilize certain items, such as medical devices, electronic devices, surfaces, processing equipment, foodstuff, and wounds). Certain implementation procedures are described generally below with additional detail provided elsewhere in the present disclosure. It shall be appreciated that these implementation mechanisms are readily combinable, and variable, to adjust for a particular item, surface, or wound to be treated in an effective fashion (e.g. tailored amount of sterilant/disinfectant, tailored time, tailored pressure, etc.) and that they can be readily combined by one of ordinary skill in the art, based on the disclosure provided herein to achieve efficacious sterilization/disinfection.

According to several embodiments, the disclosed devices, systems, and methods, are configured to reduce bioburden on an object or surface (e.g., the number of bacteria or other microorganism, fungus, etc. on a surface that has not been sterilized). In some examples, bioburden testing, also known as microbial limit testing, can be used in products or components used in the pharmaceutical or medical field to evaluate microbial levels during processing and handling or after a sterilization/disinfection cycle.

Bioburden can be a significant source of morbidity or mortality. For example, hospitalized patients (e.g. patients in an intensive care unit) may be fitted with devices for insertion into the body. As an example, a hospitalized patient can be fitted with endotracheal tubes to facilitate respiration. Such an endotracheal tube may remain in place within a patient for an extended period of time (e.g. up to 14 days). Biofilm contamination of endotracheal tubes within an intubated patient can lead to an increased rate of infection (e.g. pneumonia).

In other examples, occurrences of catheter related blood stream infection can increase as a result of the use of invasive medical devices including intravascular catheters. Such infections are one of the most common types of bloodstream infection. Several factors relating to the pathogenesis of catheter related blood stream infection have been identified. For example, the skin and hub are the most common sources of colonization of percutaneous vascular catheters. The organisms can migrate from the skin to the insertion site along the intercutaneous segment, eventually reaching the intravascular segment of the tip. As well, the hub can be a major source of colonization of the catheter lumen, which leads to bloodstream infections through luminal colonization of the intravascular segment. The catheter surface can be another factor relating to the pathogenesis of catheter related blood stream infection. Organisms that adhere to the catheter surface can maintain themselves by producing an "extracellular slime," a substance rich in exopolysaccharides, often referred to as fibrous glycocalyx or microbial biofilm. Microorganisms can bind to the surface of host proteins, such as fibrin and fibronectin, to produce biofilm.

In other examples, the prevention of colonization of bacterial and fungal organisms on the surfaces of orthopedic implants has frequently required the use of antimicrobial agents, such as antibiotics, bound to the surface of such devices. The goal of such attempts has been to produce a sufficient bacteriostatic or bactericidal action to prevent colonization. Various methods have previously been employed to coat the surfaces of medical devices with an antibiotic.

As will be discussed in more detail below, the disclosed devices, systems, and methods can be configured to reduce the bioburden of medical devices through sterilization. In addition to the use on medical devices, the disclosed devices, systems, and methods can be used to reduce the presence of bacteria and fungal organisms in other settings that require sterilization. For example, this can include, but not be limited to, hospital settings, settings where food is processed, prepared, or served, settings where individuals with a compromised or decreased immune system live or have access to, environments with a high rate of bacteria buildup (e.g. bathrooms, daycare centers, public transportation, etc.).

Sterilant/Disinfectant

In several embodiments, a liquid sterilizing/disinfecting agent, or a solid agent that is at least partially converted to a liquid during a sterilization/disinfection cycle is used. In several embodiments, a liquid sterilizing/disinfecting agent such as hydrogen peroxide solution is used. In several embodiments described herein are done so with particular reference to hydrogen peroxide as the sterilizing/disinfecting agent, it will be appreciated that the system is also applicable to other solutions and/or pure liquids, such as peracetic acid, formalin solution, aldehydes such as formaldehyde, propriolactone, chlorine dioxide, and the like.

As discussed in more detail below, in several embodiments, varied concentrations of the sterilizing/disinfecting agent are provided, with different amounts being utilized, depending on the type of sterilization/decontamination cycle. Concentrations can range, in several embodiments, from about 30% to about 60% concentration, e.g., about 30%, about 35%, about 40%, about 45%, about 50%, about 55%, or about 60% concentration. In some examples, the hydrogen peroxide (or other agent) vapor concentration can be from about 100 ppm to about 10,000 ppm or any ranges in between such as about 100 ppm to about 600 ppm, about 500 ppm to about 2500 ppm, about 1000 ppm to about 4000 ppm, about 1500 ppm to about 5000 ppm, about 2500 ppm to about 6000 ppm.

Operating Pressures

In some embodiments, the vapor pressure of the sterilant/disinfectant is maintained at or below the saturation level in the sterilization chamber (e.g., for the pressure and/or temperature inside of chamber). In several embodiments, this approach reduces or eliminates condensation buildup on the items being sterilized, on the walls of the chamber, and on other components exposed to the sterilant/disinfectant, such as hoses and fittings described herein.

In some embodiments, the disclosed devices, systems, and methods can be operated at an ambient pressure, e.g., a pressure approximately equivalent to the atmospheric pressure in a given location (e.g., sea level vs. mountain). Depending on the embodiment, the pressures employed in the systems and devices disclosed herein range from about 600 mm mercury (mmHg) to about 800 mmHg, including about 600 to about 610, about 610 to about 620, about 620 to about 630, about 630 to about 640, about 640 to about 650 about 650 to about 660, about 660 to about 670 about 670 to about 680, about 680 to about 690, about 690 to about 700, about 700 to about 710, about 710 to about 720, about 720 to about 730, about 730 to about 740, about 740 to about 750, about 750 to about 760, about 760 to about 770, about 770 to about 780, about 780 to about 790, about 790 to about 800, and any pressure there between, including endpoints. In some embodiments, the ambient pressure can be pre-programmed and/or adjustable by a user. This can allow the disclosed device, system, and method to be adaptable for a variety of different items to be sterilized. Moreover, in several embodiments, the relatively ambient pressure can be adjusted as needed to further reduce the potential for condensation formation within the chamber and/or on/in devices to be sterilized/disinfected. Additionally, while various embodiments can be utilized in approximate room pressures, in some instances, varying the speeds of blowers/distributors, conduit size/valve position, allows for use of slight negative or positive pressure. In some embodiments, a slight negative pressure may advantageously keep the effluent within the system as a safety precaution. In some embodiments, the pressure may be approximately 1 to 2 cm of $H_2O$ lower than ambient pressure.

Open and Closed Systems

In some embodiments, the disclosed devices, systems, and methods operate in a closed loop. In a closed loop system, the system does not rely on matter exchange external to the system. As such, in a closed loop sterilization system, sterilization/disinfection vapors can be recirculated. In several embodiments, this increases the efficiency of the system as the recycled vapors still provide potential sterilization/disinfection effects.

For example, as discussed herein, in a closed loop system, a carrier gas, such as air, is dried and heated prior to flowing past a vaporizer. A hydrogen peroxide aqueous solution can be introduced into the vaporizer and enables the solution to be vaporized. The resulting vapor is then combined with the carrier gas and introduced into a sterilization chamber of varying size, shape, and material. A blower can exhaust the carrier gas from the sterilization chamber and recirculate the carrier gas to the vaporizer where additional vaporized hydrogen peroxide is added.

In addition to the closed loop system, an open loop system is also provided in several embodiments, to provide free air venting. In an open loop system, the system is configured to allow gases to be vented into the external environment. For example, in an open loop system, various portions of the system can be vented before, after, or during sterilization. In some embodiments, before sterilization is conducted in the sterilant chamber, all gases can be purged and the gaseous contents of the chamber are purged to the environment.

As well, in an open loop system, various portions of the system can be configured to allow air to enter the system. In some embodiments, the open loop system can include inlets to allow independent entrance into the system. For example, each of the inlets can comprise one or more valves that provide for selective flow of air into the open loop system. In some embodiments, the open loop system can include a filter element that filters environmental air and allow it to pass into the system.

one embodiment, an open loop system is for the purpose of pre-heating (optionally) and drying the chamber 10 before and after the circulation of bactericidal effluent through the closed loop system. The open loop system uses a flow generator (e.g., an exhaust pump, an air conveyor, a fan, or a blower), exhausting to atmosphere to draw air from an air input through an input (and an optional heater). The input air may optionally be filtered by filter In one embodiment of open-loop operation, the output of the chamber is drawn out by a blower and passes through a conduit and a free radical destroyer. In several embodiments, the open loop approach is implemented initially, such that the chamber, and items within the chamber, can be dried and pre-heated before implementing closed loop operation. Likewise, after sterilization/disinfection, an open loop operation can be reinstated, depending on the embodiment.

Humidity

In several embodiments, moisture control/humidity regulation (e.g., self-regulation or control) is important to reduce or avoid unwanted condensation. Without control, in some contexts, moisture deposition can cause adverse effects on the articles being sterilized/disinfected. As one example, when electronic devices are being sterilized, excessive condensation could potentially create electrical shorts and otherwise damage the electronic devices. Similarly, residual condensation on a device can reduce the efficacy of sterilization/disinfection, or provide a "safe harbor" for future growth of microorganisms or mold during storage.

In some embodiments, a desiccant or other chemical composition that is designed to absorb moisture is provided for use in conjunction with the system. In some embodiments, the desiccant is provided within the conduits leading into, or exiting, a sterilization/disinfection chamber. In such embodiments the desiccant functions analogously to a filter for particulate matter, however serves to remove moisture from the gases entering or exiting the sterilization/disinfection chamber. In additional embodiments a desiccant reservoir is provided within the sterilization chamber to aid in controlling the relative moisture content within the chamber before, during, or after a sterilization/disinfection cycle. In several embodiments, a target humidity level is recommended for a given type of device to be sterilized/disinfected or the degree to which a device, or surface, is to be sterilized are disinfected. In several embodiments the target relative humidity range is between about 10% to about 85% including about 10% to about 15%, about 15% to about 20%, about 20% to about 25%, about 25% to about 30%, about 30% to about 35%, about 35% to about 40%, about 40% to about 45%, about 45% to about 50%, about 50% to about 55%, about 55% to about 60%, about 60% to about 65%, about 65% to about 70%, about 70% to about 75%, about 75% to about 80%, about 80% to about 85%, and any relative humidity between those listed, including endpoints. In additional embodiments greater degrees of humidity can be provided for within the sterilization chamber, in combination with a heating and/or drying cycle within the sterilization/disinfection protocol.

Temperature

As described herein, various embodiments may be operated at ambient conditions (e.g., room temperature). However, some embodiments allow for controlled or automatic regulation of the temperature in the chamber. In several embodiments, lower ambient temperatures slow the sterilization process, which may be advantageous in several embodiments. Likewise, in several embodiments, a higher ambient temperature accelerates the process. Therefore, depending on the embodiment, temperatures can range from about 50° F. to about 120° F., including about 50° F. to about 60° F., about 60° F. to about 70° F., about 70° F. to about 80° F., about 80° F. to about 90° F., about 90° F. to about 100° F., about 100° F. to about 110° F., about 110° F. to about 120° F. In several embodiments, temperatures can range from about 20° C. to about 30° C., including 20° C., 21° C., 22° C., 23° C., 24° C., 25° C., 26° C., 27° C., 28° C., 29° C., 30° C. and ranges from about 20° C. to about 25° C. and about 25° C. to about 30° C. It shall likewise be appreciated that temperatures can vary depending on the device, object, or surface (including the wound) to be sterilized/disinfected in order to provide an optimal balance of efficacy of sterilization/disinfection versus the possibility for damage to an object (e.g., electronic devices) or pain to a subject (a patient with a wound).

Activation/Cycle Time

Depending on the embodiment, the systems and devices disclosed herein can be programmed to run various types of cycles. For example, cycles designed for sterilization, high level disinfection, or low level disinfection may vary in duration—e.g., sterilization having a longer cycle time as compared to high level disinfection, which has a longer cycle time than low level disinfection. In several embodiments, the systems provided for herein also are configured to run a maintenance cycle, for example a short cycle during an extended storage. For devices that have previously been subject to sterilization/disinfection.

In some embodiments, the disclosed devices, systems, and methods can be configured to include a programmable activation time. In some examples, the activation time can be customizable and/or controlled by a user. This can allow the disclosed devices, systems, and methods to be configurable to different types of devices to be sterilized. As well, depending on the item to be sterilized, activation time can be adjusted to allow for more thorough processing.

It shall be appreciated that cycle times are readily adjustable by a given user for a given context, but generally speaking can vary between about 60 seconds and about 20 minutes, including about 60 seconds to about 90 seconds, about 90 seconds to about 120 seconds, about two minutes to about four minutes, about four minutes to about six minutes, about six minutes to about eight minutes, about eight minutes to about 10 minutes, about 10 minutes to about 15 minutes, about 15 minutes to about 20 minutes, about 20 minutes to about 30 minutes, and any time between those listed, including endpoints. Additionally, multiple cycles, or repeats, can be run on any given device or surface to be sterilized/disinfected, should additional sterilization disinfection be required Unit Level Sterilization In some embodiments, the disclosed devices, systems, and methods can be configured to provide sterilization to a plurality of individual units. For example, the system can include structures to allow for sterilization of individual and/or separate components of an item. In some embodiments, the disclosed devices, systems, and methods, can allow for the sterilization of small or hard-to-reach areas such as lumens, folds, crevices, etc. A unit level sterilization can provide for more thorough sterilization as well as lower costs.

Residue Free

In some embodiments, the disclosed devices, systems, and methods provide a sterilization/disinfection method that is residue free (also disclosed elsewhere herein are embodiments wherein a layer is deposited purposefully). In several embodiments, a residue free sterilant/disinfectant is configured to eliminate the risk of carry-over of chemical residue to patients and also to reduce the cost of chemical disposal. In some embodiments, residue free sterilant/disinfectant also ensures that no separate water rinse or post-cleaning step is required to remove excess sterilant/disinfectant from the item or surface being treated.

In addition to removing remaining sterilant chemical from the item being sterilized, the disclosed devices, systems, and methods can also ensure that the item being sterilized will dry to a clean, bright, shiny appearance with no spotting, streaking, or film residue. This can save significant time any money and can improve the appearance of the sterilized item.

Setting/Application

All of the disclosed devices, systems, and methods to provide sterilization can be used in acute care, point of care, long term care, or commercial settings. As well, the disclosed devices, systems, and methods can be used to prevent and control infection. In some embodiments, the disclosed devices, systems, and methods are configured to sterilize and/or disinfect instruments and devices. In some examples, the disclosed are configured to provide systems and methods for general sterilization and disinfection.

Sterilization System Employing Plasma and Vapor

As shown in FIG. 1A, various embodiments include a sterilization chamber 10 configured to receive sterilant and the item to be sterilized. The sterilization chamber 10 can include any type of moving or stationary chamber, non-limiting examples of which are described herein. In FIG. 1A, the chamber 10 is shown as a tumbler-type chamber, which is rotated around a longitudinal axis 54 (e.g., rotate around the x-axis), for example by motor 51, in the manner of a conventional home clothes dryer. Items to be sterilized are placed in a chamber 10. Such a tumbler-type chamber 10 would be appropriate for fabric items 56 such as towels and cloths, surgical masks and gowns, gloves, etc. The tumbler design could also be used to sterilize shredded medical waste within the teachings of the disclosure.

In some embodiments, the chamber 10 may rotate around the longitudinal axis 54 in a clockwise direction, a counter clockwise direction, or alternating between clockwise and counter clockwise directions. In some embodiments, the chamber 10 may alternate between partial rotations about the longitudinal axis 54 in one direction and partial rotations about the longitudinal axis 54 in the opposite direction. In some other embodiments, the chamber 10 may alternate between partial and complete rotations about the longitudinal axis 54.

The chamber 10 is not limited to rotations about the longitudinal axis 54, but may move in other degrees of freedom. For example, in some embodiments, the chamber 10 may rotate partially or completely about a different longitudinal axis, such as one perpendicular to longitudinal axis 54 (e.g., rotate about the y-axis or the z-axis). As another example, the chamber 10 may move back and forth along a direction parallel the longitudinal axis 54 (e.g., along the x-axis) or a different longitudinal axis (e.g., along the y-axis or the z-axis). The chamber 10 may also move in a combination of the different degrees of freedom. For example, the chamber may be a shaker, agitator, or other type of device that moves in randomized or oscillating patterns.

The chamber 10 may be made of any type of material, yet in various embodiments, the chamber 10 is made of a non-conductive material to not interfere with certain reactive species of the sterilant. For example, the chamber 10 may be made of glass, plastic (e.g., polytetrafluoroethylene), or combinations thereof (e.g., partially glass and partially plastic). In some embodiments, the chamber 10 may be transparent or partially transparent such that the contents within the chamber 10 may be viewable during the sterilization process.

The size and shape of the chamber 10 are not particularly limited, but can be tailored to the application of use. For example, in some instances, the chamber 10 may be relatively small, light-weight, and portable. In other embodiments, the chamber may be dimensioned to accommodate larger items, such as control modules for IV stands, power units for various equipment in surgical suites, end piece apparatuses used in an operating room (such as eyepieces for surgical scopes). In some embodiments, inside chamber 10 there is a container of custom size and shape based on the device or devices to be placed inside the container for sterilization, disinfection, sanitation, and/or decontamination. In other embodiments the chamber 10 can be entire room, for example an Operating Room, where the sterilant source can be placed inside or outside the room.

In some embodiments, chamber 10 further contains a container of custom size and shape based on the device or devices to be sterilized, disinfected, sanitized, and/or decontaminated inside the container. In some embodiments, the custom sized container inside chamber 10 contains only one device and the container is custom sized to fit that individual device. In some embodiments, the container inside chamber 10 contains a set of devices and the container contains recesses shaped to hold each individual device. In embodiments where chamber 10 further includes a custom sized container, an adaptor attaches to the container and delivers sterilant to the container. In some embodiments the sterilization cycle for the device is decreased due to the direct, individualized exposure to the sterilant within the custom sized container. In some embodiments, a duck bill valve forms the attachment point between the adaptor and the container. In such embodiments, the valve is predisposed to be in a closed position such that the attachment and removal of the adapter does not allow air flow to disturb the sterility of the contents inside the container. Furthermore, in such embodiments the cracking pressure of the duck bill valve is high enough to prevent air flow in or out of the container. Additionally, in such embodiments, the airtight nature of the container is further maintained by a seal on the edges of the container. The custom sized container placed inside chamber 10 allows for more direct exposure of sterilant.

In some embodiments, a set of devices will be placed in the custom sized container to remain sterile for later use. For example, in some embodiments the custom sized container contains surgical equipment and the custom sized container is removed from the chamber and taken to an operating room. In this embodiment, the surgical equipment has remained sterile within the container and contains sterilized equipment for use by the medical staff. A custom sized container meant for surgical use could contain equipment including but not limited to retractors, clips, clamps, forceps, scissors, and needle holders. In some embodiments the container is coded to convey the contents. As a non-limited example, the container could be coded with the medical procedure for its intended use.

In some embodiments, the device to be sterilized within the custom sized container placed within chamber 10 is a FDA regulated device. In such embodiments, the FDA regulated device can include but is not limited to a pacemaker, a stent, a prosthetic heart valve, a bone screw, a retractor, surgical clips, surgical clamps, forceps, surgical scissors, or surgical needle holders. In some embodiments one item is sterilized, disinfected, sanitized, and/or decontaminated in the custom sized container within chamber 10 and another item is sanitized, and/or decontaminated in the remaining open space in chamber 10. In this embodiment, chamber 10 is dual purposed to sterilize two different devices, one within the custom sized container requiring a direct flow of sterilant and one outside the custom sized container. In such embodiments, the item placed inside the custom sized container requires more absolute sterilization than the item placed in the general space. In some embodiments of dual sterilization, the item placed inside the custom sized container is a FDA regulated device. In some embodiments of dual sterilization, the item placed in the open space of chamber 10 is an EPA regulated device such as an iPad or a phone. In some embodiments of dual sterilization, the item placed in the open space of chamber 10 is a low risk FDA regulated device such as a stethoscope or a blood pressure cuff. In some embodiments of dual sterilization, the item placed inside the custom sized container is a high risk FDA regulated device such as a stent or a pacemaker.

In some embodiments, chamber 10 is an entire room. In one embodiment of room decontamination, the room has sealed vents, such as AC vents and any other air vents, for example air heating vents. In some examples, the door must be sealed in order to prevent escape of the sterilant to other parts of the building. In some embodiments, a temporary airlock attaches to the door. The sterilant can be delivered to the room from the device/source that is located in the room or through the conduits, input and output, connected to the device that is outside of the room. In another embodiment of room decontamination, the room is sealed off from the outside to prevent the escape of the sterilant to other parts of the building. In one such embodiment a reversible sealing mechanism such as a tent is used to prevent the flow of air outside the room.

Endoscope Rack

Some embodiments comprise a rack that sterilizes and disinfects endoscopes and similar devices including other lumen containing devices. In several embodiments, the rack is configured to combine the need to dry endoscopes (or other devices with lumens) and the ability to disinfect or sterilize the scopes and associated lumens while ensuring the disinfection integrity of the scopes in storage subsequent to disinfection or sterilization. In some examples the endoscope rack can be used with scopes related to the following fields, gastroenterology, endoscopic ultrasound scopes, pulmonology, ENT (ear, nose, and throat), speech, and urology. In some embodiments scopes with working channels such as for biopsy or suction can be used with the endoscope rack.

In some embodiments, a single endoscope rack can hold and process up to 40 endoscopes. In some embodiments the endoscopes are dried and stored in the endoscope rack and maintain sterility while inside the unit. In some embodiments the scopes will be hung lengthwise either proximal end up or distal end up in the endoscope rack.

In some embodiments, the endoscope will be placed in the endoscope rack after they have gone through a disinfection cycle by another means such as an Olympus or Medivator liquid disinfection system. In such embodiments, the endoscope would be attached to a universal adapter, for example a clamshell or other valve/fitting that blows air into the working channel of the endoscope until it is dry. The drying process can be, for example, between 10 and 90 seconds; in some examples, the drying process can be between 0-5 seconds, between 5-10 seconds, between 10-15 seconds, between 15-20 seconds, between 20-25 seconds, between 25-30 seconds, between 30-35 seconds, between 35-40 seconds, between 40-45 seconds, between 45-50 seconds, between 50-55 seconds, between 55-60 seconds, between 60-65 seconds, between 65-70 seconds, between 70-75 seconds, between 75-80 seconds, between 80-85 seconds, or 85-90 seconds; in some examples, the drying process can be approximately 0 seconds, 1 second, 2 seconds, 3 seconds 4 seconds, 5 seconds, 6 seconds, 7 seconds, 8 seconds, 9 seconds, 10 seconds, 11 seconds, 12 seconds, 13 seconds, 14 seconds, 15 seconds, 16 seconds, 17 seconds, 18 seconds, 19 seconds, 20 seconds, 25 seconds, 30 seconds, 35 seconds, 40 seconds, 45 seconds, 50 seconds, 55 seconds, 60 seconds, 65 seconds, 70 seconds, 75 seconds, 80 seconds, 85 seconds, or 90 seconds. In some embodiments the dry cycle can use air, sterilant (e.g. RONS, $H_2O_2$, or other streams). In several embodiments, a dryer (or dry cycle) is not present or utilized. In some embodiments the dryer will be a standalone unit. In some embodiments the endoscope will be placed in the endoscope rack as the first step in the disinfection process. In these embodiments, exposure of the endoscope to sterilant sterilizes the endoscope.

In some embodiments, the sterility of the endoscope will be maintained through the placement of a single use, form fit barrier pouch (the endoscope pouch) that is placed over the endoscope in a loose fit and seals the endoscope off from the surrounding environment. In several embodiments, the pouch is large enough to avoid tight contact between the scope and the pouch "wall." In some embodiments, the inner wall of the pouch is made of a material such as TYVEK or a similar material to allow the effluent to penetrate the space where the endoscope touches the wall. In one embodiment, the endoscope pouch is made of clear material to allow viewing of the endo scope make, model, and bar code while the endoscope is still inside the endoscope container. In several embodiments, the endoscope pouch is impermeable to gas and retains effluent that is introduced into the pouch. Another advantage of the endoscope pouch is that once the endoscope sterilization cycle is completed, the endoscope can be transported to the exam room inside the pouch thereby remaining sterile.

In some embodiments, the sterility of the endoscopes is verified through the use of chemical indicators built into the pouch to monitor the level of effluent. Additionally, biological indicators can be assessed in the morning and at night to determine if there is a proper level of biological kill.

In some embodiments, continuous circulation of the effluent is achieved by having an inlet and outlet adapter whereby effluent is moved into and out of the pouch. In such embodiments, the inlet adapter will channel effluent directly into all lumens of the endoscope. In some embodiments, the adapter for the effluent inlet will have two ports, one with a direct connection to the lumen or lumens and one to direct effluent into the pouch.

In such embodiment, the inputs will be decoupled in order to maintain proper pressure at each port. The lumen port will deliver the effluent to sterilize the lumens and the other port, the one directing effluent to the pouch, will deliver effluent to sterilize other parts of the endoscope. The outlet adapter will channel the old, used effluent back to the location of the evaporator and the plasma generator for re-processing. Unlike the input connectors, there will be only one common output. In some embodiments, the output adapter is at the other end of the pouch from the input adapter. A similar process can be used to sterilize/disinfect an endoscope that does not have a lumen wherein the entire endoscope will still be exposed to effluent.

In some embodiments the endoscope rack has multiple cycle settings. For example, cycles designed for sterilization, high level disinfection, and maintenance of sterility for endoscope storage. The sterilization and high level disinfection cycles vary by the length of the cycle time with a longer cycle used for the sterilization cycle. The maintenance cycle is designed to maintain the sterility/disinfection of the endoscope during storage and before use. For example, the endoscope could be placed in the endoscope rack and sterilized at night and stored for use in the morning. Use of the maintenance cycle on the endoscope rack would ensure that the endoscope is sterile/disinfected for use in morning procedures. The maintenance cycle could be run, for example, once every four hours while the endoscopes are stored overnight. A set timer could be used to initiate maintenance cycles throughout the night or the duration of storage in the endoscope rack. In some embodiments each endoscope rack would have light indications that coordinate with the current cycle of the endoscope rack. For example, a red light would indicate that the endoscope rack is currently undergoing a sterilization/disinfection cycle, a yellow light would mean that a maintenance cycle is underway, and a green light would mean that no cycles are currently processing and the endoscopes are ready for use. In some embodiments the endoscope drying rack is modular and it is possible to start and stop a cycle on a particular scope at different times. In some contexts, a single endoscope will be placed in and removed from the endoscope rack about 3 to 4 times per day under normal hospital use.

Figure 26A:
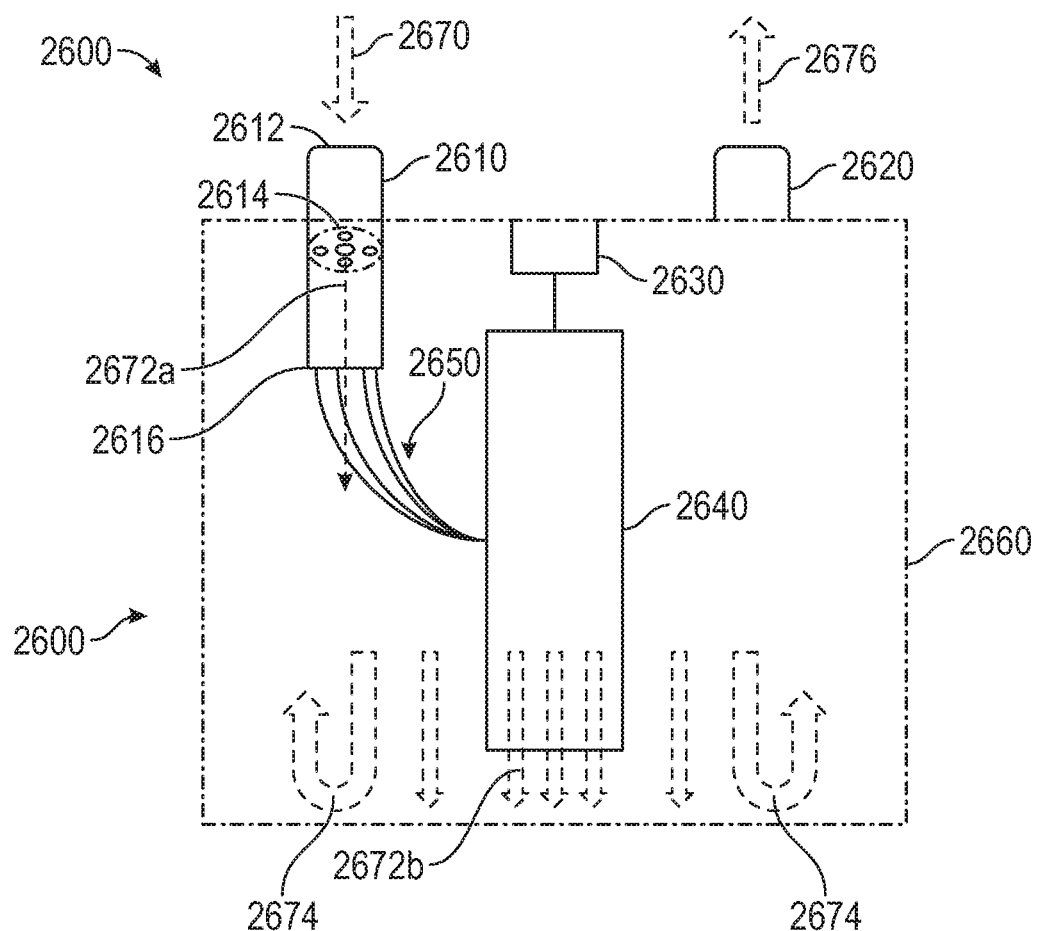
FIGS. 26A-26B show an embodiment of a system for sterilizing and/or disinfecting endoscopes and similar devices with lumens. In this embodiment, effluent is pushed through the lumens of the device as well as directly into the chamber housing the devices with lumens.
Figure 26B:
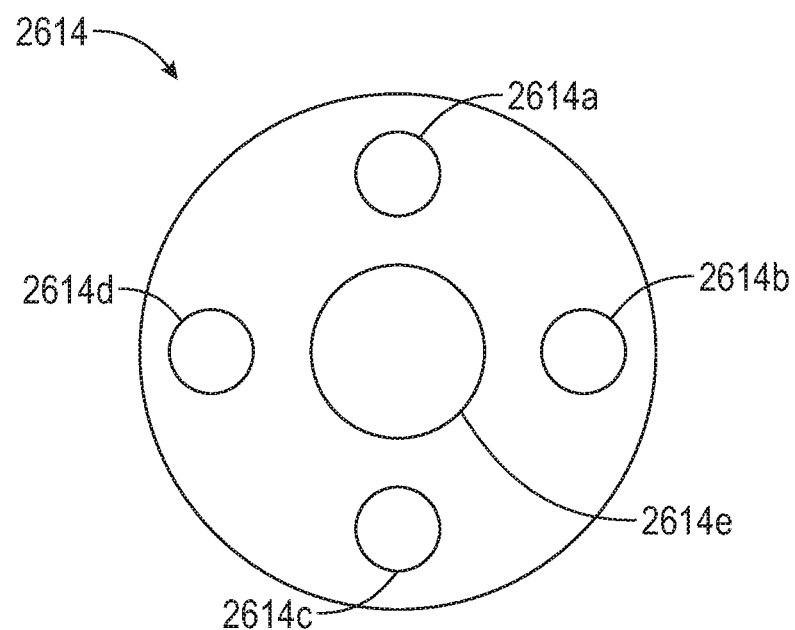
Figure 26C:
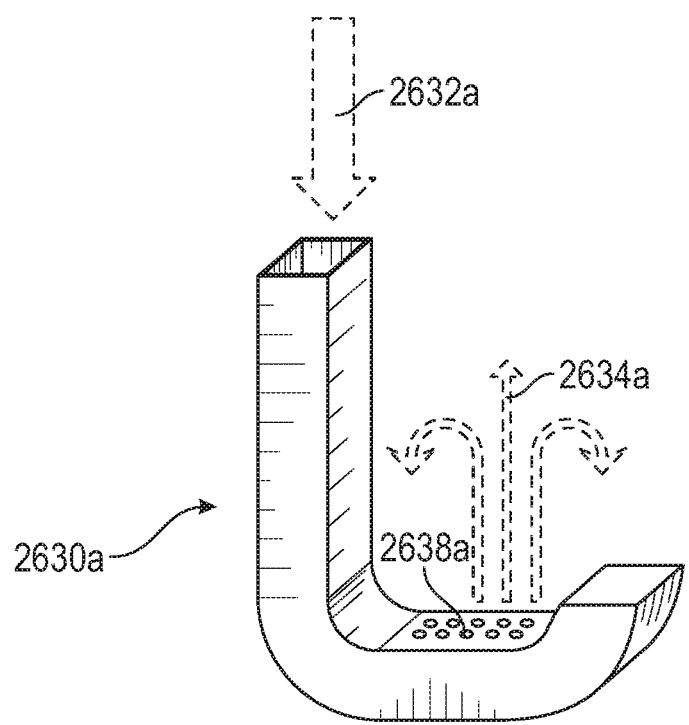
FIG. 26C shows an embodiment of a retaining structure for retaining and/or securing a device for sterilization and/or disinfection in the system for sterilizing and/or disinfecting illustrated in FIG. 26A. The retaining structure illustrated in FIG. 26C is configured to provide for effluent to pass through the surface of the retaining structure.
Figure 26D:
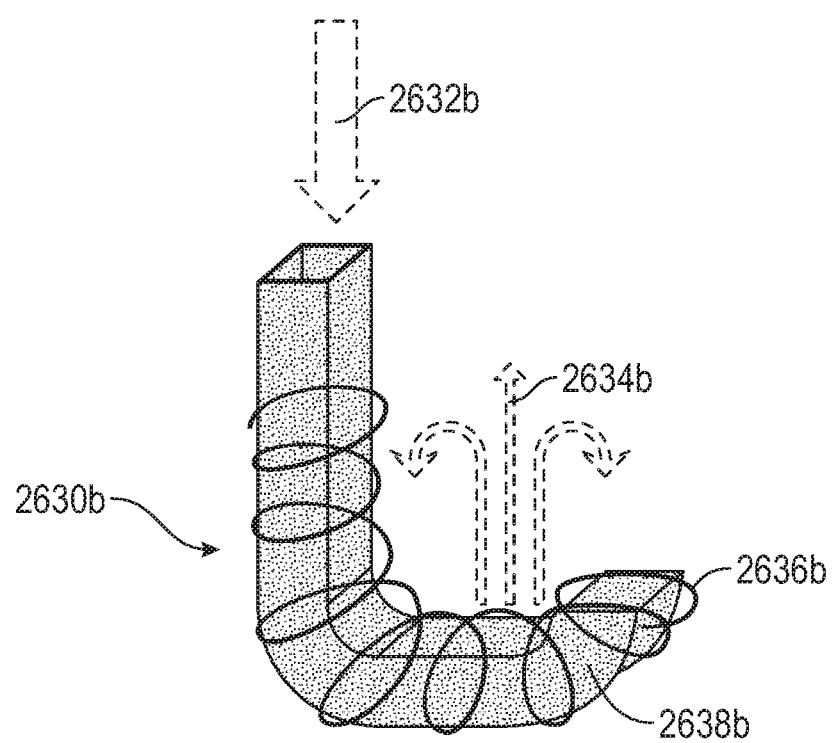
FIG. 26D shows an embodiment of a retaining structure for retaining and/or securing a device for sterilization and/or disinfection in the system for sterilizing and/or disinfecting illustrated in FIG. 26A. The retaining structure illustrated in FIG. 26D is wrapped in a porous material.
Figure 27A:
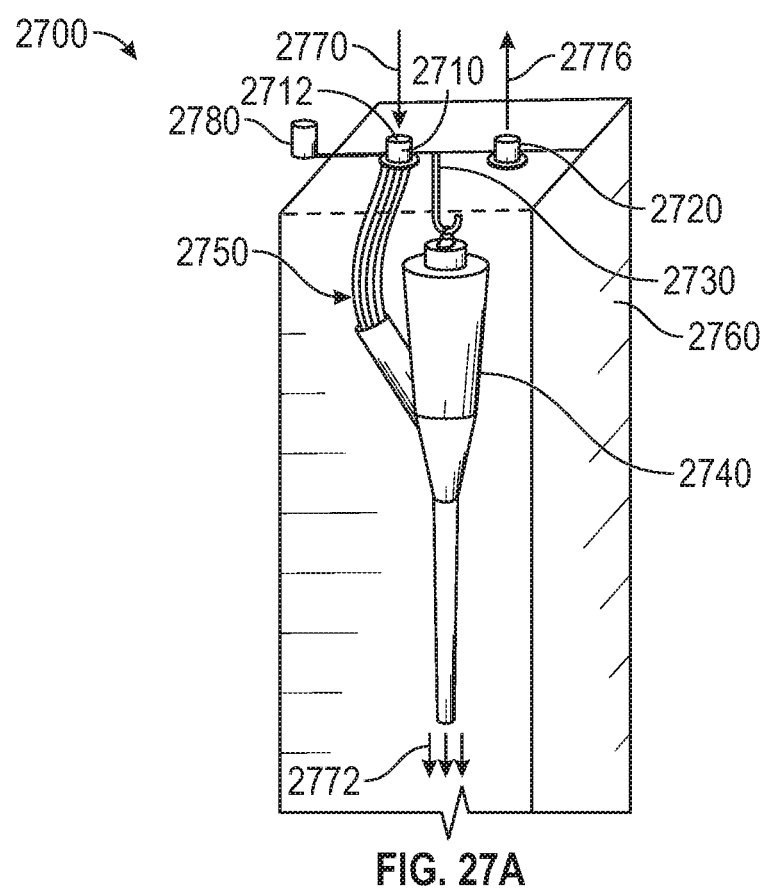
FIG. 27A shows an alternative embodiment of a system for sterilizing and/or disinfecting endoscopes and similar devices with lumens. The system for sterilizing and/or disinfecting endoscopes and similar devices with lumens of FIG. 27A (or other embodiments disclosed herein) can be configured such that effluent is delivered to the lumens and the chamber simultaneously.
Figure 27B:
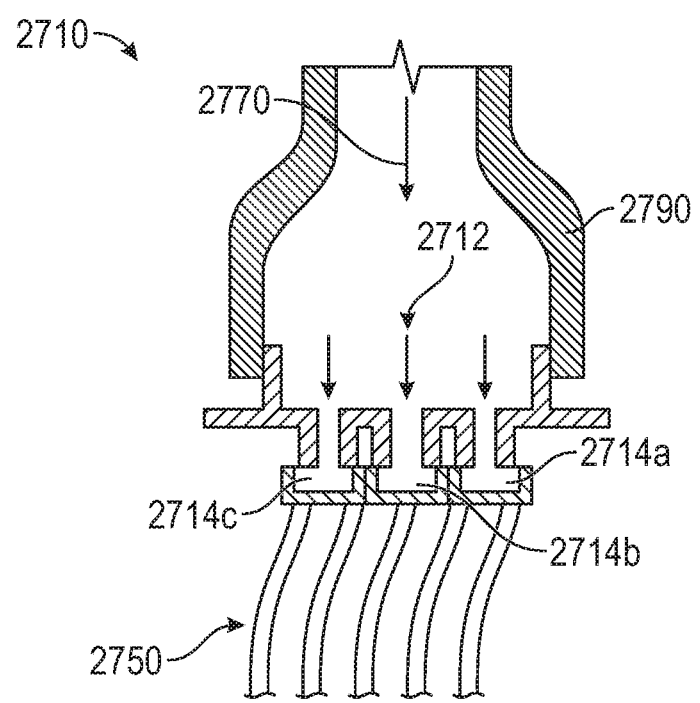
FIG. 27B shows an embodiment of an inlet port for pushing effluent through the lumens of a device retained in the system illustrated in FIG. 27A.

FIGS. 26A-26D and 27A-27B illustrate an embodiment of a system for sterilization and/or disinfection of devices comprising lumens. FIGS. 26A-26b illustrate a schematic of a system for sterilization and/or disinfection of devices comprising lumens 2600 while FIG. 27A-27B illustrates a first embodiment of the system for sterilization and/or disinfection of devices comprising lumens 2700. As will be described in more detail below, the systems described with regard to FIGS. 26A-26D and 27A-27B are configured to "push" effluent through the lumens of a device.

Turning first to the system for sterilization and/or disinfection of devices comprising lumens 2600 illustrated in FIG. 26A, the system includes a container 2660 with an input 2610 and an output 2620. The container 2660 includes a retaining structure 2630 that is configured to retain and/or secure a device 2640. In some embodiments, the device 2640 includes one or a plurality of lumens 2650. As will be discussed in more detail below, each of the lumens 2650 can be fluidly connected to the input 2610.

The container 2660 can be a variety of sizes and shapes and can comprise a rigid or flexible material. In some embodiments, the container 2660 can be configured to retain its shape such that an inserted device can be retained, sterilized and/or disinfected, and subsequently stored and/or transported. In some examples, the container 2660 can comprise a flexible material that is disposed over a rigid frame. As will be discussed below, the container 2660 can comprise a sufficiently rigid material such an internal negative pressure applied to the container 2660 does not cause the container 2660 to collapse. In some embodiments, the container 2660 can comprise a non-porous material such as polyethylene, PETG (polyethylene terephthalate), aluminized mylar, Tyvek, chlorinated polyvinyl chloride (CPVC), polyvinyl chloride (PVC), Ultem™, etc. In some embodiments, the container 2660 can comprise a material that prevents oxidation. In some embodiments, the container 2660 can be clear to allow the user to see the type of device 2640 within the container 2660.

In some embodiments, the container 2660 can be configured to withstand a negative pressure within the container 2660. In several embodiments, the application of negative pressure to the container 2660 prevents effluent from escaping if the container were to be structurally or physically compromised prior to, or during, a sterilization cycle. In this way, should a leak develop in the container 2660, air from the surrounding environment would be pulled into the container 2660 rather than having effluent escape. In some embodiments, the negative pressure within the container 2660 can be between −0.03 to −1 psi; in some embodiments the negative pressure can be between −0.00 to −0.05 psi, −0.05 to −0.10 psi, −0.10 to −0.15 psi, −0.15 to −0.20 psi, −0.20 to −0.25 psi, −0.25 to −0.30 psi, −0.30 psi to −0.35 psi, −0.35 psi to −0.40 psi, −0.40 psi to −0.45 psi, −0.45 psi to −0.50 psi, −0.50 psi to −0.55 psi, −0.55 psi to −0.60 psi, −0.60 psi to −0.65 psi, −0.65 psi to −0.70 psi, −0.70 psi to −0.75 psi, −0.75 psi to −0.80 psi, −0.80 psi to −0.85 psi, −0.85 psi to −0.90 psi, −0.90 psi to −0.95 psi, or −0.95 psi to −1.0 psi; in some embodiments, the negative pressure can be −0.03 psi, −0.05 psi, −0.10 psi, −0.15 psi, −0.20 psi, −0.25 psi, −0.30 psi, −0.35 psi, −0.40 psi, −0.45 psi, −0.50 psi, −0.55 psi, −0.60 psi, −0.65 psi, −0.70 psi, −0.75 psi, −0.80 psi, −0.85 psi, −0.90 psi, −0.95 psi, or −1.0 psi. In some examples, the negative pressure can be between 2 cm $H_2O$ to about 80 cm $H_2O$ or any ranges in between such as about 2 cm $H_2O$ to about 3 cm $H_2O$, about 3 cm $H_2O$ to about 4 cm H$_2$O, about 4 cm H$_2$O to about 5 cm H$_2$O, about 5 cm H$_2$O to about 6 cm H$_2$O, about 6 cm H$_2$O to about 7 cm H$_2$O, about 7 cm H$_2$O to about 8 cm H$_2$O, about 8 cm H$_2$O to about 9 cm H$_2$O, about 9 cm H$_2$O to about 10 cm H$_2$O, about 2 cm H$_2$O to about 10 cm H$_2$O, about 10 cm H$_2$O to about 20 cm H$_2$O, about 20 cm H$_2$O to about 30 cm H$_2$O, about 30 cm H$_2$O to about 40 cm H$_2$O, about 40 cm H$_2$O to about 50 cm H$_2$O, about 50 cm H$_2$O to about 60 cm H$_2$O, about 60 cm H$_2$O to about 70 cm H$_2$O, and about 70 cm H$_2$O to about 80 cm H$_2$O.

As shown in FIG. 26A, the input 2610 and the output 2620 can be located on a surface of the container 2660 and are fluidly connected with the container 2660. Depending on the embodiment, the input 2610 and output 2620 are located in different positions from one another, for example to allow a customized configuration for a particular application. In several embodiments, the inlet and outlet are location on opposing surfaces of the container. In some embodiments, the input 2610 and the output 2620 are configured to allow for effluent to flow into and out of the container 2660 respectively. As will be discussed in more detail below, the input 2610 can be configured to receive an effluent input (e.g., a sterilant or disinfectant such as H$_2$O$_2$ and/or ozone) that can push effluent through any of the lumens 2650 of the device 2640 that is hooked up to the input 2610.

FIG. 26B illustrates an embodiment of a cross-section 2614 of the input 2610. As shown, in some embodiments, the input 2610 can include a plurality of openings that are configured to allow for fluid flow from an external effluent source and through the input 2610. The cross-section 2614 of the input 2610 can be configured to include any number of openings to accommodate any number of lumens. In the embodiment illustrated in FIG. 26B, the cross-section 2614 of the input 2610 includes a lumen connection 2614a, a lumen connection 2614b, a lumen connection 2614c, a lumen connection 2614d, and an opening 2614e. In some examples, each of the lumen connections 2614a, 2614b, 2614c, 2614d are configured to be fluidly connected to one of the plurality of lumens 2650 of the device 2640. An endoscope and similar devices can include a plurality of lumens that provide various functions—for example a lumen providing air, a lumen providing water to clear the lens of the scope, a lumen for providing suction, or a lumen for providing a tool pathway. Each of the plurality of lumens can be hooked onto one of the lumen connections 2614a, 2614b, 2614c, 2614d such that each of the lumens are sterilized and/or disinfected by the system 2600. The opening 2614e can be configured to allow effluent to pass through the input 2610 and into the container 2660.

FIG. 26A illustrates an example of the effluent flow through the system for sterilization and/or disinfection of devices comprising lumens 2600. In some examples, the system for sterilization and/or disinfection of devices comprising lumens 2600 has an input flow 2670 that pushes effluent through the input 2610. As discussed above with regard to the cross-section 2614 of the input 2610, the input flow 2670 pushes effluent through each of the attached lumens 2650 as well as pushing the flow of effluent 2672a through the opening 2614e and into the interior of the container 2660. Similarly, in some examples, the effluent can be configured to push through each of the lumens 2650 and also into the interior of the container 2660 through the flow of effluent 2672b through the device 2640. By allowing the input flow 2670 of effluent to be pushed into the interior of the container 2660, the effluent can be circulated through the entirety of the system 2600 such that the exterior of the device 2640 can also be sterilized and/or disinfected. The circulation of effluent 2674 through the interior of the container 2660 is shown through in the arrows of the container 2660.

In some examples, once the effluent is circulated through the interior of the container 2660, the effluent can be configured to leave the output 2620 through the output flow 2676 shown in FIG. 26B. As mentioned above, in some embodiments, the container 2660 can have sufficient structure or be sufficiently rigid such that negative pressure can be generated but is not sufficient to collapse the container 2660. In several embodiments, the container is configured to deform under negative pressure by less than about 25% (from its original position), less than about 20%, less than about 15%, less than about 10%, or less than about 5%.

As discussed above, in some embodiments, the device 2640 is secured and retained within the container 2660 by the retaining structure 2630. However, with structures configured to secure a device (e.g. a hook) within the sterilization/disinfection system, it remains important to sterilize or disinfect the portion of the device that is in contact with the device securement structure. For example, if an endoscope is hung from a hook within the system (e.g., the hooks shown in FIGS. 26C and 26D) for sterilization/disinfection, how is the portion of the endoscope in contact with the hook to be sterilized/disinfected?

FIGS. 26C and 26D illustrate two non-limiting embodiments of the retaining structure 2630 that address this issue. Turning first to the retaining structure 2630a illustrated in FIG. 26C, the retaining structure 2630a can be a hook that is configured to allow an endoscope or other similar device 2640 to be hung from during the sterilization/disinfection process. The retaining structure 2630a can be hollow so as to provide for the input flow 2632a of effluent through the retaining structure 2630a. In some examples, the surface of the retaining structure 2630a can include a plurality of openings 2638a where the device 2640 is in contact with the retaining structure 2630a. Each of the plurality of openings 2638a is configured to allow for the output flow 2634a of effluent out from the retaining structure 2630a and onto the surface of the device 2640 in contact with the retaining structure 2630a.

FIG. 26D illustrates retaining structure 2630b, another embodiment of the retaining structure 2630. Not unlike the retaining structure 2630a, in some examples, the retaining structure 2630b can be configured to be shaped like a hook that is configured to allow an endoscope or other similar device 2640 to be hung from during the sterilization/disinfection process. The retaining structure 2630b can be hollow so as to provide for the input flow 2632b of effluent through the retaining structure 2630b. In some examples, the surface of the retaining structure 2630b can be covered in a plurality of openings 2638b such that output flow 2634b of effluent occurs on the entirety of the surface of the retaining structure 2630b. In some embodiments, the entirety of the retaining structure 2630b can be wrapped in a porous material 2636b. In some examples the porous wrap material 2636b can be Tyvek, Teflon (PTFE), etc. When a device 2640 is hung on the retaining structure 2630b, the surface of the device 2640 in contact with the retaining structure 2630b can be sterilized/disinfected as effluent passes through the retaining structure 2630b, through the surface of the openings 2638b, and passes through the porous wrap material 2636b, thereby disinfecting the device.

In some embodiments, the retaining structures 2630a, 2630b can be configured to sterilize/disinfect the retaining structure 2640 using UV light. Therefore, instead of, or in addition to, having an input flow 2632a, 2632b and output flow 2634a, 2634b of effluent, UV light can instead be fed through the retaining structures 2630a, 2630b. Each of the retaining structures 2630a, 2630b could be illuminated to provide the UV light. In some embodiments, the wavelengths of the UV light could be UV-A (315 to 400 nm), UV-B (280-315 nm) or UV-C (100 to 280 nm). In some examples, the use of UV-C wavelength UV light is preferable.

In some embodiments, prior to beginning the sterilization and disinfection system for the system for sterilization and/or disinfection of devices comprising lumens 2600, the instruments need to be dry. In many instances, a previous cleaning process is used to reduce the bioburden. In some examples, a scrub and/or flush of alcohol may be performed on a device 2640 before it is used in the system 2600. In order to ensure that the device 2640 is sufficiently dry, the system 2600 can be configured to provide a drying process (e.g., high pressure, dried and/or heated air, etc.). The drying process can be configured to ensure that all moisture is eliminated from the surface of the device 2640 and from the exterior and interior of each of the lumens 2650. Once this is completed, the sterilization/disinfection process of the system 2600 can begin.

In some examples, the system 2600 is configured to be sealed after the device 2640 is placed within the container 2660. In some embodiments, a heat sealer can be used to seal the container 2660. Prior to beginning the sterilization/disinfection cycle within the system 2600, a pressure check can be conducted to ensure that the container 2660 does not have any leaks. In some examples, testing is conducted by slowly filling the container 2660 with air at a relatively slow rate of fill, to for example, between 0.1 psi to 3.0 psi. Rates of fill can range from between about 0.5 and 10 psi per minute, including about 0.5 psi/min, about 1 psi/min, about 2 psi/min, about 3 psi/min, about 5 psi/min, about 6 psi/min, about 8 psi/min, about 9 psi/min, and any rate therebetween. In some embodiments, the fill rate can be between 20-500 L/min, between 20-50 L/min, 50-100 L/min, 100-150 L/min, 150-200 L/min, 200-250 L/min, 250-300 L/min, 300-350 L/min, 350-400 L/min, 400-450 L/min, 450-500 L/min. Rates of fill can include, for example, about 20 L/min, 30 L/min, 40 L/min, 50 L/min, 60 L/min, 70 L/min, 80 L/min, 90 L/min, 100 L/min, 110 L/min, 120 L/min, 130 L/min, 140 L/min, 150 L/min, 160 L/min, 170 L/min, 180 L/min, 190 L/min, 200 L/min, 210 L/min, 220 L/min 230 L/min, 240 L/min, 250 L/min, 260 L/min, 270 L/min, 280 L/min, 290 L/min, 300 L/min, 310 L/min, 320 L/min, 330 L/min, 340 L/min, 350 L/min, 360 L/min, 370 L/min, 380 L/min, 390 L/min, 400 L/min, 410 L/min, 420 L/min, 430 L/min, 440 L/min, 450 L/min, 460 L/min, 470 L/min, 480 L/min, 490 L/min, 500 L/min, and any rate therebetween. In some embodiments, the container 2660 can be pressurized in less than 1 minute or even less than 30 seconds. Target pressures include about 0.1 psi, 0.3 psi, 0.5 psi, 0.7 psi, 1 psi, 1.5 psi, 2.0 psi, 2.5 psi, 3 psi and any pressure therebetween. The fill can stop at a predetermined pressure for a predetermined time. Hold times can range from about 10 to about 60 seconds, including about 10 seconds, about 15, seconds, about 20 seconds, about 30 seconds, about 40 seconds, about 50 seconds, or about 60 seconds. For example, in one embodiment the rate of fill in is between about 1 and 10 psi per minute and a holding pressure of 0.8 psi with a holding time of 30 seconds. The air can then be released from the container 2660 to reduce the air pressure. The aforementioned pressure check can be a quality check at manufacturing, or before allowing effluent into the container 2660. In some embodiments, the seals on the container 2660 can be spring loaded or a retention structure (e.g. a cap).

FIGS. 27A-27B illustrate another embodiment of the system for sterilization and/or disinfection of devices comprising lumens 2700. The system 2700 resembles or is identical to the system 2600 in many respects. Accordingly, numerals used to identify components of the system for sterilization and/or disinfection of devices comprising lumens 2600 are incremented by a factor of one hundred to identify like features of the system for sterilization and/or disinfection of devices comprising lumens 2700. Any component or step disclosed in any embodiment in this specification can be used in any other embodiment.

As described with regard to the system for sterilization and/or disinfection of devices comprising lumens 2600, the system for sterilization and/or disinfection of devices comprising lumens 2700 illustrated in FIG. 27A can include a container 2760 with an input 2710 and an output 2720. The container 2760 can include a retaining structure 2730 that is configured to retain and/or secure a device 2740. In some embodiments, the device 2740 can include one or a plurality of lumens 2750. As discussed above, in some examples, each of the lumens 2750 can be fluidly connected to the input 2710. As discussed with regard to the system 2600, the system 2700 illustrated in FIG. 27A is configured to "push" effluent through the lumens of the device 2740.

The container 2760 can be similar to the container 2660 and is not limited in size or shape. In some embodiments, the container 2760 can be configured to retain its shape such that the device 2740 can be retained, sterilized/disinfected, and or subsequently stored and/or transported. In some embodiments, the container 2760 can be clear to allow the user to see the type of device 2740 within the container 2760. As illustrated in FIG. 27A, in some embodiments, the container 2760 can comprise a flexible material that is disposed over a rigid frame. The rigid frame of the container 2760 can be configured such that the internal negative pressure of the container 2760 does not cause the container 2760 to collapse and prevents effluent from escaping if a leak is developed in the container 2760. In some embodiments, the negative pressure within the container 2660 can be between −0.03 to −1 psi; in some embodiments the negative pressure can be between −0.00 to −0.05 psi, −0.05 to −0.10 psi, −0.10 to −0.15 psi, −0.15 to −0.20 psi, −0.20 to −0.25 psi, −0.25 to −0.30 psi, −0.30 psi to −0.35 psi, −0.35 psi to −0.40 psi, −0.40 psi to −0.45 psi, −0.45 psi to −0.50 psi, −0.50 psi to −0.55 psi, −0.55 psi to −0.60 psi, −0.60 psi to −0.65 psi, −0.65 psi to −0.70 psi, −0.70 psi to −0.75 psi, −0.75 psi to −0.80 psi, −0.80 psi to −0.85 psi, −0.85 psi to −0.90 psi, −0.90 psi to −0.95 psi, or −0.95 psi to −1.0 psi; in some embodiments, the negative pressure can be −0.03 psi, −0.05 psi, −0.10 psi, −0.15 psi, −0.20 psi, −0.25 psi, −0.30 psi, −0.35 psi, −0.40 psi, −0.45 psi, −0.50 psi, −0.55 psi, −0.60 psi, −0.65 psi, −0.70 psi, −0.75 psi, −0.80 psi, −0.85 psi, −0.90 psi, −0.95 psi, or −1.0 psi.

In some examples, the input 2710 and the output 2720 can be located on a surface of the container 2760 and, like in the container 2660, are fluidly connected with the interior of the container 2760. In some examples, the input 2710 and the output 2720 are configured to allow for effluent to flow into and out of the container 2760 respectively. In some embodiments, the input 2710 can include a cap 2780 and the output 2720 can include a cap (not illustrated) that are configured to seal the interior of the container 2760. As will be discussed with regard to FIG. 27B, the input 2710 can be configured to receive an effluent input (e.g., a sterilant or disinfectant such as $H_2O_2$ and/or ozone) that can push effluent through any of the lumens 2750 of the device 2740 that is hooked up to the input 2710.

FIG. 27B illustrates an enlarged cross-sectional view of the input 2710. As discussed with regard to the input 2610, in some embodiments, the input 2710 can include a plurality of openings that are configured to allow for fluid flow from an external effluent source and through the input 2710. In some examples, the proximal end 2712 of the input 2710 can be configured to engage with an input line 2790. The input line 2790 can be composed of a flexible material, such as PVC, PVC with plasticizer, CPVC, Teflon, etc.

The input 2710 can be configured to include any number of openings to accommodate any number of lumens. In the embodiment illustrated in FIG. 27B, the input 2710 can include a lumen connection 2714a, a lumen connection 2714b, and a lumen connection 2714c. Any of the lumen connections 2714a, 2714b, 2714c, can be configured to be fluidly connected to one of the plurality of lumens 2750 of the device 2740. The device 2740 can be an endoscope or a similar device that includes a plurality of lumens that each provide one of a variety of functions. These can include, for example, a lumen providing air, a lumen providing water to clear the lens of the scope, a lumen for providing suction, or a lumen for providing a tool pathway. Each of the above lumens of the device 2740 can be hooked onto one of the lumen connections 2714a, 2714b, 2714c. As the input flow 2770 of effluent travels from the input line 2790 and into the proximal end 2712 of the input 2710, effluent can be pushed through each of the connected lumens 2750. In some embodiments, any of the lumen connections 2714a, 2714b, 2714c can be configured to instead allow effluent to pass from the input line 2790 and into the interior of the container 2760.

In some examples, the effluent flow through the system for sterilization and/or disinfection of devices comprising lumens 2700 can be similar with the system 2600. For example, the system for sterilization and/or disinfection of devices comprising lumens 2700 can have an input flow that pushes effluent through the input 2710. As illustrated in FIG. 27B, the input flow 2770 can push effluent through each of the attached lumens 2750 as well as pushing the flow of effluent through an opening and into the interior of the container 2760. Similarly, in some examples, the effluent can be configured to push through each of the lumens 2750 and subsequently into the interior of the container 2760. By providing for the input flow of effluent to be pushed into the interior of the container 2760, the effluent can be circulated through the entirety of the 2700, such that the exterior of the device 2740 can also be sterilized and/or disinfected.

In some embodiments, after effluent is circulated through the interior of the container 2760, the effluent can be configured to be drawn out of the output 2720. As mentioned above, in some embodiments, the container 2760 can have sufficient structure or be sufficiently rigid such that negative pressure can be generated. However, the generated negative pressure should not be sufficiently great so as to collapse the container 2760.

As discussed with regard to the retaining structure 2630, the retaining structure 2730 of the system for sterilization and/or disinfection of devices comprising lumens 2700 can be configured to secure and retain the device 2740 within the container 2760. In some embodiments, as illustrated in FIGS. 26C and 26D, the retaining structure 2730 of the system for sterilization and/or disinfection of devices comprising lumens 2700 can be configured to sterilize/disinfect the surface of the device 2740 in contact with the retaining structure 2730.

Figure 27C:
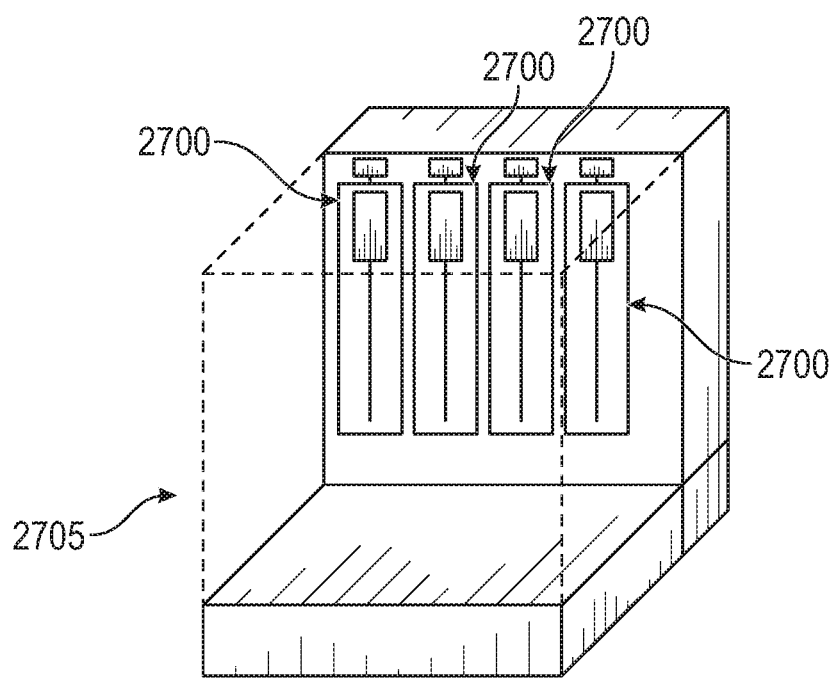
FIG. 27C shows an example of a plurality of the systems illustrated in FIGS. 26A and 27A aligned in a rack.
Figure 27D:
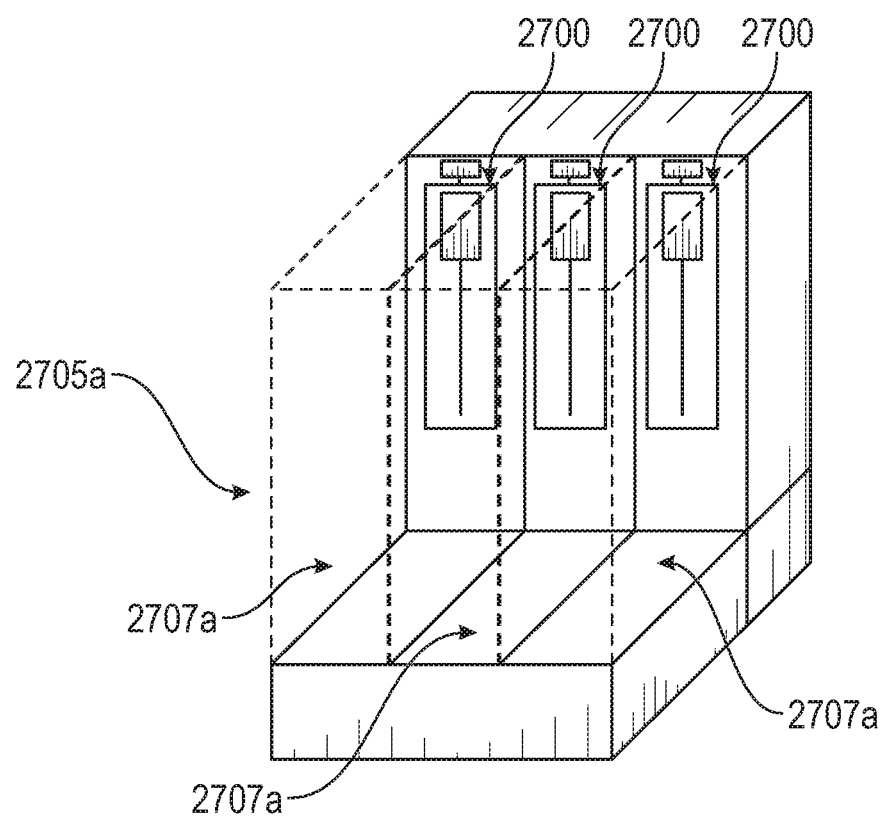
FIG. 27D shows another embodiment wherein each of a plurality of systems according to an embodiment are retained in individual compartments.

In some examples, each of the systems 2600, 2700 illustrated in FIGS. 26A and 27A can be part of a rack system to allow for the processing of multiple devices at a time. FIGS. 27C and 27D illustrate two embodiments of a rack configured to sterilize or disinfect a plurality of containers 2660, 2760.

Turning first to FIG. 27C, illustrated is an embodiment of a cabinet 2705 that is configured to sterilize and/or disinfect a plurality of containers 2660, 2760 in a batch set up. In the illustrated embodiment, the cabinet 2705 is configured to receive a plurality of containers 2660, 2760 that are in a reversibly closable structure. The cabinet 2705 can include a door or other sealing structure that prevents fluid (e.g. air, effluent) from escaping from the interior of the cabinet 2705 once closed. Once each of the plurality of containers 2660, 2760 are secured within the cabinet 2705 (e.g. a rack) and the door is closed to the cabinet 2705, the process for sterilization and/or disinfection can be initiated. In the embodiment illustrated in FIG. 27C, each of the containers 2660, 2760 can include a separate effluent source. However, in addition to an effluent source to each of the plurality of containers 2660, 2760, an effluent source can be provided for the interior of the cabinet 2705. This effluent source can not only serve to sterilize each of the exteriors of the containers 2660, 2760 but also ensure that should a leak occur in any of the containers 2660, 2760, the effluent in the external environment would enter each of the containers 2660, 2760. As effluent is sealed within the cabinet 2705 during the sterilization and/or disinfection process, the door to the cabinet 2705 is not configured to open until the sterilization and/or disinfection process is completed, or until effluent is purged from the interior of the cabinet 2705. In some examples, to ensure that moisture is not trapped inside the containers 2660, 2760 and creating a breeding ground for bacteria, the sterilization and/or disinfection system can be configured to run in short pulses to prevent the growth of bacteria. These short pulses would refresh the bag while it is being stored. For example, a number of short cycles (e.g. 5-6 cycles) could be run in a 12 hour time period.

In other embodiments, a sterilization and/or disinfection cycle can be run over shorter time periods—for example a short cycle can be run every 5 minutes, 10 minutes, 15 minutes, 20 minutes, etc. This can be important because bacteria, when in favorable growth conditions, can undergo exponential growth in minutes. In some examples, the sterilization and/or disinfection cycle can be run once every 2-6 hours until the device (or devices) within the system is used. The sterilization and/or disinfection cycle that is run every 2-6 hours can be short (e.g. 1-5 minutes) depending on the device being sterilized/disinfected. In some embodiments, when a device is retained within the containers 2660, 2760 for a period longer than 24-48 hours without being removed, the sterilization and/or disinfection cycle can be run once every 6 hours.

FIG. 27D illustrates another embodiment of a cabinet 2705a that is configured to sterilize and/or disinfect a plurality of containers 2660, 2760. In contrast to the cabinet 2705 illustrated in FIG. 27C, the cabinet 2705 of FIG. 27D can include a plurality of lockers 2707a, wherein each of the lockers 2707a is configured to receive one of the containers 2660, 2760. Each of the lockers 2707a of the cabinet 2705a can include a separate door or sealing structure that prevents fluid (e.g. air, effluent) from escaping from the interior of each of the lockers 2707a when closed. The cabinet 2705a illustrated in FIG. 27D provides for asynchronous sterilization and/or disinfection of the containers 2660, 2760. Each of the separate lockers 2707a can initiate a separate process for sterilization and/or disinfection. In some examples, each of the lockers 2707a can include a separate effluent source for each of the separate containers 2660, 2760 housed. The asynchronous sterilization and/or disinfection of the containers 2660, 2760 allows a user flexibility in sterilizing and/or disinfecting devices as they are being used. In some embodiments, as with the cabinet 2705 illustrated in FIG. 27C, to ensure that moisture is not trapped inside the containers 2660, 2760 to create a breeding ground for bacteria, the sterilization and/or disinfection system can be configured to run in short pulses to prevent the growth of bacteria while stored. For example, a number of short cycles (e.g. 5-6 cycles) could be run in a 12 hour time period.

In other embodiments, a sterilization and/or disinfection cycle can be run over shorter time periods—for example a short cycle can be run every 5 minutes, 10 minutes, 15 minutes, 20 minutes, etc. This can be important because bacteria, when in favorable growth conditions, can experience exponential growth in minutes. In some examples, the sterilization and/or disinfection cycle can be run once every 2-6 hours until the device within the system is used. The sterilization and/or disinfection cycle that is run every 2-6 hours can be short (e.g. 1-5 minutes) depending on the device being sterilized/disinfected. In some embodiments, when a device is retained within the containers 2660, 2760 for a period longer than 24-48 hours without being removed, the sterilization and/or disinfection cycle can be run once every 6 hours.

Figure 28:
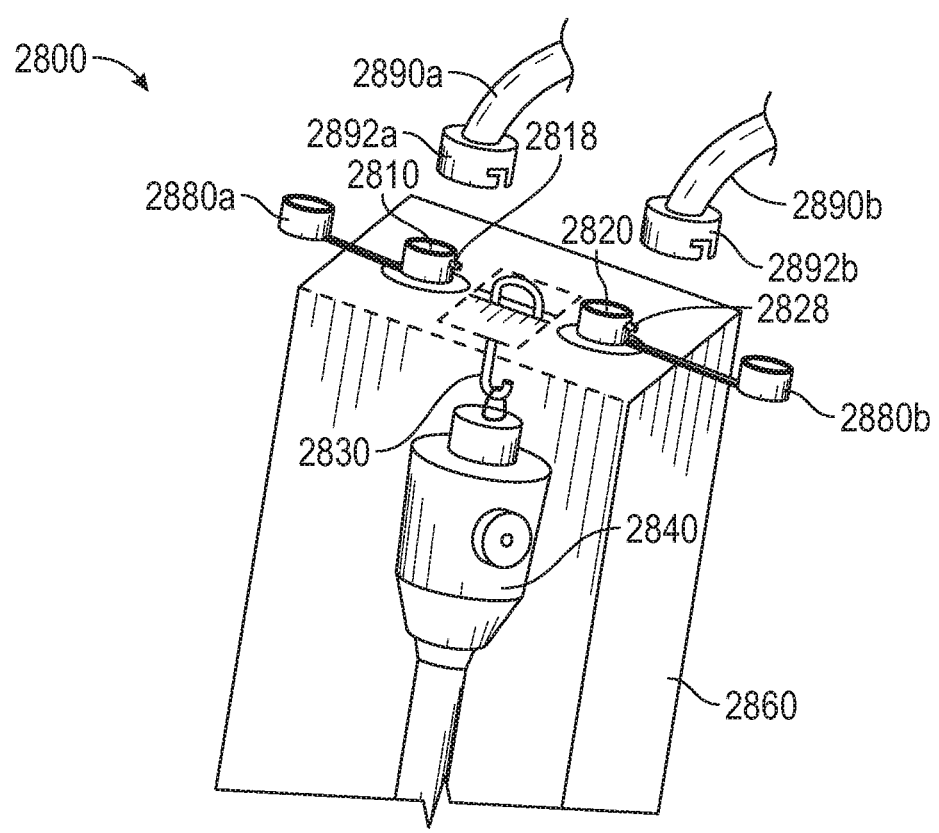
FIG. 28 shows an embodiment of a system for sterilizing and/or disinfecting endoscopes and similar devices without lumens.

FIG. 28 illustrates an embodiment of a system for sterilization and/or disinfection of devices 2800. As will be discussed in more detail below, although the system 2800 is configured to sterilize and/or disinfect devices without lumens, the system 2800 can resemble the systems 2600 or 2700 in some aspects. Accordingly, numerals used to identify components of the system 2600 and 2700 are incremented by a factor of one hundred to identify like features of the system for sterilization and/or disinfection of devices 2800. Any component or step disclosed in any embodiment in this specification can be used in any other embodiment.

In some embodiments, the system for sterilization and/or disinfection of devices 2800 can include a container 2860 with an input 2810 and an output 2820. The container 2860 can include a retaining structure 2830 that is configured to retain and/or secure a device 2840. Similar to the system 2600, 2700, the system for sterilization and/or disinfection of devices 2800 is also a system configured to "push" effluent through the interior of the container 2860.

In some examples, the container 2860 can be similar to the container 2660 and is not limited in size or shape. In some embodiments the container 2860 can be configured to retain its shape such that the 2850 can be retained, sterilized and/or disinfected, and or subsequently stored and/or transported. As illustrated in FIG. 28, in some embodiments, the container 2860 can comprise a flexible material that is disposed over a rigid frame. The rigid frame of the container 2860 can be configured such that the internal negative pressure of the container 2860 does not cause the container 2860 to collapse. As noted with regard to the container 2660, this can prevent effluent from escaping from the interior of the container 2860 should a leak develop. In some embodiments, the negative pressure within the container 2860 can be between −0.03 to −1 psi; in some embodiments the negative pressure can be between −0.00 to −0.05 psi, −0.05 to −0.10 psi, −0.10 to −0.15 psi, −0.15 to −0.20 psi, −0.20 to −0.25 psi, −0.25 to −0.30 psi, −0.30 psi to −0.35 psi, −0.35 psi to −0.40 psi, −0.40 psi to −0.45 psi, −0.45 psi to −0.50 psi, −0.50 psi to −0.55 psi, −0.55 psi to −0.60 psi, −0.60 psi to −0.65 psi, −0.65 psi to −0.70 psi, −0.70 psi to −0.75 psi, −0.75 psi to −0.80 psi, −0.80 psi to −0.85 psi, −0.85 psi to −0.90 psi, −0.90 psi to −0.95 psi, or −0.95 psi to −1.0 psi; in some embodiments, the negative pressure can be −0.03 psi, −0.05 psi, −0.10 psi, −0.15 psi, −0.20 psi, −0.25 psi, −0.30 psi, −0.35 psi, −0.40 psi, −0.45 psi, −0.50 psi, −0.55 psi, −0.60 psi, −0.65 psi, −0.70 psi, −0.75 psi, −0.80 psi, −0.85 psi, −0.90 psi, −0.95 psi, or −1.0 psi.

In some embodiments, the container 2860 could instead be pressurized such that the interior surface of the container 2860 moves away from (e.g. is not in contact with) the device 2840. In some embodiments, the use of positive pressure in the container 2860 (or any of the containers disclosed herein), can be configured to maintain space around the device 2840 (or any processed items). This can enable the sterilant to circulate completely across the surface of items to be sterilized and/or disinfected and minimizes dead spots where the sterilant and/or disinfectant might not contact all the surfaces of the items to be sterilized and/or disinfected. In some examples, the positive pressure may be used independent of the generator or as part of the generator to maintain positive space within the chamber (e.g. container 2860). In some examples, the use of negative pressure can be configured to prevent leaks from the generator during the cycle. Particularly when used with the cabinets 2705, 2705a illustrated in FIGS. 27C-27D, as each of the cabinets 2705, 2705a are sealed, a leak in the container 2860 would not be problematic (e.g., sterilant would not escape into the external atmosphere). As the device 2840 only needs to hang from within the container 2860, a wide range of materials can be used for constructing the container 2860. In some embodiments, the container 2860 can be clear to allow the user to see the type of device 2840 within the container 2860.

In some examples, the input 2810 and the output 2820 can be located on a surface of the container 2860 and be fluidly connected with the interior of the container 2860. In some examples, the input 2810 and the output 2820 are configured to allow for effluent to flow into and out of the container 2860 respectively. In some embodiments, each of the input 2810 and the output 2820 can include a cap 2880a and cap 2880b that are configured to seal the interior of the container 2860. As illustrated in FIG. 28, in some embodiments, the input 2810 can include an engagement structure 2818 that is configured to engage with a corresponding engagement structure 2892a on a distal end of the input line 2890a. Similarly, the output 2820 can include an engagement structure 2828 that is configured to engage with a corresponding engagement structure 2892b on a distal end of the output line 2890b.

The system for sterilization and/or disinfection of devices 2800 can have an effluent flow that enters from the input line 2890a, through the input 2810, and into the interior of the container 2860. The effluent can circulate throughout the interior of the container 2860 to sterilize and/or disinfect the exterior surface of the device 2840 before being drawn out of the output 2720 and through the output line 2890b. In some embodiments, the container 2860 can have sufficient rigidity such that, while negative pressure is generated, the container 2860 does not collapse. This can prevent the walls from the container 2860 from being in contact with the device 2840.

The container 2860 of the system for sterilization and/or disinfection of devices 2800, like the containers 2660, 2760, can be sterilized and/or disinfected in either of the cabinets 2705, 2705a illustrated in FIGS. 27C-27D and described above.

Figure 29:
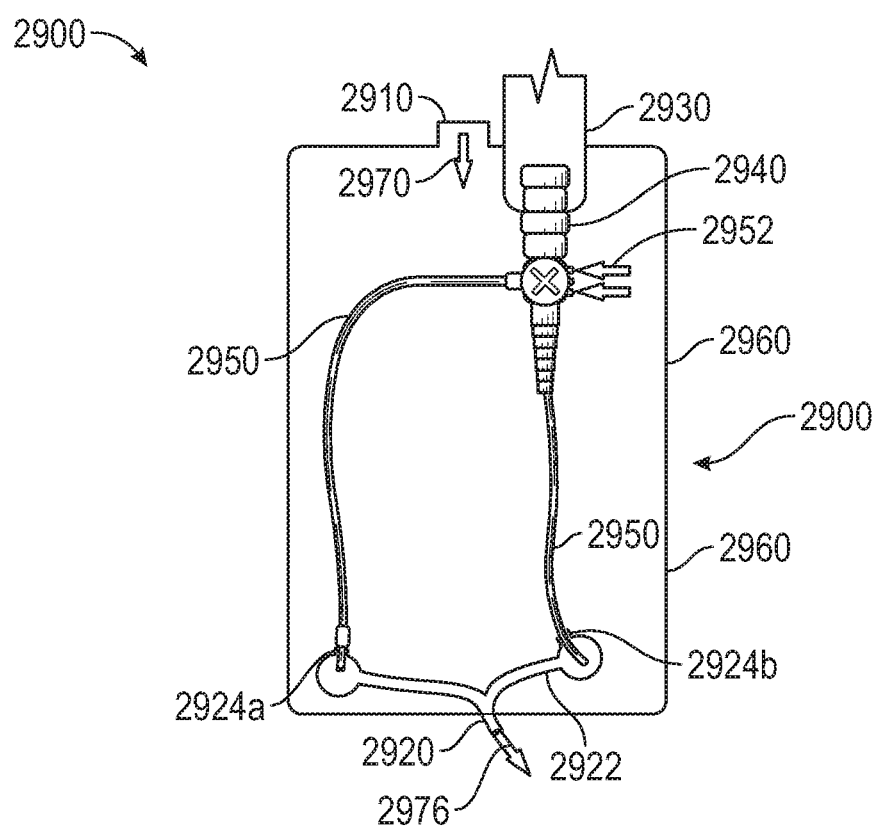
FIG. 29 shows an embodiment of a system for sterilizing and/or disinfecting endoscopes and similar devices with lumens. In this embodiment, effluent is pulled through the lumens of the device.

FIG. 29 illustrates an embodiment of a system for sterilization and/or disinfection of devices comprising lumens 2900. The system for sterilization and/or disinfection of devices comprising lumens 2900 illustrates another method for sterilizing a plurality of lumens on a device. In the system 2900, effluent is "pulled" through each of the plurality of lumens as will be described in detail below.

Although the system 2900 is configured to sterilize and/or disinfect devices with lumens using a "pulling" method, the system 2900 can resemble the systems 2600 or 2700 in some aspects. Accordingly, numerals used to identify components of the system 2600 and 2700 can be incremented by a factor of one hundred to identify like features of the system for sterilization and/or disinfection of devices comprising lumens 2900. However, any component or step disclosed in any embodiment in this specification can be used in any other embodiment.

In some examples, the system for sterilization and/or disinfection of devices comprising lumens 2900 can include a container 2960 with an input 2910 and an output 2920. The container 2960 can include a retaining structure 2930 that is configured to retain and/or secure a device 2940. In some embodiments, the device 2940 can include one or a plurality of lumens 2950.

The container 2960 can be similar to the containers 2660, 2670 and is not limited in size or shape. In some embodiments, the container 2960 can be configured to retain its shape such that the device 2940 can be retained, sterilized/disinfected, and or subsequently stored and/or transported. In some embodiments, the container 2960 can be clear to allow the user to see the type of device 2940 within the container 2960. In some embodiments, the container 2960 can comprise a flexible material that is disposed over a rigid frame. In other embodiments, the container 2960 can comprise a rigid chamber.

In some examples, the input 2910 and the output 2920 can be fluidly connected with the interior of the container 2960. In some examples, the input 2910 and the output 2920 are configured to allow for effluent to flow into and out of the container 2960 respectively. As will be discussed in more detail below, the input 2910 can be configured to receive an effluent input (e.g., a sterilant or disinfectant such as $H_2O_2$ and/or ozone) that can be pulled through any of the lumens 2950 of the lumens 2950. Each of the distal ends of the lumens 2950 can be configured to engage with a plurality of fitting rings 2924a, 2924b such that each of the lumens 2950 are fluidly connected to the output lumens 2922.

As noted above, the system for sterilization and/or disinfection of devices comprising lumens 2900 is configured to "pull" effluent through each of the lumens 2950 to sterilize and/or disinfect the interior of each of the lumens 2950. By "pulling" effluent through each of the lumens 2950 of the device 2940, the device 2940 can be sterilized without needing to hook up each of the plurality of lumens 2950 with the input.

As illustrated in FIG. 29, the input 2910 of the container 2960 receives an input flow 2970 of effluent. In some examples, the interior of the container 2960 is maintained at a higher pressure than the exterior of the container 2960. In some embodiments, the pressure can be maintained between 20 to 100 cm of $H_2O$; in some embodiments, the pressure can be maintained between 20-30 cm of $H_2O$, between 30-40 cm of $H_2O$, between 40-50 cm of $H_2O$, between 50-60 cm of $H_2O$, between 70-80 cm of $H_2O$, between 80-90 cm of $H_2O$, or between 90-100 cm of $H_2O$; in some embodiments, the pressure can be maintained at about 20 cm of $H_2O$, about 25 cm of $H_2O$, at about 30 cm of $H_2O$, at about 35 cm of $H_2O$, at about 40 cm of $H_2O$, at about 45 cm of $H_2O$, at about 50 cm of $H_2O$, at about 55 cm of $H_2O$, at about 60 cm of $H_2O$, at about 65 cm of $H_2O$, at about 70 cm of $H_2O$, at about 75 cm of $H_2O$, at about 80 cm of $H_2O$, at about 85 cm of $H_2O$, at about 90 cm of $H_2O$, at about 95 cm of $H_2O$, or at about 100 cm of $H_2O$. The pressure differential can cause effluent to be pulled into the device 2940 as shown in the arrows illustrating the input flow 2952 of the effluent through the device 2940. In some examples, the effluent is pulled through the device 2940 and through each of the lumens 2950 to exit from the distal ends of the lumens 2950. In some embodiments, the effluent can then travel through the output lumens 2922 where an output flow 2676 exits through the output 2920. In some embodiments, the output flow 2676 is equivalent to the input flow 2952.

In some examples, the container 2960 of the system for sterilization and/or disinfection of devices comprising lumens 2900, like the containers 2660, 2760, can be sterilized and/or disinfected in either of the cabinets 2705, 2705a illustrated in FIGS. 27C-27D and described above.

In some embodiments there is a controller unit that houses, the plasma generator, the evaporator, the hydrogen peroxide cartridge, fans, as well as the electronics and control boards for the device. In some embodiments, the controller unit would be small enough in size to be placed on a wall or counter. In some embodiments, the chamber and the control unit would be separate units that are connected by tubing. In these embodiments, tubing would carry sterilant both from the control unit to the chamber and then from the chamber back to the control unit to be reprocessed. The basic device of the control unit can be used to sterilize/decontaminate a variety of objects dependent on the chamber attached to the control unit. For example, in some embodiments the control unit is connected to an endoscope drying and treatment rack where endoscopes are sterilized. In some embodiments the same control unit is connected to a chamber designed to hold communication devices where iPad, cell phones, personal communication devices (e.g., nurse phones), and pagers, for example, can be sterilized/decontaminated. In some embodiments the control unit is used to determine the sterilization cycle of the device based on the objects placed in the attached chamber. For example, in some embodiments the chamber holds endo scopes and the controller unit will be set to sterilization. In another example, the chamber will hold communication devices and the controller unit will be set to rapid disinfection.

An effluent generator 46 is used for production of effluent for sterilization or decontamination of the chamber and its contents and for powering the circulation of effluent in the closed loop, to be described later. The effluent generator 46 includes a flow generator (e.g., a circulating pump, a positive displacement pump, an air conveyor, a fan, or a blower with flow distributor 14), a free radical supply unit (e.g., a cold plasma generator such as a plasma electric free radical generator 30, ozone generator or any other type of system that generates free radicals, such as a dielectric barrier discharge system), and a vapor supply unit (e.g., an evaporator or vaporizer 32). The flow generator can include a controllable-speed type (e.g., variable speeds) or a single-speed type. Although various embodiments can be utilized in room pressures, in some instances, varying the speeds may allow use of slight negative or positive pressure. In some embodiments, a slight negative pressure may advantageously keep the effluent within the system as a safety precaution. In some embodiments, the pressure may be approximately 1 to 2 cm of $H_2O$ lower than ambient pressure.

The plasma free radical generator 30 can be any kind of dielectric barrier discharge device, electrical corona device, a glow discharge device, or a microwave generator. One non-limiting example of a device which can be used within the teachings of the disclosure is an ozone generator such as, for example, ozone generator cell SY-G20 manufactured by Longma Industrial Zone, Bao'an District, Shenzhen, 518108, P.R.C.

In several embodiments, the vaporizer 32 contains liquid sterilizing agent such as hydrogen peroxide solution, though other agents known to those of ordinary skill could be used, as discussed below. Additionally, in several embodiments, a solid agent could be used that is converted into a liquid during the sterilization cycle. The gas entering the vaporizer, comes into contact with the solution, and produces an effluent comprising reactive oxygen species (e.g., bactericidal effluent). While certain embodiments are described with particular reference to hydrogen peroxide as the sterilizing agent, it will be appreciated that the system is also applicable to other solutions and pure liquids, such as peracetic acid or formalin solution.

The vaporizer 32 can be in the form of a "bubbler", in which the gas passes through a container of liquid, or the vaporizer could use plates or wicks over which the gas passes. Preferably, the vaporizer 32 uses a measured amount of sterilizing agent, preferably in a pre-measured cartridge which can be inserted into the vaporizer, such that the agent is substantially or completely consumed in the course of a sterilizing run. The vaporizer can thus supply a specific small amount of hydrogen peroxide to the evaporator from a cartridge which is emptied and dried during the sterilization process. In some embodiments, the hydrogen peroxide concentration can be from about 30% to about 60% concentration, e.g., about 30%, about 35%, about 40%, about 45%, about 50%, about 55%, or about 60% concentration. In some examples, the hydrogen peroxide vapor or microdroplets concentration can be from about 100 ppm to about 10,000 ppm or any ranges in between such as about 100 ppm to about 600 ppm. At the end of the sterilization cycle, the final hydrogen peroxide vapor or microdroplets concentration can be about 600 ppm or less (e.g., about 550 ppm or less, about 525 ppm or less, about 500 ppm or less, about 475 ppm or less, about 450 ppm or less, about 425 ppm or less, or about 400 ppm or less) in some embodiments, allowing for less condensation and better material compatibility. The drying of the cartridge is accomplished by heating it using a small heater or dryer and a limited filtered air flow through the cartridge into the system. This way there is reduced or no danger that hydrogen peroxide liquid is present in the cartridge at the end of the cycle when a person/operator will insert a new cartridge for next cycle. In alternative embodiments, a cartridge is provided that contains enough sterilant for a certain number of cycles (e.g., 5 cycles, 10 cycles, etc.), for use in circumstances where there are a higher number of cycles used on a regular basis. In some embodiments, each cycle uses about 1 mL or less than 1 mL of sterilant (e.g. hydrogen peroxide) in one cycle. In such embodiments, as above, the cartridge is optionally dried before a system lock allows the cartridge to be removed by a user. In still additional embodiments, akin to an "all in one" espresso machine, certain embodiments dispose of the cartridge internally to the machine, reducing the risk to users, and a new cartridge is inserted in its place when prompted by the system. In some examples, the cartridge can have enough sterilant (e.g. hydrogen peroxide) such that it can be replaced approximately two times a week.

In some examples, the cartridge can have approximately 250 mL of sterilant (e.g. hydrogen peroxide). In some embodiments, approximately 0.40 mL to 0.45 mL including 0.40 mL, 0.41 mL, 0.42 mL, 0.43 mL, 0.44 mL, and 0.45 mL of sterilant (e.g. hydrogen peroxide) is used in each cycle.

In some embodiments, the cartridge can have between about 250 mL to about 500 mL of sterilant, including 250 mL, 300 mL, 350 mL, 400 mL, 450 mL, and 500 mL, and including ranges in between such as about 250 mL to about 300 mL, about 300 mL to about 350 mL, about 350 mL to about 400 mL, about 400 mL to about 450 mL, and about 450 mL to about 500 mL. In some embodiments, the cartridge can be configured to provide enough sterilant for between about 500-1500 cycles of disinfection/sterilization, including 500, 600, 700, 800, 900, 1000, 1100, 1200, 1300, 1400, 1500 cycles. In some examples, the cartridge is configured to provide enough sterilant for ranges in between 500-1500 cycles including about 500 to about 600 cycles, about 600 to about 700 cycles, about 700 to about 800 cycles, about 800 to about 900 cycles, about 900 to about 1000 cycles, about 1000 cycles to about 1100 cycles, about 1100 to about 1200 cycles, about 1200 to about 1300 cycles, about 1300 to about 1400 cycles, and about 1400 to about 1500 cycles.

In some embodiments, the vaporizer 32 may be filled with hydrogen peroxide liquid before each cycle to a certain prescribed level so that there is enough liquid to last to the end of the cycle. In such embodiments, the cycle may be continuously in free radical saturation. The remaining liquid in the vaporizer 32 can be utilized in the next cycle because hydrogen peroxide does not decompose between cycles (e.g., if the time between cycles is not long such as more than two weeks, three weeks, four weeks, or months). In some embodiments, if the liquid (e.g., hydrogen peroxide) in the vaporizer decomposes below an acceptable level (e.g., 5% below the original level) the liquid is drained from the vaporizer and discarded.

The blower with the flow distributor 14 takes recirculated effluent from the chamber 10 via conduit 36, and distributes it proportionally through conduit 40, which is coupled, optionally through a filter 50, into the plasma generator 30, and through conduit 38, again through optional filter 50, into vaporizer 32. The recirculated effluent is preferably distributed in proportions of approximately 30% to conduit 40, and approximately 70% to conduit 38, although other proportions could be used within the teaching of the disclosure. For example, in some embodiments, the effluent can be distributed in portions of approximately ⅓ to the plasma generator 30 and approximately ⅔ to the vaporizer 32 by having a single conduit 40 leading to the plasma generator 30 and two conduits 38 leading to the vaporizer 32. Other embodiments employ ratios of about 10:90, 20:80, 40:60; 50:50, 60:40, 70:30, 80:20, and the like.

With the proportions noted above, most of the recirculated effluent bypasses the plasma generator 30, passing only through vaporizer 32. The lesser proportion of the effluent passes through plasma generator 30, picking up new free radicals, and is mixed back in the rest of the effluent from the vaporizer 32 at junction 48. Accordingly, the sterilant can be rejuvenated multiple times without filtering out the active species and/or free radicals resulting in a sterilization process comprising a single cycle of continuous flow. By rejuvenating the sterilant without filtering out the reactive species and free radicals, various embodiments can achieve constant peak efficiency. For example, various embodiments can maintain a peak free radical mixture in a relatively short cycle time, as opposed to other technologies that refresh the sterilant throughout the process, thereby requiring longer times to completion.

The effluent produced in the effluent generator 46 is then introduced into the chamber 10, completing the closed loop of the system. In FIG. 1A, the free radicals from the plasma generator 30 and the effluent from the vaporizer 32 are mixed from the sterilant prior to introduction into the chamber 10. In various embodiments, the sterilant includes substantially only free radicals and humidity such that there is no condensation of hydrogen peroxide and exposure to the item being sterilized. In other embodiments, the plasma generator 30 and the effluent from the vaporizer 32 may be mixed within the chamber 10, e.g., by use of a baffle. In such embodiments, the plasma may be advantageously generated within the chamber 10 without application of a radio frequency (RF) field into the chamber 10. In FIG. 1A, the plasma generator 30 and the vaporizer 32 are disposed in parallel. In other embodiments, the vaporizer 32 and the plasma generator 30 are disposed in series, e.g., with the vaporizer 32 placed prior or after the plasma generator 30. In some such embodiments, a dryer may be placed a prior to the plasma generator 30.

In various embodiments, the generated atmospheres in the chamber 10 have sterilizing (or disinfecting, sanitizing, decontaminating, and/or therapeutic aspects). Advantageously, the generated atmospheres in several embodiments undergo a relatively gentle process that is compatible with all natural and manmade materials. In some embodiments, the generated atmospheres are produced with a "green" process, e.g., utilizing relatively low power consumption and producing non-toxic products and by-products.

Quality control and/or regulatory compliance indicators (e.g., disposable after every cycle, semi-disposable for use after a number of cycles, or non-disposable) may be incorporated in many embodiments. For example, indicators can provide information to an operator of proper delivery, amount, and/or mix of sterilant to the chamber 10. An example includes a chemical strip in a holder within the chamber 10. For a semi-disposable strip for a certain number of cycles (e.g., 2, 3, 4, 5, 6, 7, 8, 9, 10, 12, 15, 20, etc.), in some embodiments, only a portion of the strip may be exposed for each cycle. As another example, a chemical strip may be incorporated into a label for a chamber such as for the case where the chamber is a plastic bag (e.g., a Tyvek® bag). In some such embodiments, the indicator may travel with the item (e.g., when placed or removed from the chamber). As yet another example, a sensor (e.g., a hydrogen peroxide sensor) may be incorporated in an automated fashion. Other examples are possible.

In addition to the closed loop system, an open loop system is also provided. In one embodiment, an open loop system is for the purpose of pre-heating (optionally) and drying the chamber 10 before and after the circulation of bactericidal effluent through the closed loop system. The open loop system uses a flow generator (e.g., an exhaust pump, an air conveyor, a fan, or a blower 16), exhausting to atmosphere 56, to draw air from an air input 58 through an input controller (e.g., an input valve 18) and an optional heater 26 into chamber 10. The input air may be filtered by filter 20, which is preferably of the high efficiency particulate air (HEPA) variety or a military grade filter.

The fresh (heated or not heated), filtered air is introduced into the chamber 10 through conduit 42.

In the open-loop operation mode, the output of the chamber 10 is drawn out by blower 16 and passes through conduit 44 and a Free Radical Destroyer (FRD) 24, which destroys any free radicals which might remain before the air is exhausted 56. A second filter 22, again preferably of the HEPA type, can be provided in conduit 44 to filter out any particles which would otherwise enter the FRD or be exhausted to the atmosphere. The presence of HEPA filters 20 and 22 at the input and exhaust ensures that there is substantially no microorganism transfer between the ambient air and the sterilization system and vice versa. The order of the filter 22, FRD 24, and blower 16 can be in any order.

The simplest FRD is an activated carbon filter, for example, the Vent Pure "D" from General Carbon Corp. of Paterson, N.J. Other examples include filters comprising a noble metal (e.g., platinum, silver, gold, etc.) or ceramic. In some embodiments, a catalytic converter might be used to convert harmful compounds to less harmful ones.

By opening valve 18 and turning on heater 26 and blower 16, the chamber 10, and items 56 within the chamber, can be dried and pre-heated before the closed loop operation is begun. Once the pre-heating and drying step is completed, valve 18 is closed and heater 26 is turned off Preferably, blower 16 is of a controllable-speed type, so that it may be operated at a reduced speed during closed-loop operation. In some embodiments, this will induce a slight negative pressure in the chamber 10, preventing leakage of effluent from the chamber. However, the blower could be a single-speed blower, in which case it would be turned off after the pre-heating step.

After optionally pre-heating, in several embodiments, the system is operated in closed-loop mode by starting blower/distributor 14 and plasma generator 30. The effluent mixture circulates continuously through the loop, from generator 46 through conduit 34, through chamber 10 and conduit 36, back to the generator 46.

When this cycle is finished plasma generator 30 is turned off, valve 18 is opened, and blower 16 is turned on full speed in order to remove the active free radicals from the effluent using FRD 24, and to dry the chamber 10 and the sterilized equipment 56 or 62.

The closed loop blower/distributor 14 may remain on, if desired, so as to circulate air through the closed loop to dry the free radical source 46 and vaporizer 32. Heater 26 may optionally be turned on at this stage, as well, so that heated air is circulated through the vaporizer in order to evaporate residual remains of liquid solution of hydrogen peroxide. Alternatively, blower/distributor 14 may be turned off if it is not desired to circulate air through the closed loop portion of the system during this drying step.

A controller 12 is provided in order to control the operation of the various parts of the system.

As described herein, various embodiments may be operated at ambient conditions (e.g., room temperature). Such embodiments may be advantageous in hospital settings where air conditions and humidity are controlled. However, some embodiments may adjust the conditions within the chamber 10 to a more effective environment. For example, if the ambient temperature were too cool or too warm, some embodiments are configured to self-regulate or control the temperature in the chamber 10 to a desired temperature (e.g., within an operating range for sterilant effectiveness). Another aspect of the sterilizing cycle is to control Relative Humidity in the chamber. The humidity can be varied during the cycle from lower humidity at the beginning of the cycle to higher humidity toward the end of the cycle depending on the initial conditions of the items to be sterilized. For example, some items may contain residual moisture from washing or were stored in moist environment. In such case it is necessary to remove the residual moisture from the items in order to accomplish full sterilization.

In general, a lower ambient temperature may slow the sterilization process, while a higher ambient temperature may speed up the process. As will be described herein, various embodiments may self-regulate or control humidity such that the humidity of incoming air does not adversely affect the humidity in the chamber 10. Hydrogen peroxide can replace water in the atmosphere and water can condense out. Under many anticipated environmental conditions (e.g., hospital conditions), self-regulation and control measures can be incorporated. In more severe environment conditions (e.g., jungle environments), additional purge valves and methods may be incorporated, such as to purge the vaporizer 32 at various intervals and to bled out hydrogen peroxide (e.g., in case of shipping or transport or when the hydrogen peroxide decomposes below the desired w/w % level)).

In various applications, moisture control (e.g., self-regulation or control) may be important to reduce or avoid unwanted condensation. Absent adequate moisture control, there may be the potential of water vapor and/or hydrogen peroxide vapor condensation forming on the walls of the chamber 10 as well as on articles in the chamber 10. The resulting layer of water and hydrogen peroxide condensation can cause adverse effects on the articles being sterilized in some instances. As one example, when electronic devices are being sterilized, excessive condensation could potentially create electrical shorts and otherwise damage the electronic devices.

Moisture control is also important in the sterilization process when items or their parts to be sterilized are wet and pathogens are "hiding" under a layer of moisture preventing the access of free radicals in the sterilant to the pathogens. In such conditions part of the sterilization cycle is to maintain the circulating sterilant at much lower relative humidity level in order to remove the remnants of the moisture from the article. In some embodiments where there is a layer of moisture preventing access of free radicals in the sterilant to the pathogens, the target relative humidity level is maintained at 20-30% for some amount of time before the sterilization process is started.

Figure 1B:
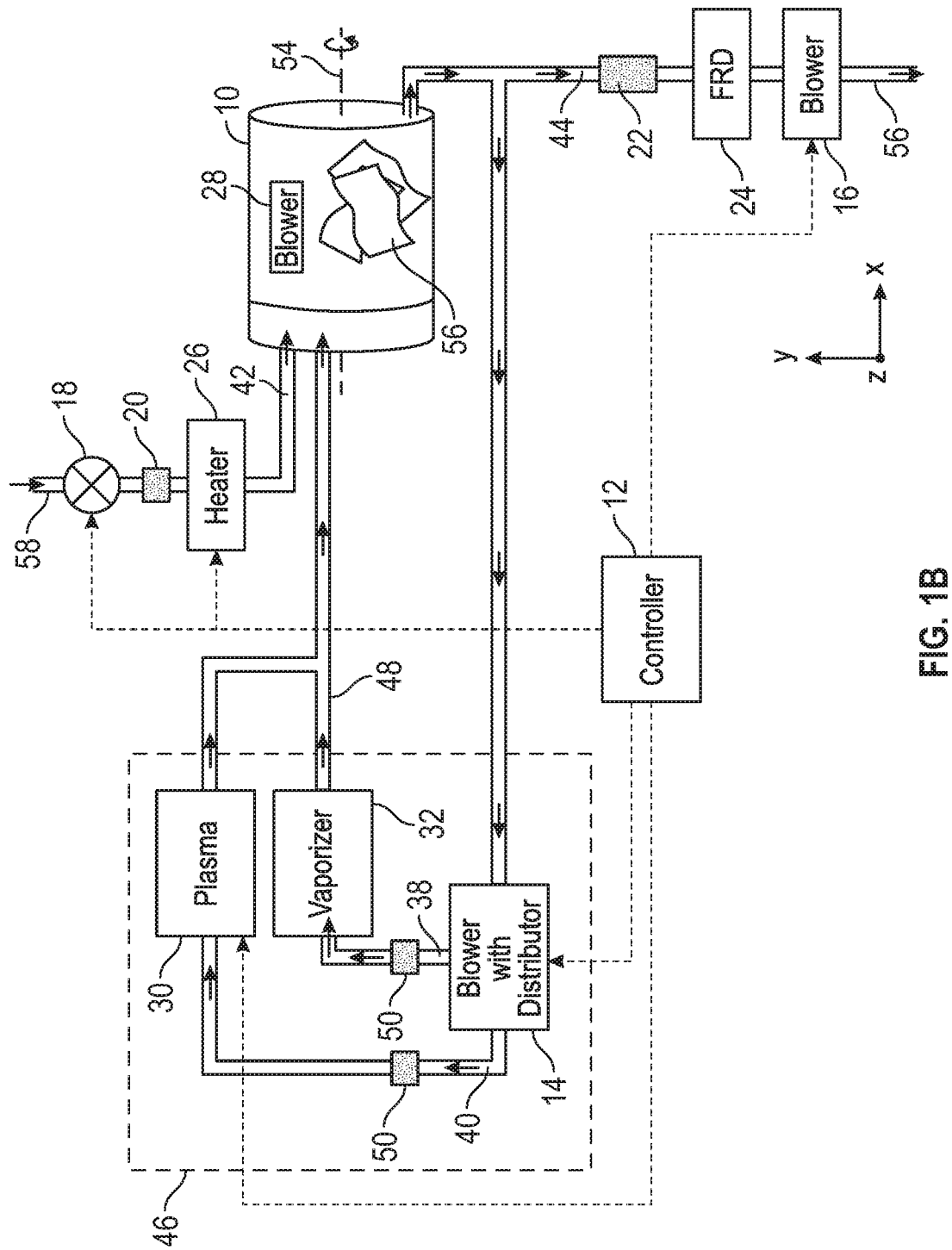
FIG. 1B shows another embodiment of the disclosure with a tumbler-type chamber, that does not include a motor or a circulating blower.
Figure 1C:
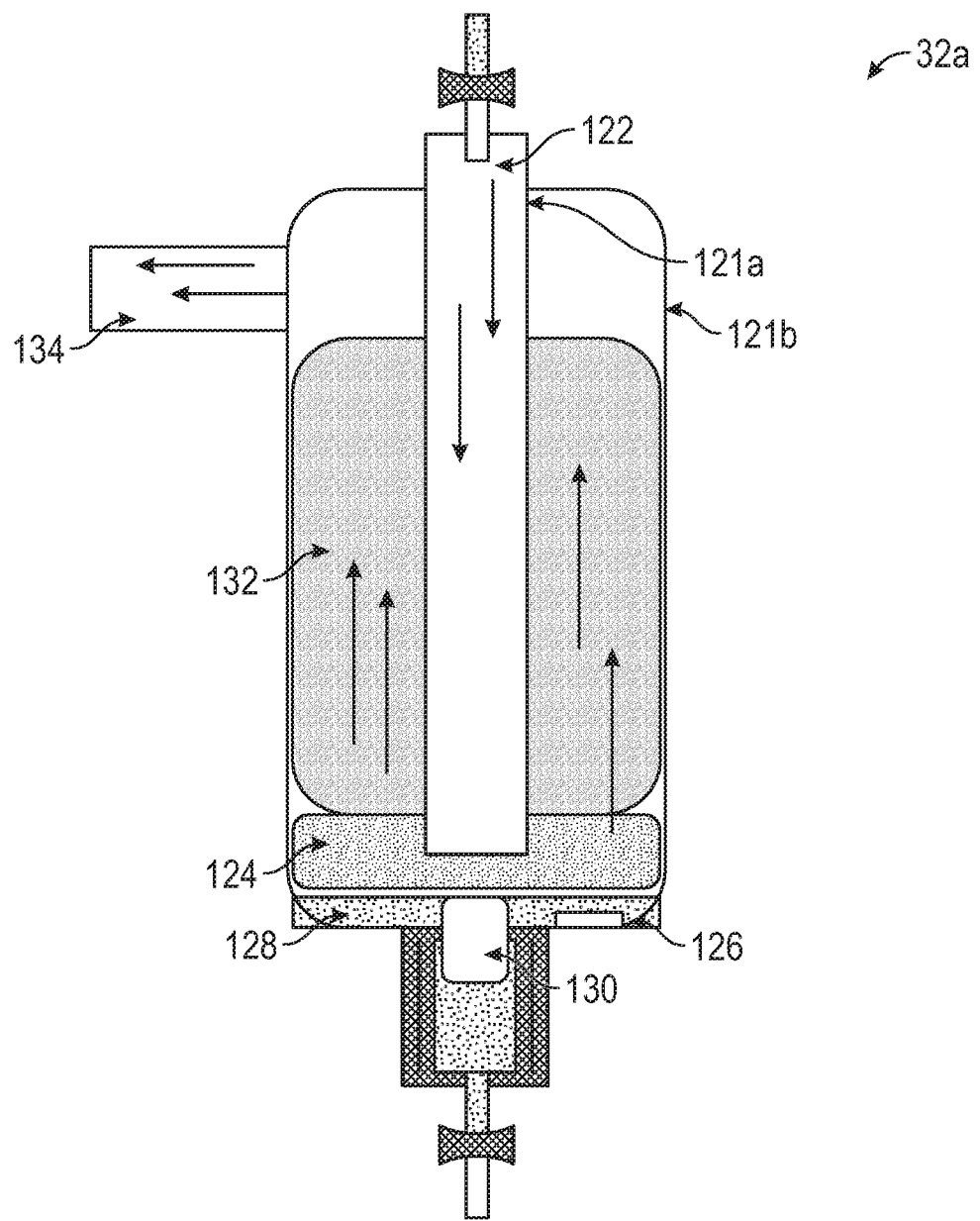
FIG. 1C shows an example evaporator configured to generate sterilant at vapor pressures at or below saturation levels that is configured to control the sterilizing agent (e.g. liquid sterilant) level in the evaporator chamber; the evaporator may use a piezoelectric transducer to create a sterilant mist.
Figure 1D:
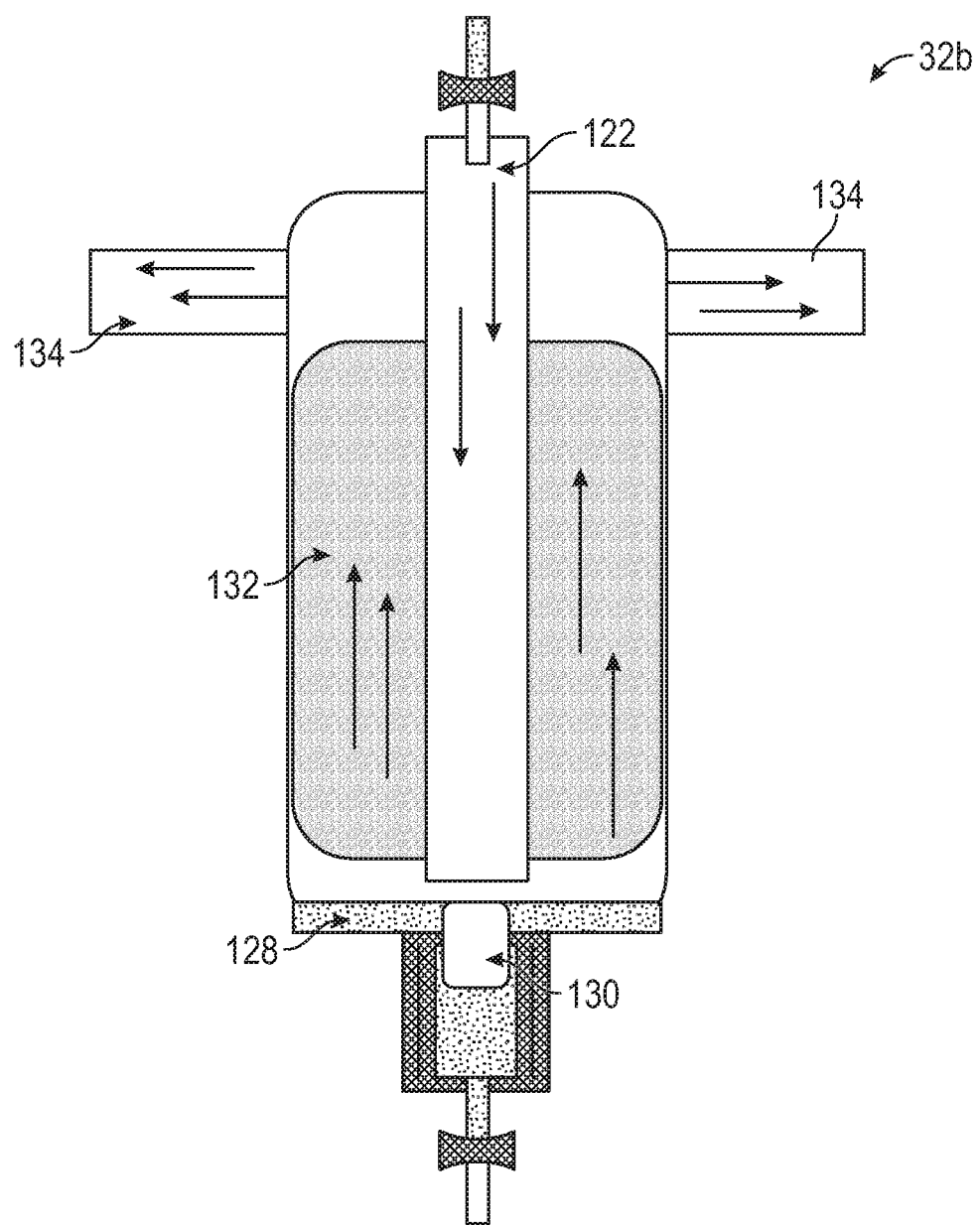
FIG. 1D shows an example evaporator configured to generate sterilant at vapor pressures at or below saturation levels is configured to control the sterilizing agent (e.g. liquid sterilant) level in the evaporator chamber; the evaporator that may omit the piezoelectric transducer.
Figure 1E:
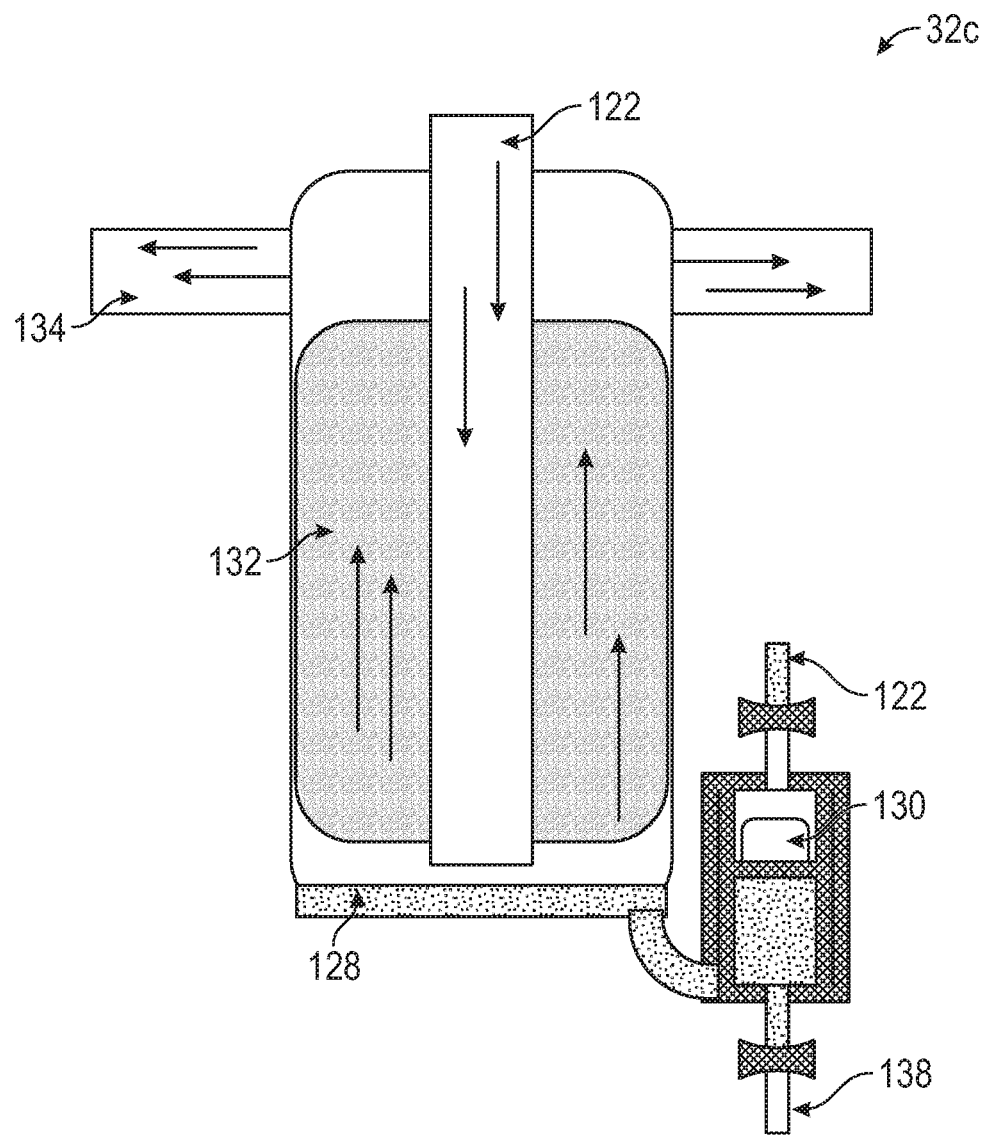
FIG. 1E shows an example evaporator configured to generate sterilant at vapor pressures at or below saturation levels and that may include a drain for removing sterilizing agent.

FIG. 1B illustrates another embodiment wherein the sterilization system does not include a motor or a circulating blower.

In some embodiments, the vapor pressure of the sterilant may be maintained at or below the saturation level in the sterilization chamber (e.g., for the pressure and/or temperature inside of chamber 10). By doing so, various embodiments can reduce or eliminate condensation buildup on the items being sterilized, on the walls of the chamber 10, and on other components exposed to the sterilant, such as hoses and fittings described herein. FIGS. 1C-1E illustrate some examples of evaporators 32a, 32b, and 32c configured to control the vapor pressure of the sterilant. Each of evaporators 32a, 32b, and 32c is usable as the vaporizer 32 in all of the embodiments described herein and may produce, in many instances, a substantially non-condensing output.

As shown in FIG. 1C, evaporator 32a may comprise two concentric tubes 121a, 121b with a wicking material 132 disposed between the tubes 121a, 121b. In operation, the evaporator 32a can receive sterilizing agent 128 (e.g., hydrogen peroxide solution or other suitable sterilizing agent liquid) for example, forming a pool of liquid near the bottom of the evaporator 32a. The evaporator 32a may include a float 130 to regulate the level of the sterilizing agent 128. For example, a controller (e.g., controller 12 shown in FIG. 1) can electronically monitor the position of the float 130. The float 130 can include a magnetic switch float such as, for example, 9FS01-0112 manufactured by Strain Measurement Devices, Inc. 55 Barnes Park North, Wallingford, Conn. 06492. Based on the position of the float 130, the controller 12 can open or close an intake valve to maintain the desired level of sterilizing agent 128.

In some embodiments, the evaporator 32a may comprise a piezoelectric transducer 126 (or other suitable vibration element). The piezoelectric transducer 126 may be configured to create a mist 124 of the sterilizing agent 128, which may be absorbed by wicking material 132.

As indicated by the arrows in FIG. 1C, the evaporator 32a may take in gas (e.g., air or other medium) at intake 122. If desired, the intake 122 may extend below the level of the sterilizing agent 128, such that the incoming gas bubbles through the sterilizing agent 128, encouraging evaporation and misting. The gas may then pass through mist 124. In at least some arrangements, the flow of the gas may assist in the formation of mist 124. In other words, the flow of the gas may cause some of the sterilizing agent 128 to move into the lower regions of the wicking material 132. Evaporation of the sterilizing agent 128 may occur primarily within the wicking material 132, which is at least partially saturated with sterilizing agent 128. In other words, the wicking material 132 may be formed from a porous material that, due to its porous nature, has a large internal surface area which enhances evaporation.

In at least some arrangements, by saturating the lower portions of wicking material 132, the upper portions of wicking material 132 (e.g., the portions further from the pool of sterilizing agent 128) may remain relatively dry. As such, the wicking material 132 may serve to both encourage evaporation and to reduce/avoid producing vapor that is over-saturated (e.g., to avoid or minimize formation of droplets or mists of the sterilizing agent 128 at the output 134 of the evaporator 32a). Put another way, even if the evaporator 32a were to produce over-saturated sterilant vapor in the lower regions of the wicking material 132, the upper portions of the wicking material 132 would drive formation of condensation and then absorb the condensation, such that the final output would be merely saturated or below saturation levels.

As another example, the float 130 may include a level control float sensor/switch 130 configured to regulate the level of sterilizing agent 128. In operation, sterilizing agent 128 may be received through the float switch 130. As sterilizing agent 128 is evaporated into the gas flow, float sensor/switch 130 may sense a drop in the level of the sterilizing agent 128 and open an intake valve to refill the sterilizing agent 128 in the evaporator 32a.

Alternatives for maintaining the level of sterilizing agent 128 may be used. As one example, a sensor may be provided that measures the level of sterilizing agent 128 and a controller (e.g., controller 12 shown in FIG. 1A) may open or close an intake valve in response to measurements from the sensor at the beginning of each cycle. Other examples of liquid level measurement devices include using a laser or a mechanical switch.

In various embodiments, the wicking material 132 and other components of the evaporator 32a that may come into contact with the sterilizing agent 128 may comprise materials that are resistant to the sterilizing agent 128 (e.g., hydrogen peroxide). In arrangements also including a plasma generator 30 (e.g., an ozone generator) and in which the sterilant is recirculated, the wicking material 132 and other components of the evaporator 32a that may come into contact with the recirculated sterilant may comprise materials that are also resistant to the sterilant (e.g., which may include ozone).

FIG. 1C illustrates an evaporator 32b in which the piezoelectric transducer 126 is omitted. In some such arrangements, the liquid sterilizing agent 128 may be transferred to the wicking material 132 by the gas flowing through the evaporator 32b (e.g., by bubbling, by direct liquid surface deformation, etc.). If desired, wicking material 132 may be extended into sterilizing agent 128 (e.g., the sterilizing agent 128 may be maintained at a level that is in contact with wicking material 132) such that no bubbling or misting is required to draw the sterilizing agent 128 into the wicking material 132. In other embodiments, multiple layers of wicking material may be used, e.g., a first wicking material that contacts the sterilant directly and is interwoven or overlaid (optionally reversibly) with another wicking material (optionally of the same type as the first) that is relatively permanent to the device (though it is optionally replaceable). Such techniques may also be utilized in embodiments including piezoelectric transducer 126. FIG. 1C also illustrates that the output 134 may be arranged in a different way.

FIG. 1E illustrates an evaporator 32c that may include an input 136 and/or a drain 138 for the sterilizing agent 128. During operation, float switch 130 or other suitable mechanism may maintain the level of the sterilizing agent 128 in the evaporator 32c by adding sterilizing agent 128 from input 136 and/or by removing sterilizing agent 128 from drain 128. In addition, when the evaporator 32c is shut off or during desired portions of a sterilizing process, the evaporator 32c may be drained through drain 138. By draining the sterilizing agent 128 through drain 138, the evaporator 32c can, if desired, be quickly dried out (e.g., to reduce any danger of any remaining hydrogen peroxide). Drying out the evaporator 32c may include passing air through the wicking material 132 to absorb any remaining sterilizing agent 128. Additionally, maintaining a particular level of sterilant, in several embodiments, optimizes the overall process, as too much or too little sterilant being incorporated into the effluent can lead to inefficient sterilization, while too much may damage the items to be sterilized.

In various embodiments described herein, evaporation can occur passively (e.g., without heat) by the flow of air through the wet wicking material. In some instances, equilibrium between liquid and vapor can be reached at or below the saturation level. Accordingly, various embodiments may simply adjust the saturation level of the sterilizing agent 128, but need not adjust the concentration of the sterilizing agent 128. Also, by controlling the level of moisture, certain embodiments do not require the use of heat in the vaporizer 32.

Figure 1F:
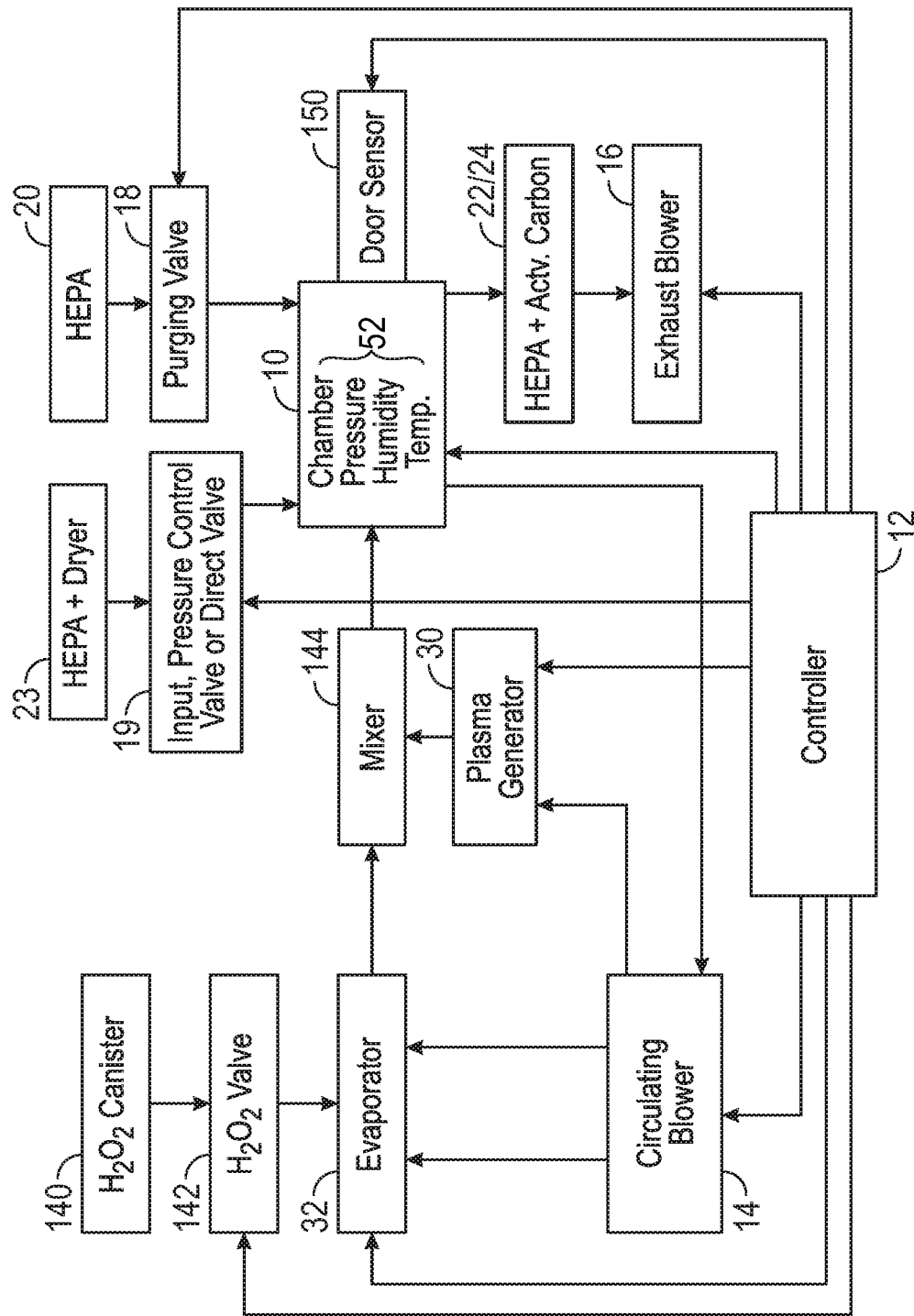
FIG. 1F shows a block diagram of an example embodiment using a regulated input of fresh, dry air and associated exhausting of circulating effluent to reduce or prevent buildup of condensation in the chamber.

FIG. 1F illustrates an example embodiment that may be used to regulate the water vapor saturation level as well as the sterilant vapor saturation level within the sterilization chamber 10. Some embodiments include other features as described herein such as a hydrogen peroxide canister 140, a hydrogen peroxide valve 142 that feeds hydrogen peroxide into evaporator 32, and a door sensor 150 that determines when chamber 10 is open and/or closed. Some embodiments may also include a mixer 144 in which the sterilant vapor and plasma effluent are mixed before entering chamber 10.

As shown in the example of FIG. 1F, various embodiments may include a sensor 52 in the chamber 10. The sensor 52 may include one or more humidity sensors (sometimes referred to as hygrometers), one or more temperature sensors, and/or one or more pressure sensors. Some embodiments may also include an input pressure control valve 19. In operation, controller 12 may use sensor 52 to determine when the vapor saturation level within chamber 10 is approaching a threshold level likely to produce undesired condensation (e.g., when the vapor level is approaching saturation). For example, when the pressure difference between the chamber 10 and the outside environment reaches a set value (e.g., the threshold level), controller 12 may send an appropriate control signal to increase the power of the exhaust blower 16. This opens the input pressure control valve 19 to allow fresh, dry air (e.g., air dried by dryer 23) into the chamber 10 to reinstate the pressure in the chamber 10.

Alternatively, some embodiments may include a direct valve 19 instead of the input pressure control valve. When the pressure difference between the chamber 10 and the outside environment reaches a set value (e.g., the threshold level), controller 12 may send an appropriate control signal to open the direct valve 19 to allow fresh, dry air (e.g., air dried by dryer 23) into the chamber 10. The exhaust blower 16 removes effluent from the chamber 10 to maintain the prescribed pressure difference between the chamber 10 and ambient environment.

In some other arrangements, controller 12 may activate or increase (or decrease) the speed of exhaust blower 16, may activate or increase (or decrease) the speed of an intake blower such as dryer 23, may activate or increase (or decrease) the heating power of a drying unit attached to the air intake such as dryer 23, may partially or fully open the purging valve 18, may take other suitable steps, or may take any combinations of these and other steps. As additional fresh, dry air enters chamber 10 and is recirculated by blower 14, the vapor saturation will be reduced. In some arrangements, controller 12 may cycle the introduction of fresh air (e.g., stop adding fresh after the vapor levels fall to a second and lower threshold). In other arrangements, controller 12 may modulate the amount of fresh air introduced into the system in real time in order to maintain the vapor levels at a desired level or within a desired range.

Figure 1G:
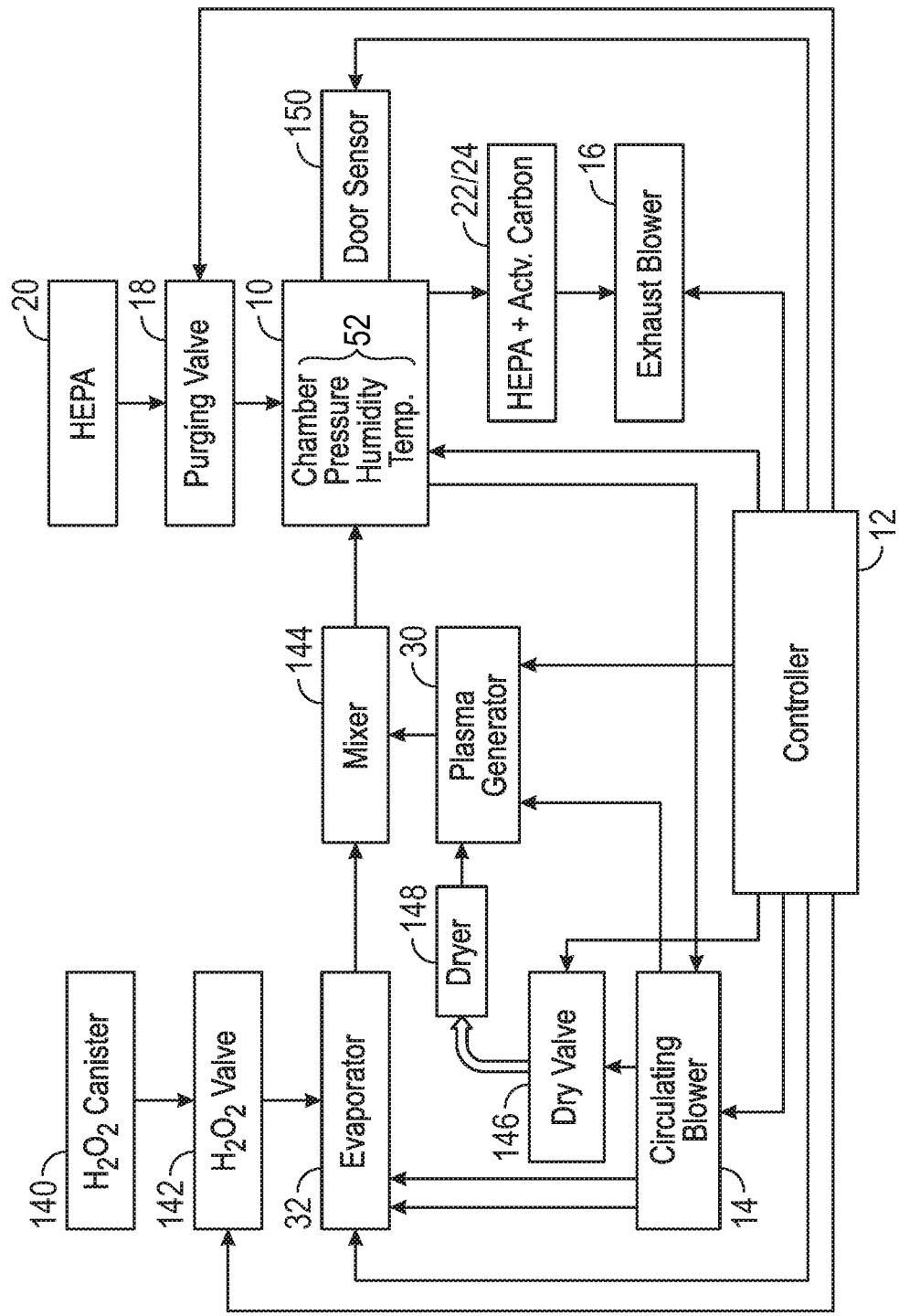
FIG. 1G shows a block diagram of an example embodiment using a dryer in a partial bypass of the effluent supply to the plasma generator to prevent or reduce condensation in the chamber.

FIGS. 1G and 1H illustrate additional example embodiments configured to help maintain desired vapor saturation levels to reduce or avoid undesired condensation. Such embodiments may control the vapor saturation level within the sterilization chamber 10 by incorporating a dryer 148 in the recirculating loop of sterilant, e.g., prior to the plasma generator 30. In such examples, the circulating vapor that exits the plasma generator 30 may be slightly dryer than the vapor exiting the evaporator 32 resulting in a dilution of the vapors in the mixer 144 and lowering the saturation level to below the set level (e.g., the condensation level). Dryer 148 may be any suitable dryer. As examples, dryer 148 may be a desiccant dryer or a dehumidifier utilizing a refrigeration system.

As shown in FIG. 1G, dryer 148 may be disposed in a partial bypass of the intake to the plasma generator 30. In other words, a portion of the recirculating gas may be routed directly from the circulating blower 14 to plasma generator 30, while a second portion may be selectively routed from blower 14, through dryer 148, and then to generator 30. In the manner discussed in connection with FIG. 1F, controller 12 may use a sensor 52 to monitor the humidity levels and other factors (e.g., to determine the risk of unwanted condensation) and may control dryer 148 and bypass valve 146 in response. In particular, when humidity levels reach saturation (or some other desired threshold), controller 12 may open bypass valve 146 enabling the flow of gas through dryer 148 and controller 12 may also activate dryer 148. In some arrangements, controller 12 may maintain a desired humidity level by regulating the amount of bypass through valve 146 (e.g., by varying the amount or time that valve 146 is open), by regulating the drying effect of dyer 148 (e.g., by varying the drying power of dryer 148), by other methods such as those described in FIG. 1F, or by some combination of these and other techniques.

As shown in FIG. 1H, some embodiments may be capable of having dryer 148 in a full bypass arrangement. In particular, the system may include plasma valve 152. In response to the humidity levels in chamber 10 and other suitable criteria, controller 12 may partially or fully shut plasma valve 152 while partially or fully opening dry valve 146. In other words, controller 12 may have some or even all of the gas fed to plasma generator 30 pass first through dryer 148. In the manner noted above, controller 12 may then regulate dryer 148 to maintain desired humidity levels in chamber 10 and thereby avoid undesired condensation. In some embodiments, another option to regulate humidity in the chamber is to introduce controlled amount of fresh air that is drawn to the chamber through a desiccant/dryer. A non-limiting example of this is illustrated in FIG. 1F.

Systems Employing a Residual Coating Device

Figure 1I:
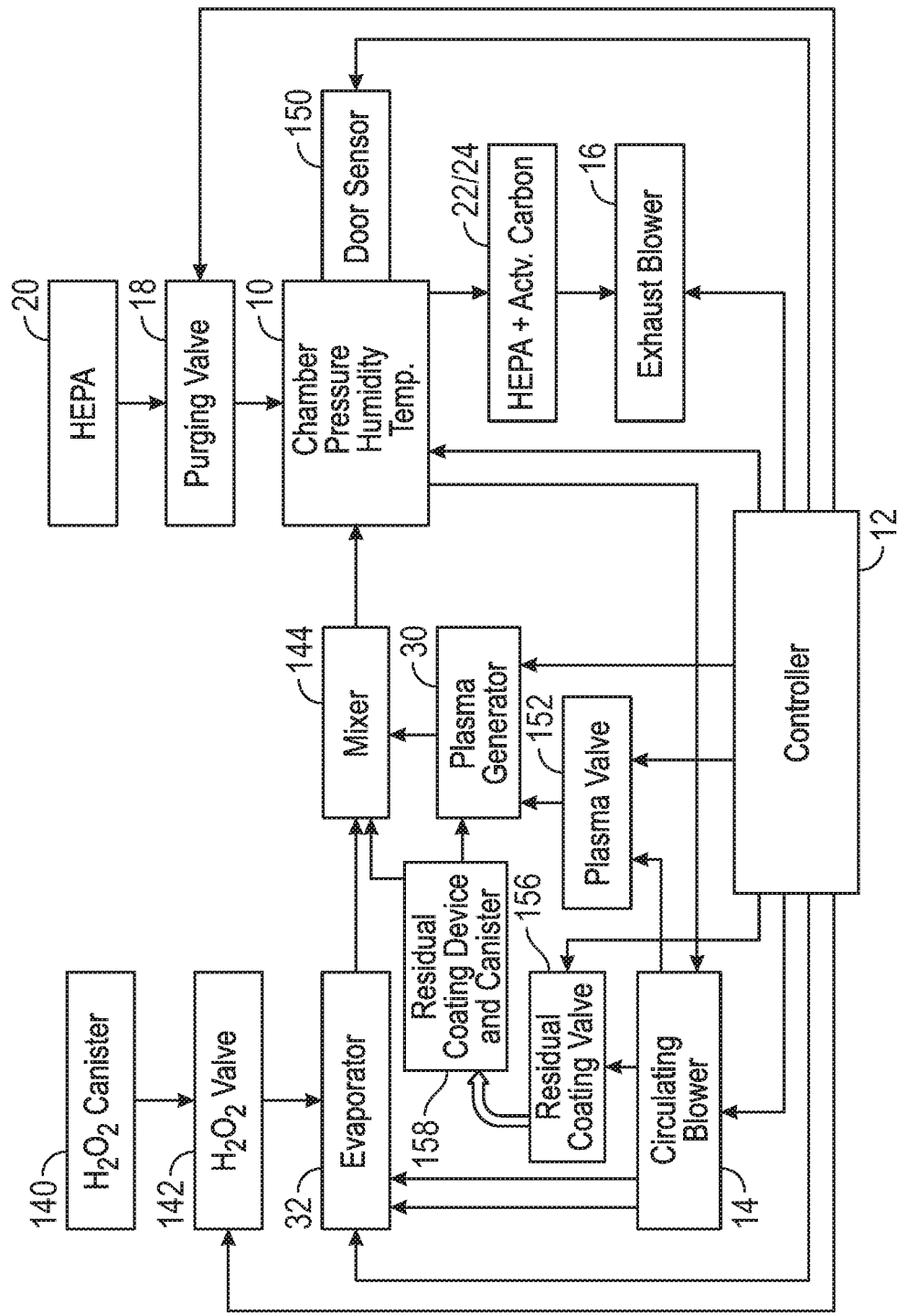
FIG. 1I shows a block diagram of an example embodiment using a residual coating deposition device to deposit a protective coating on items in the chamber.

FIG. 1I illustrates an additional embodiment including a residual coating device 158 that deposits a residual coating on items in chamber 10. In particular, the system may include a residual coating device and canister 158 and an optional residual coating valve 156. The residual coating device 158 may be used to deposit a residual coating on items in chamber 10. As an example, the residual coating device 158 may form a residual coating that is bactericidal, that is sacrificial and removable after potential contamination, etc.

In several embodiments, the residual coating device 158 generates a residual coating liquid or vapor that is conveyed to chamber 10 and deposited on items within chamber 10. The residual coating may be a material that has bactericidal properties such as silver, copper, or a combination of bactericidal materials. The residual coating may be formed from materials that are compatible with the items the coating is deposited on and may also be biocompatible with human subjects, especially in arrangements in which the items the coating is deposited on are items that come into contact with patients or other persons (e.g., surgical tools, endoscopes, dental products, infant care products, etc.). The residual coating material contained in canister 158 may be a gas, a liquid, a solid agent that is converted into a liquid during the coating cycle, or other suitable material. Gas entering the coating device 158 may come into contact with the residual coating material and the device 158 may then produce an effluent including coating material. In at least some arrangements, coating material may be aerosolized, sprayed or painted onto items in chamber 10 by device 158. While shown in FIG. 1I as being in a closed loop path of the type described herein, residual coating device 158 may also be integrated into chamber 10 or disposed in an open and non-recirculating path.

The residual coating device 158 may apply residual coatings to various products in chamber 10 including, but not limited to, cosmetics, eye ware, dental products, home use products for a medical condition (e.g., CPAP masks), infant care products, and pet care products. In general, the present disclosure applies to various industries that include but are not limited to, health care, sports medicine, veterinary care, dental care, agriculture, food processing, research, packaging, pharmaceuticals, packaging of pharmaceuticals, home health, day care, senior care, private and public services, and military/emergency field care. The process of residual coating, along with the other processes described herein, may be utilized in any field in which sanitization, disinfection, and/or sterilization is desirable.

The residual coating may serve to inhibit or prevent future growth of mold, bacteria, or other contaminants on items (which may be items that have been or will be sterilized in chamber 10). The residual coating may also include a sacrificial material that forms a barrier between the items in chamber 10 and external contaminants. The residual coating may be a layer that lasts for multiple sterilization cycles through chamber 10, or may be a layer that lasts as few as a single sterilization cycle, depending at least in part upon the material contained in canister 158 and deposited by device 158 and the sterilization process details (e.g., duration of sterilization, use of evaporated sterilant, use of a plasma generator, etc.).

Residual coating device 158 may include a canister containing coating material (i.e., a consumable canister). While FIG. 1I illustrates the canister and coating device schematically as one unit, the residual coating canister may be provided separately. In at least some embodiments, the residual coating canister, the hydrogen peroxide canister 140, and any other consumable canisters in the system may be provided in a combined canister system (i.e., replaceable as a whole) or may be provided as individually-replaceable canisters.

As shown in FIG. 1I, some embodiments may include a residual coating valve such as valve 156. Controller 12 may selectively open valve 156 during coating operations (e.g., when the system is coating objects in chamber 10 with a residual protective coating).

Systems Employing Plasma or Vaporizer Only and No Pre-Heater

Figure 4:
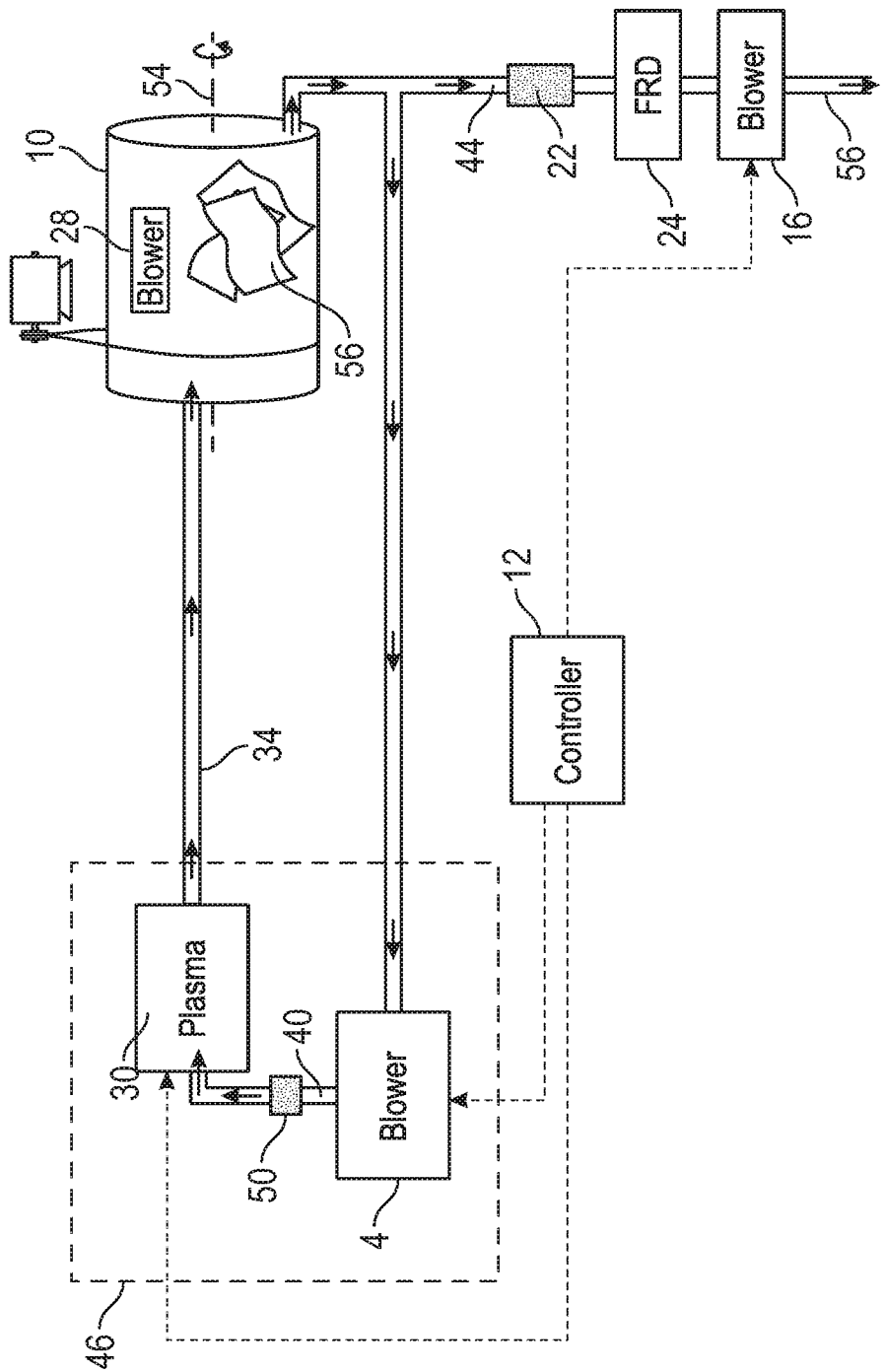
FIG. 4 shows a block diagram of a variation on the embodiment of FIG. 1, omitting the preheater, distributor and vaporizer.
Figure 5:
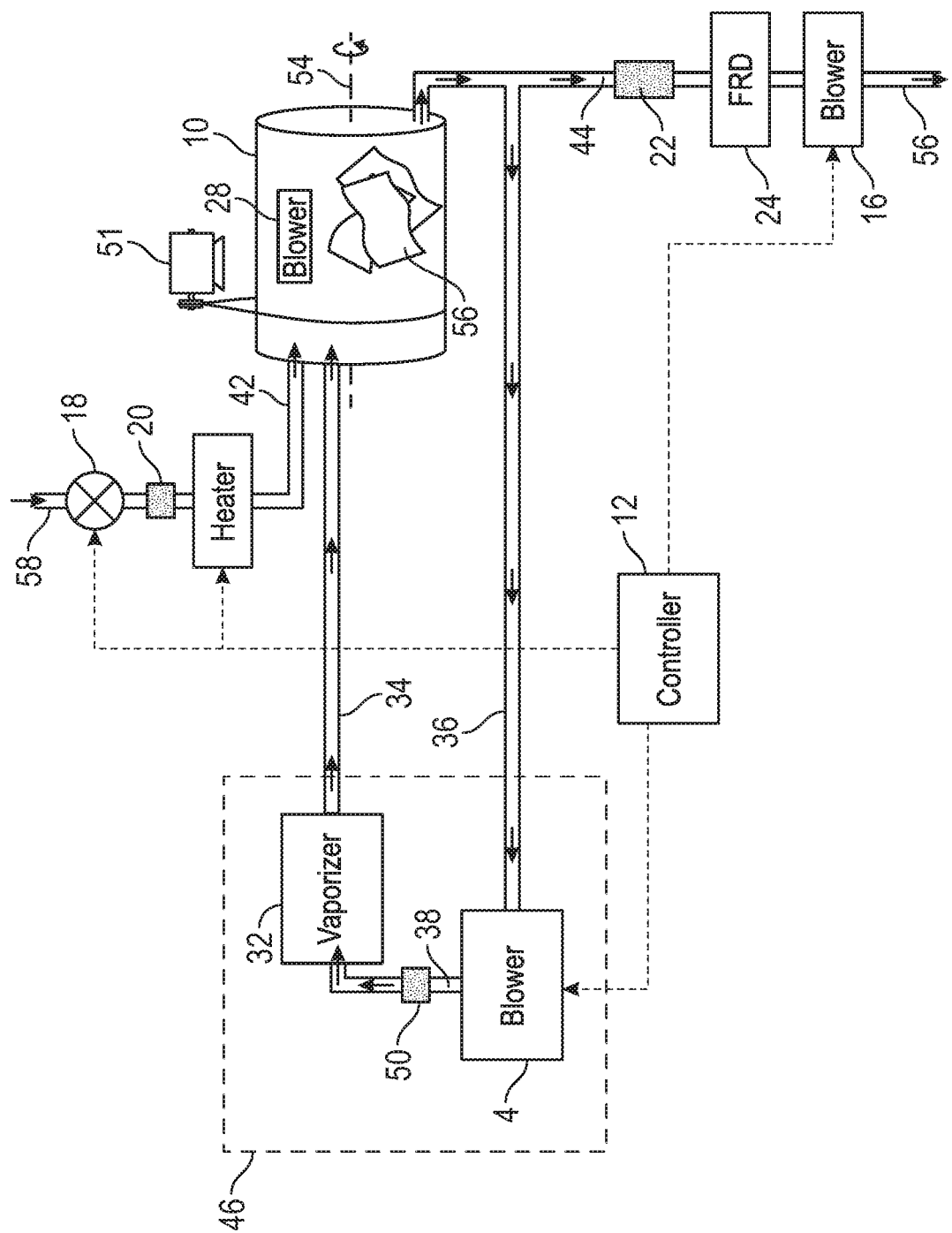
FIG. 5 shows a block diagram of a variation on the embodiment of FIG. 1, omitting the distributor and plasma generator.

As shown in FIGS. 4 and 5, in two additional embodiments, the effluent generator 46 could be made with only one of the sources—either a plasma generator 30 (FIG. 4) or a vaporizer (FIG. 5). In these variations, the blower/distributor 14 from FIG. 1A is replaced by a blower 4, since with only one source there is no need for distribution. However, in several embodiments, a blower distributor may still be used, in order to generate modular systems that can be varied between use of plasma or vapor at one point, and plasma and vapor at another point.

In the embodiment depicted in FIG. 4, the open loop pre-heater system with its heater 26, filter 20 and valve 18 is omitted as well, to illustrate a variation where there is no pre-heat capability. In some embodiments, the system illustrated in FIG. 4 can include a dryer.

In the embodiment depicted in FIG. 5, the system heater 26 can be omitted. In some examples, the system of FIG. 5 can include a dryer.

It will be understood that these variations could also be applied to any of the other embodiments disclosed herein, although this is not explicitly illustrated in a figure.

In either of the variations, and in many of the embodiments, the sterilizer of certain embodiments operates in the closed-loop mode by recirculating the effluent through the chamber and the effluent generator without passing the effluent through a free-radical destroyer in the closed loop. In addition, the variations can control moisture levels as described herein with respect to FIG. 1A. In addition, regarding the embodiment shown in FIG. 5, as described herein with respect to FIG. 1A, evaporation can occur passively (e.g., without heat) by the flow of air through a wet wicking material.

Alternative Embodiment—Another Chamber With Both Plasma and Vapor

Figure 2A:
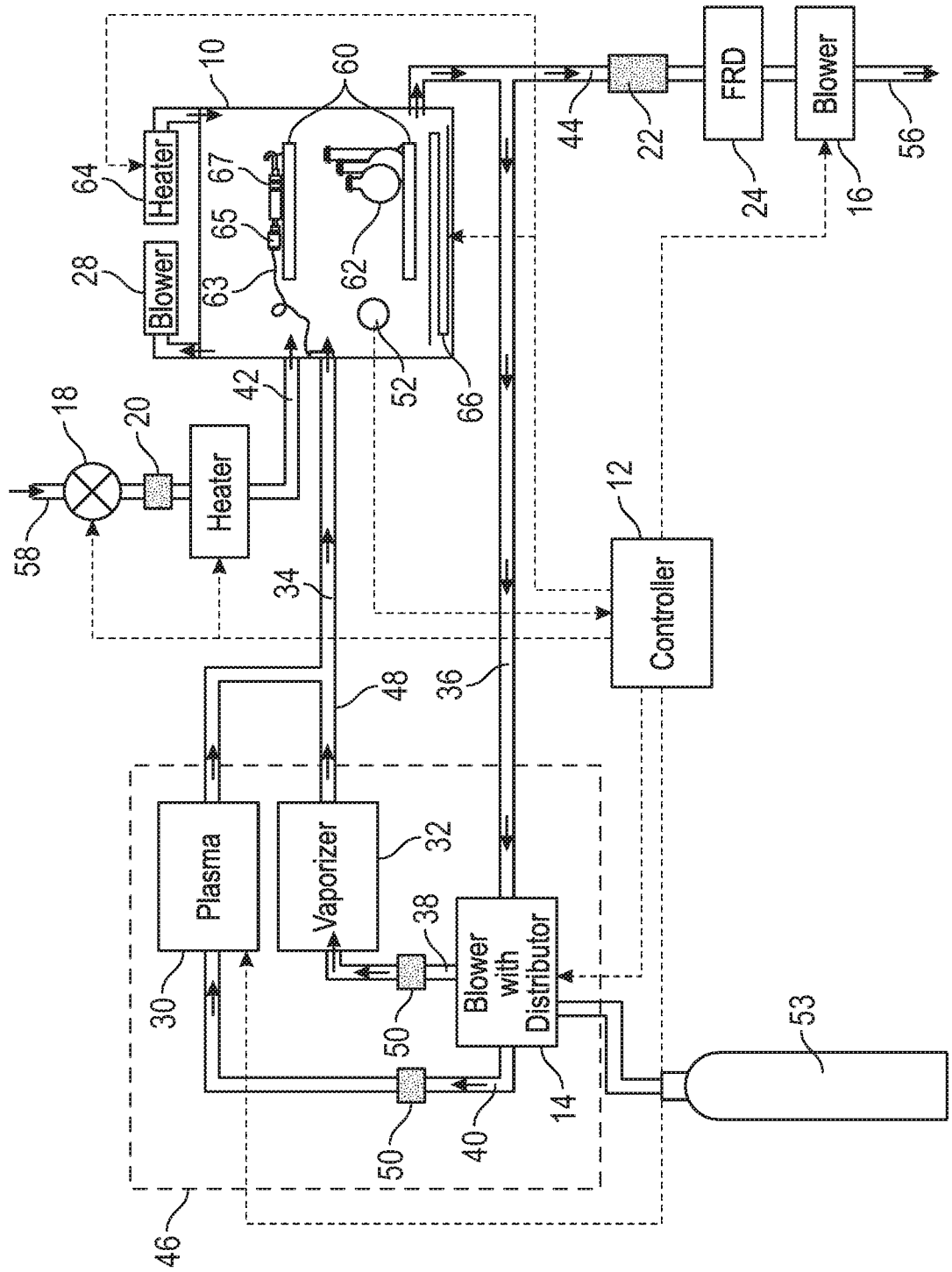
FIG. 2A shows a block diagram of a second embodiment of the disclosure with a stationary chamber with heating.

FIG. 2A illustrates an embodiment appropriate for more rigid items 62, such as laboratory glassware, surgical implements, dental tools, etc. The items 62 may be put on shelves 60, the shelves preferably being made of wire or perforated to allow free circulation of effluent around the items 62.

For the sterilization of instruments with internal conduits or lumens such as endoscopes, catheters, or dental handpieces 67, a portion of the sterilant gas can be forced through the instruments 67, while the outer surfaces of the instruments 67 are sterilized by the effluent in the chamber, as discussed below. To do this, one or more additional conduits can be supplied with sterilant gas from the effluent input conduit 34—this is shown in FIG. 2A as tubing (e.g., a flexible hose 63). The hose 63 is equipped with one or more appropriate adapters and/or connectors 65 to plug into the handpiece 67. The tubing can be made of any material, e.g., a material that is resistant to free radicals and/or reactive species (e.g., of hydrogen peroxide). For example, in some embodiments, the tubing can be made of Tygon®, Teflon®, and or polyvinyl chloride. In some other embodiments, the tubing can be made of any material having an inner coating or sleeve of such resistant material.

Additionally a circulating blower 28 can be used to increase effluent turbulence in the chamber. The blower 28 can be placed in the chamber 10, as shown in FIG. 1A, or outside, connected to the chamber by ducts, as shown in FIG. 2A. As described herein, various embodiments can be used at ambient temperature. Optionally, a heater 64 can be put in the ducts to heat the air circulated by the blower 28, or, alternatively, the chamber may be directly heated by elements 66 either in the chamber or attached to the walls of the chamber. A heater can be used in any of the embodiments described herein although not shown in the figures.

In the embodiment of FIG. 2A, a sensor (e.g., a temperature sensor 52) is provided in the chamber 10. The controller 12 can then maintain a selected temperature in the chamber 10 by reading the temperature through sensor 52 and controlling chamber heaters 64 and/or 66 as needed. Other sensors (e.g., pressure, humidity, etc.) can also be used.

Optionally, a carrier gas 53, such as air, oxygen, nitrogen, carbon dioxide, helium, argon, or a combination of carrier gases, can be introduced into the effluent generator 46 to be mixed with the effluent in the closed system. This can be done as an additional input to blower/distributor 14, as shown in FIG. 2A.

Figure 2B:
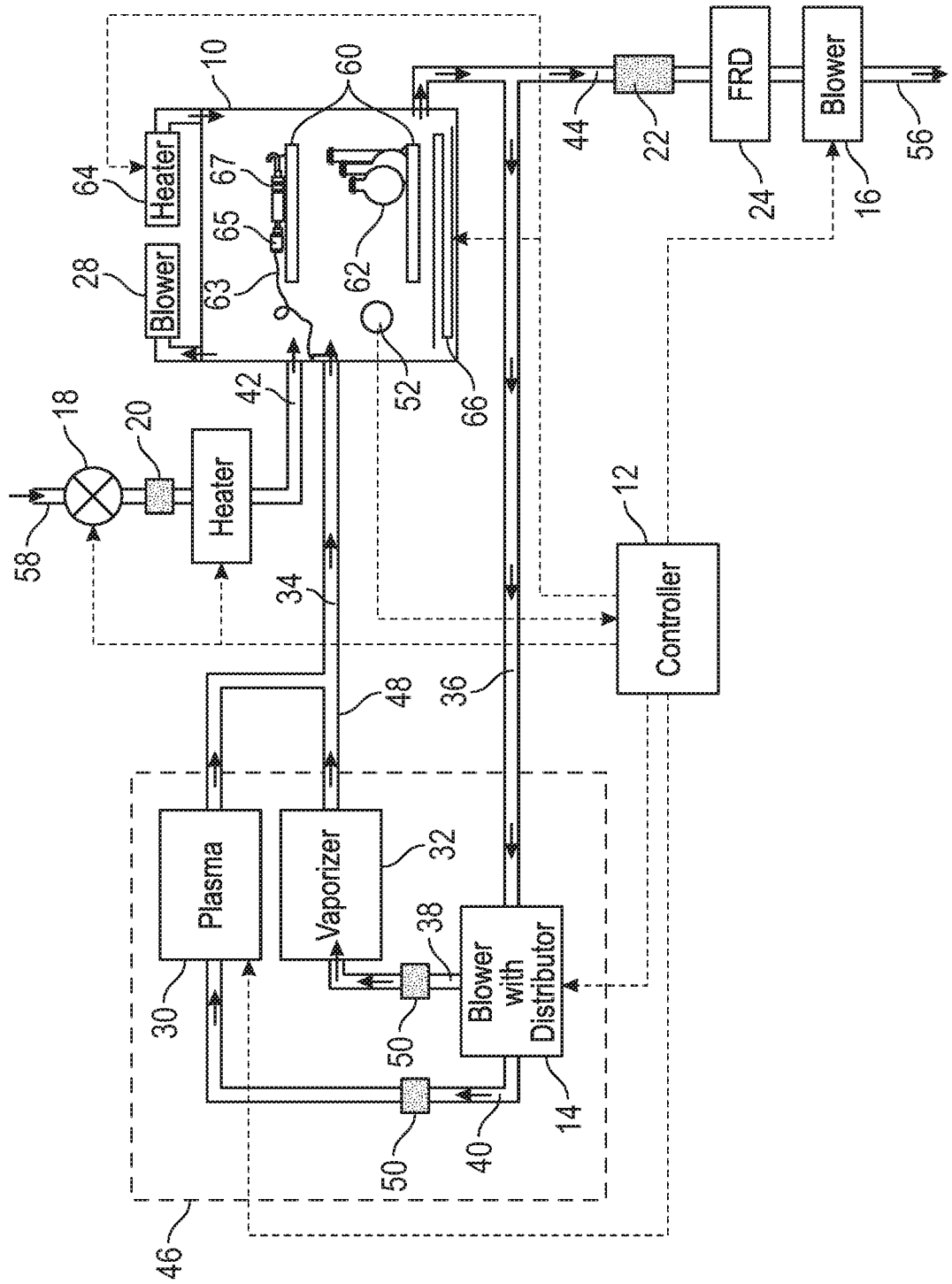
FIG. 2B shows another embodiment of the block diagram of FIG. 2A without a carrier gas 53.

FIG. 2B illustrates another embodiment of a sterilization and disinfection system for use on rigid items such as laboratory glassware, surgical implements, dental tools, etc. In the embodiment illustrate in FIG. 2B, the system does not include a carrier gas 53. In some embodiments, the system also does not include a heater. In some examples, the system can include an independent blower for the plasma and/or an independent blower for the evaporator. In some embodiments, the system can include a dryer.

Additional Systems and Devices Using Centrifugal Multiple-Outlet Blower

Figure 6:
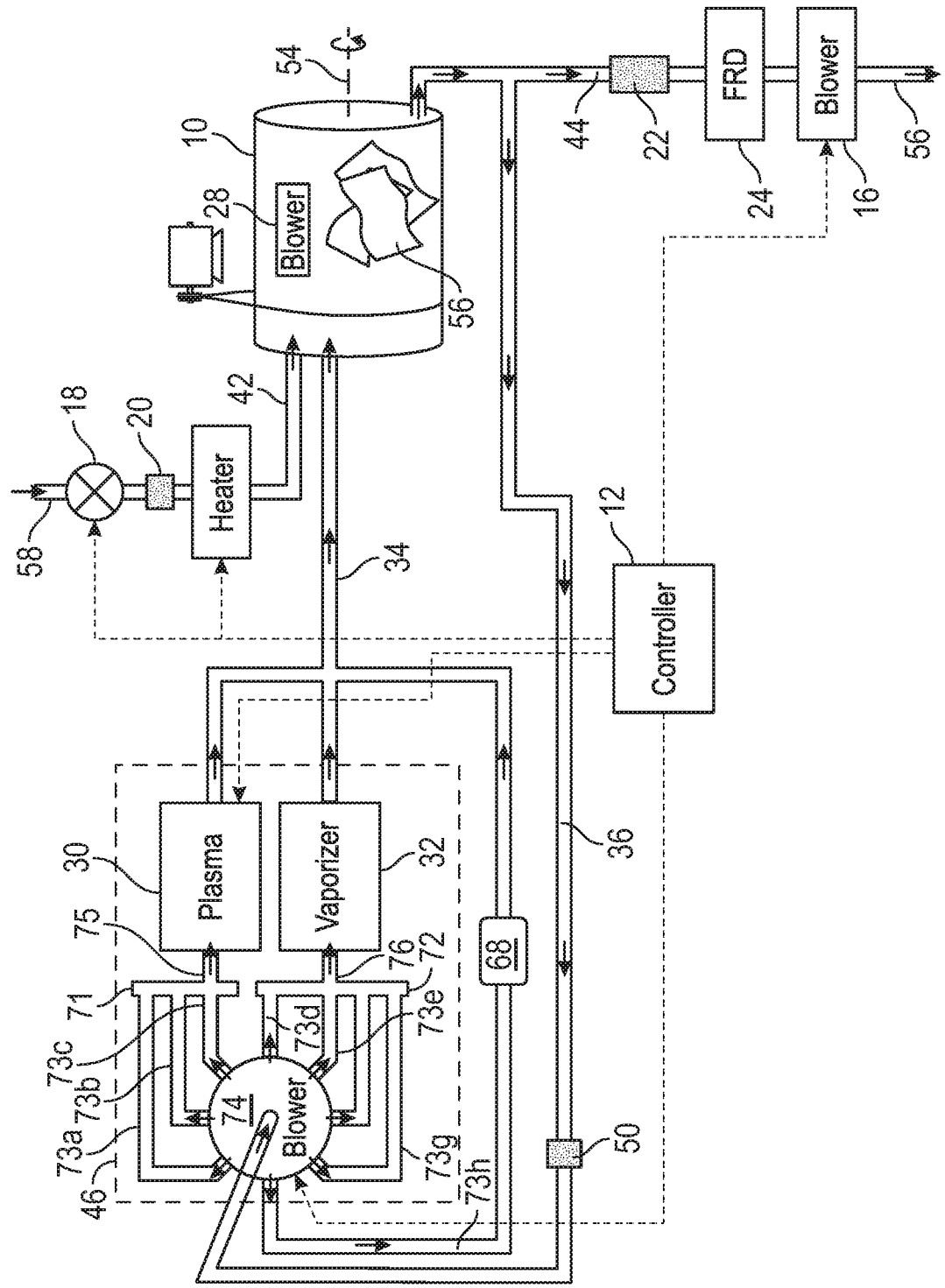
FIG. 6 shows a block diagram of a third embodiment of the disclosure, using a centrifugal multiple-outlet blower in place of the blower-distributor and adding a bypass heater.
Figure 7:
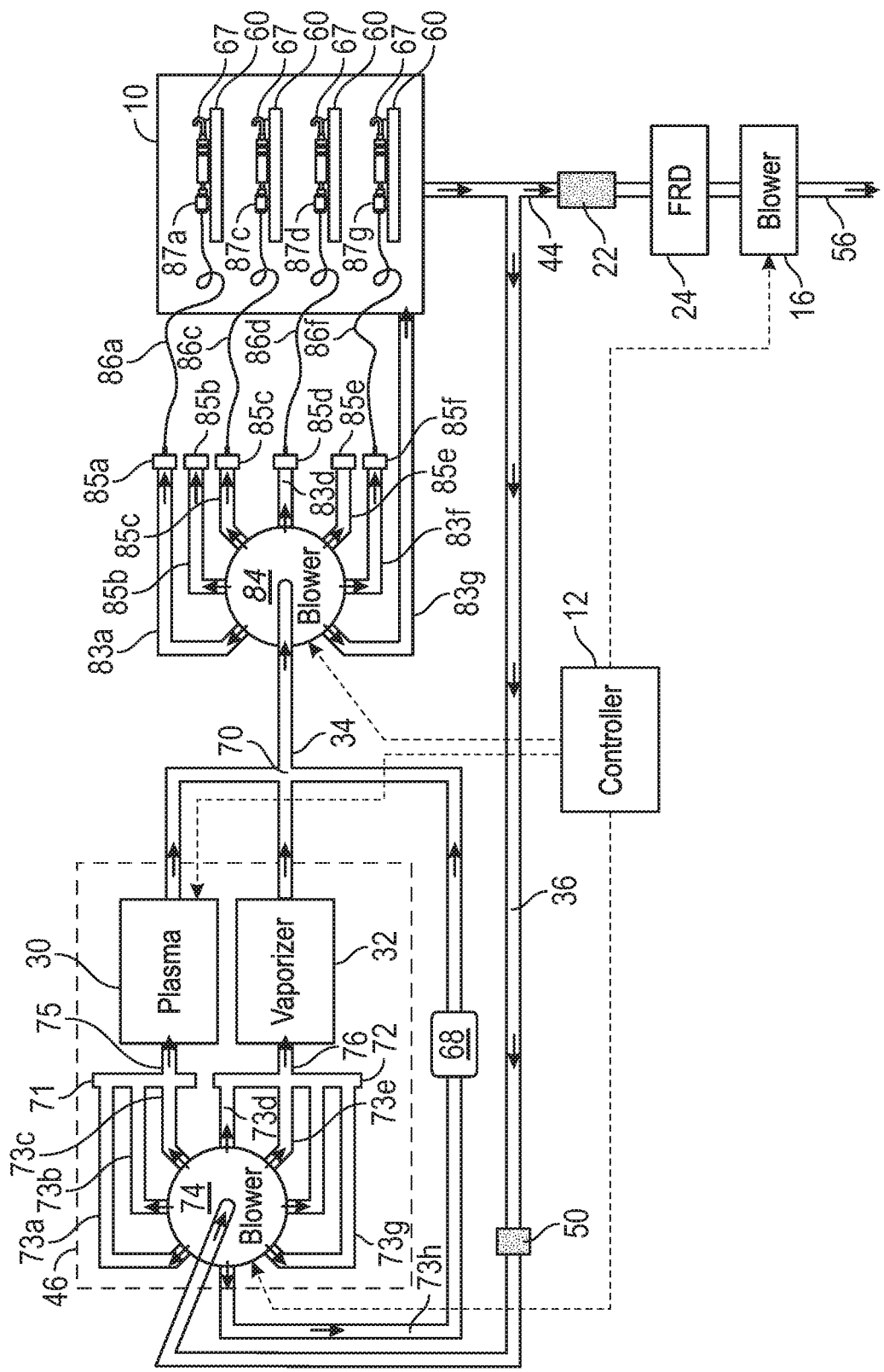
FIG. 7 shows a variation on the embodiment of FIG. 6, using two centrifugal multiple-outlet blowers to provide multiple outlets for recirculation.
Figure 8:
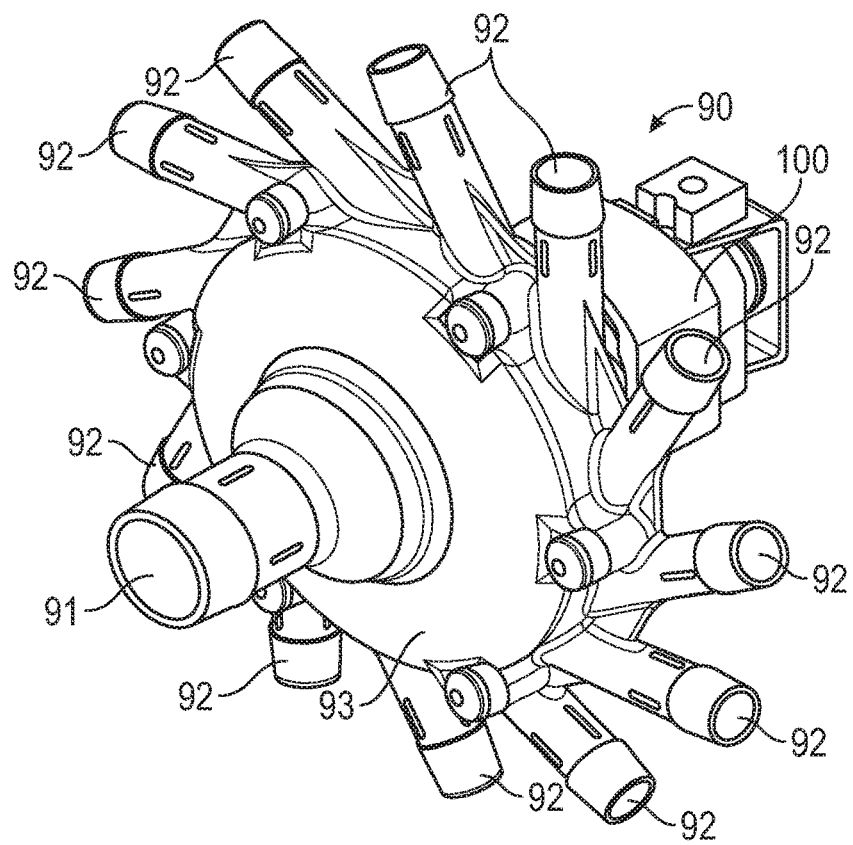
FIG. 8 shows a centrifugal multiple outlet blower as used in the embodiment of FIGS. 6 and 7.
Figure 9:
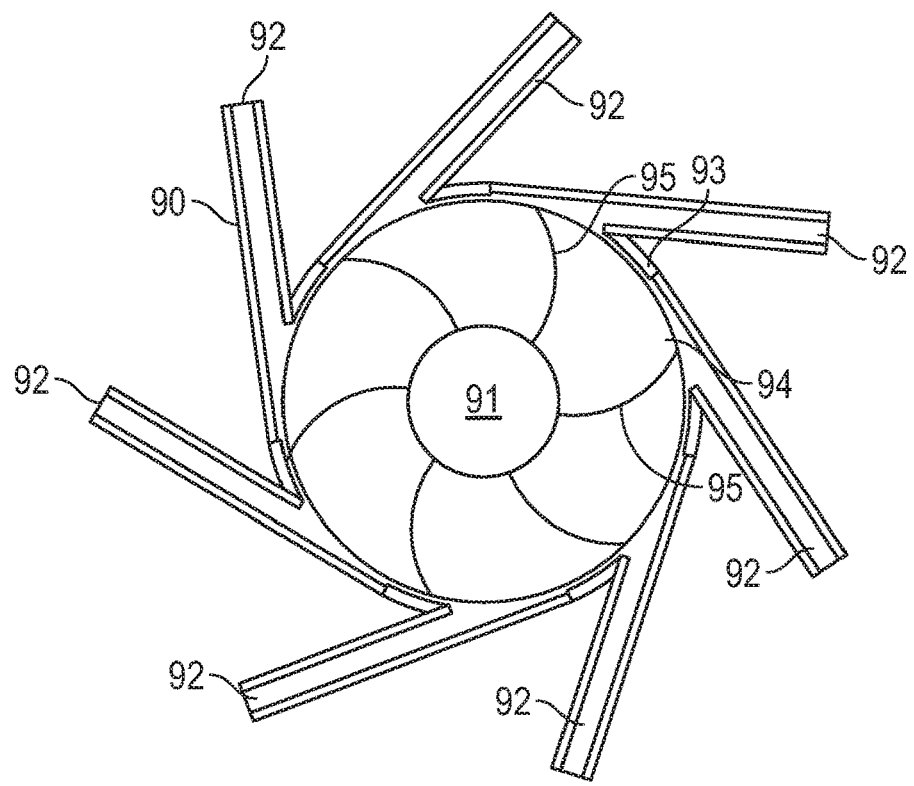
FIG. 9 shows a cut-away diagram of the blower of FIG. 8.

FIGS. 8 and 9 show a multiple-output centrifugal blower which is used with the embodiments as shown in FIGS. 6 and 7. The centrifugal blower used in this embodiment is a novel development on the centrifugal blowers and "squirrel-cage" type blowers.

As can be seen in FIGS. 8 and 9, the blower 90 has a central input 91 for drawing gas to be distributed by the blower 90 into the blower housing 93. A plurality of tangential outputs 92 are provided, each output providing a stream of gas in approximately equal amounts. The number of outputs 92 can vary within the teachings of the disclosure, depending on the requirements of the design. As examples, twelve outputs are shown in FIG. 8 and seven in FIG. 9, while blower 74 in FIGS. 6 and 7 has eight outputs and blower 84 has seven outputs. Other embodiments can employ alternative numbers of inputs and/or outputs.

A central impeller 94 inside the housing 93 is rotated by a conventional motor 100. The motor can be electric, or powered by hydraulic fluid or compressed air, or any other motive force known to the art. The impeller 94 is here shown as centrifugal impeller" type, which has a plurality of curved blades 95. As the impeller 94 is rotated at high speed, air from input 91 is flung outward by centrifugal force and the action of the blades 95, and is expelled through tangential outputs 92. In some embodiments, the impeller 94 may be designed with plastic, but other materials may be used, e.g., non-reactive metals, etc.

FIG. 6 shows how a multiple-output blower can be used within the teachings of the disclosure as the blower-distributor 14 of FIG. 1A.

In this embodiment, the effluent generator 46 uses multiple-output blower 74 to apportion the effluent returning from chamber 10 through conduit 36 between the plasma generator 30, the vaporizer 32, and an optional bypass heater 68. The outputs of the plasma generator 30, vaporizer 32 and bypass heater 68 are combined together at a junction 70, the combined effluent streams flowing into the chamber 10 through conduit 34 as in previous figures.

The outputs 73a-73h of the blower 74 each carry an output flow which is a fraction of the total output flow of the blower approximately equal to the total flow divided by the number of outlets. Therefore a desired portion of the effluent can be chosen by combining an appropriate choice of the number of outputs, with the output of the manifold being approximately equal to the number of blower outputs being combined divided by the total number of outlets available. Multiple outputs can be combined using manifolds, such as manifold 71 to which outputs 73a-73c are input, or manifold 72 which combines the flow from outputs 73d-73g. Output 73h is connected directly to the bypass heater 68.

In the example of FIG. 6, blower 74 has eight outputs 73a-73h, so each output carries approximately one eighth or 12.5% of the total output of the blower. Therefore, in the arrangement of this example, manifold 71 receives three eighths (37.5%) of the flow, and the output of the manifold feeds this flow to plasma generator 30 through conduit 75. Similarly, manifold 72 receives four eighths (or one half) (50%) of the flow through conduit 76, the output of which is connected to vaporizer 32. Bypass heater 68 receives one eighth (12.5%) of the flow directly from a single output 73h, which could be thought of as a manifold with a single input. Other proportions between the plasma generator 30, vaporizer 32, and/or bypass heater 68 are possible.

In some embodiments, the system of FIG. 6 can be configured to omit the heater. In some examples, the system of FIG. 6 can be configured to omit the output blower. In some embodiments, the system of FIG. 6 can include an independent blower associated with the plasma generator 30 and/or an independent blower associated with the vaporizer 32.

FIG. 7 shows the third embodiment used with a fixed chamber for sterilizing items such as endoscopes, catheters, or dental handpieces 67 (or other medical tools having lumens or other interior conduits or spaces which should be sterilized), as in the second embodiment of FIG. 2A. Shelves 60 can be provided to support the tools 67, as needed.

In FIG. 7, rather than feeding the chamber 10 directly, the effluent conduit 34 is used to feed a second multiple-outlet centrifugal blower 84. In this variation, the multiple outputs 83a-83g of blower 84 are used individually to feed multiple users of the effluent, rather than being combined to apportion flow as with outputs 73a-73h of blower 74.

The outputs 83a-83f of blower 84 are fitted with shut-off valves or quick-disconnect fittings 85a-85f, of any kind known to the art. Flexible hoses 86a-86f are plugged into fittings 85a-85f to convey effluent from the fittings 85a-85f to connectors or adaptors 87a-87f, into which the handpieces 67 can be plugged to sterilize the insides of the handpieces. Output 83g of blower 84 is routed directly to chamber 10, to supply effluent to the chamber for sterilizing the outside of the handpieces 67, as well as any other contents of the chamber.

In other embodiments, the outputs 83a-83f of blower 84 can be fed directly into the chamber 10 with the hoses 86a-86f connected inside the chamber 10. In some such instances, the chamber 10 may be separated into multiple chambers such that it may be possible to adjust and/or remove one item from within the chamber 10 without affecting another item within the chamber 10. As another example, some embodiments may include a separate exiting rigid or flexible chamber such that one of the items can be conveyed to the exiting chamber prior to removal without affecting another item within the chamber 10.

Some embodiments may incorporate quality control and/or regulatory compliance indicators. For example, some embodiments may provide an indicator (e.g., disposable, semi-disposable, or non-disposable) on the shelf 60 for each item (e.g., instrument 67). As another example, some embodiments may provide a removable holder for each separate item with the indicator place within or on the holder. The holder can be placed within the chamber 10 and connected accordingly. In some such embodiments, each item can have its own indicator and traveling container. Other examples are possible.

In some embodiments, the system of FIG. 7 can be configured to omit the blower 74. In some examples, the system of FIG. 7 can instead include an independent blower associated with the plasma generator 30 and/or an independent blower associated with the vaporizer 32.

Systems and Devices Employing a Wound Chamber

Figure 10:
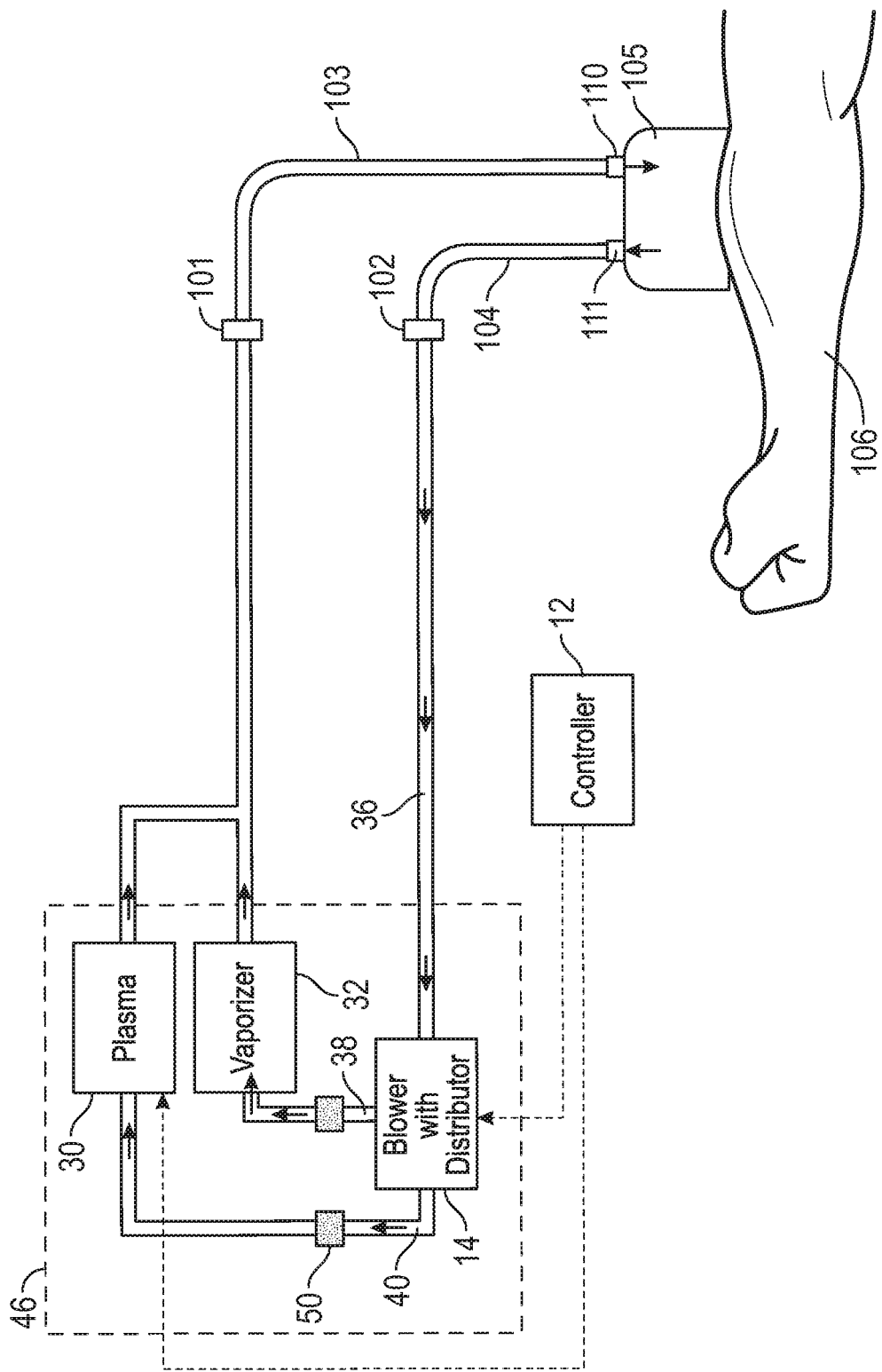
FIG. 10 shows a fourth embodiment of the disclosure, showing use with a wound chamber.
Figure 11:
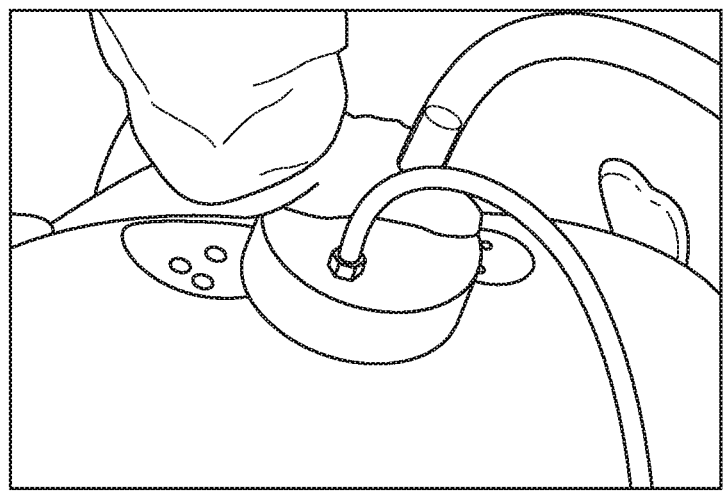
FIG. 11 shows a picture of a wound chamber in use.
Figure 12:
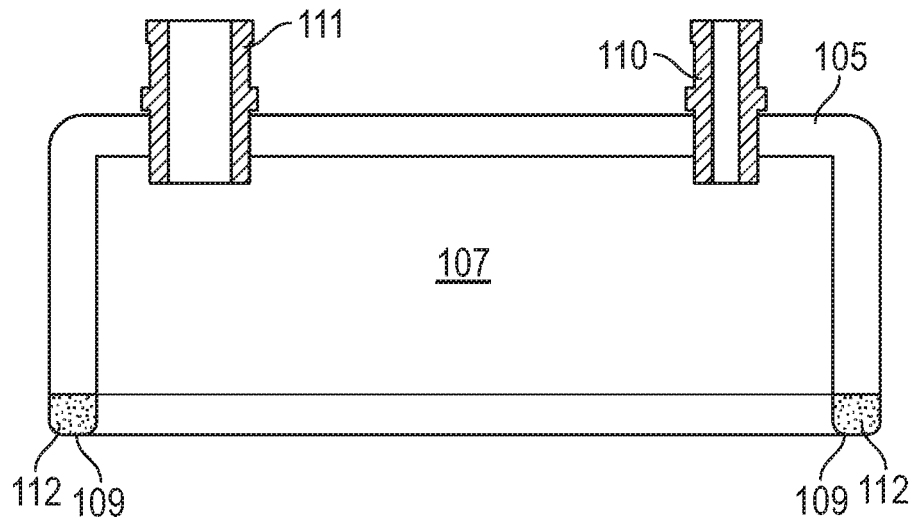
FIG. 12 shows a cut-through side view of a wound chamber.

FIGS. 10-12 show how certain embodiments can be used with an open-sided portable wound chamber 105 to apply effluent to an open wound on a patient. Such application has been shown in experiments to promote healing.

FIG. 10 shows how the system of some embodiments is used in this application. Effluent generator 46 recirculates effluent from conduit 36 to conduit 34, as described in the preceding embodiments. It will be understood that while the effluent generator 46 is shown in FIG. 10 in the version used in FIGS. 1A and 2, the effluent generator 46 could also be any of the other versions described herein or in application Ser. No. 12/510,341 (now U.S. Pat. No. 8,221,679), incorporated herein by reference. If desired, plasma generator 30 or vaporizer 32 may be omitted. In various arrangements, medication or other treatment may be added to the circulating sterilant.

In some embodiments, the system of FIG. 10 can be configured to omit the blower/distributor 14. In some examples, the system of FIG. 10 can include an independent blower associated with the plasma generator 30 and/or an independent blower associated with the vaporizer 32.

The wound chamber 105 is shown in FIG. 12 in a sectional view. The chamber 105 has a body 107 with an open bottom 108. The edges 109 around the open bottom 108 can be simply rounded off, or could be provided with flexible or resilient sealing material 112 to facilitate a tight seal against a surface. Connectors 110 and 111 provide mechanisms for connecting input and output hoses, respectively, to route the flow of effluent to and from the chamber. The connectors could be the same size, or, as shown in FIG. 12, the input connector 110 could be of smaller diameter than the output connector 111.

In this embodiment, the output conduit 34 of the effluent generator feeds a wound chamber 105 through a flexible hose 103 which connects to appropriate connectors 101 and 110 at each end. Return effluent from the wound chamber 105 passes through flexible hose 104 with connectors 102 and 111 into return conduit 36, to be recirculated back through the effluent generator 46. In use, the chamber 105 is placed upon the body of the patient (here shown as an arm 106), over the wound to be treated. The chamber 105 is pressed firmly against the body 106, and the sterilizer is operated for a selected period of time.

Figure 14:
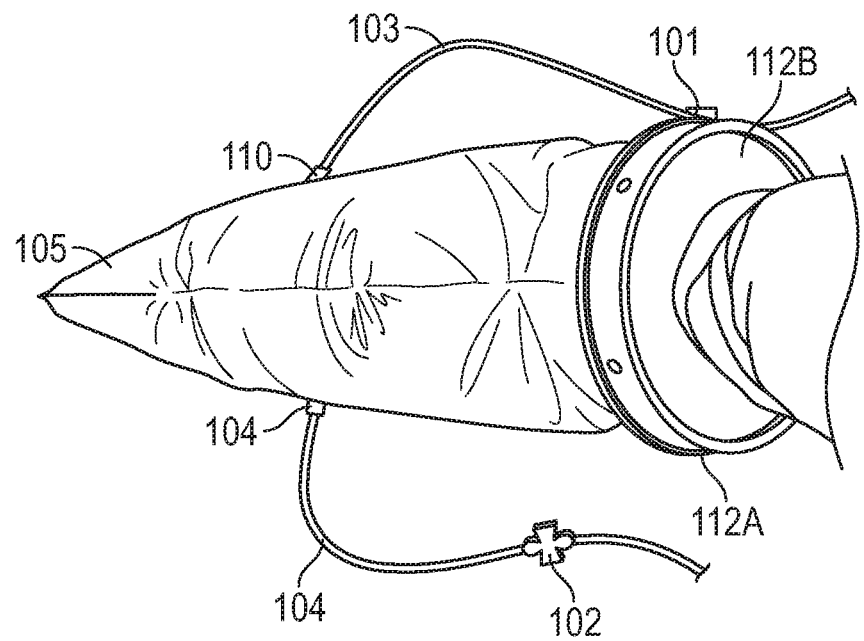
FIG. 14 shows a picture of an example inflatable wound chamber in use.
Figure 15:
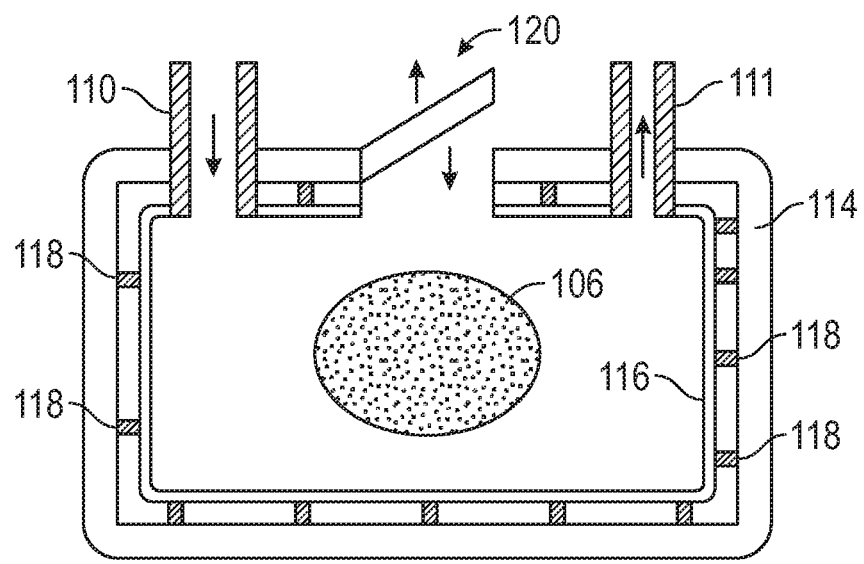
FIG. 15 shows a cross-sectional view of an example wound chamber that includes structures configured to maintain separation between the wound chamber and the patient.

As shown in FIGS. 14 and 15, the wound chamber 105 may be designed to maintain separation from the patient's wound(s). In a first arrangement, the wound chamber 105 may be filled with circulating sterilant at a positive pressure, thereby inflating the wound chamber 105. Wound chamber 105 may include structures as collar 112A and cuff 112B that enable chamber 105 to be placed over a limb and sealed to the limb. In general, any suitable mechanisms for sealing the wound chamber 105 to a patient may be used. Examples of such suitable mechanisms include flexible cuffs, tape, straps, zippers, snaps, clips, buttons, and other mechanical implementations. Similar mechanisms may also be used to provide access to the patient's wound during, before, or after treatment, as shown by access port 120 in FIG. 15. Access ports such as access port 120 may be provided for the placement of a sensor inside of chamber 105 (e.g., to provide sealed pathways for cabling to and from such sensor) and to provide medical providers with access to the patient's wounds for any purpose.

The wound chamber, sealing mechanism, and associated hoses, couplings, and accessories may be formed from any suitable materials. In general, materials that come into contact with the sterilant should be safe to contain the sterilant and materials that come into contact with patients should be biocompatible. While FIG. 14 illustrates wound chamber 105 sized for a patient's arm, wound chamber 105 may be provided in alternative forms sized for patients of different sizes and ages, a patient's leg, a chest, or even an entire body (with an opening enabling the patient to breathe).

As shown in FIG. 14, wound chamber 105 may include structures that provide rigidity to the wound chamber. Such structures may, in some arrangements, enable wound chamber to be operated at a slightly negative pressure, while still maintaining separation from the patient's wound and enabling the free circulation of sterilant. Operating chamber 105 at a slightly negative pressure has an added benefit of reducing the likelihood of the circulating sterilant escaping into the surrounding atmosphere, which may, as an example, increase the safety of chamber 105 in situations in which the sterilant is hazardous, perhaps when inhaled. These structures may include, as a first example, ribs 118 which may be rigid or inflatable. As a second example, these structures may include a two-chamber design including outer wall 114 and inner wall 116 where the space between the walls may be pressurized to form a rigid shell. Even when wound chamber 105 is operated at a positive pressure, wound chamber 105 may include any of the features described herein that provide rigidity.

Figure 21:
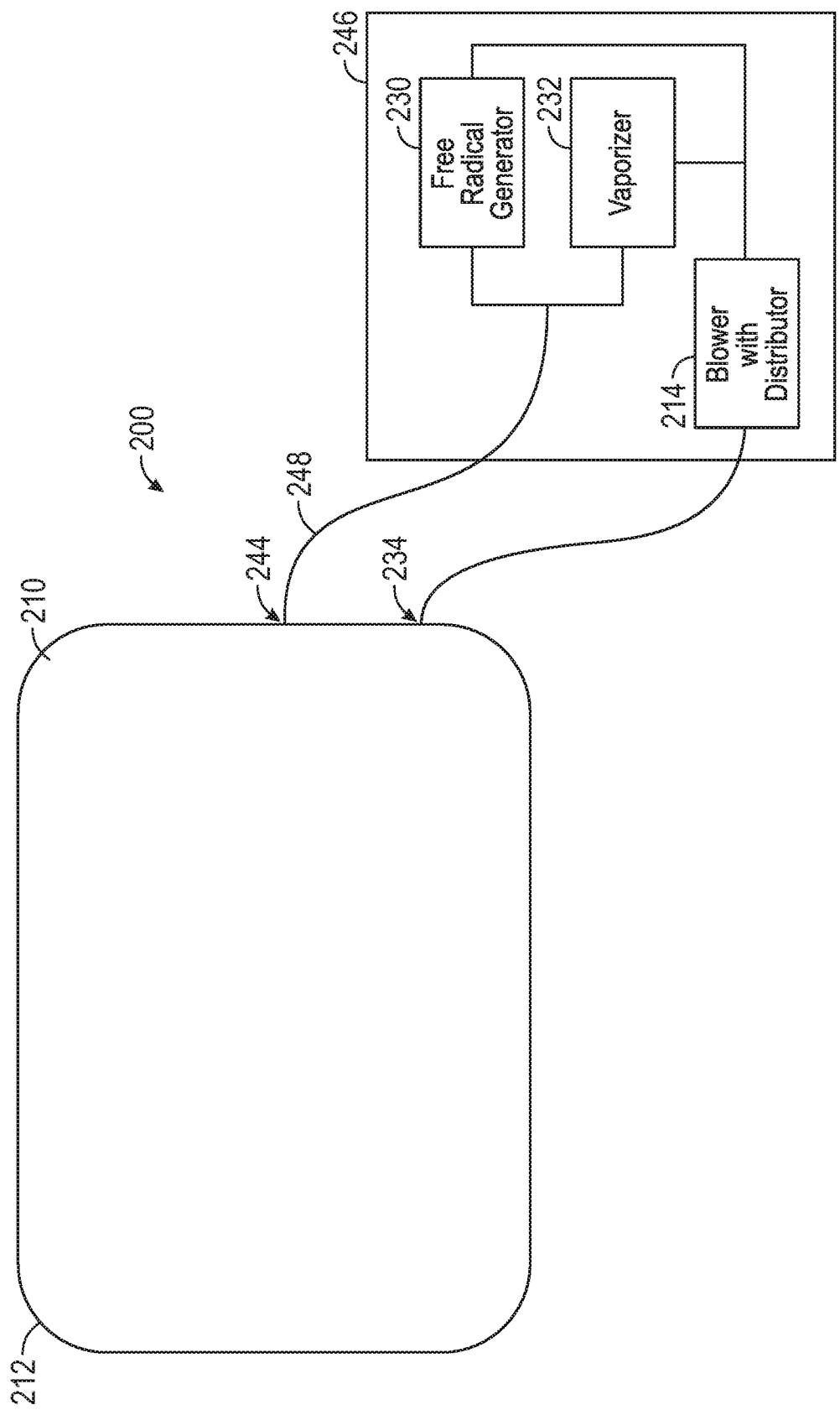
FIG. 21 shows another embodiment of the system for sterilization and disinfection.

FIG. 21 illustrates another embodiment of the system for sterilization and disinfection 200. As with the examples provided above, the system for sterilization and disinfection 200 can include a chamber 210 that is fluidly connected to an effluent generator 246. In some embodiments, the chamber 210 can have an inlet 244 and an outlet 234 that are connected to the effluent generator 246 through an inlet conduit 248 and an outlet conduit 236 respectively to form a closed system. As discussed above, the effluent generator 246 can include a free radical generator 230, a vaporizer 232, and a blower with distributor 214.

Figure 22B:
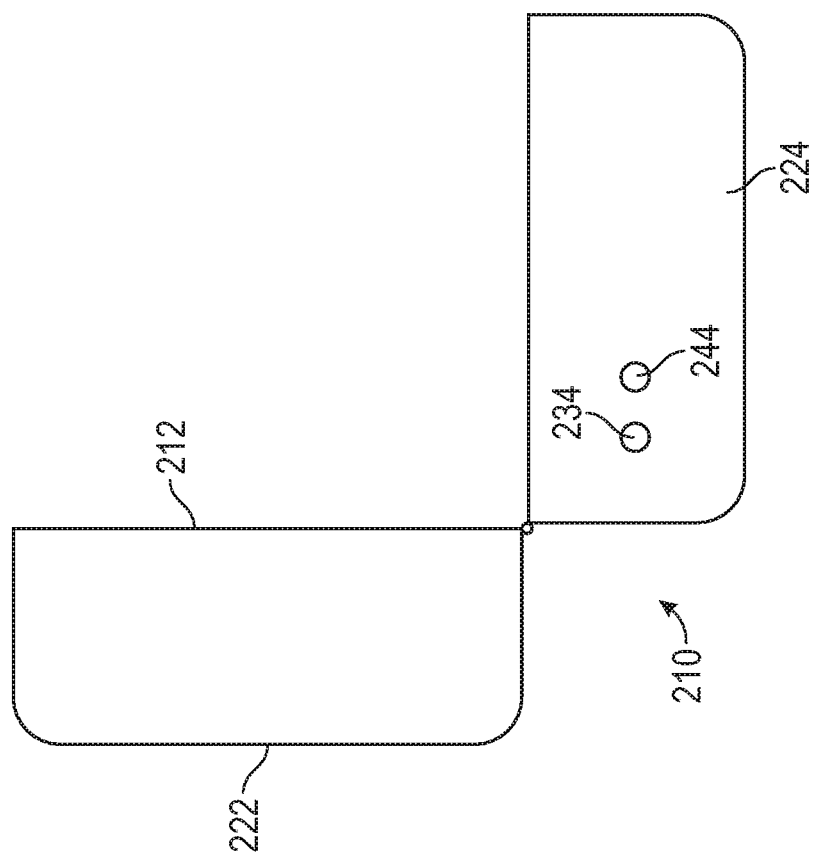
FIGS. 22A-22B shows a plurality of views of an embodiment of a chamber that can be used in a system for sterilization and disinfection.
Figure 22A:
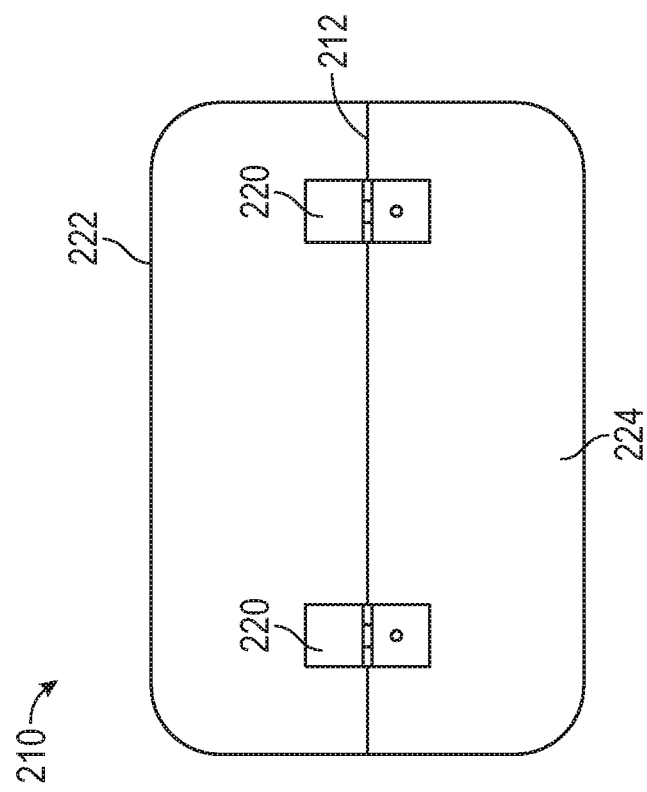

The chamber 210 can be configured to receive sterilant and the item to be sterilized. As illustrated in FIGS. 22A-B, the chamber 210 can be configured to receive and store an item before and after sterilization. In some examples, the chamber 210 can include a top portion 222 and a bottom portion 224 that can be opened and closed to secure an item to be sterilized within. In some embodiments, the top portion 222 and the bottom portion 224 are configured to form a seal 212 when closed. As well, the chamber 210 can include engagement structures 220 that are configured to secure the top portion 222 with the bottom portion 224 such that the interior of the chamber 210 remains sterilized and disinfected. In some embodiments, the engagement structure 220 can be a clasp, a lock, or any other structure that can secure the two halves of the chamber 210. In some examples, the inlet 244 and the outlet 234 are located on the exterior of the chamber 210 to allow sterilant to be received and circulated into and out of the chamber 210.

The chamber 210 may be made of any type of material, such as a non-conductive material to prevent interference with certain reactive species of the sterilant. For example, the chamber 210 can be made of glass, plastic (e.g., polytetrafluoroethylene), or combinations thereof (e.g., partially glass and partially plastic). In some embodiments, the chamber 210 may be transparent or partially transparent such that the contents within the chamber 210 may be viewable during the sterilization process.

As illustrated, the size and shape of the chamber 210 are not particularly limited, but can be tailored to the application of use. For example, in some instances, the chamber 210 may be relatively small, light-weight, and portable. In other embodiments, the chamber may be dimensioned to accommodate larger items, such as control modules for IV stands, power units for various equipment in surgical suites, end piece apparatuses used in an operating room (such as eyepieces for surgical scopes).

Figure 23A:
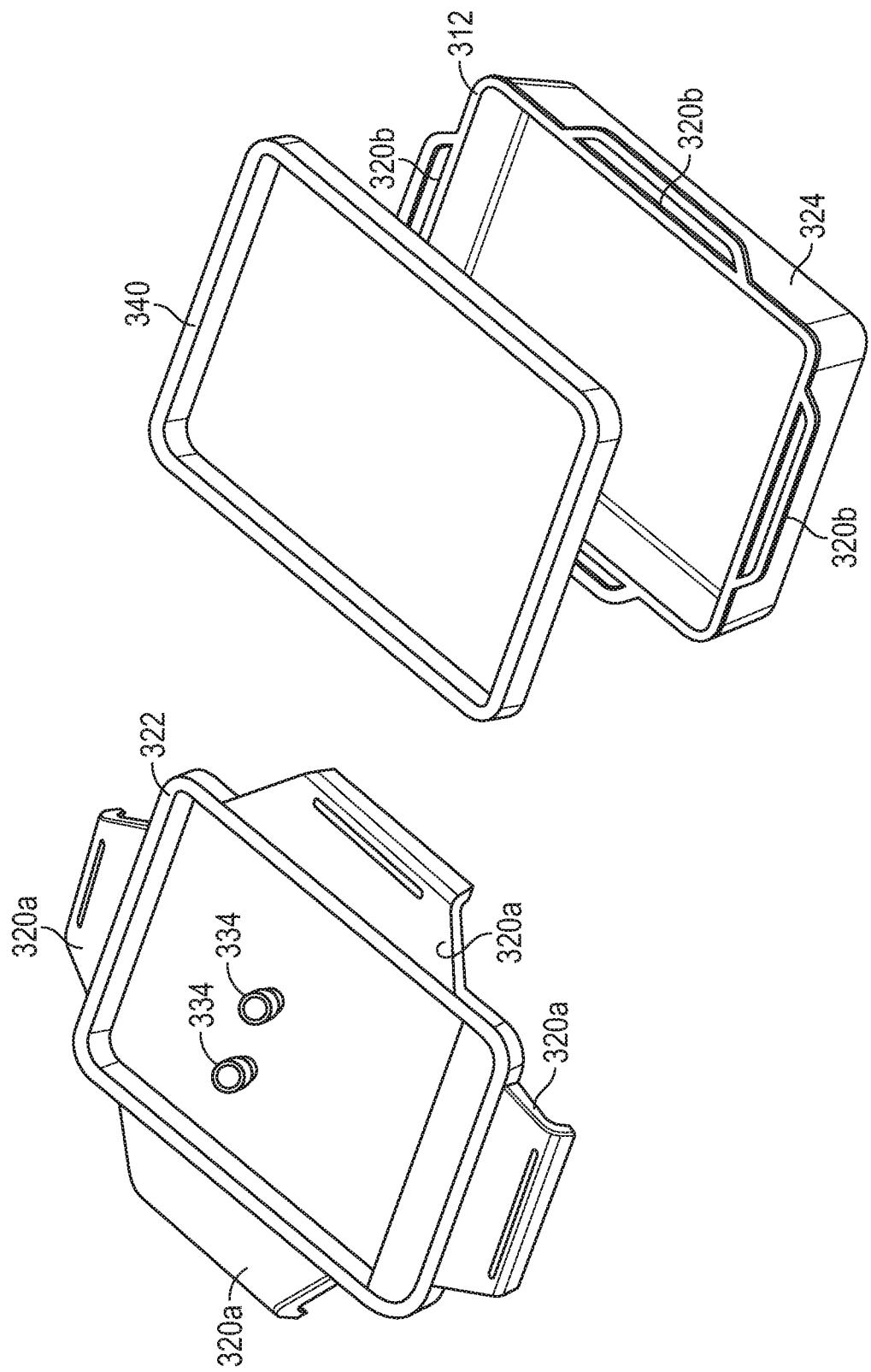
FIG. 23A shows an exploded view of an embodiment of a chamber including an insert that can be used in a system for sterilization and/or disinfection.
Figure 23B:
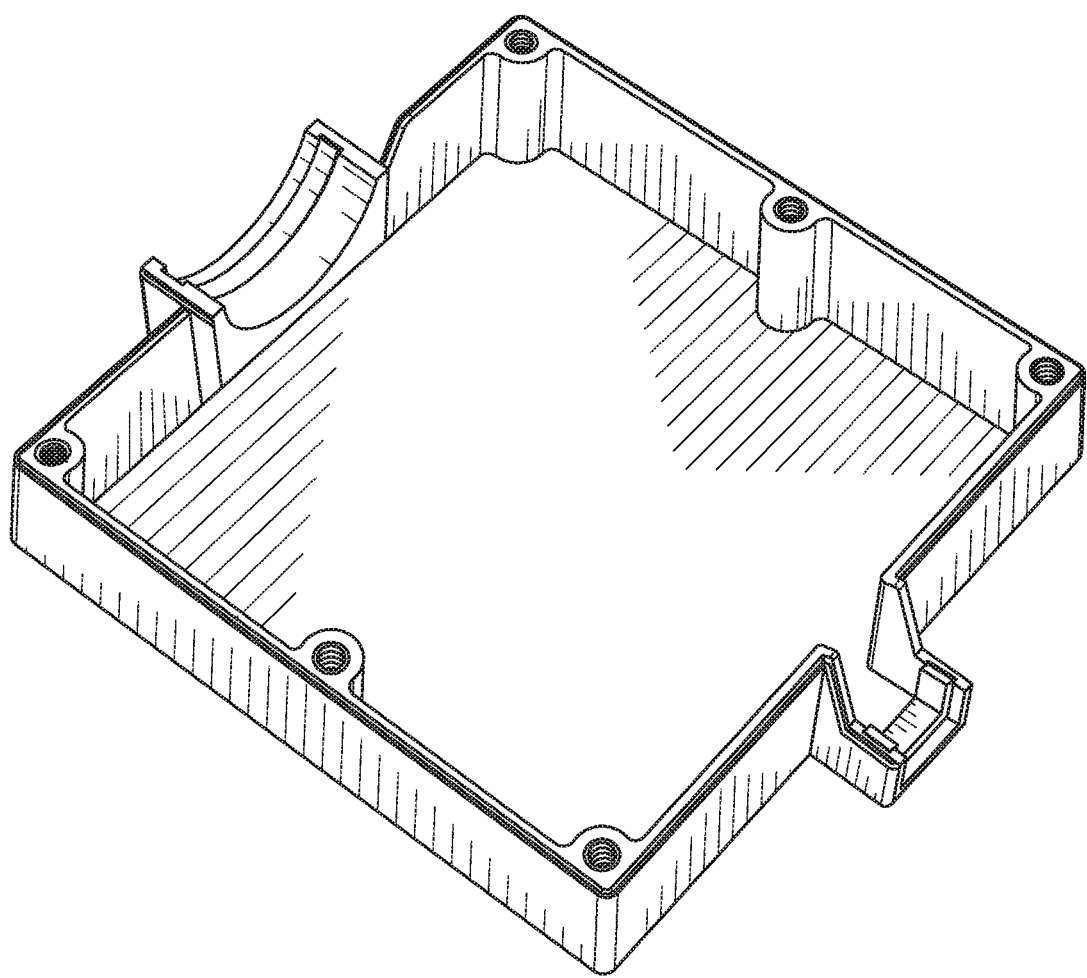
FIGS. 23B-23G illustrates another embodiment of a chamber configured to provide a system for UV sterilization and/or disinfection. The system for UV sterilization and/or disinfection of FIGS. 23B-23G (as well as other embodiments disclosed herein) can be used for sterilizing and/or disinfecting sensitive electronic parts (e.g. for a medical instrument).
Figure 23C:
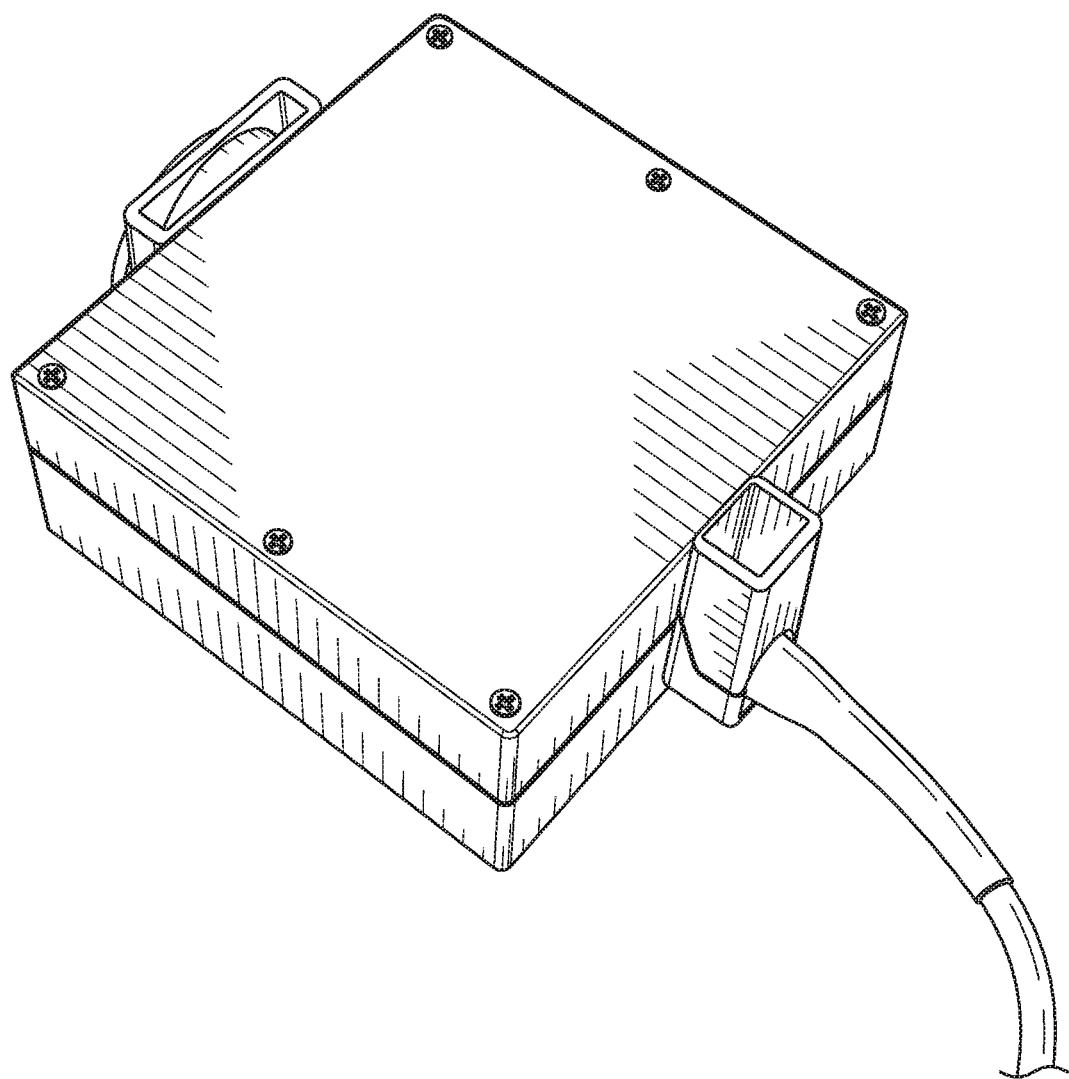
Figure 23D:
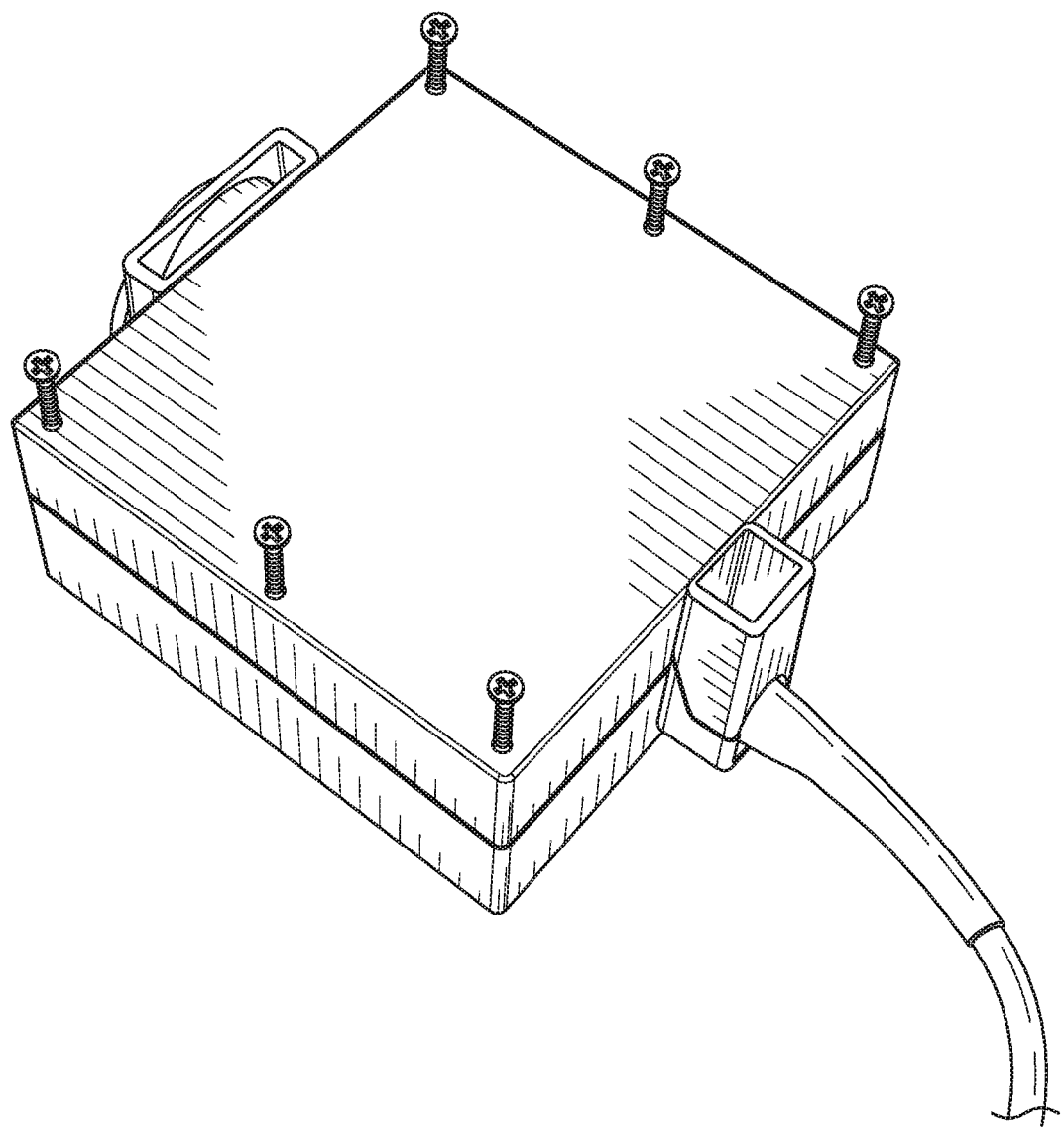
Figure 23E:
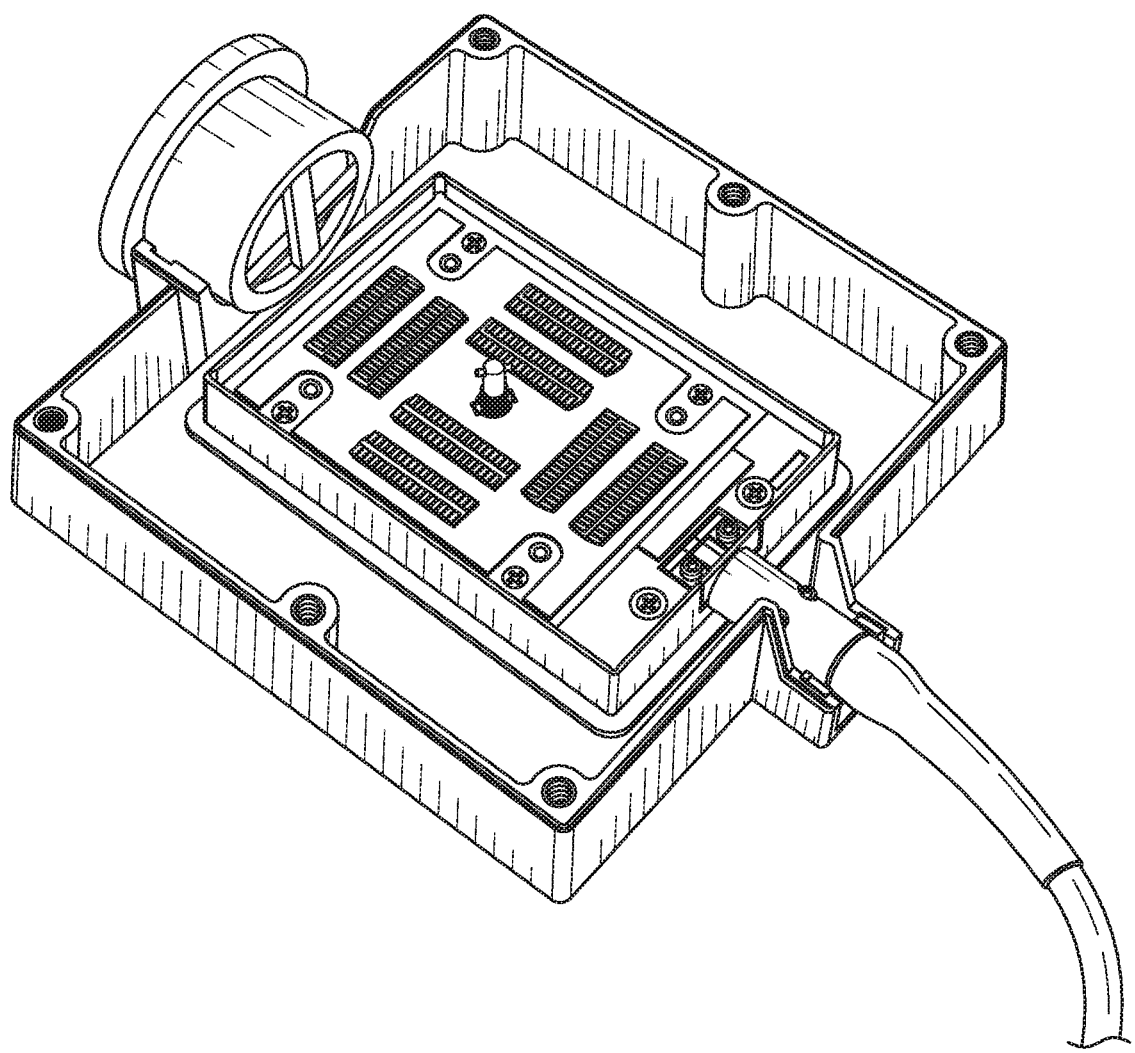
Figure 23F:
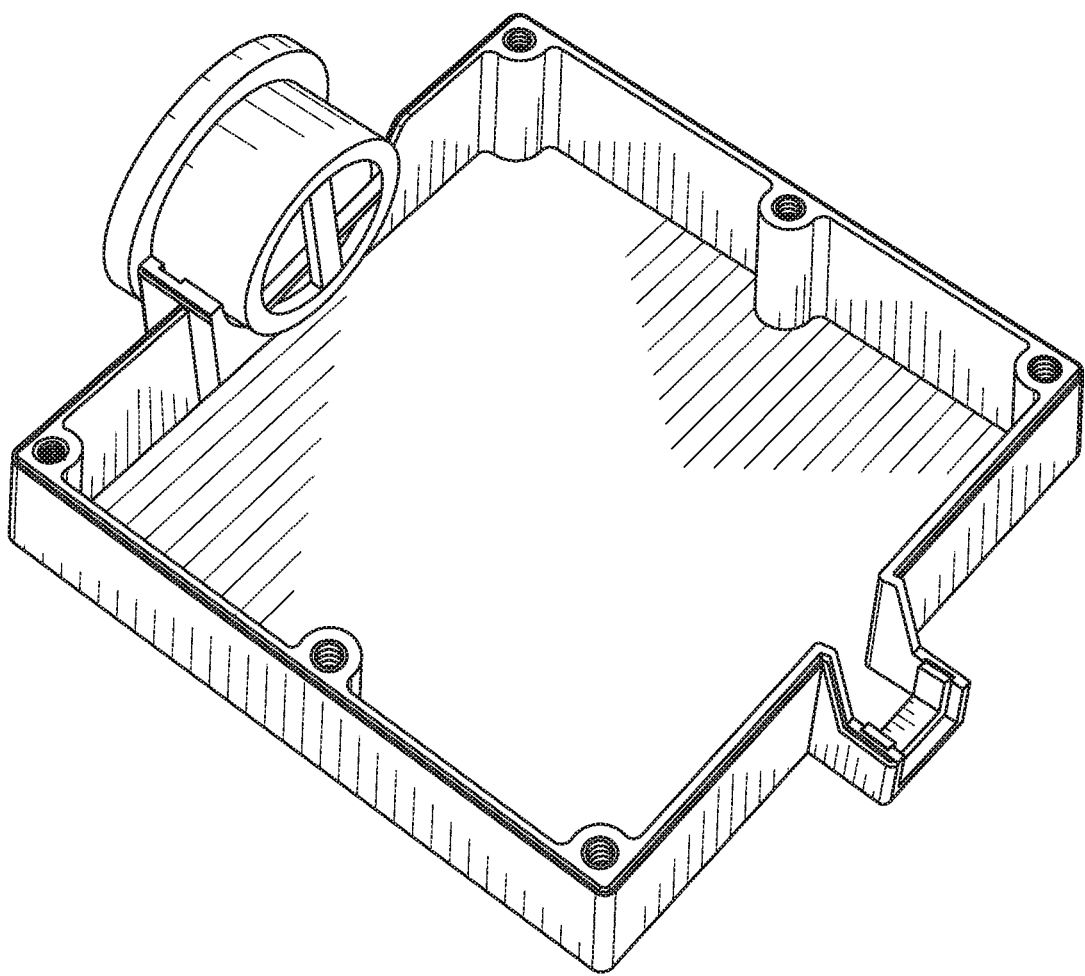
Figure 23G:
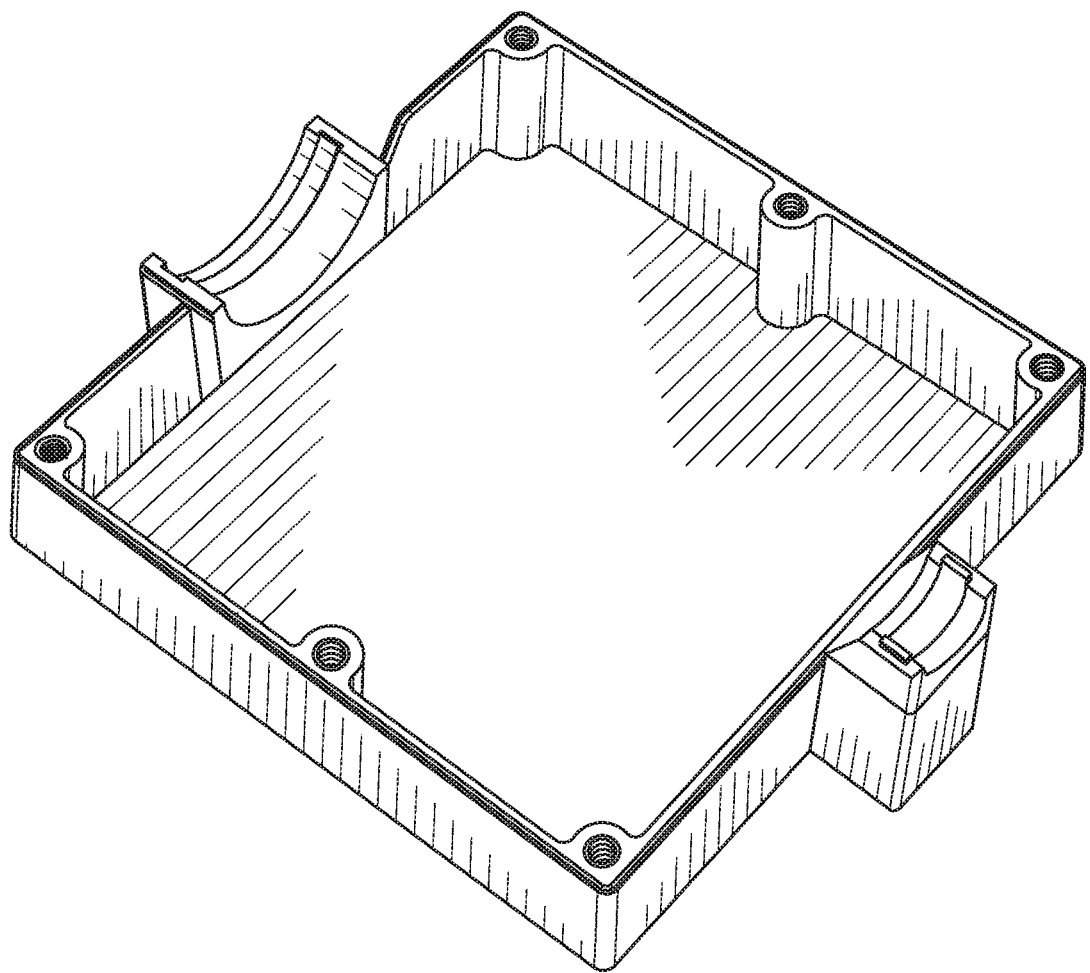

In some embodiments, the chamber can include a container of custom size and shape based on the device or devices to be placed inside the container for sterilization, disinfection, sanitation, and/or decontamination. FIG. 23A illustrates an embodiment of the chamber 310 further including an insert 340. The disclosed insert 340 can be used in any of the chambers disclosed above. The chamber 310 can include a top portion 322 and a bottom portion 324 that are configured to receive the insert 340. The top portion 322 of the chamber 310 can include a plurality of engagement structures 320a that are configured to engage with the plurality of engagement structures 320b of the bottom portion 324. In some examples, when the plurality of engagement structures 320a are secured with the plurality of engagement structures 320b, a seal 312 can be formed between the top portion 322, bottom portion 324 to secure and seal the insert 340 located within. In some embodiments the top portion 322 further includes an inlet 344 and an outlet 334. The outlet 334 and the inlet 344 are located on the top portion 322 such that sterilant can be circulated about the devices placed in the insert 340. However, the outlet 334 and the inlet 344 can be located anywhere on the chamber 310—whether on the top portion 322 or the bottom portion 324.

In some examples, many devices that need sterilization or disinfection can contain circuit boards or other electronic components that are sensitive to moisture (e.g. water vapor and hydrogen peroxide vapor) and oxidative species (e.g. $H_2O_2,O_3$), for example (e.g. copper). In such devices, the use of $H_2O_2$ and/or $O_3$ for sterilization/disinfection can damage the underlying device to be sterilized/disinfected. To accommodate this, in some examples, a sub-chamber of the system for sterilization and disinfection can provide for UV sterilization/disinfection. For example, the sub-chamber 310 illustrated in FIG. 23A, can be configured to provide UV sterilization/disinfection. FIGS. 23B-23G illustrates another embodiment for a system configured to provide UV sterilization/disinfection.

The UV could be limited to a specific part of the device to be processed to ensure that the oxidation of the process does not impact the component (e.g., printed circuit board, small circuit board, ultrasound probe, etc.) that is moisture sensitive. In some examples, a bag or other enclosure can be placed around the moisture sensitive portion of the device to be sterilized/disinfected so as to protect it from the oxidation of the system. In some embodiments, the UV sterilization/disinfection can be provided in a separate sub-chamber from the portion of the device providing $H_2O_2$ and/or ozone. In other examples, UV sterilization/disinfection and $H_2O_2$ and/or ozone sterilization/disinfection can be provided within the same chamber.

In some embodiments, the sterilization/disinfection of devices that are sensitive to moisture, $H_2O_2$, and/or $O_3$ can be sterilized/disinfected with a wide range of wavelengths of light. For example, the wavelengths of light used can be within the UV range (e.g. 10 nm to 400 nm), the visible light range (390 nm to 700 nm), etc. In some examples, the use of UV-C wavelength UV light (100 to 280 nm) is preferable.

Figure 24:
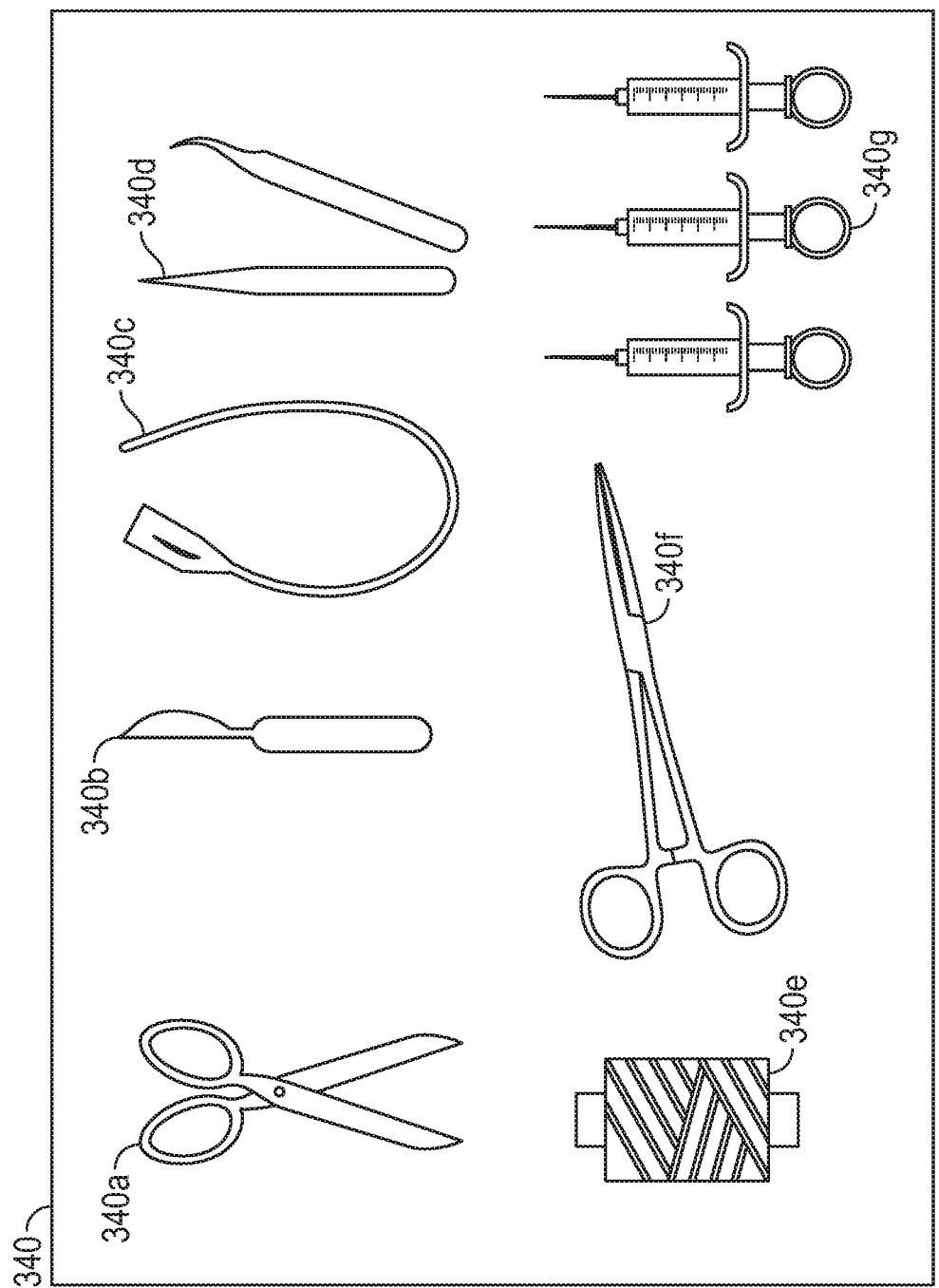
FIG. 24 shows an embodiment of an inset to be used in a chamber.

In some embodiments, the insert 340 can be configured to provide a custom sized fit for receiving a plurality of devices. For example, the insert 340 inside chamber 310 can contain recesses shaped to hold each of a plurality of devices. FIG. 24 illustrates an example of an insert 340 configured to receive and secure a plurality of devices for sterilization/disinfection. This can include, for example, a sterile kit that includes a plurality of items such as a first item 340a (e.g., scissors), a second item 340b (e.g., scalpel), a third item 340c (e.g., catheter), a fourth item 340d (e.g., forceps), a fifth item 340e (e.g., suture), a sixth item 340f (e.g., hemostat), and a seventh item 340g (e.g., syringes).

The insert 340 can allow an item to be packaged, sterilized and/or disinfected and then transported, all the while remaining sterilized and/or disinfected prior to use. Particularly in the field of medical devices, the configuration of the system for sterilization and disinfection 300 with insert 340 can provide for easy packaging of an item to be used during a surgical procedure (e.g., a medical device or a medical kit) and easy sterilization/disinfection thereafter. Once packaged, the item, through the inlet 344 and the outlet 334, can be sterilized and/or disinfected and subsequently stored until ready for use. The seal 312 of the chamber 310 can ensure that the item within the chamber 310 remains sterilized and/or disinfected during storage and transportation. In this way, when the item is brought out for use in a sterile environment, the item does not need to be sterilized and/or disinfected again.

Figure 25A:
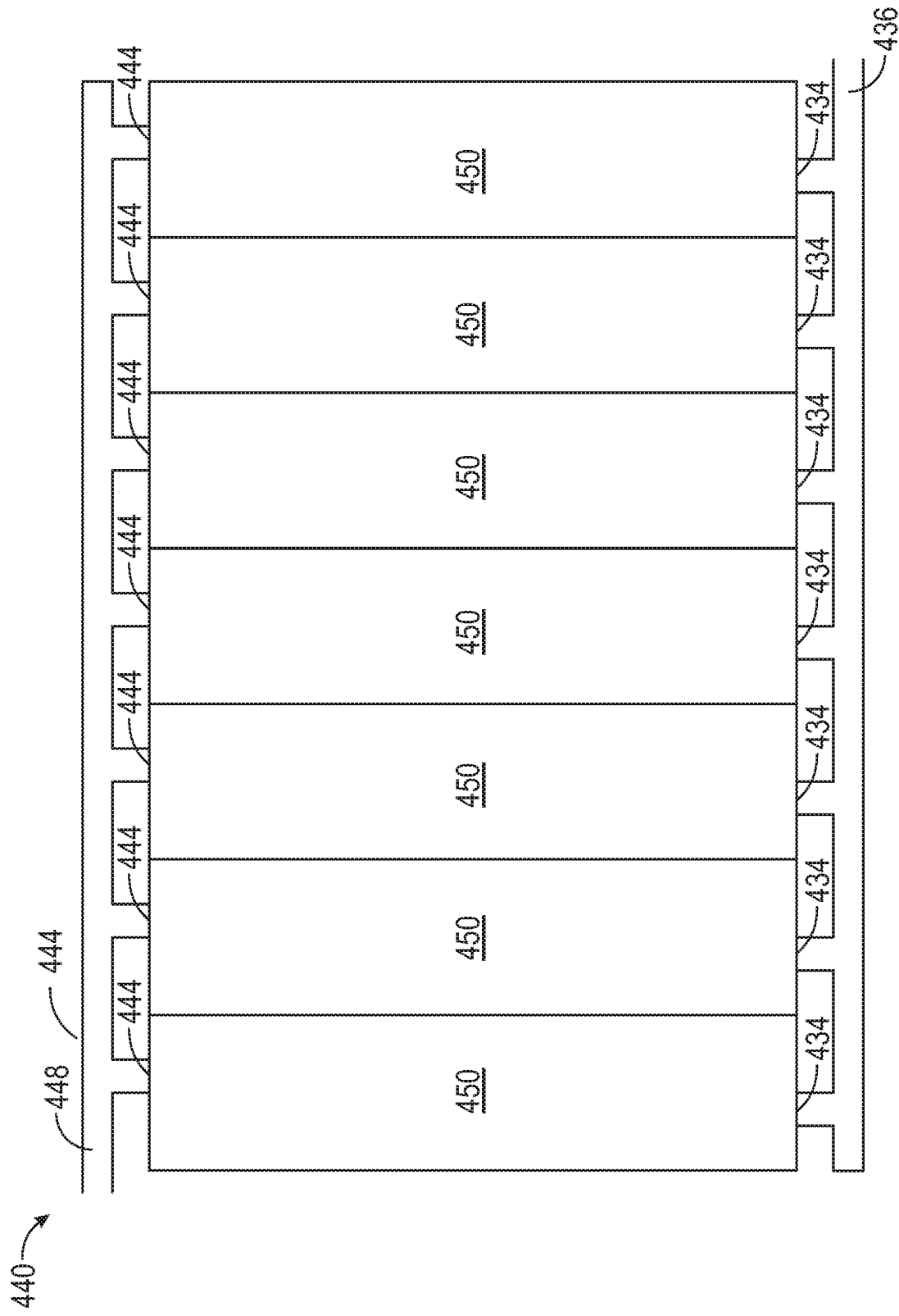
FIG. 25A-25B shows another embodiment of a chamber that can be used in a system for sterilization and disinfection.
Figure 25B:
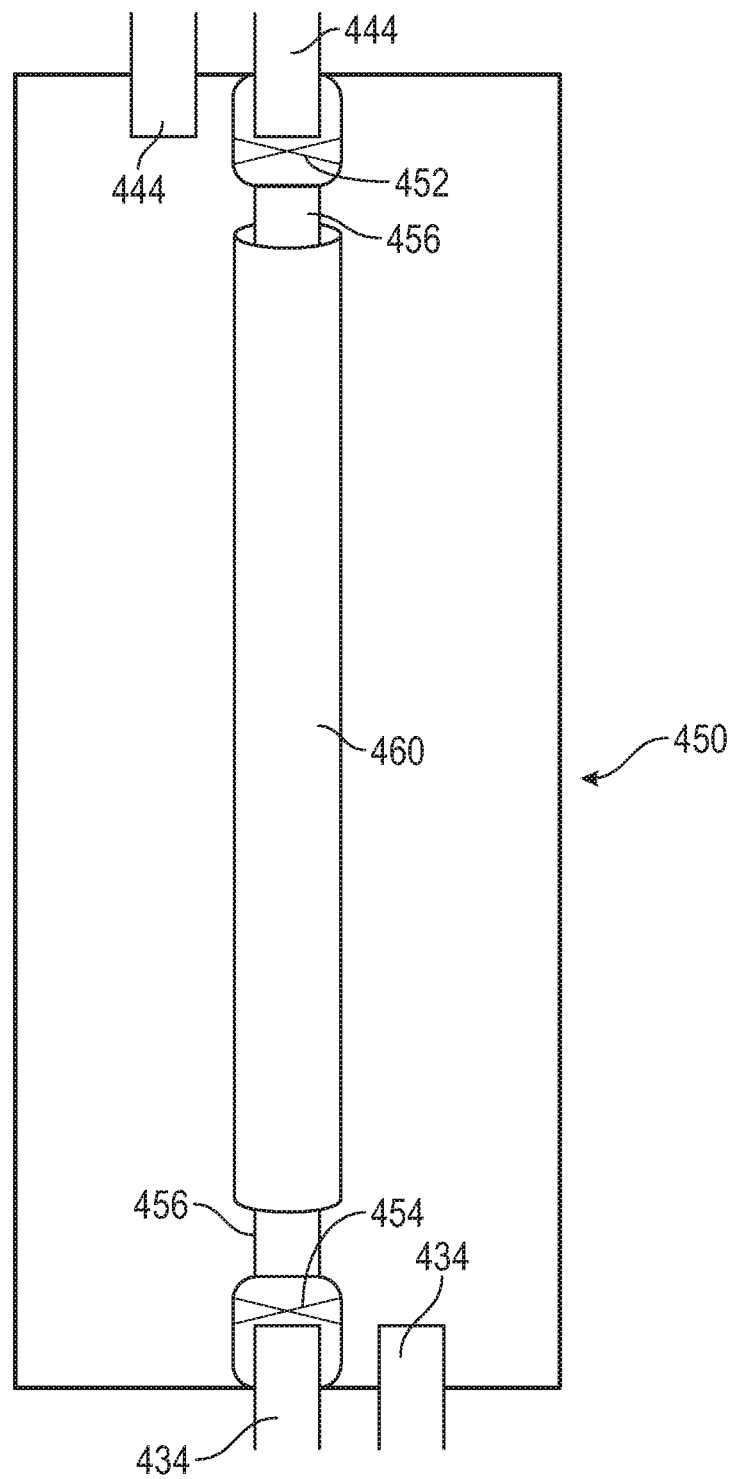

FIGS. 25A-25B illustrate another embodiment of the system for sterilization and disinfection 400 wherein the interior of the chamber 410 (not illustrated) includes a plurality of compartments 450. In some embodiments, each of the plurality of compartments 450 includes a plurality of inlets 444 and outlets 434. The plurality of inlets 444 can be fluidly connected by an inlet conduit 448 such that sterilant can be provided to all of the plurality of compartments 450 at the same time. Similarly, in some examples, the plurality of outlets 434 can be fluidly connected by an outlet conduit 436 such that sterilant can be circulated out of the plurality of compartments 450 at the same time. In other embodiments, the flow of sterilant into and out of each of the plurality of compartments 450 can occur independently of the remaining plurality of compartments 450. In some examples, each of the plurality of compartments 450 are removable and/or insertable and includes individual seals such that each of the plurality of compartments 450 remains sterilized/disinfected even when removed from the chamber 410 of the system for sterilization and disinfection 400.

FIG. 25B illustrates a cross-section of an embodiment of an individual compartment of the plurality of compartments 450. In some embodiments, the plurality of compartments 450 is configured with a plurality of inlets 444 and a plurality of outlets 434. This configuration can allow each of the plurality of compartments 450 to be dual purposed. For example, each of the plurality of compartments 450 can be configured to sterilize an interior of an item placed within the compartment 450 and anything located external to the item (e.g., the exterior of the item or a separate item placed in the compartment 450).

In some examples, the dual purposed sterilization/disinfection can be accomplished by including a sterilization lumen 456 having an inlet valve 452 and an outlet valve 454 that are attached with the inlet 444 and the outlet 434 respectively. In some embodiments the inlet valve 452 and the outlet valve 454 are duck bill valves that form attachment points between the inlet 444 and the outlet 434 and the sterilization lumen 456 disposed therein. In some examples, the inlet valve 452 and the outlet valve 454 are predisposed to be in a closed position such that attachment and removal of each of the plurality of compartments 450 from the system for sterilization and disinfection 400 does not allow air flow to disturb the sterility of the contents inside the container. Furthermore, in such embodiments the cracking pressure of the inlet valve 452 and the outlet valve 454 are high enough to prevent air flow in or out of the container.

As shown in FIG. 25B, the inlet valve 452, the outlet valve 454, and the sterilization lumen 456 allow for a device having a lumen 460 to be sterilized. The sterilization lumen 456 is configured to sterilize devices having tubular configurations (e.g., catheters) that have interior surfaces that are difficult to reach, clean, or sterilize/disinfect. In some embodiments, the sterilization lumen 456 can have a plurality of openings along the length of the sterilization lumen 456 such that sterilant can be circulated through the interior of the lumen of the device 460. In some embodiments the sterilization lumen 456 comprises a first half adjacent to the inlet valve 452 and a second half adjacent to the outlet valve 454. The first half of the sterilization lumen 456 can be received within a first end of the lumen of the device 460, while the second half of the sterilization lumen 456 can be received within a second end of the lumen of the device 460. Sterilant can therefore be received through the first end of the device having a lumen 460 and circulated out through the second half of the sterilization lumen 456.

In some embodiments, each of the plurality of compartments 450 are sterilized/disinfected by circulating sterilant through each of the inlets 444—sterilant is therefore circulated into the interior of the plurality of compartments 450 to both sterilize/disinfect the exterior of the device having a lumen 460 and the interior of the lumen of the device having a lumen 460. At the end of the cycle, the sterilant is circulated out of the plurality of compartments 450 through the outlet 434 and the outlet 434 adjacent to the outlet valve 454. Each of the plurality of compartments 450 can then be transported and stored—wherein the item located within each of the plurality of compartments 450 remains sterile/disinfected until use.

Use of the Sterilizer and Wound Chamber

FIG. 11 shows a photograph of the wound chamber in use in an experiment on a pig. In the example, multiple deep dermal partial thickness burn injuries were induced in Yorkshire pigs weighing 40-45 kilograms. After the burn wounds were produced, the wounds were inoculated with both *Staphylococcus aureus* and *Pseudomonas aeruginosa* to create a polymicrobial wound infection. These microorganisms were chosen as these two organisms are commonly found in infected burn wounds in humans.

Figure 13:
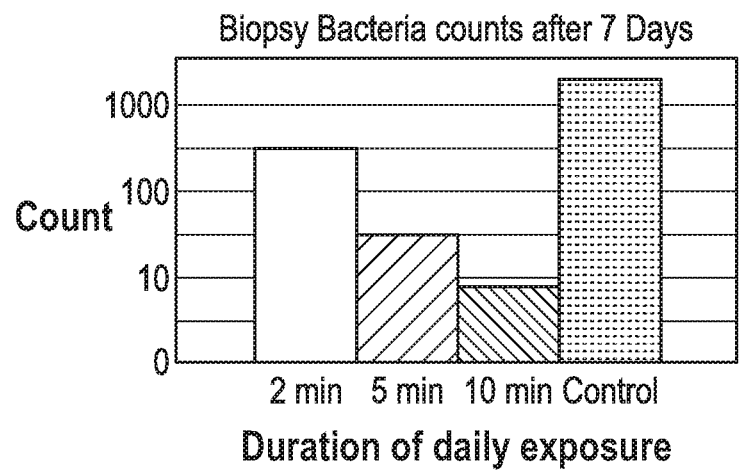
FIG. 13 shows a bar graph of results from a method of wound treatment using the fourth embodiment of the disclosure.

Burn wounds were exposed to disinfecting effluent produced by the sterilizer of the disclosure by placing the wound chamber over the wounds and operating the sterilizer for 2, 5 and 10 minutes each day for seven days. The wounds were examined on a daily basis. The results of the seventh day bacterial count compared with the control (not treated) are shown in FIG. 13, which has a logarithmic scale of bacteria count on the vertical axis, and bars along the horizontal axis showing counts in areas exposed for 2 minutes, 5 minutes and 10 minutes, as well as a bar showing counts in an untreated (control) area. As can be seen in this figure, the bacteria counts are significantly lower in areas treated using certain embodiments described herein—the ten-minute treatment count being more than 100 times smaller than the control.

Example Method of Operation

Figure 3A:
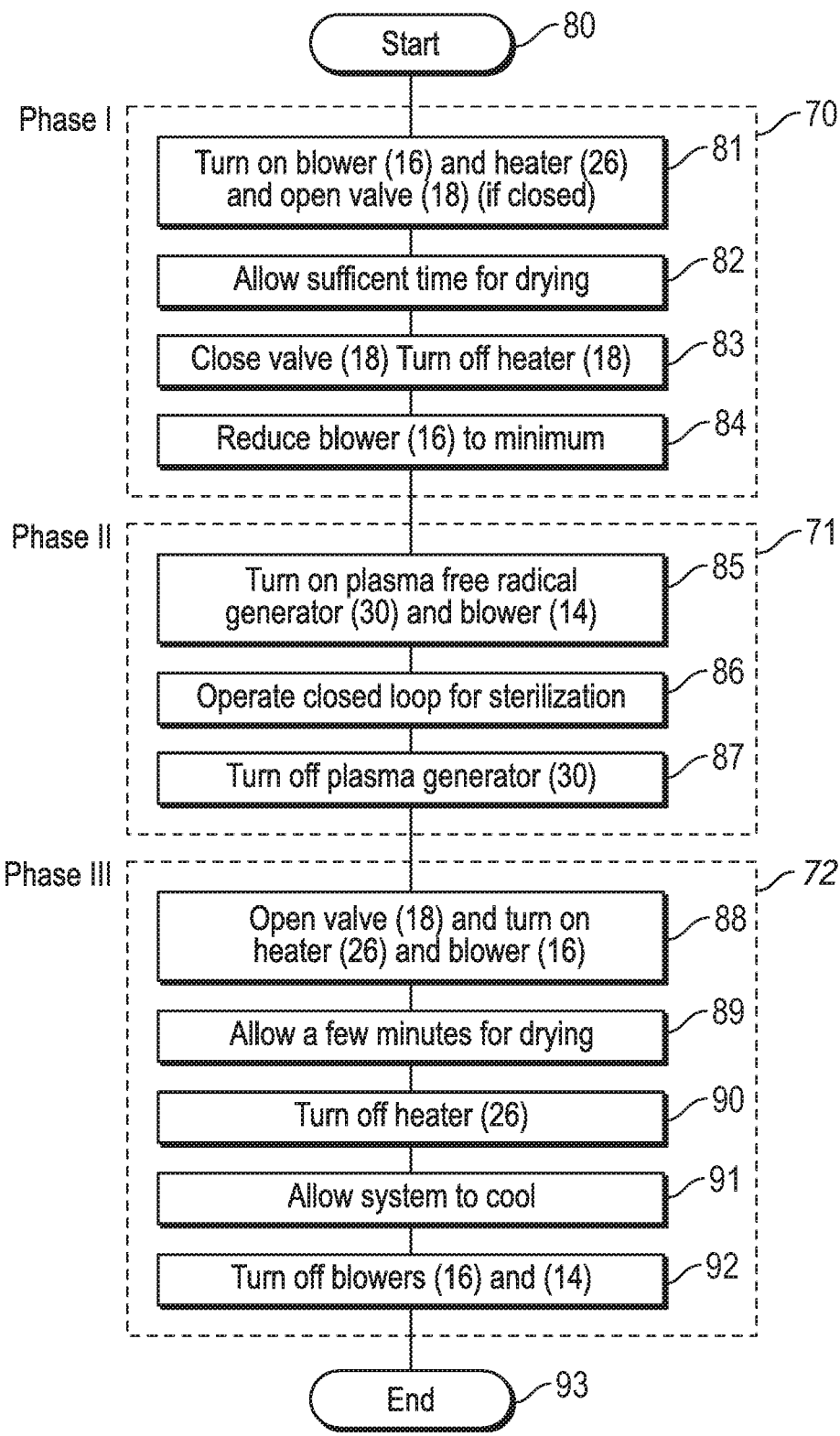
FIG. 3A shows a flowchart of an example method of the disclosure.

As shown in FIG. 3A, the sterilization process using the embodiments of the disclosure which have pre-heaters and/or exhaust systems, may include one, tow, or three phases:

80—Start the method

70—Phase I—Pre-sterilization drying and optionally heating (Open Loop)

81—During this phase the exhaust blower 16 is turned on, the valve 18 is opened (if closed) and the heater 26 is turned on. This causes fresh air from the inlet 58 to flow through valve 18, optional HEPA filter 20, and heater 26 into chamber 10 via conduit 42. The heated air dries and heats the sterilized items and is expelled through conduit 42 via optional filter 22, free radical destroyer 24 and exhaust blower 16.

82—The drying and heating is continued for a sufficient time, for example approximately 5 minutes. However, in several embodiments, the drying portion of the cycle is eliminated. If desired, a heat sensor or humidity sensor (not shown) could be provided at the exhaust 56 or in conduit 44, coupled to the controller 12, so that the duration of the pre-heating could be controlled based on empirical data rather than an arbitrary elapsed time. Optionally, if a chamber temperature sensor 52 is provided, the controller 12 may operate heater 26 and, if provided, chamber heaters 64 and/or 66 to maintain a desired pre-heat temperature in the chamber.

83—After the chamber and the sterilized items are dried and heated the input valve 18 is closed.

84—The exhaust blower 16 is turned off (or reduced to minimum speed, if this ability is available)

71—Phase II—Sterilization (Closed Loop)

85—The plasma generator 30 and/or the vaporizer 32, and the closed loop blower/distributor 14 are turned on. This causes the air to circulate in the closed loop through the effluent generator 46 and the chamber 10, as described in the description of the apparatus, above.

86—The closed loop system produces continuously free radical rich effluent that sterilizes items in the chamber 10. The closed loop operation continues for a time sufficient for sterilization. As an example, a duration of approximately 20-30 minutes should be sufficient for adequate sterilization of most items. In several embodiments, cycle times range from about 3 to about 40 minutes (e.g., about 3 to 5 minutes, about 5 to 7 minutes, about 7 to 10 minutes, about 10-15 minutes, about 15-20 minutes, about 20-30 minutes, about 30-40 minutes, and any time between those listed. If provided, the controller 12 will activate chamber heaters 64 and/or 66 to maintain a desired temperature in chamber 10, as measured by sensor 52.

87—At the end of the sterilization period, the plasma generator 30 and/or vaporizer 32 is turned off.

72—Phase III—Post-sterilization drying and clearing (Open Loop)

88—Input valve 18 is opened, heater 26 is turned on and the exhaust blower 16 is turned on. The closed loop blower/distributor 14 may remain on during this Phase III in order to dry free radical source 46, or, if desired, blower/distributor may be turned off in step 87. The air flows from the input 58 via conduit 42 into the chamber 10 drying the items and, if blower 14 remains on, the free radical source 46. The moist air is expelled into the atmosphere via filter 22 and free radical destroyer 24.

89—The open loop operation is maintained for a time sufficient to dry and clear the chamber 10. The drying operation may be maintained for a sufficient period to warm and/or dry the items 56/62 in chamber 10, thereby limiting or preventing bacterial growth on the items. If desired, a closed loop drying operation may be utilized (e.g., in which a desiccant or other dryer and/or heater are provided in a closed loop path). A period of, for example, five minutes should suffice.

90—Heater 26 is turned off, with blower 16 (and blower 14, if desired) remaining on.

91—Fresh air is passed through the system for a sufficient time to cool down to the ambient temperature. For example, a few minutes operation would suffice for cooling. Optionally, if sensor 52 is provided in the chamber, the controller 12 could be programmed to continue this cooling until a desired temperature is reached.

92—Blower 16 is turned off, as well as blower 14 if it is still on. Valve 18 may be closed at this time, or left open for the next run.

93—The method ends. The chamber 10 may now be opened and the items 56/62 removed. New items may be put in the chamber, if desired, and the process repeated again from 80. Additional filters, blowers, sensors (e.g., temperature, pressure, humidity, etc.), and/or controls may be incorporated into various embodiments. Furthermore, various embodiments may incorporate a bar code reader, a print out, and/or other accessories and/or methods, e.g., to enhance quality control and/or regulatory compliance.

Another Example Method of Operation—Without Heating

The sterilization cycle has varied humidity; during the initial part of the cycle the sterilant has low humidity, for example about 50%. During this part of the cycle the excessive residual moisture on the sterilized items is removed. The later part of the cycle delivers the circulating sterilant to the items at much higher humidity, for example about 80% to 90%, that speeds up the sterilization process.

Additional Example Method of Operation—Residual Coating Device

Figure 3B:
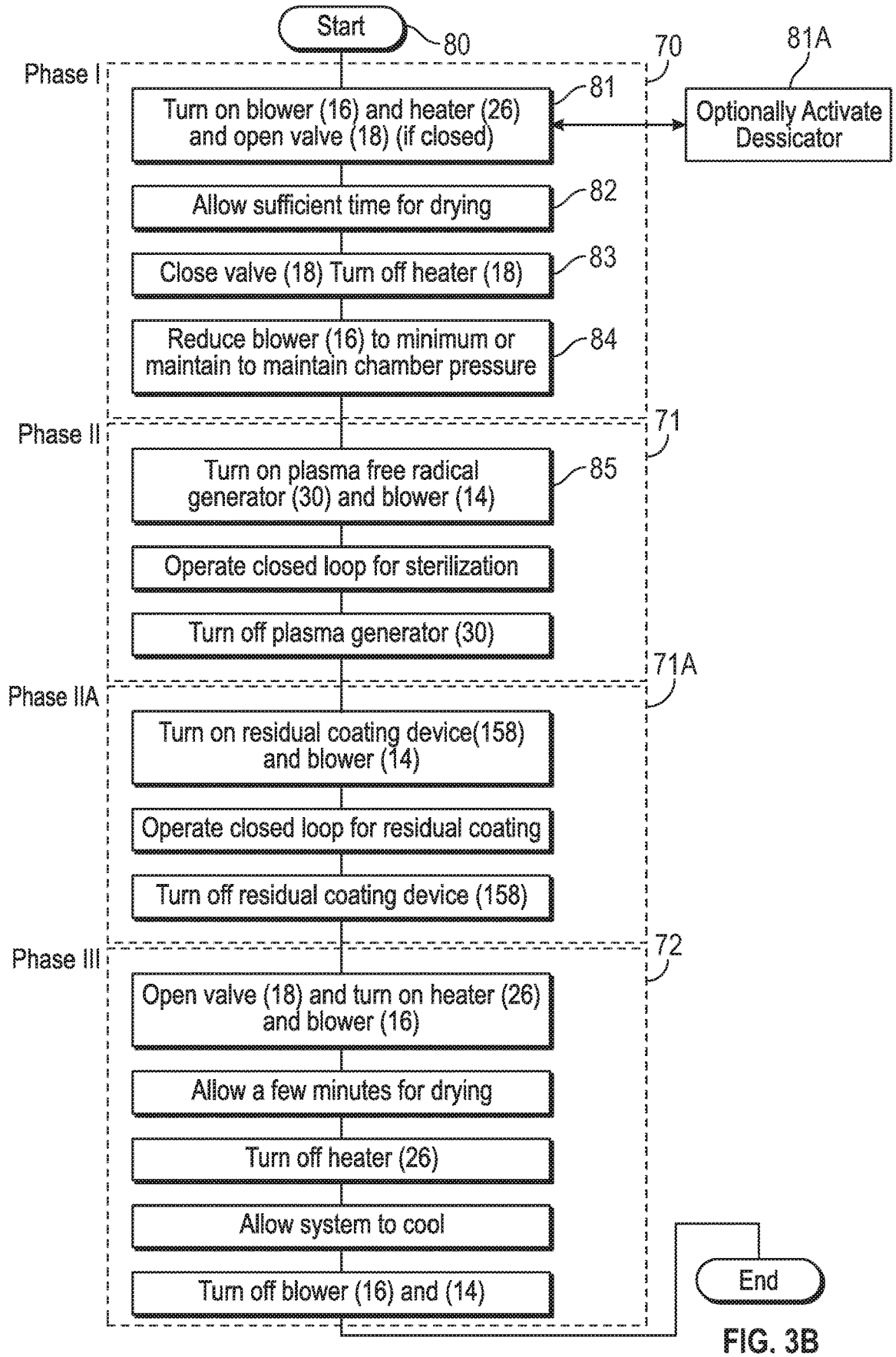
FIG. 3B shows a flowchart of an example method of the disclosure with an optional step of extended drying of items in the chamber and with an optional step of depositing a protective coating on items in the chamber.

As shown in FIG. 3B, processes using the embodiments of the disclosure, may include a residual coating phase:

71A—Phase IIA—Residual Coating

85A—The residual coating device 158 and the closed loop blower/distributor 14 are turned on and the residual coating valve 156 is opened. This causes gas to circulate, in a closed loop, through the residual coating device 158 and the chamber 10, as described in the description of the apparatus, above.

86A—The closed loop system produces continuously residual coating rich effluent that coats items in the chamber 10. The closed loop operation continues for a time sufficient for coating. As an example, a duration of approximately 1-5, 5-10, 10-15, 15-20, or 20-30 minutes should be sufficient for adequate coating of most items. If provided, the controller 12 will activate chamber heaters 64 and/or 66 to maintain a desired temperature in chamber 10, as measured by sensor 52.

87A—At the end of the residual coating period, the residual coating device 158 is turned off.

The residual coating process may be performed in addition to or instead of the sterilization phase and other phases described herein. For example, in arrangements in which previously-sterilized items are available, the residual coating process may be performed without a sterilization phase to deposit the additional residual coating on those items.

Additional Example Method of Operation—Device for Relative Humidity Cycling

Figure 3C:
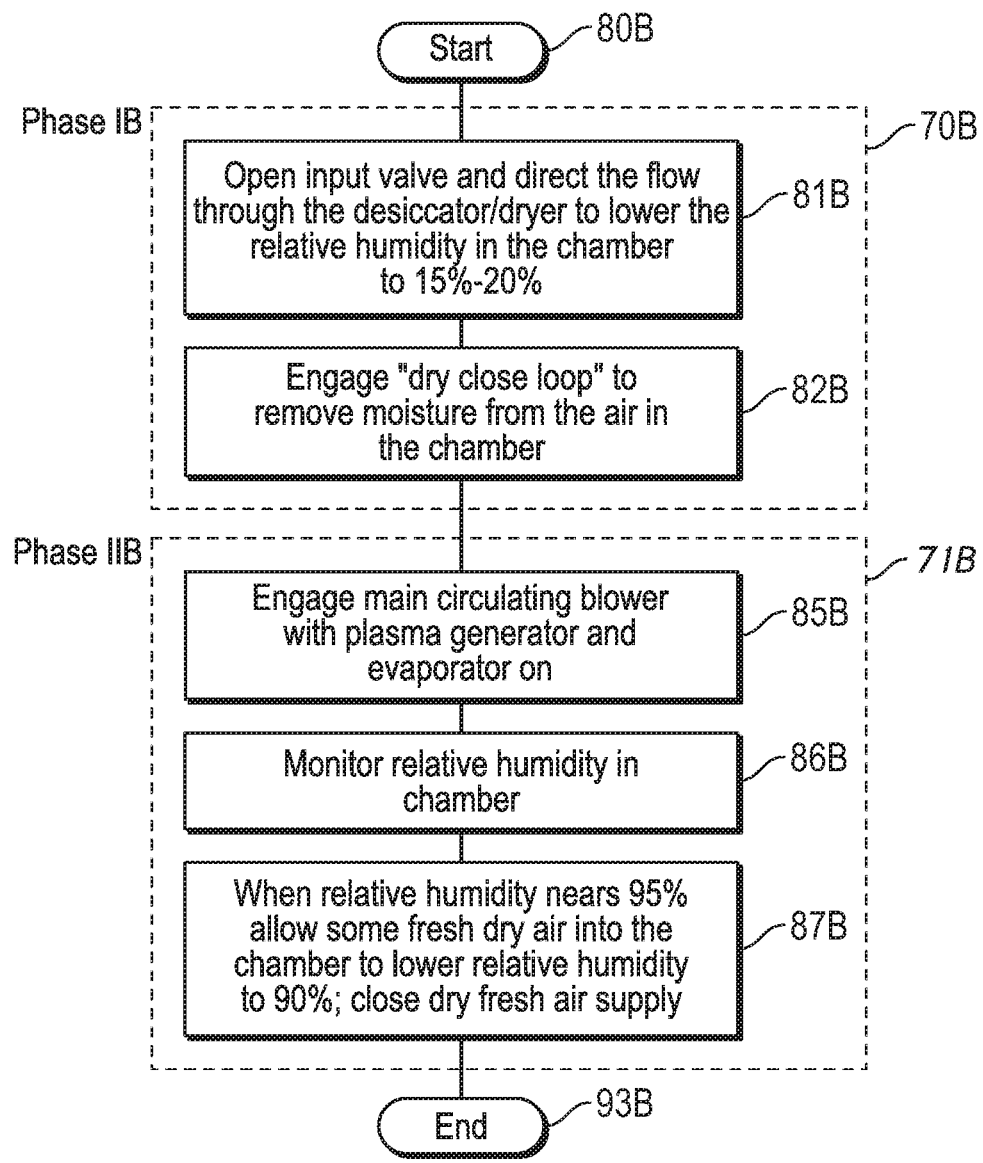
FIG. 3C shows a flowchart of another example method of the disclosure.

As shown in FIG. 3C, processes using the embodiments of the disclosure, may be used to obtain a desired relative humidity:

80B—Start the method

70B—Phase IB—Obtaining the desired initial low relative humidity

81B—Open the input valve and direct the flow through the desiccator/dryer to lower the relative humidity in the chamber to 15%-20% level.

82B—Engage the "dry close loop" to remove moisture from the air in the chamber. In some embodiments, this can be a separate closed loop that circulates the air between the chamber and the desiccator/dryer.

71B—Phase IIB—Proper Sterilization Cycle

85B—Engage a main circulating blower with plasma generator and evaporator on

86B—Monitor relative humidity in the chamber

87B—When the relative humidity nears 95%, allow some fresh dry air (through the desiccator/dryer) into the chamber to lower the relative humidity to 90%. Subsequently close the dry fresh air supply.

Figure 3D:
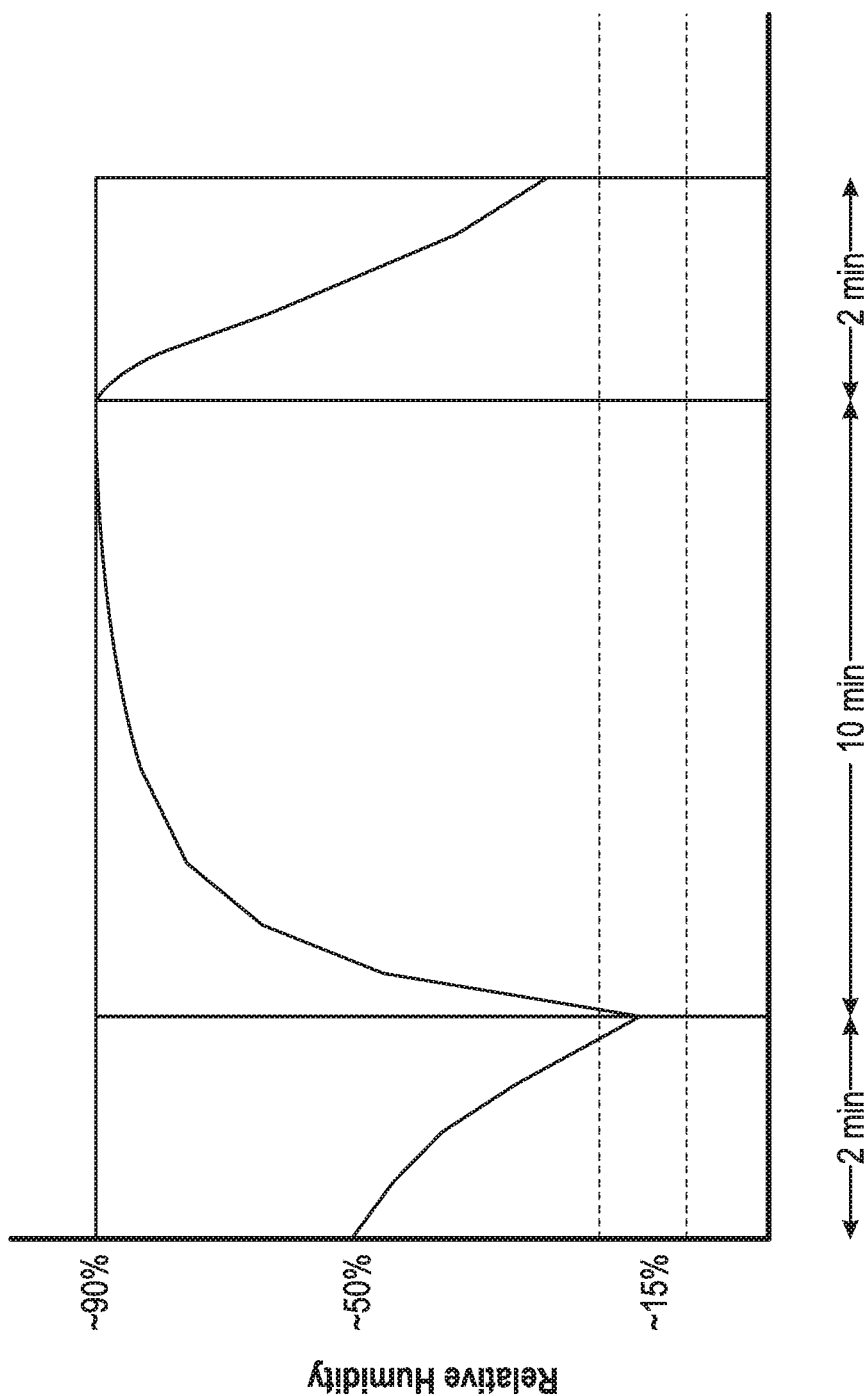
FIG. 3D shows a chart illustrated the proposed relative humidity levels in the chamber during one embodiments of the disclosed sterilization/disinfection cycle.

FIG. 3D illustrates an example of the proposed relative humidity levels in the chamber during the sterilization/disinfection cycle. Please note that the 2 minute and 10 minute marks are arbitrary.

Incorporation into an Appliance having a Closed Space

Certain appliances may harbor various sorts of fungi or pathogens (e.g., microbes). Growth of such fungi and pathogens may be from moisture or other enabling process conditions. Accordingly, various embodiments described herein can be incorporated into an appliance having a closed space. For example, in washing machines, especially front loading washing machines, there is a potential for undesirable growth of mold, fungus, mildew, slime, or some combination thereof (collectively and/or individually referred to herein as "mold" for purposes of brevity). Most front loading washing machines require a water-tight seal when the door is shut, in order to prevent water leakage during the wash cycle. Many front loading washing machines also include a gasket assembly between the door and the wash drum, primarily to keep clothing within the drum. Due to these features, front loading washing machines often are not completely drained of detergent, wash water, and/or rinse water after a wash cycle. Some liquid remains pooled in various areas of the washer, often in and around the gasket and the drum, door, and gasket interfaces. This pooled liquid has a high probability of becoming polluted and contaminated over time, resulting in the growth of mold and odors, which are unpleasant, unsightly, and unsanitary. Various mold-preventative remedies have been suggested or implemented such as drying the gasket assemblies after use, running a hot water cleaning cycle with bleach, leaving the washer door open to dry out the interior, and running a dehumidifier in the space the washer is being used. However, such remedies have not fully addressed the problem and mold remains and continues to present a problem in front loading washing machines.

As illustrated in FIG. 16, some embodiments as described herein may be incorporated into a washing machine. Although various aspects are described in the washing machine, it would be appreciated that such features can apply to other appliances with a closed space, such as dishwashers, dryers, or refrigerators (e.g., in the fruit and vegetable containment compartments). When incorporated into a front loading washing machine, the sterilization system (or disinfection, sanitization, or decontamination system) can substantially reduce or eliminate the mold problem typically found in front loading washing machines or other system with a closed space. In such arrangements, the sterilization chamber 10 of the systems described herein becomes the washing machine chamber 154, including the washing drum, gasket assembly, interior of the front door, other components exposed to the wash environment, as well as potentially other components in the washing machine such as the detergent loading equipment (which may be a tray or other device).

In some embodiments, the sanitization of the washing machine chamber 154 can be accomplished by circulation of a sterilant (e.g. free radical effluent) through the chamber 154. In operation, the gaseous sterilant produced by evaporator 32 and plasma generator 30, individually or in combination, is circulated by blower 14 through the washing machine chamber 154. In some examples, the continuous circulation through the evaporator 32 and the plasma generator 30 can provide maximum free radical saturation level in the sterilant. Due to the gaseous nature of the sterilant, the sterilant is easily spread to substantially all of the exposed surfaces of the washing machine chamber 154 and substantially all surfaces that can harbor mold or other pathogens in crevices, including difficult to reach spaces through diffusion of the gaseous sterilant. In this manner, the problem of mold in front loading washing machines and other systems with closed spaces can be reduced or even eliminated. Moreover, since front loading washing machines are generally water-tight, the recirculating sterilant can be substantially contained within the chamber, especially when operating at a slightly negative pressure.

In some embodiments, the input and the output of the sterilant into and out of the chamber 154 can be designed in such a way such that water is not stored in the conduits as a result of the washing cycle. In some embodiments, this can be accomplished by having the input and the output conduit at an angle that is at least horizontal or slightly/almost vertical. In some embodiments, the angle of the input and output conduit can range between about 0° and 90°; in some embodiments the angle can range between about 0°-10°, 10°-20°, 20°-30°, 30°-40°, 40°-50°, 50°-60°, 60°-70°, 70°-80°, or 80°-90°; in some embodiments, the angle can be approximately 0°, 5°, 10°, 15°, 20°, 25°, 30°, 35°, 40°, 45°, 50°, 55°, 60°, 65°, 70°, 75°, 80°, 85°, or 90°. Ensuring that the input and output flow of the sterilant does not carry out any remnants of the water from the washing cycle ensures that the efficacy of the sanitization is not decreased. In some embodiments, the tumbler-type chamber 10 of the machine (e.g. washing machine) should be in motion during the sanitization cycle to assure some turbulence within the chamber.

When incorporated into a washing machine, the evaporator 32 (and associated components) and plasma generator 30 may both be included or, if desired, one of the evaporator 32 and the plasma generator 30 may be omitted. For example, similar to FIG. 5, FIG. 17 illustrates an example embodiment in which the sterilant is generated by an evaporator 32 and without a plasma generator 30. The sterilant may include hydrogen peroxide vapor or microdroplets. The vapor can interact with surfaces within the chamber 154 killing pathogens it encounters. Even if a surface in the chamber is wet, some of the sterilant vapor may penetrate the surface to kill the pathogens because it is in equilibrium with the liquid solution in the evaporator 32 and thus the vapor may attempt to be in similar equilibrium with the surface.

Similar to FIG. 4, some embodiments may utilize sterilant generated by a plasma generator 30 and without an evaporator 32. The sterilant may include active species produced in the plasma generator 30, such as excited oxygen species (e.g., $O_2$, $O_3$, and/or O) and nitrogen oxide ($N_2O$ or $NO_2$).

The preferred embodiment may depend on factors such as the time devoted for sanitization and/or the recommended cycle to be utilized. For example, in some embodiments, using both a plasma generator 30 and an evaporator 32 may produce the more potent sterilant than using the plasma generator 30 or evaporator 32 alone. As another example, using less sterilizing agent solution (e.g., hydrogen peroxide) in the evaporator 32 may in some cases result in longer operation times.

Figure 18A:
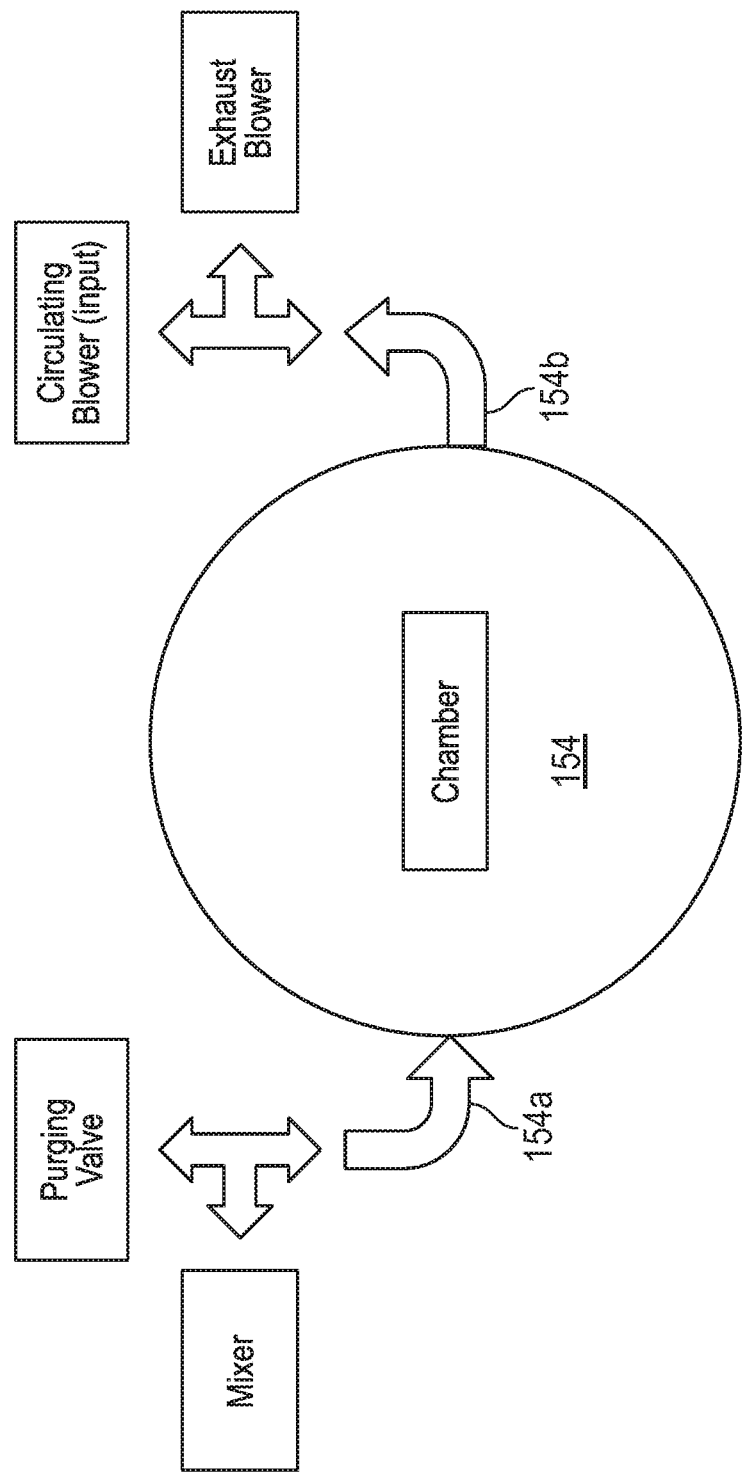
FIG. 18A shows the input and output of a washing machine chamber of some embodiments.

In various embodiments, the moisture control features described in connection with FIGS. 1F-1H may be included or omitted, as desired. Omitting the dryer of FIGS. 1G-1H might reduce the cost of the system; while incorporating the dryer might help in enabling a drying component of the sterilization cycle (e.g., drying can further reduce the risks of mold developing). FIG. 18A illustrates the input 154a and output 154b of the chamber 154 in some embodiments. It may be desirable to arrange the sterilant recirculation lines, particularly the lines of the input 154a and output connected to chamber 154, such that water is not stored in the lines as a result of the washing cycle (such water could tend to decrease the efficacy of the sanitization system). It may also be desirable to activate the tumbling of the washing drum during sanitization to create turbulence with the chamber.

A sterilization cycle may be performed whenever the door is closed, as determined by door sensor 150. If desired, the washing machine may also include a sensor such as a pressure sensor, which determines if the washing drum is empty or full of clothing or other materials. In such an arrangement, the washing machine may prevent activation of the sterilization cycle unless empty. The sterilization cycle may be user initiated or may be automatically initiated based on programmed criteria (e.g., once a day, once a week, once a month, at the end of a wash cycle, after a certain number of wash cycles, if a time between wash cycles exceeds a threshold, some combination of these and other criteria, etc.).

A sterilization cycle may, as an example, include some or all of the following steps (in any order). First, controller 12 may open hydrogen peroxide valve 142 and activate evaporator 32 (unless evaporator 32 and its associated components are omitted). Then, controller 12 may activate exhaust blower 16 to establish a negative pressure within washing machine chamber 154 and may activate circulating blower 14. (Controller 12 may continuously adjust exhaust blower 16 based on readings from sensors 52 to maintain the desired negative pressure.) A few seconds (e.g., 5 seconds) after turning on the circulating blower 14, controller 12 may activate plasma generator 30 (unless plasma generator 30 is omitted). Controller 12 may then wait for the primary duration of the cycle (the duration may be adjustable by controller 12 or by a user). As the end of the cycle nears, controller 12 may turn off the plasma generator 30, if present. A few seconds (e.g., 3 seconds) after the plasma generator 30 is turned off, controller 12 may turn up the exhaust blower 16 (perhaps to full power) and open input purging valve 18 in order to purge the sterilant from the washing chamber 154. The controller 12 may continue purging the chamber for any desired length of time (e.g., 5 seconds, 10 seconds, 20 seconds, etc.).

If desired, the controller 12 may monitor the door sensor 150 and, if the door is opened at any point in the cycle, close the hydrogen peroxide valve 142, deactivate plasma generator 30, and activate the exhaust blower 16 at full power for a desired amount of time (e.g., 5 seconds, 10 seconds, 20 seconds, etc.). Controller 12 may also, in such situations, close the intake purging valve 18. By closing purging valve 18, the exhaust blower will draw the circulating sterilant away from the opened door, further reducing any potential safety risks associated with the sterilant escaping through the opened door.

Figure 18B:
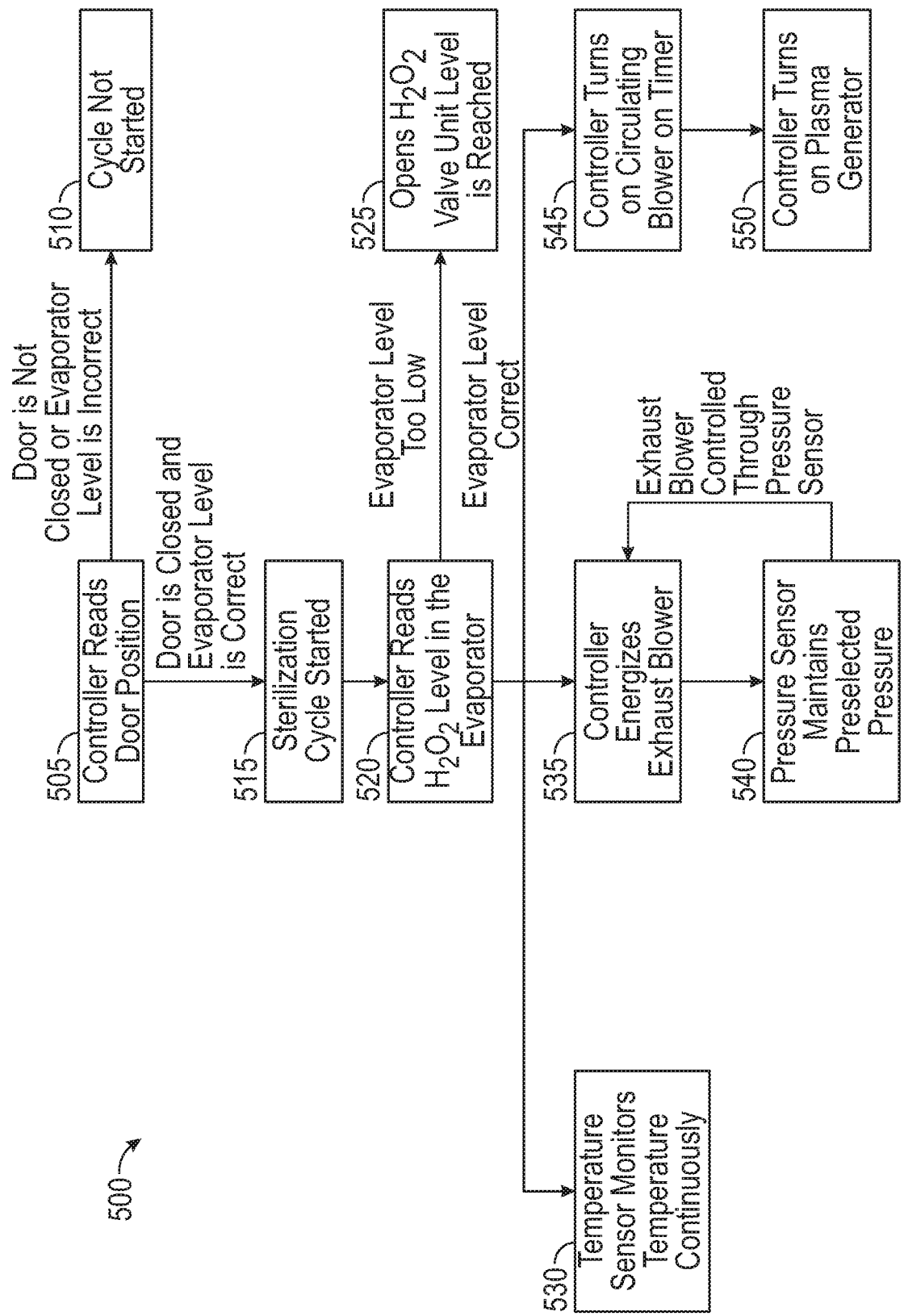
FIGS. 18B-18C show a flow chart of embodiments of a method for sterilization of a machine, for example a washing machine.

FIG. 18B illustrates an embodiment of a method for sterilization of a machine 500 or other reversible closable enclosed structure (e.g. a "locker" or container as referred to herein, a washing machine, dishwasher). In some embodiments, the method for sterilization of a machine 500 includes step 505 wherein the controller is configured to read the door position. In some examples, as shown in step 510, if the door is not closed or the evaporator level is incorrect, the sterilization cycle contained within the method for sterilization of a machine 500 is not started. In some examples, as shown in step 515, if the controller determines that the door is closed and that the evaporator level is correct, the sterilization cycle begins.

In some embodiments, the method for sterilization of a machine 500 includes step 520 wherein the controller is configured to read the $H_2O_2$ level in the evaporator. If the controller determines that the $H_2O_2$ in the evaporator level is too low, step 525 illustrates that the controller opens the $H_2O_2$ valve until the appropriate level is reached. In some examples, the appropriate level of $H_2O_2$ can be between 5-20 mL depending on the size of the chamber; the appropriate level of $H_2O_2$ can be between 5-6 mL, between 6-7 mL, between 7-8 mL, between 8-9 mL, between 9-10 mL, between 10-11 mL, between 11-12 mL, between 12-13 mL, between 13-14 mL, between 14-15 mL, between 15-16 mL, between 16-17 mL, between 17-18 mL, between 18-19 mL, or between 19-20 mL depending on the size of the chamber; the appropriate level of $H_2O_2$ can be 5 mL, 6 mL, 7 mL, 8 mL, 9 mL, 10 mL, 11 mL, 12 mL, 13 mL, 14 mL, 15 mL, 16 mL, 17 mL, 18 mL, 19 mL, or 20 mL depending on the size of the chamber. In some examples, if the controller determines that the $H_2O_2$ in the evaporator level is correct, the method for sterilization of a machine 500 can proceed to any or all of steps 530-555 illustrated in FIG. 18B. In several embodiments, a sensor (optionally in addition to the controller discussed above) is present to measure the amount of $H_2O_2$ vapor in the system. In some embodiments, the appropriate level is reached when the level of $H_2O_2$ is right below saturation.

In some embodiments, once the controller determines that the proper $H_2O_2$ level in the evaporator has been reached, the method can proceed to step 530 wherein a temperature sensor is configured to monitor temperature continuously. In some embodiments, the controller is configured to maintain the temperature between about 15-50° C.; in some embodiments, the temperature is maintained between about 15-20° C., 20-25° C., 25-30° C., 30-35° C., 35-40° C., 40-45° C., 45-50° C.; in some embodiments, the temperature is maintained at approximately 15° C., 20° C., 25° C., 30° C., 35° C., 40° C., 45° C., 50° C. In some examples, if the temperature is above or below the predetermined threshold noted above, the controller is configured to wait until the proper temperature is reestablished. This can be, for example, at the ambient temperature. In some embodiments, once the controller determines that the proper $H_2O_2$ level in the evaporator has been reached, the method can proceed to step 535 wherein the controller is configured to energize the exhaust blower. In some examples, the exhaust blower can be energized at full power. In some embodiments, full power can be approximately 150 W, 110V AC. In some examples, the exhaust blower can be energized at full power for between 2 to 10 seconds. In some embodiments, the exhaust blower can be energized at full power until approximately 3 volume exchanges of the chamber air has been accomplished. Other amounts are used, depending on the embodiment. For example, one, 2, 4 or 5 volume exchanges can be performed, depending on the embodiment. In some examples, as seen in step 540, the exhaust blower can be controlled through the pressure sensor in the chamber during plasma operation. The pressure in the chamber can be maintained at a preselected pressure. For example, this preselected pressure can be lower than ambient air by approximately 1-2 cm of $H_2O$.

In some embodiments, once the controller determines that the proper $H_2O_2$ level in the evaporator has been reached, the method can proceed to step 545 wherein the controller turns on the circulating blower. In some examples, the circulating blower is on a timer. In some embodiments, the circulating blower can operate at a maximum of 2 Amps and 110V AC. In some examples, the circulating blower can operate to accomplish at least 5-10 volume exchanges per minute, 5-6 volume exchanges per minute, 6-7 volume exchanges per minute, 7-8 volume exchanges per minute, 8-9 volume exchanges per minute, 9-10 volume exchanges per minute; in some examples, the circulating blower can operate to accomplish 5 volume exchanges per minute, 6 volume exchanges per minute, 7 volume exchanges per minute, 8 volume exchanges per minute, 9 volume exchanges per minute, 10 volume exchanges per minute. In some embodiments, after the circulating blower is turned on for a predetermined time, as shown in step 550, the controller can be configured to turn on the plasma generator. In some examples, the predetermined time can be 5 seconds. In some embodiments, the controller can be configured to turn on the plasma generator immediately after the circulating blower is turned on.

Figure 18C:
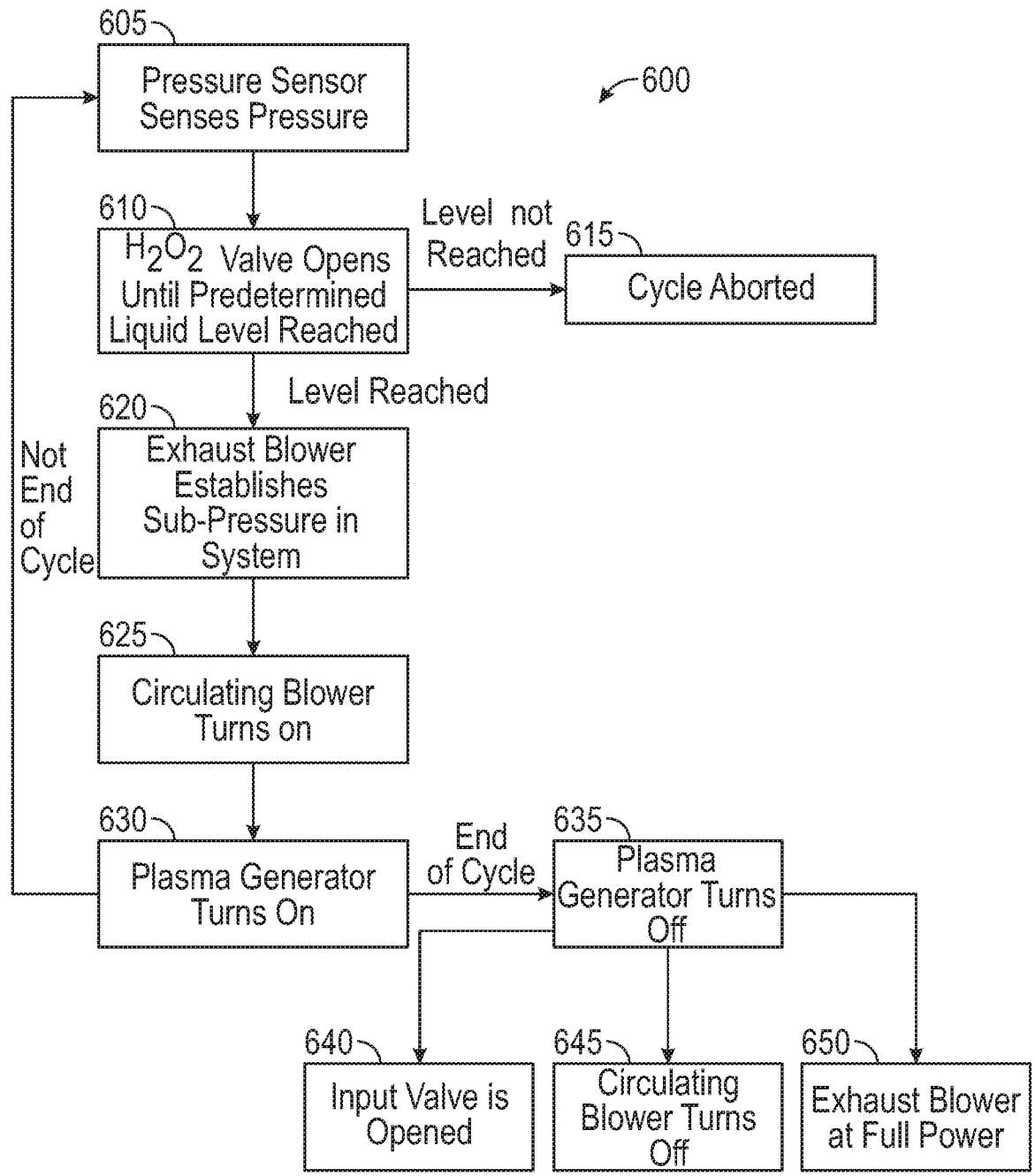
Figure 19:
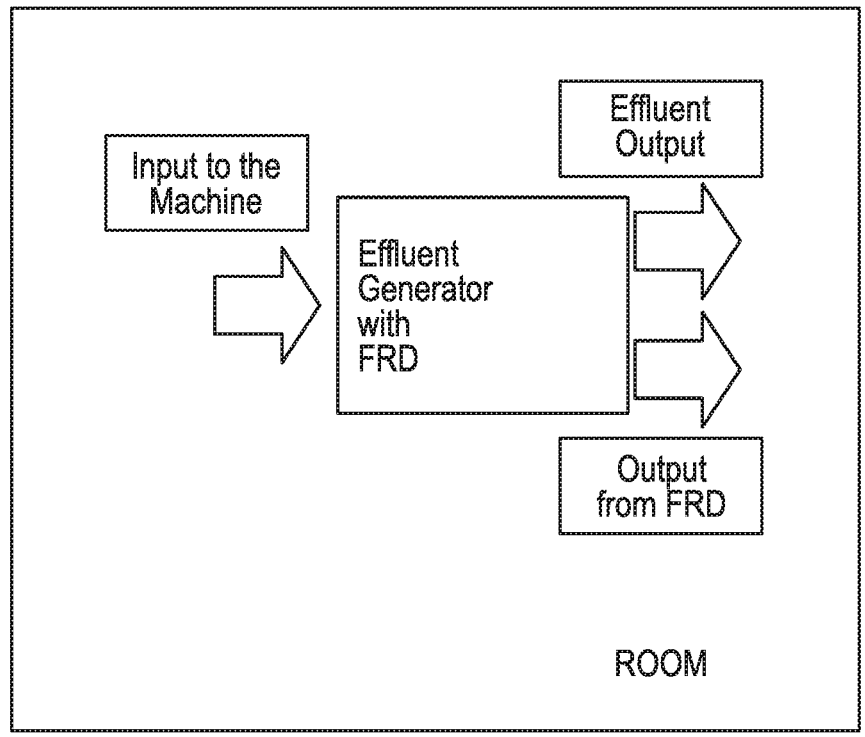
FIG. 19 shows a block diagram of an example embodiment where the sterilant is delivered to the room from an effluent generator with a Free Radical Destroyer (FRD) located in the room.
Figure 20:
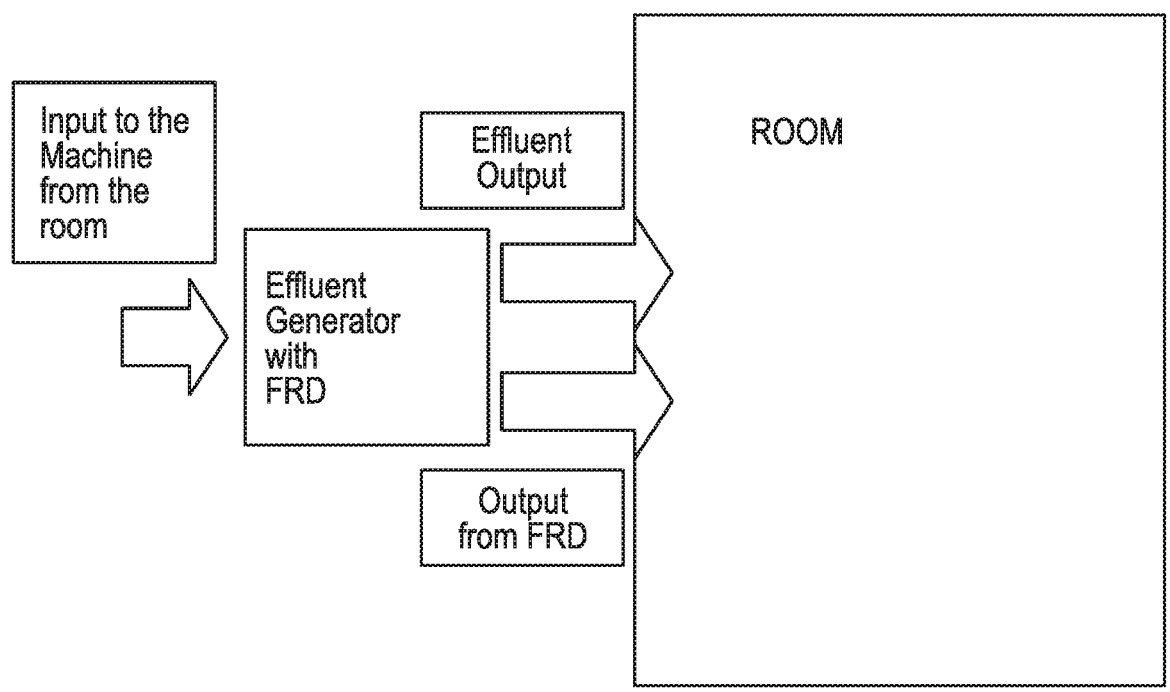
FIG. 20 shows a block diagram of an example embodiment where the sterilant is delivered to the room from an effluent generator with a Free Radical Destroyer (FRD) through the conduits, input and output, connected to the device that is outside of the room.

As discussed above, in some embodiments, the exhaust blower can be controlled through the pressure sensor, wherein the pressure sensor feeds input back into the exhaust blower while the sterilization cycle is active (e.g. the plasma generator is on). An example of the pressure sensor input cycle 600 is illustrated in FIG. 18C. In some embodiments, the pressure sensor input cycle 600 can include step 605 wherein the pressure sensor senses the pressure within the machine 500. In some examples, a sub-pressure in the system can be established at the beginning of the cycle— before the evaporator is filled or after the evaporator is filled. In some embodiments, the system has to be at the predetermined sub-pressure before the circulating blower is turned on. In some embodiments, as shown in step 610, the $H_2O_2$ valve of the canister is configured to open for a predetermined amount of time until a predetermined liquid level is reached. In some embodiments, the predetermined amount of time can be between 0-10 seconds; in some embodiments, the predetermined amount of time can be around 0 seconds, 1 second, 2 seconds, 3 seconds, 4 seconds, 5 seconds, 6 seconds, 7 seconds, 8 seconds, 9 seconds, or 10 seconds. In some examples, the predetermined liquid level can be approximately 1-2 cm of $H_2O$.

In some examples, if the predetermined liquid level is reached, the pressure sensor input cycle 600 is terminated as shown in step 615. In some examples, if the predetermined pressure is reached, the pressure sensor input cycle 600 progresses to step 620. As noted above, and as shown in FIG. 18C, in some examples, the exhaust blower can be configured to establish a sub-pressure within the system. In some embodiments, the sub-pressure in the system can be about 1-2 cm $H_2O$ below ambient. In some embodiments, the exhaust blower is configured to run continuously.

In some embodiments, the pressure sensor input cycle 600 includes step 625 wherein the circulating blower is configured to turn on. Once turned on, in some examples, after a predetermined time of having the circulating blower on, the plasma generator can be configured to turn on, as shown in step 630.

In some examples, near the end of the pressure sensor input cycle 600, the plasma generator can be configured to turn off for a predetermined amount of time as shown in step 635. In some examples, the predetermined amount of time can be between 0-3 seconds; in some examples the predetermined amount of time can be around 0 seconds, 1 second, 2 seconds, or 3 seconds. In some embodiments, the pressure sensor input cycle 600 can then proceed to any one, or all of steps 640, 645, or 650. As shown in FIG. 18C, at step 640, the input valve is opened for a predetermined amount of time. In some embodiments, the predetermined amount of time can be between 0-20 seconds; in some embodiments, the predetermined amount of time can be around 0 seconds, 1 second, 2 seconds, 3 seconds, 4 seconds, 5 seconds, 6 seconds, 7 seconds, 8 seconds, 9 seconds, or 10 seconds. At step 645, the circulating blower can be turned off after the plasma generator is turned off for a predetermined amount of time. At step 650, the exhaust blower can be configured to operate at full power for a predetermined amount of time after the plasma generator is turned off for a predetermined amount of time. In some embodiments, the predetermined amount of time can be between 0-5 seconds; in some embodiments, the predetermined amount of time can be around 0 seconds, 1 second, 2 seconds, 3 seconds, 4 seconds, or 5 seconds.

In some embodiments, the method for sterilization of a machine 500 is configured to include a safety device mounted on the door. The safety device can be configured such that if the door is opened, the method for sterilization of a machine 500 cannot begin or operate. In some embodiments, the safety device can be a switch or a sensor. In some examples, when the door is opened, either or both of the plasma generator and the circulating blower must be turned off and the exhaust blower is put on full power for a predetermined amount of time. In some embodiments, the predetermined amount of time can be between 0-5 seconds; in some embodiments, the predetermined amount of time can be around 0 seconds, 1 second, 2 seconds, 3 seconds, 4 seconds, or 5 seconds. In some examples, the purpose of the exhaust blower is to maintain a negative pressure within the machine or chamber of a device. For example, in the context of a washing machine the exhaust blower can maintain a pressure in the system that yields a water level of between about 0.25 to 1.0 inch below a water level that would exist when pressure is ambient.

In some examples, any of the aforementioned systems for sterilization and/or disinfection can include a safety switch/sensor mounted on the door. In some embodiments, if the door is opened, the system cannot be started operate. In some examples, when the door is opened, the plasma generator and the circulating blower are turned off. In some examples, when the door is opened, the exhaust blower can be put on full power for 5 seconds.

In some examples, the method for sterilization of a machine 500 can optionally include a drying step (e.g., use of a desiccant) to ensure that all moisture is removed from the system for sterilization/disinfection to allow effluent to reach all surfaces, as a layer of water or moisture can impeded the ability for the effluent to kill microorganisms at the surface. In some embodiments, a pulsing approach can be used to remove moisture and to keep bacteria at low levels. In other embodiments, short cycles can be run over short time periods—for example a sterilization and/or disinfection cycle can be run every 5 minutes, 10 minutes, 15 minutes, 20 minutes, etc. This can be important because bacteria, when in favorable growth conditions, can experience exponential growth in minutes.

Low Level Disinfection

Figure 42A:
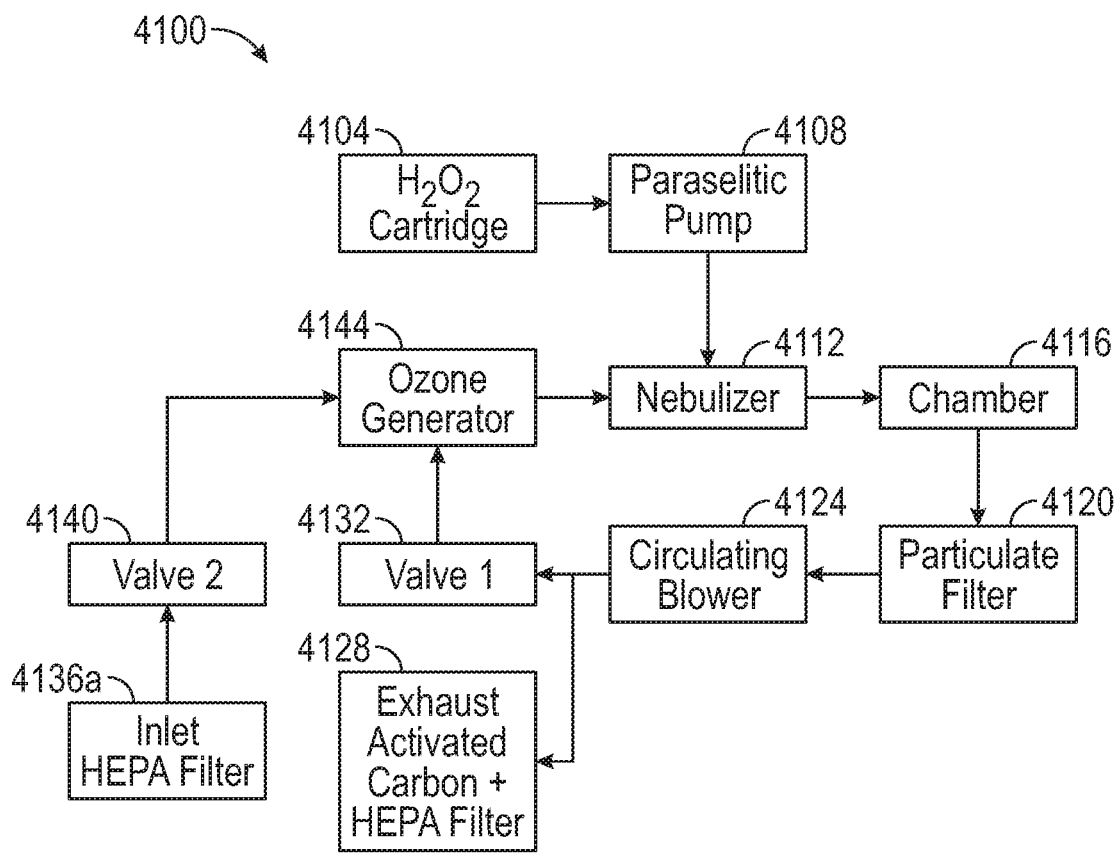
FIG. 42A illustrates a schematic embodiment of a disinfection/sterilization system (e.g. low level/high level disinfection or sterilization system).
Figure 42B:
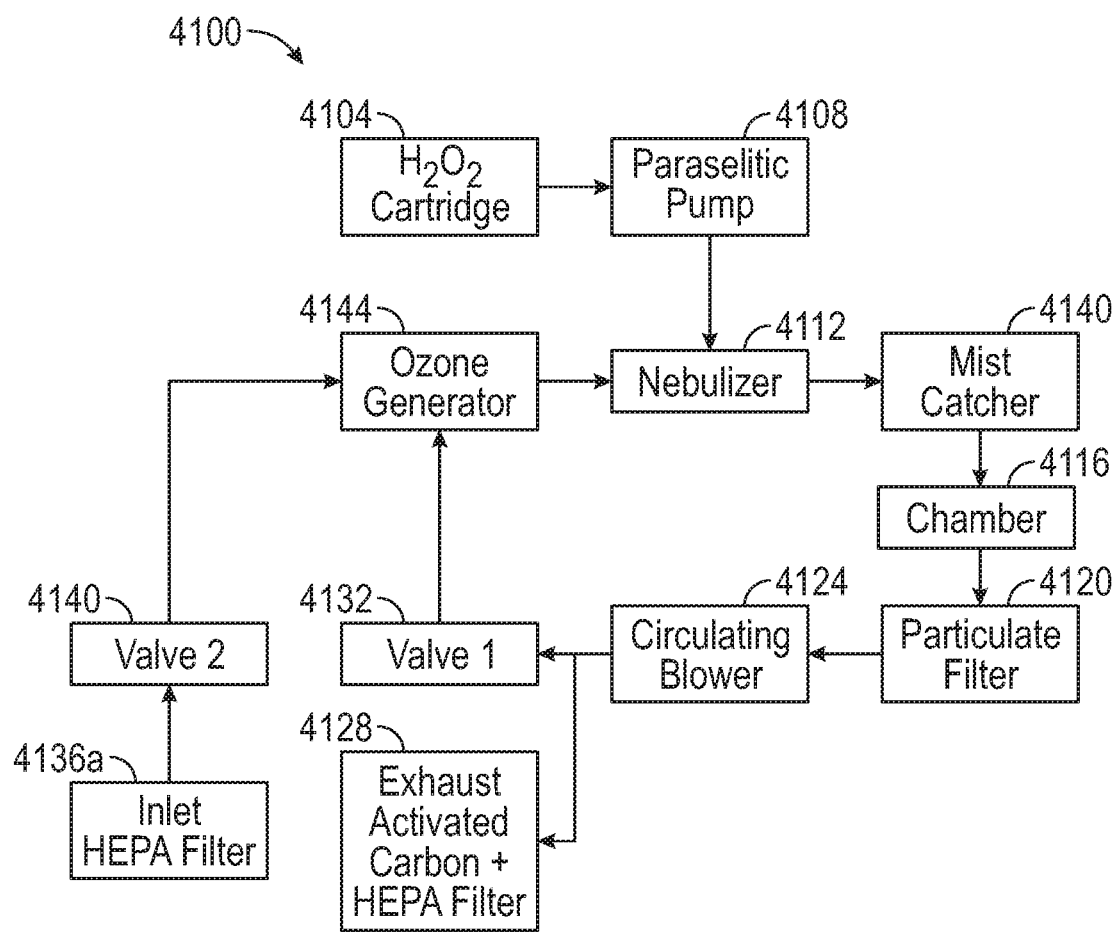
FIG. 42B illustrates another schematic embodiment of a disinfection/sterilization system (e.g. low level/high level disinfection or sterilization system) that includes a mist catcher.

FIGS. 42A-42B illustrate a plurality of embodiments of a disinfection/sterilization system (e.g. low level/high level disinfection system or sterilization system) and associated method for disinfection/sterilization system. FIG. 42A illustrates a schematic of the disinfection/sterilization system 4100. In some embodiments, the disinfection/sterilization system 4100 can include a nebulizer 4112, a disinfection chamber 4116, and a circulating blower 4124. In some examples, the nebulizer 4112 can be fluidly connected with a paraselitic pump 4108 that receives a $H_2O_2$ cartridge 4104. In some embodiments, the nebulizer 4112 can be fluidly connected with an ozone generator 4144.

In some examples the disinfection/sterilization system 4100 can include a circulating blower 4124. Fluid flow can travel from the disinfection chamber 4116 through a particulate filter 4120 to the circulating blower 4124. In some embodiments, the circulating blower 4124 can be configured to blow air through the ozone generator 4144. In some examples, a valve1 4132 controls fluid flow between the circulating blower 4124 and the ozone generator 4144.

In some examples the disinfection/sterilization system 4100 can include an exhaust 4128 and an inlet 4136a. In some embodiments, the exhaust 4128 is fluidly connected to the circulating blower 4124 such that when the valve1 4132 is closed, fluid flow from the circulating blower is blown through the exhaust 4128. In some examples, the exhaust 4128 includes an activated carbon and HEPA filter. In some embodiments, the filter is configured to convert effluent into water vapor and oxygen. In some embodiments, the inlet 4136a is fluidly connected to the ozone generator 4144. In some examples, a valve2 4140 controls fluid flow between the inlet 4136a and the ozone generator 4144. For example, when the valve2 4140 is opened, fluid flow is allowed from the inlet 4136a into the ozone generator 4144. In other examples, when the valve2 4140 is closed, the ozone generator 4144 is sealed from the inlet 4136a. In some embodiments, the inlet 4136a includes a HEPA filter. In some embodiments, the filter is configured to convert effluent into water vapor and oxygen.

Figure 42C:
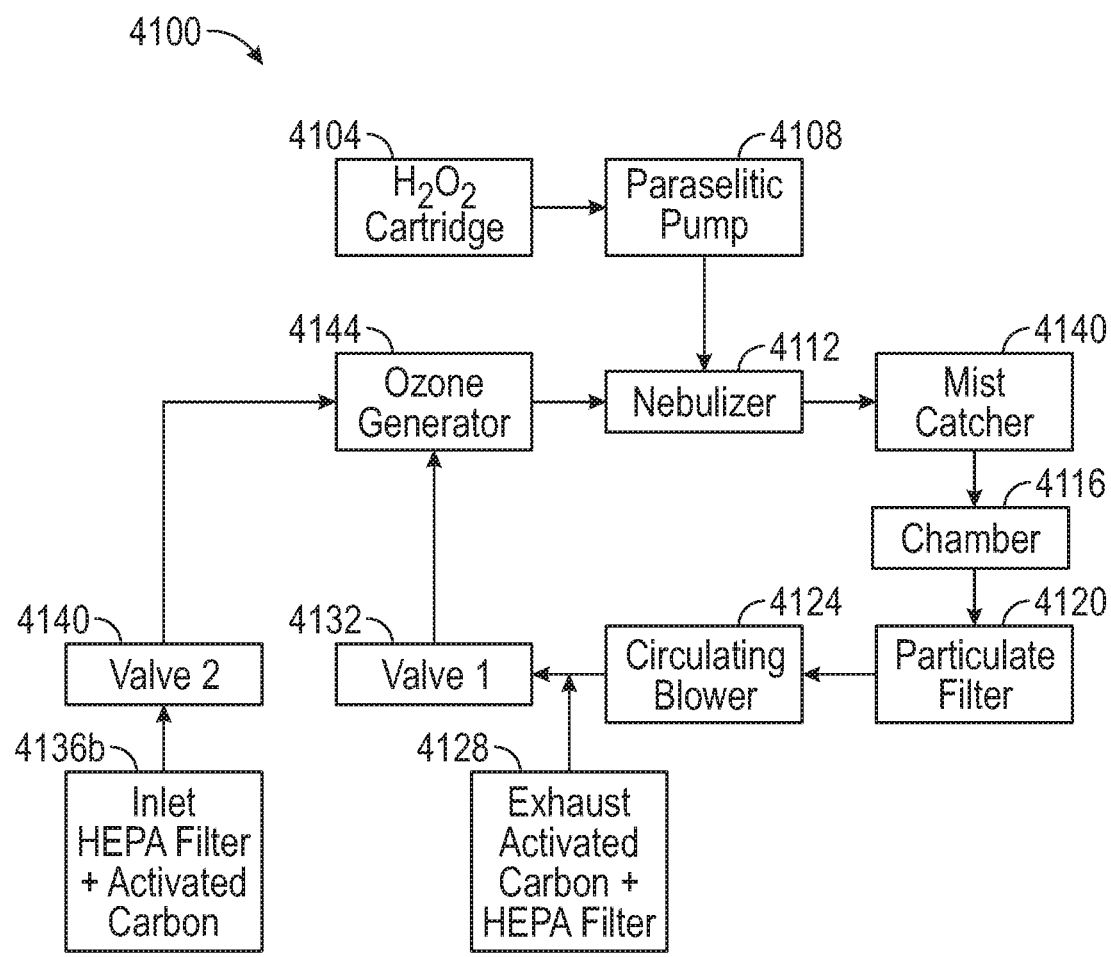
FIG. 42C illustrates another schematic embodiment of a disinfection/sterilization system (e.g. low level/high level disinfection or sterilization system) that includes a mist catcher and wherein the disinfection/sterilization system is configured to operate in contaminated environment by chemical or biological agents.
Figure 42D:
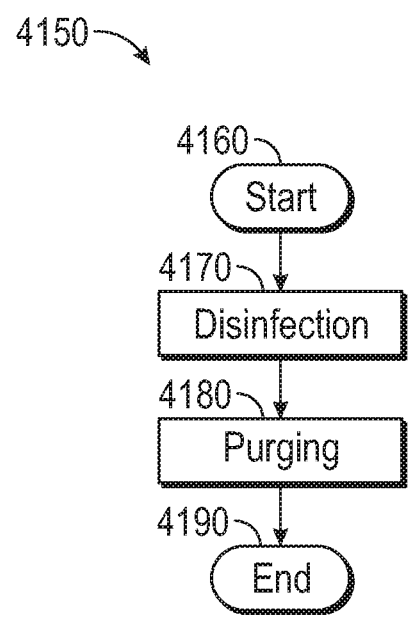
FIG. 42D illustrates a flowchart of a method for disinfection/sterilization according to the embodiment illustrated in FIG. 42A.

FIG. 42D illustrates a flow chart of a method for disinfection/sterilization 4150. Once the method is turned on at start 4160, the method for disinfection/sterilization 4150 can include a disinfection step 4170. At the disinfection step 4170, valve1 4132 can be in the open state while the valve 2 4140 can be in the closed state. At step 4170, the circulating blower 4124 is configured to circulate effluent through the system 4100. In some embodiments, the effluent can flow through the system 4100 from the valve1 4132 to the ozone generator 4144, from the ozone generator 4144 to the nebulizer 4112, from the nebulizer 4112 to the disinfection chamber 4116, and from the disinfection chamber 4116 through the particulate filter 4120 and into the circulating blower 4124. In some examples, the ozone generator 4144 and the nebulizer 4112 can be configured to work on a scheduled time and duty cycle to keep the effluent at an optimized disinfection condition. In some embodiments, the paraselitic pump 4108 is configured to deliver a precise quantity of hydrogen peroxide solution from the $H_2O_2$ cartridge 4104 to the nebulizer 4112. In some examples, the nebulizer delivers the ozone and the sterilant separately. This can be done, for example, through the nebulizer or through a different vaporizing unit. In some embodiments, the ozone generator is not in direct communication with the nebulizer.

In some embodiments, the method for disinfection/sterilization 4150 can include a purging step 4180. At the purging step 4180, valve1 4132 can be closed and valve2 4140 can be opened. In some examples, at the purging step 4180, the circulating blower 4124 pushes the effluent into the exhaust filter 4128 and fresh air is introduced into the disinfection/sterilization system 4100 through the inlet filter 4136. This can help to remove active radicals and/or molecules from the disinfection/sterilization system 4100. The method for disinfection/sterilization 4150 ends at step 4190.

FIG. 42B illustrates another embodiment of the disinfection/sterilization system 4100. As illustrated in FIG. 42B, in some examples, the disinfection/sterilization system 4100 can include a mist catcher 4140. In some embodiments, the mist catcher 4140 is fluidly connected to the nebulizer 4112. In some examples, the mist catcher 4140 is located downstream of the nebulizer 4112. In some embodiments, the mist catcher is configured to collect unvaporized mist from the nebulizer 4112. This can prevent mist deposition in the chamber 4116 and on the surface of the treated items. In some examples, the mist catcher 4140 can be a wicking material that has minimal or a zero pressure drop across and stores small mist droplets. In some embodiments, flowing effluent through the mist catcher 4140 evaporates the stored liquid before the end of the disinfection/sterilization cycle.

In some examples, the nebulizer delivers the ozone and the sterilant separately. This can be done, for example, through the nebulizer or through a different vaporizing unit. In some embodiments, the ozone generator is not in direct communication with the nebulizer. FIG. 42C illustrates another embodiment of the disinfection/sterilization system 4100 illustrated in FIG. 42B. As illustrated in FIG. 42C, in some examples, the disinfection/sterilization system 4100, can be configured to operate in a contaminated environment containing chemical or biological agents. In order to perform in such an environment, the disinfection/sterilization system 4100 can include an inlet 4136b that includes a filter further including activated carbon.

Figure 44A:
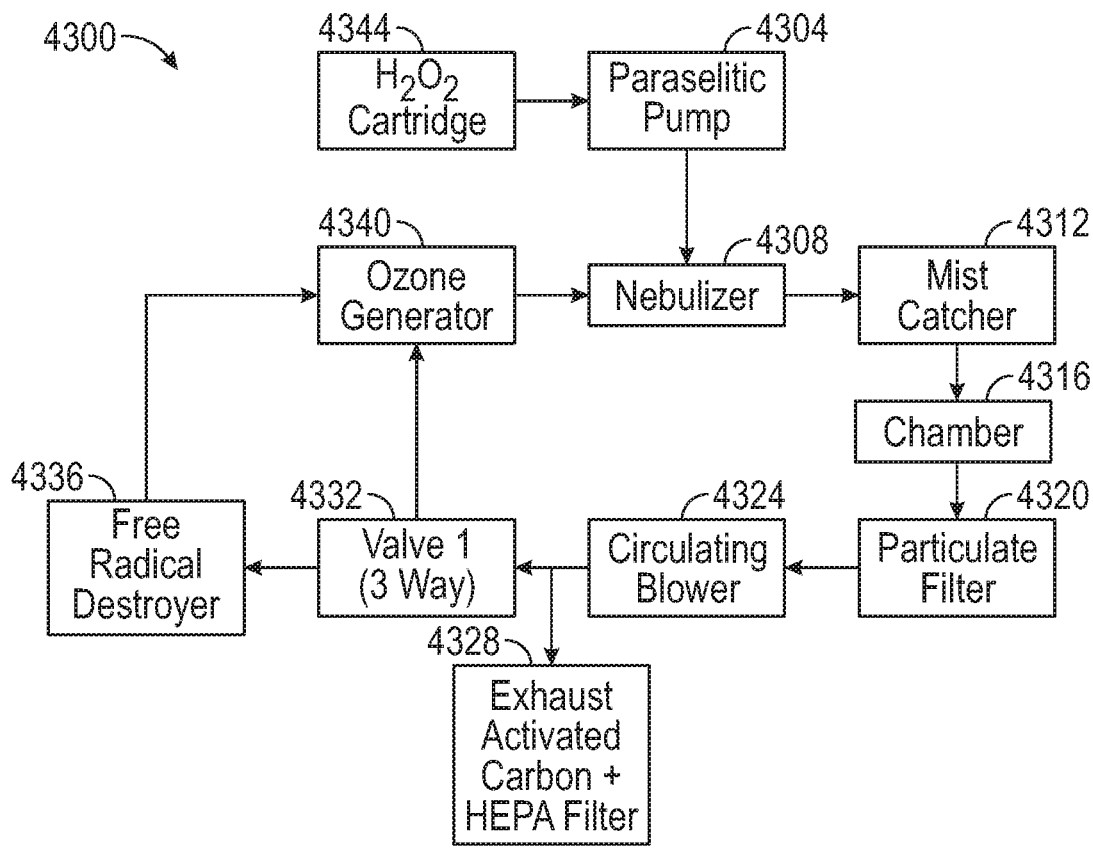
FIG. 44A illustrates a schematic embodiment of another embodiment of a disinfection/sterilization system (e.g. low level/high level disinfection or sterilization system).
Figure 44B:
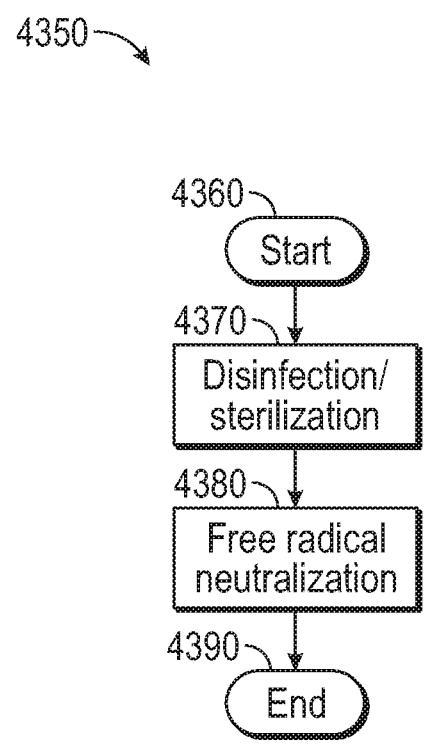
FIG. 44B illustrates a flowchart of a method for disinfection/sterilization according to the embodiment illustrated in FIG. 44A.

FIGS. 44A-44B illustrate another embodiment of a disinfection/sterilization system (e.g. low level/high level disinfection system or sterilization system) and associated method for disinfection/sterilization system. In some embodiments, the disinfection/sterilization system and associated method illustrated in FIGS. 44A-44B is configured to be in a closed environment. The disinfection/sterilization system illustrated can be configured to be operated in an austere, contaminated environment—for example a contaminated environment that includes biological or chemical agents. FIG. 44A illustrates a schematic of the disinfection/sterilization system 4300. In some embodiments, the disinfection/sterilization system 4300 can include a nebulizer 4308, a disinfection chamber 4316, and a circulating blower 4316. In some examples, the nebulizer 4308 can be fluidly connected with a paraselitic pump 4304 that receives a $H_2O_2$ cartridge 4344. In some embodiments, the nebulizer 4308 can be fluidly connected with an ozone generator 4340.

In some examples, the nebulizer delivers the ozone and the sterilant separately. This can be done, for example, through the nebulizer or through a different vaporizing unit. In some embodiments, the ozone generator is not in direct communication with the nebulizer.

In some examples, the disinfection/sterilization system 4300 can include a circulating blower 4324. Fluid flow can travel from the disinfection chamber 4316 through a particulate filter 4320 to the circulating blower 4324. In some embodiments, the circulating blower 4324 can be configured to blow air through the ozone generator 4340.

In some embodiments, the valve1 4332 is a three-way valve. The three-way valve of valve1 4332 can be configured to control fluid flow between the circulating blower 4324 and the ozone generator 4340.

In some examples, the disinfection/sterilization system 4300 can include an exhaust 4328. In some embodiments, the exhaust 4328 is fluidly connected to the circulating blower 4324 such that when the valve1 4332 is closed, fluid flow form the circulating blower 4324 is blown through the exhaust 4328. In some examples, the exhaust 4328 includes an activated carbon and HEPA filter. In some embodiments, the filter is configured to convert effluent into water vapor and oxygen.

In some embodiments, the disinfection/sterilization system 4300 can include a free radical destroyer 4336. The free radical destroyer 4336 can be fluidly connected to the circulating blower 4324 when the valve1 4332 is opened. In some examples, the free radical destroyer 4336 is fluidly connected with the ozone generator 4340.

In some examples, the disinfection/sterilization system 4300 can include a mist catcher 4312. In some embodiments, the mist catcher 4312 is fluidly connected to the nebulizer 4308. In some examples, the mist catcher 4312 is located downstream of the nebulizer 4308. In some embodiments, the mist is configured to collect unvaporized mist from the nebulizer 4208.

FIG. 44B illustrates a flow chart of a method for disinfection/sterilization 4350. Once the method is turned on at start 4360, the method for disinfection/sterilization 4350 can include a disinfection/sterilization step 4370. At the disinfection/sterilization step 4370, valve1 4332 can be opened and configured to direct the flow into the ozone generator 4340. In some examples, during the disinfection/sterilization step 4370, a portion of the valve1 4332 is closed such that the system 4300 is closed. During the disinfection/sterilization step 4370, the effluent can circulate through the system 4300. In some embodiments, the effluent can flow from the circulating blower 4324 to the valve1 4332, from the valve1 4332 to the ozone generator 4340, form the ozone generator 4340 to the nebulizer 4308, from the nebulizer 4308 to the mist catcher 4312, from the mist catcher 4312 to the disinfection/sterilization chamber 4316, from the disinfection/sterilization chamber 4316 to the particulate filter 4320, and from the particulate filter 4320 to the circulating blower 4324. In some embodiments, the paraselitic pump 4304 is configured to deliver a precise quantity of hydrogen peroxide solution from the $H_2O_2$ cartridge 4344 to the nebulizer 4308.

As noted above, in some examples the mist catcher 4312 is fluidly connected to the nebulizer 4308. As illustrated in FIG. 44A, in some embodiments, the mist catcher 4312 is located downstream of the nebulizer 4308. The mist catcher 4230 can be configured to collect unvaporized mist from the nebulizer 4308. This can prevent mist deposition in the chamber 4316 and on the surface of the treated items. In some examples, the mist catcher 4312 can be a wicking material that has minimal or a zero pressure drop across and stores small mist droplets. In several embodiments, the wicking material (whether for the mist catcher or other elements of the systems disclosed herein) is a synthetic fiber. In several embodiments, the synthetic fiber comprises polyester fibers. Optionally the fibers comprise a moisture-absorbing finish. In several embodiments, the wicking material comprises a combination of both hydrophobic (water-repellent) and hydrophilic (water-attracting) fibers. In some embodiments, flowing effluent through the mist catcher 4312 evaporates the stored liquid before the end of the disinfection/sterilization cycle.

In some embodiments, the method for disinfection/sterilization 4350 can involve a free radical neutralization step 4380. At the free radical neutralization step, the valve1 4332 is configured to direct the circulating effluent to the free radical destroyer 4336. In some examples, during the free radical neutralization step 4380, the ozone generator 4340 and the nebulizer 4308 can be turned off.

High Level Disinfection

Figure 43A:
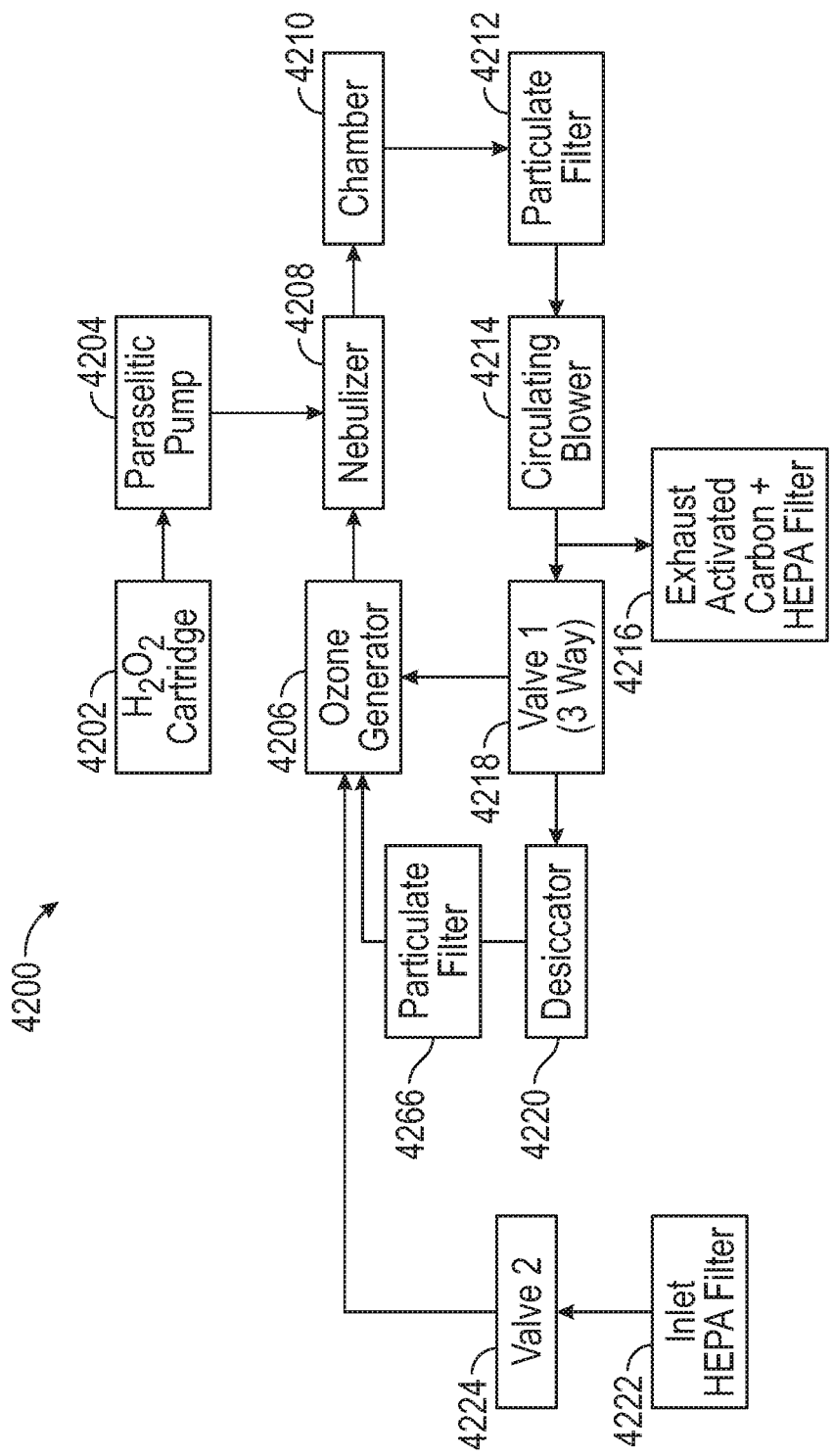
FIG. 43A illustrates a schematic embodiment of a high level disinfection and sterilization system.
Figure 43B:
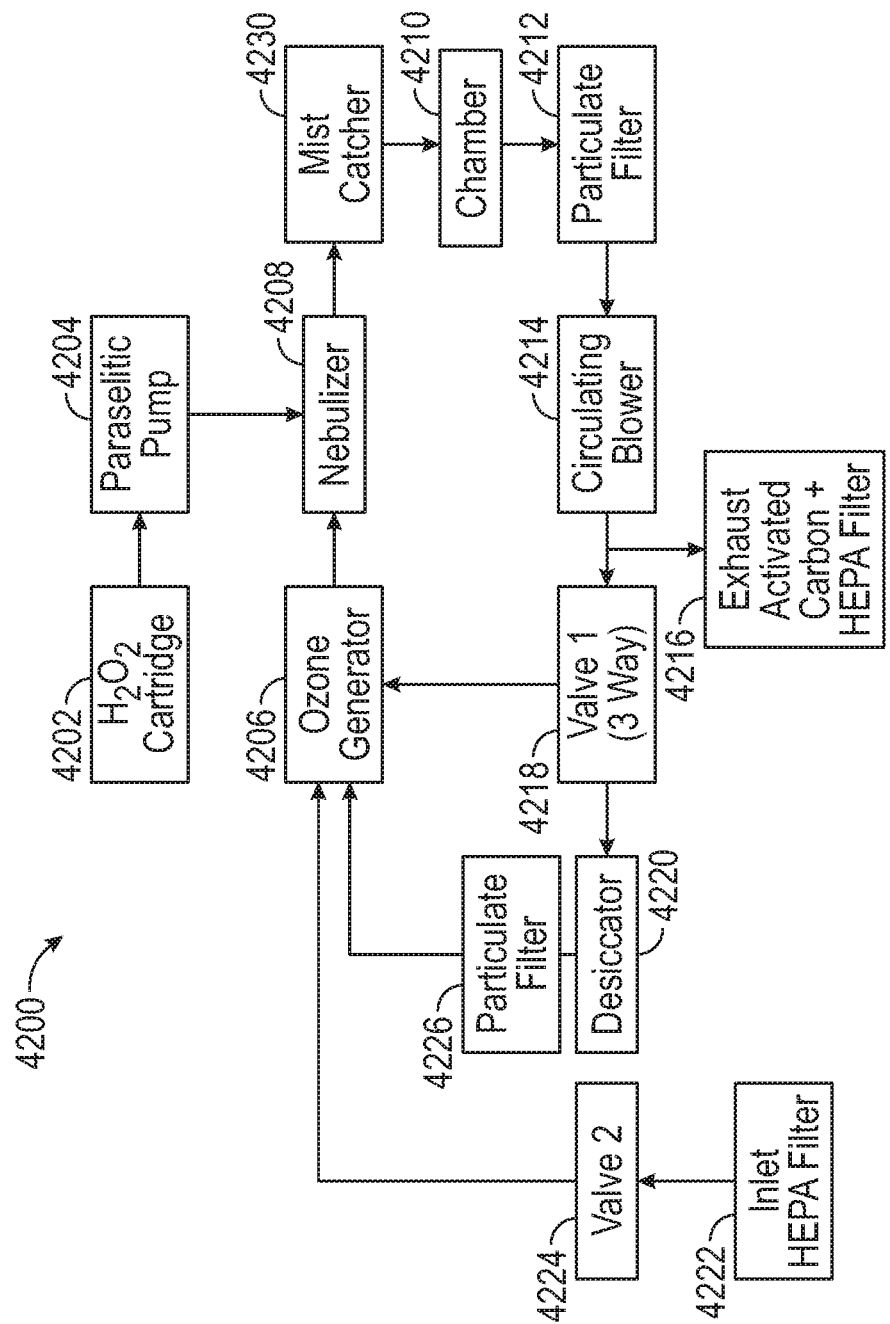
FIG. 43B illustrates another schematic embodiment of a high level disinfection and sterilization system that includes a mist catcher.
Figure 43C:
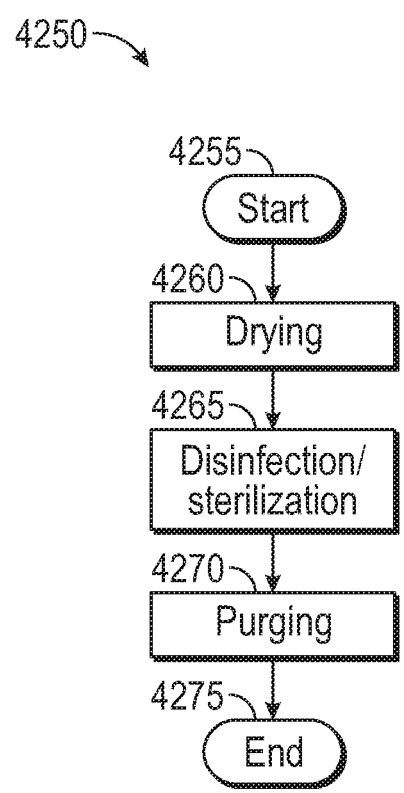
FIG. 43C illustrates a flowchart of a method for high level disinfection and sterilization according to the embodiment illustrated in FIG. 43A.

FIGS. 43A-43C illustrate an embodiment of a high level disinfection/sterilization system and associated method for high level disinfection/sterilization. The high level disinfection/sterilization system and associated method of FIGS. 43A-43B is largely similar to the disinfection/sterilization system of FIGS. 42A-42B with a few exceptions. For example, as shown in FIG. 43A, the high level disinfection/sterilization system includes a desiccator 4220. Similarly, as shown in FIG. 43C, the method for high level disinfection/sterilization includes a drying step 4255 not present in the method for disinfection/sterilization.

FIG. 43A illustrates a schematic of the high level disinfection/sterilization system 4200. In some embodiments, the high level disinfection/sterilization system 4200 can include a nebulizer 4208, a disinfection/sterilization chamber 4210, and a circulating blower 4214. In some examples, the nebulizer 4208 can be fluidly connected with a paraselitic pump 4204 that receives a $H_2O_2$ cartridge 4202. In some embodiments, the nebulizer 4208 can be fluidly connected with an ozone generator 4206.

In some examples, the nebulizer delivers the ozone and the sterilant separately. This can be done, for example, through the nebulizer or through a different vaporizing unit. In some examples, the high level disinfection/sterilization system 4200 can include a circulating blower 4214. Fluid flow can travel through the sterilization/disinfection chamber 4210 through a particulate filter 4212 to the circulating blower 4214. In some embodiments, the circulating blower 4214 can be configured to blow air through the ozone generator 4206. In some examples a valve1 4218 controls fluid flow between the circulating blower 4214 and the ozone generator 4206.

In some embodiments, the valve1 4218 is a three-way valve. The three-way valve of valve1 4218 can be configured to control fluid flow between the circulating blower 4214 and the ozone generator 4206 or dessicator 4220.

In some examples, the high level disinfection/sterilization system 4200 can include an exhaust 4216 and an inlet 4222. In some embodiments, the exhaust 4216 is fluidly connected to the circulating blower 4214 such that when the valve1 4218 is closed, fluid flow from the circulating blower is blown through the exhaust 4216. In some examples, the exhaust 4216 includes an activated carbon and HEPA filter. In some embodiments, the filter is configured to convert effluent into water vapor and oxygen. In some embodiments, the inlet 4222 is fluidly connected to the ozone generator 4226. In some examples, a valve2 4224 controls fluid flow between the inlet 4222 and the ozone generator 4206. For example, when the valve2 4224 is opened, fluid flow is allowed from the inlet 4222 into the ozone generator 4206. In other examples, when the valve2 4224 is closed, the ozone generator 4206 is sealed from the inlet 4222. In some embodiments, the inlet 4222 includes a HEPA filter. In some embodiments, the filter is configured to convert effluent into water vapor and oxygen.

In some embodiments, the high level disinfection/sterilization system 4200 can include a desiccator 4220. The desiccator 4220 can be fluidly connected to the circulating blower 4214 when the valve1 4218 is opened. In some examples, the desiccator 4220 is fluidly connected with the ozone generator 4206. In some embodiments, a particulate filter 4226 is located between the desiccator 4220 and the ozone generator 4206.

FIG. 43C illustrates a flow chart of a method for high level disinfection/sterilization 4250. Once the method is turned on at start 4255, the method for high level disinfection/sterilization 4250. Once the method is turned on at start 4255, the method for high level disinfection/sterilization 4250 can include drying step 4260. At the drying step 4260, valve1 4218 is configured to be in a position to direct fluid flow through the desiccator 4220 so as to dry the air flowing through the system 4200 of FIG. 43A. In some examples, so as to create a closed system and prevent the inflow of fluid from the outside environment, the valve2 424 can be closed. During the drying step 4260, the circulating blower 4214 can circulate the effluent through the system 4200. In some embodiments, the effluent can flow from the circulating blower 4214 through the valve1 4218, from the valve1 4218 to the desiccator 4220, from the desiccator 4220 to the ozone generator 4206, from the ozone generator 4206 to the nebulizer 4208, from the nebulizer 4208 to the disinfection/sterilization chamber 4210, from the disinfection/sterilization chamber 4210 to the particulate filter 4212, and from the particulate filter 4212 to the circulating blower 4214.

In some embodiments, the method for high level disinfection/sterilization 4250 can include a disinfection/sterilization step 4265. At the disinfection/sterilization step 4265, valve1 4218 can be opened and configured to direct the flow into the ozone generator 4206. As the valve1 4218 is opened to allow fluid flow into the ozone generator 4206, this bypasses the desiccator 4220. In some examples, during the disinfection/sterilization step 4265 the valve2 4224 is closed such that the system 4200 is closed and no fluid is allowed through the inlet during this step. During the disinfection/sterilization step 4265, the effluent can circulate through the system 4200. In some embodiments, the effluent can flow from the circulating blower 4214 to the valve1 4218, from the valve1 4218 to the ozone generator 4206, from the ozone generator 4206 to the nebulizer 4208, from the nebulizer 4208 to the disinfection/sterilization chamber 4210, from the disinfection/sterilization chamber 4210 to the particulate filter 4212, and from the particulate filter 4212 to the circulating blower 4214. In some examples, the ozone generator 4206 and the nebulizer 4208 can be configured to work on a scheduled time and duty cycle to keep the effluent at an optimized disinfection/sterilization condition. In some embodiments, the paraselitic pump 4204 is configured to deliver a precise quantity of hydrogen peroxide solution from the $H_2O_2$ cartridge 4202 to the nebulizer 4208.

In some examples, the nebulizer delivers the ozone and the sterilant separately. This can be done, for example, through the nebulizer or through a different vaporizing unit. In some embodiments, the ozone generator is not in direct communication with the nebulizer.

In some embodiments, the method for high level disinfection/sterilization 4250 can include a purging step 4270. At the purging step 4270, valve1 4218 can be closed and valve2 4224 can be opened. In some examples, at the purging step 4270, the circulating blower 4214 pushes the effluent into the exhaust filter 4216 and fresh air is introduced into the high level disinfection/sterilization system 4200 through the inlet filter 4222. This can help to remove active radicals and/or molecules form the high level disinfection/sterilization system 4200. The method for high level disinfection/sterilization 4250 ends at step 4275.

FIG. 43B illustrates another embodiment of the high level disinfection/sterilization system 4200. As illustrated in FIG. 43B, in some examples, the high level disinfection/sterilization system 4200 can include a mist catcher 4230. In some embodiments, the mist catcher 4230 is fluidly connected to the nebulizer 4208. In some examples, the mist catcher 4230 is located downstream of the nebulizer 4208. In some embodiments, the mist catcher is configured to collect unvaporized mist from the nebulizer 4208. This can prevent mist deposition in the chamber 4210 and on the surface of the treated items. In some examples, the mist catcher 4230 can be a wicking material that has minimal or a zero pressure drop across and stores small mist droplets. In some embodiments, flowing effluent through the mist catcher 4140 evaporates the stored liquid before the end of the disinfection/sterilization cycle.

UV Based Ozone Generator

In many disinfection and sterilization systems, a dielectric barrier discharge (DBD) is used for ozone generation—particularly in low level disinfection systems. Generally, DBD systems are prone to generate, in addition to ozone, small amounts (e.g. 20 ppm) of nitrogen oxide species that can frequently lead to the formation of nitric acid ($HNO_3$). Nitric acid is generally not a desirable component as it causes corrosion, particularly in metals and circuit boards. As a result, material compatibility can frequently be a problem in systems with DBD. That is to say, the use of DBD may not be desirable for the sterilization of high value instruments that contain metals or circuit boards.

In order to improve material compatibility in disinfection and sterilization systems—particularly for high value medical instruments—elimination or significant decrease of nitric acid production by ozone generator is needed. In some embodiments, for example the low level disinfection system and high level disinfection/sterilization system of FIGS. 42A-42B and 43A-43B, the ozone generator can be UV based.

In some embodiments, the ozone generator is a low pressure mercury ozone generator. In some examples, a low pressure mercury ozone generator can be configured to be used in water ozonation application and can have good bactericidal properties.

In some embodiments, the ozone generator is a $Xe_2$ Excimer ozone generator. In some examples, the $Xe_2$ Excimer ozone generator can be configured to have significantly better ozone generation efficiency (e.g. 40%) and the amount of nitric acid produced can be 0.2 ppm which is approximately 100 times lower than using DBD ozone generator. In some embodiments, the small amount of nitric acid produced can improve material compatibility significantly.

Additional Embodiments

In some embodiments, the disclosed system for sterilization/disinfection can be used in a variety of settings. To allow for use in various settings, the disclosed systems can be tailored for use in various environments where space or mobility is a concern.

For example, the systems provided for herein can be configured to be self-contained, variable size, light-weight and/or portable. In some instances, some embodiments can be battery operated or powered by hand or can be scaled to larger volume. The systems disclosed herein can be height adjustable and/or portable. These embodiments can, for example, be small enough to be moved from one site to another, or provided on a rolling cart or other mobile accessory.

The systems disclosed herein, can be front loading, top loading, or loaded by any other approach. In some examples, the system can include a sliding container comprising items to be sterilized/disinfected in the sterilizing/disinfecting chamber.

In some embodiments, the system can be self-contained with respect to its conduit plumbing. In other embodiments, the systems can be hard-plumbed, such that the various conduits external to the system are provided by a pre-existing infrastructure. For example, the system can include pre-existing infrastructure that outputs to the environment, is provided with air input, includes a heater or dryer, and can include a sterilant or disinfectant source.

As illustrated, as non-limiting examples of embodiments disclosed herein, in FIGS. 30A-30I, 31A-31C, 32A-32H, 33A-33B, 34A-34B, and 35A-35C, the system for sterilization/disinfection can be embodied in a variety of devices for use in various environments. Each of these embodiments will be discussed in turn.

Desktop Unit

In some embodiments, the system for sterilization and disinfection can be a desktop unit. As illustrated in FIGS.

30A-30B, in some embodiments, the desktop unit can be self-contained and placed on a surface. The size of the desktop unit can allow the system to be used in a variety of environments. For example, the desktop sterilization and disinfection unit can be used in a commercial setting (e.g., healthcare) or other industrial applications. FIGS. 30C-30D provides an example of the desktop unit in a healthcare setting.

Figure 30A:
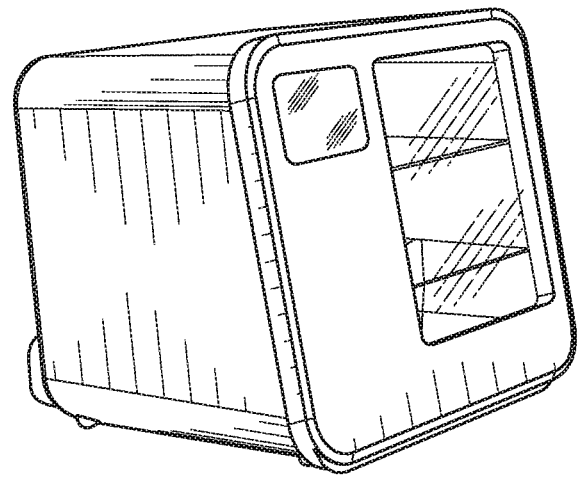
FIGS. 30A-30D show an embodiment of a system for sterilization and/or disinfection for use on a countertop.
Figure 30B:
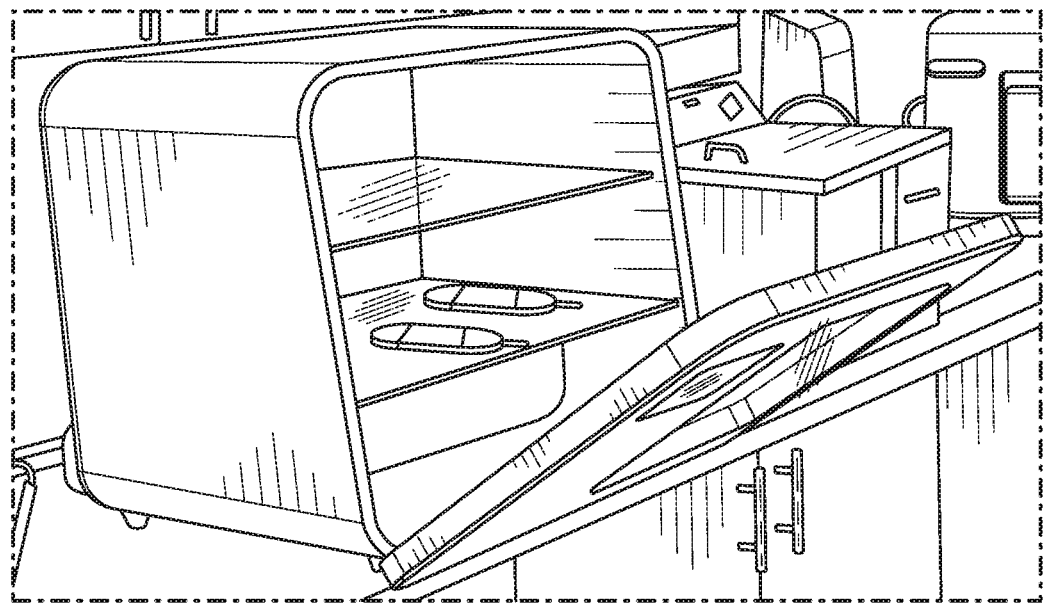
Figure 30C:
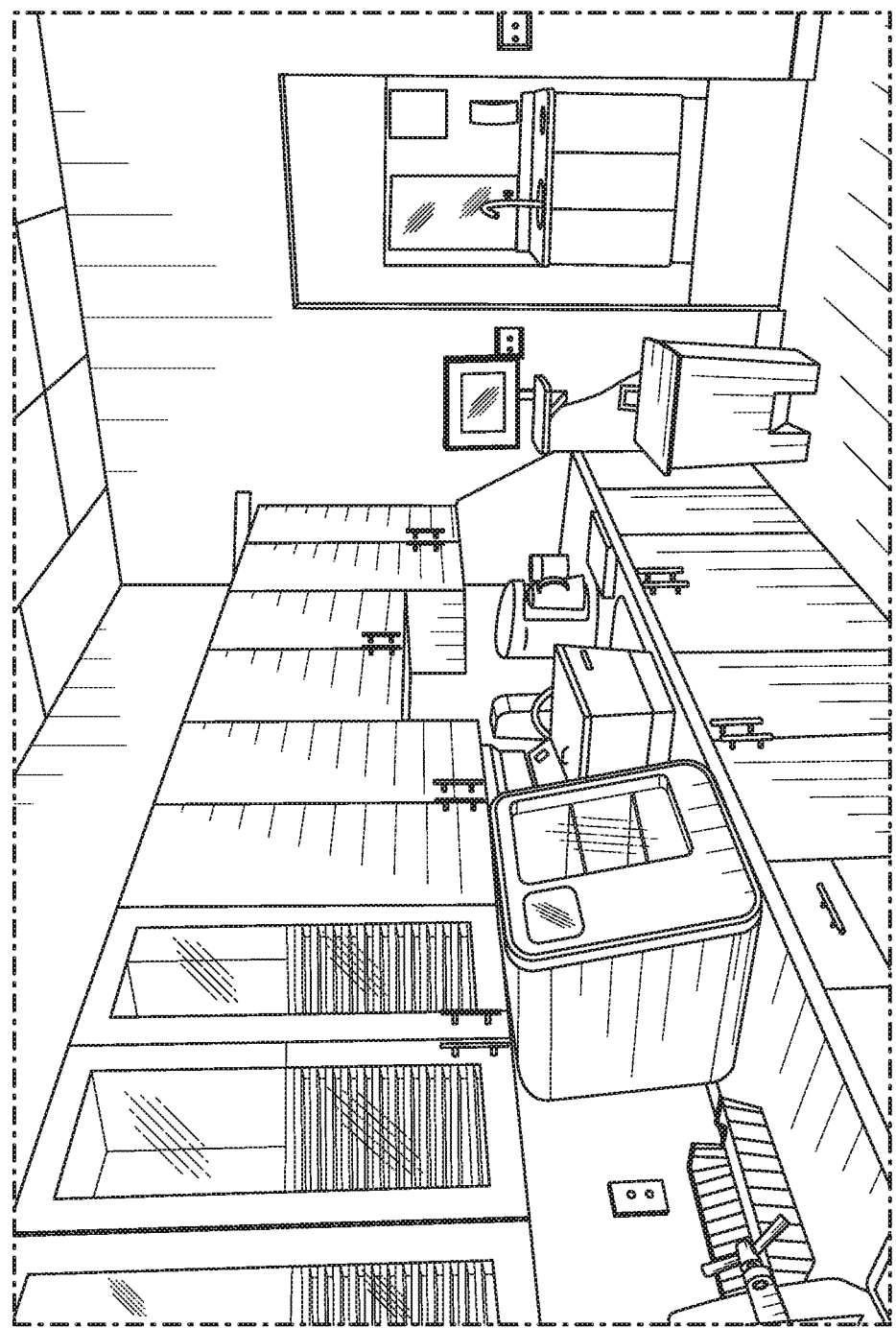
Figure 30D:
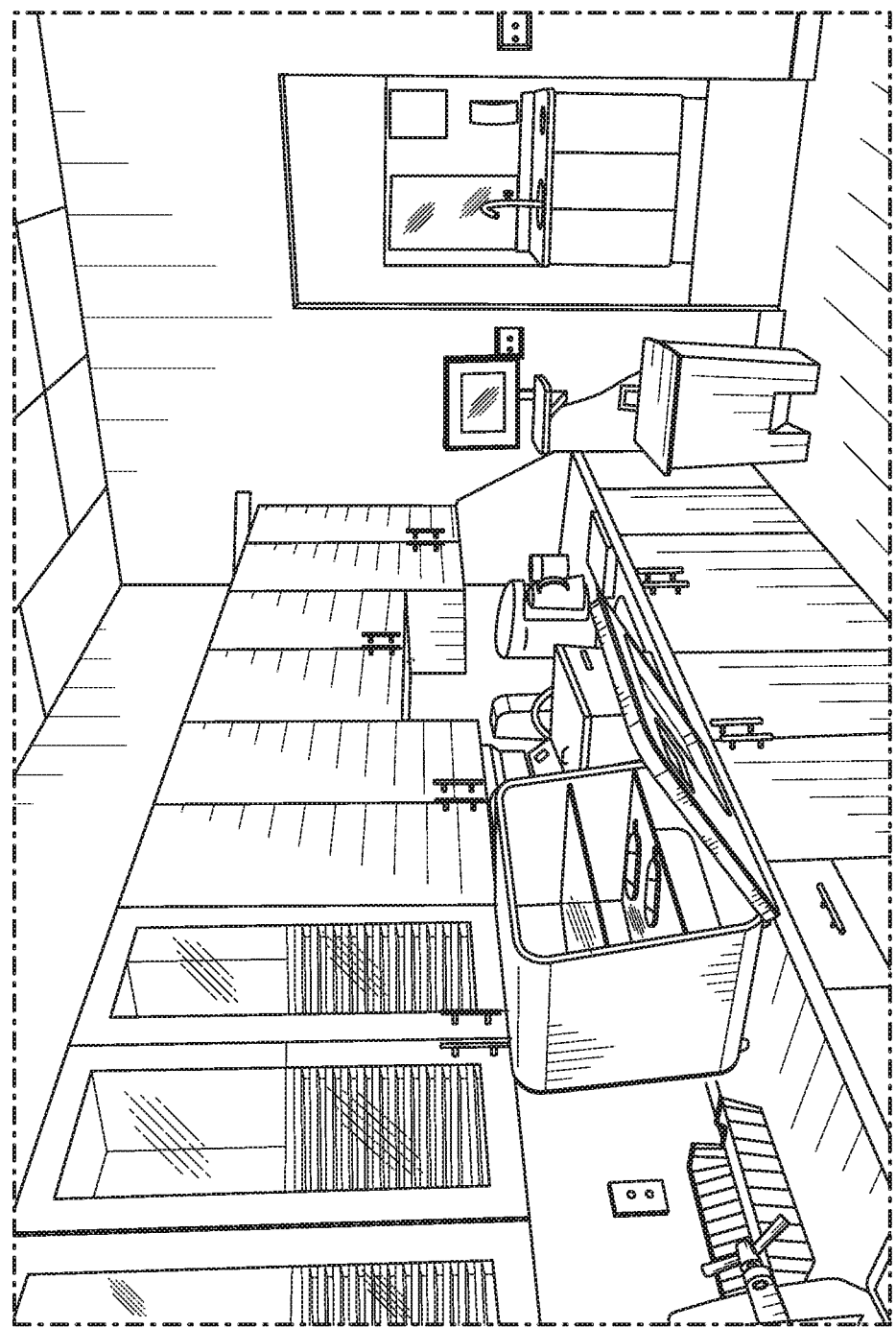

FIGS. 30B and 30D illustrate an example of the embodiment of the system with the door opened. In some embodiments, as illustrated in FIGS. 30B and 30D, the desktop unit has a front-loading hinged door. However, the desktop unit can have any type of opening that allows a user to have easy access to the interior of the system for sterilization/disinfection. For example, the desktop unit can be top-loading, front loading, include a window sash, or open from either side of the desktop unit. In some embodiments, the desktop unit can have built in shelving units. This can, for example, provide for convenient sterilization of multiple items (e.g. electronic devices). This can allow personal items brought into a setting is sterilized and disinfected.

Figure 30E:
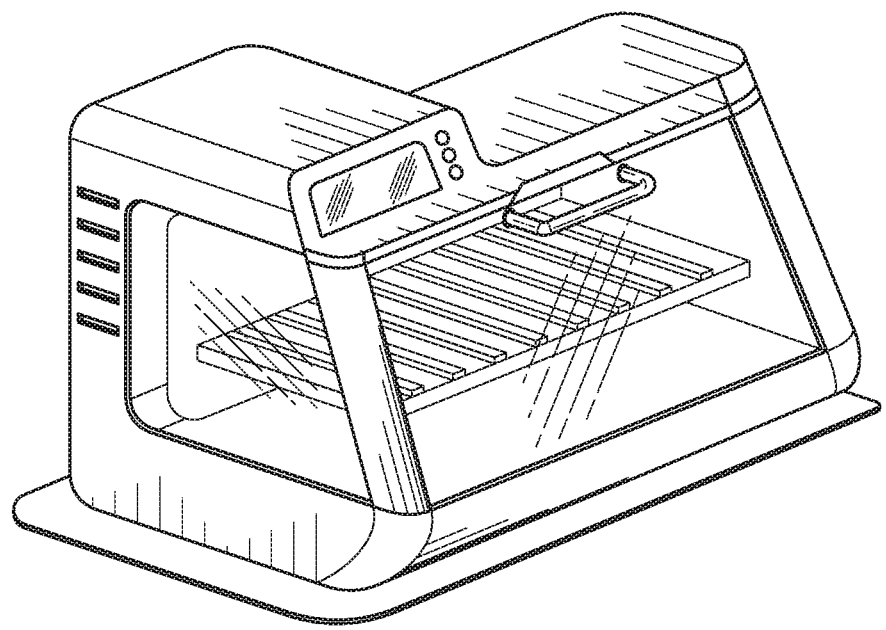
FIGS. 30E-30I show a plurality of other embodiments of the system for sterilization and/or disinfection for use on a countertop.
Figure 30F:
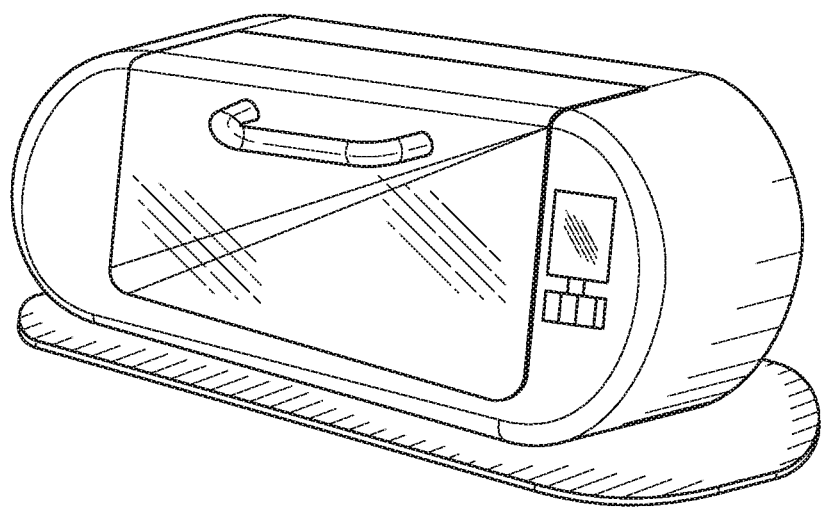
Figure 30G:
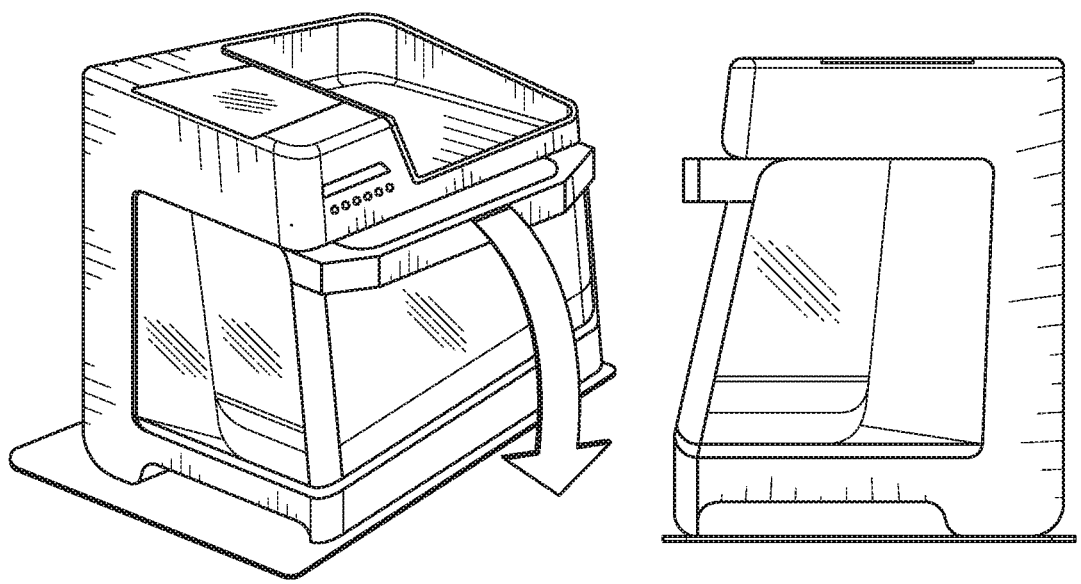
Figure 30H:
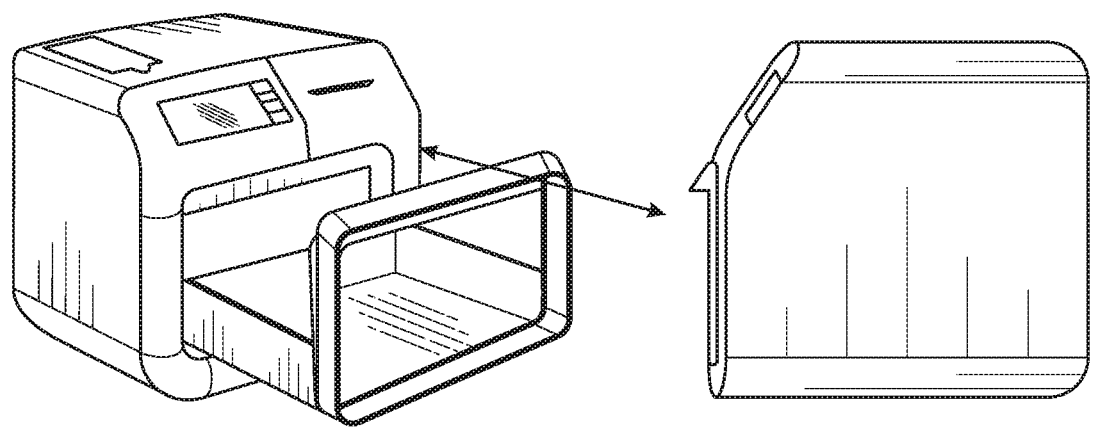
Figure 30I:
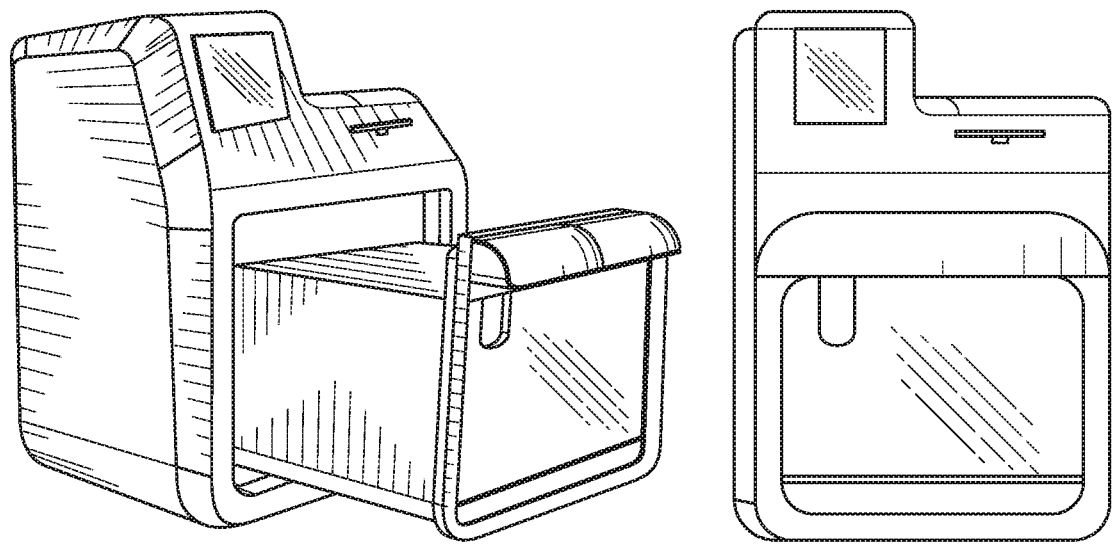

FIGS. 30E-30I illustrate alternative embodiments of desktop units that are configured to provide sterilization/disinfection of items. As with the embodiment illustrated in FIGS. 30A-30D, the desktop units of FIGS. 30E-30G can be compact such that they can be placed on the surface of a setting to allow for the sterilization/disinfection of, for example, personal or unclean items brought into an environment. As noted above, the desktop unit can have any type of opening that allows a user to have easy access to the interior of the system for sterilization/disinfection. For example, the embodiments illustrated in FIGS. 30E-30G illustrate embodiments of desktop units that have a hinged front-loading door. The embodiments illustrated in FIGS. 30H-30I illustrate desktop units with a front pull-out drawer.

Consumer Unit

FIGS. 27A-27C illustrate another embodiment of a desktop unit. As noted above, the desktop sterilization/disinfection unit can provide a compact sterilization/disinfection system that can be used in a variety of environments. In some embodiments, the desktop unit can be a consumer unit that can be used in a home or in an office setting. As with the desktop unit disclosed above, the consumer unit can be used to sterilize or disinfect personal items such as mobile phones, toys, notebooks, writing utensils, etc.

As described with regard to the desktop unit above, the consumer unit can have any type of opening that allows a user to have easy access to the interior of the system for sterilization/disinfection. For example, the desktop unit can be top-loading, front loading, include a window sash, or open from either sides of the desktop unit. As illustrated in FIGS. 27A-27C, the consumer unit can have a pull-out drawer to provide for the loading of items for sterilization/disinfection.

Figure 31A:
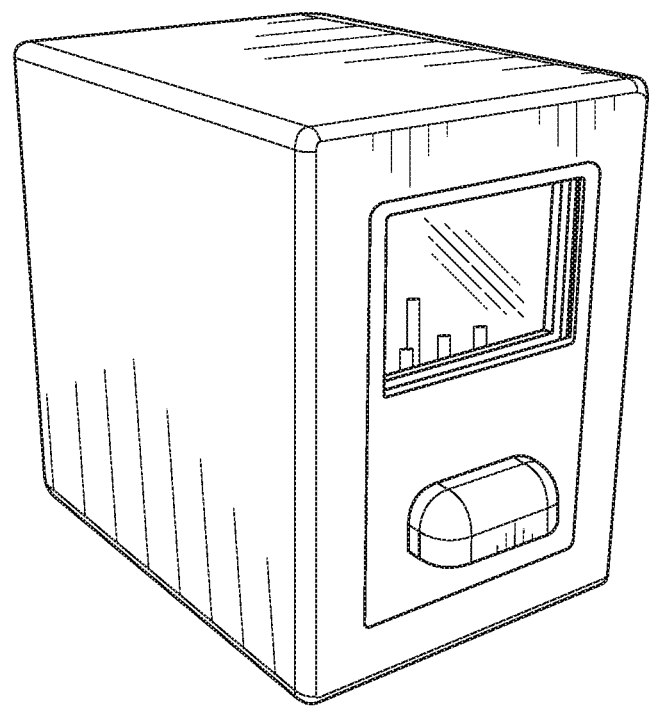
FIGS. 31A-31C show an embodiment of a desktop system for sterilization and/or disinfection for consumer use. For example, the embodiment illustrated in FIGS. 31A-31C can be used for cleaning baby bottles.
Figure 31B:
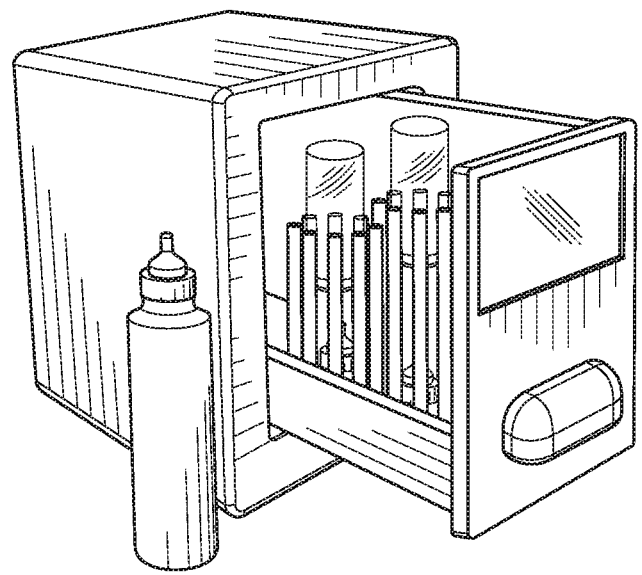
Figure 31C:
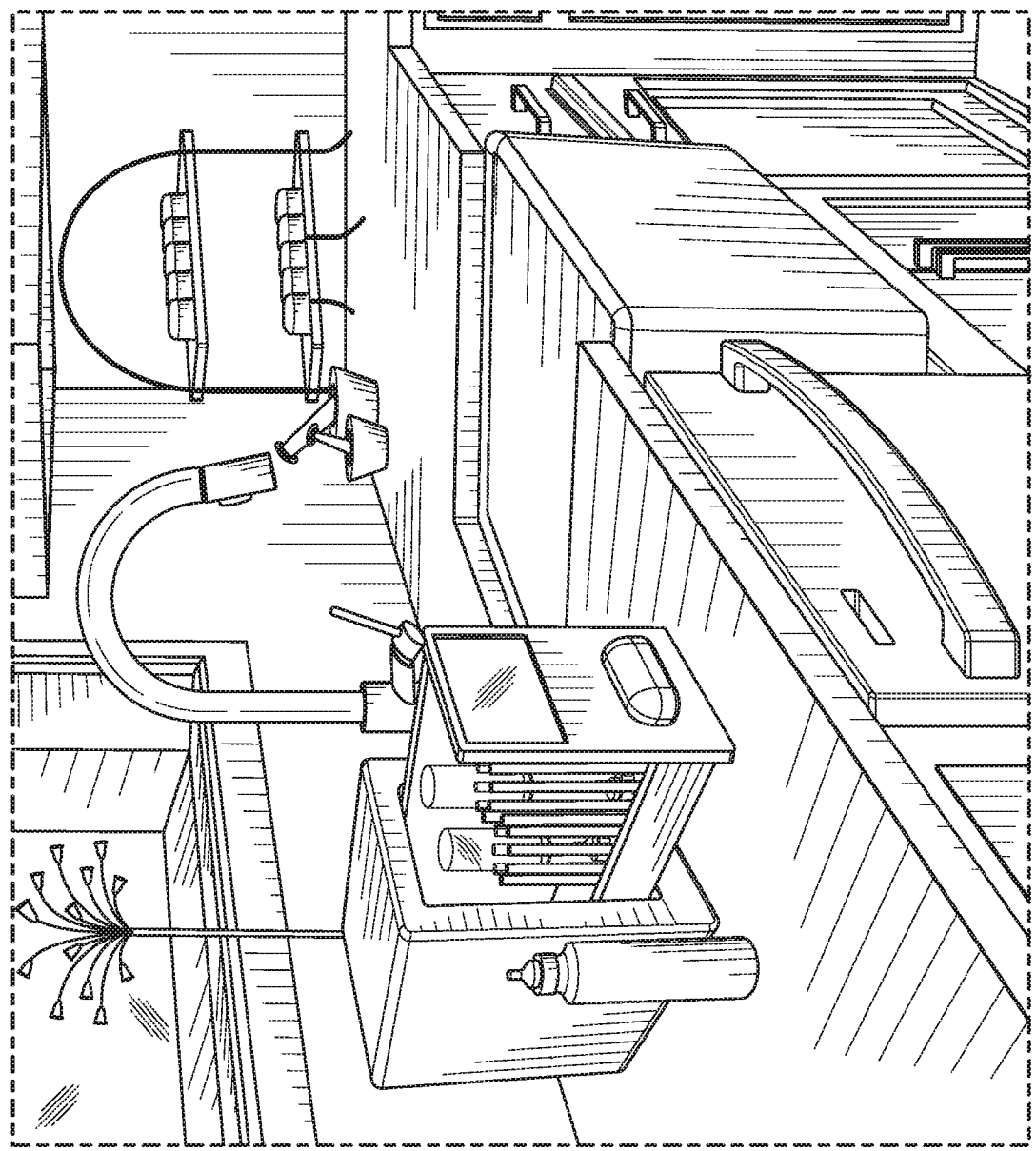

Although any of the previously disclosed desktop units of FIGS. 30A-30I can be used in a consumer setting, in some embodiments, the desktop unit can be configured or tailored for specific household or office uses. For example, the embodiment illustrated in FIGS. 31A-31C can be configured specifically to disinfect and/or sterilize baby bottles. In some embodiments, the consumer unit illustrated in FIGS. 31A-31C can include a plurality of poles that can be configured to hold inverted baby bottles. Each of the plurality of poles can be configured to include effluent output vents to enable sterilant to access the inside of the bottle. The poles enable the entire length of the inside of the baby bottle to be sterilized/disinfected while also allowing the baby bottle to dry out by allowing effluent to either evaporate or drain from the inside of the baby bottle. As illustrated in FIGS. 31B and 31C, the consumer unit can be configured to include additional space such that other components of the baby bottle (e.g., the nipple or the cap) can be placed inside the unit to be sterilized and/or disinfected as well.

Wall Mounted Unit

Figure 32A:
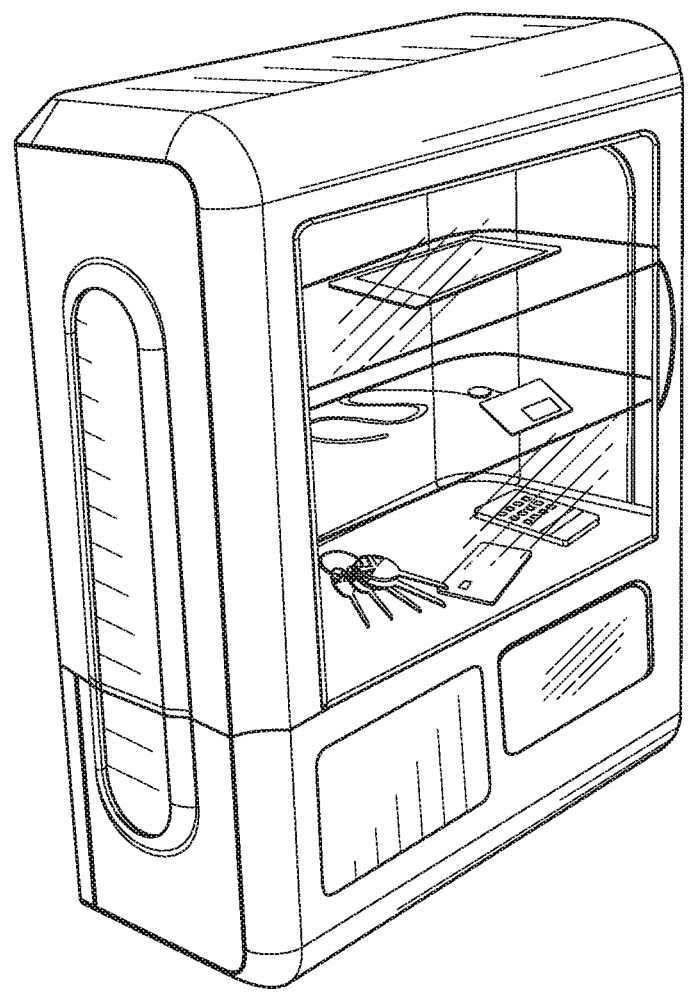
FIG. 32A shows an embodiment of a system for sterilization and/or disinfection configured for mounting on a wall.
Figure 32B:
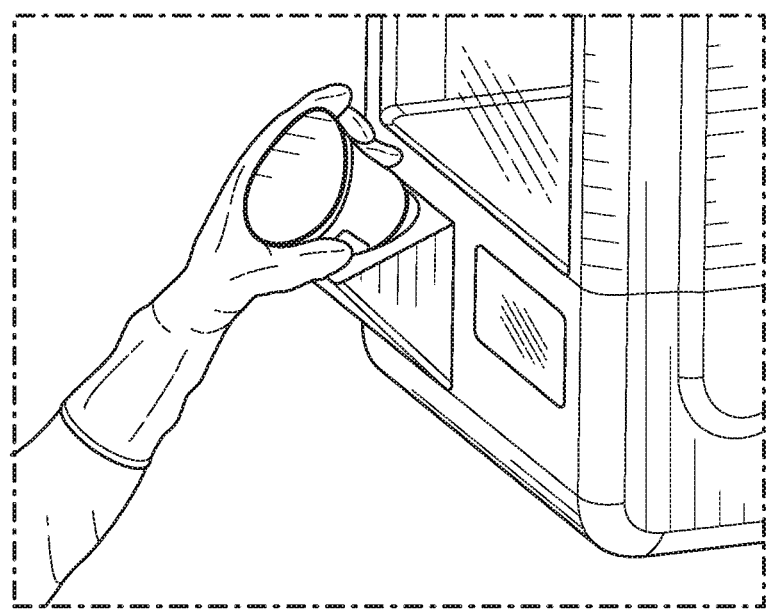
FIG. 32B shows the embodiment of the system for sterilization and/or disinfection illustrated in FIG. 32A configured to provide for loading and/or reloading of a sterilant. In some embodiments, the sterilant is a cartridge containing hydrogen peroxide.
Figure 32C:
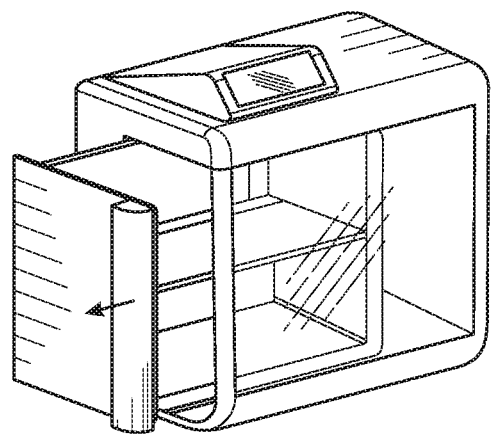
FIGS. 32C-32E show a plurality of alternative embodiments of the system for sterilization and/or disinfection configured for mounting on a wall.
Figure 32D:
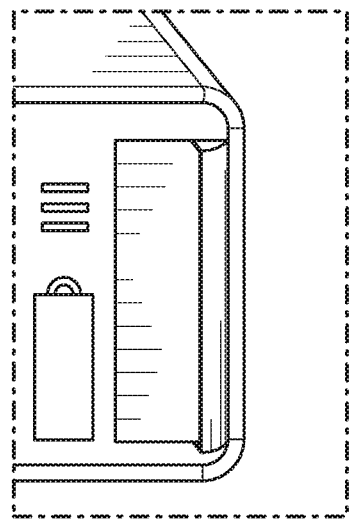
Figure 32E:
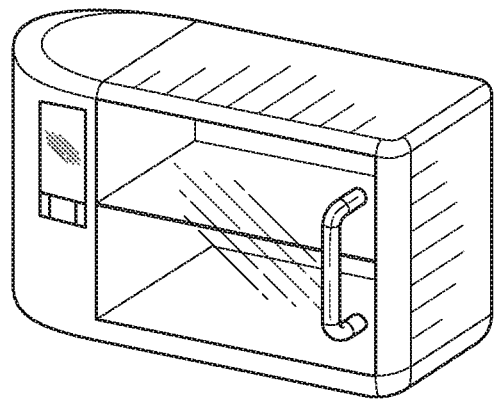
Figure 32F:
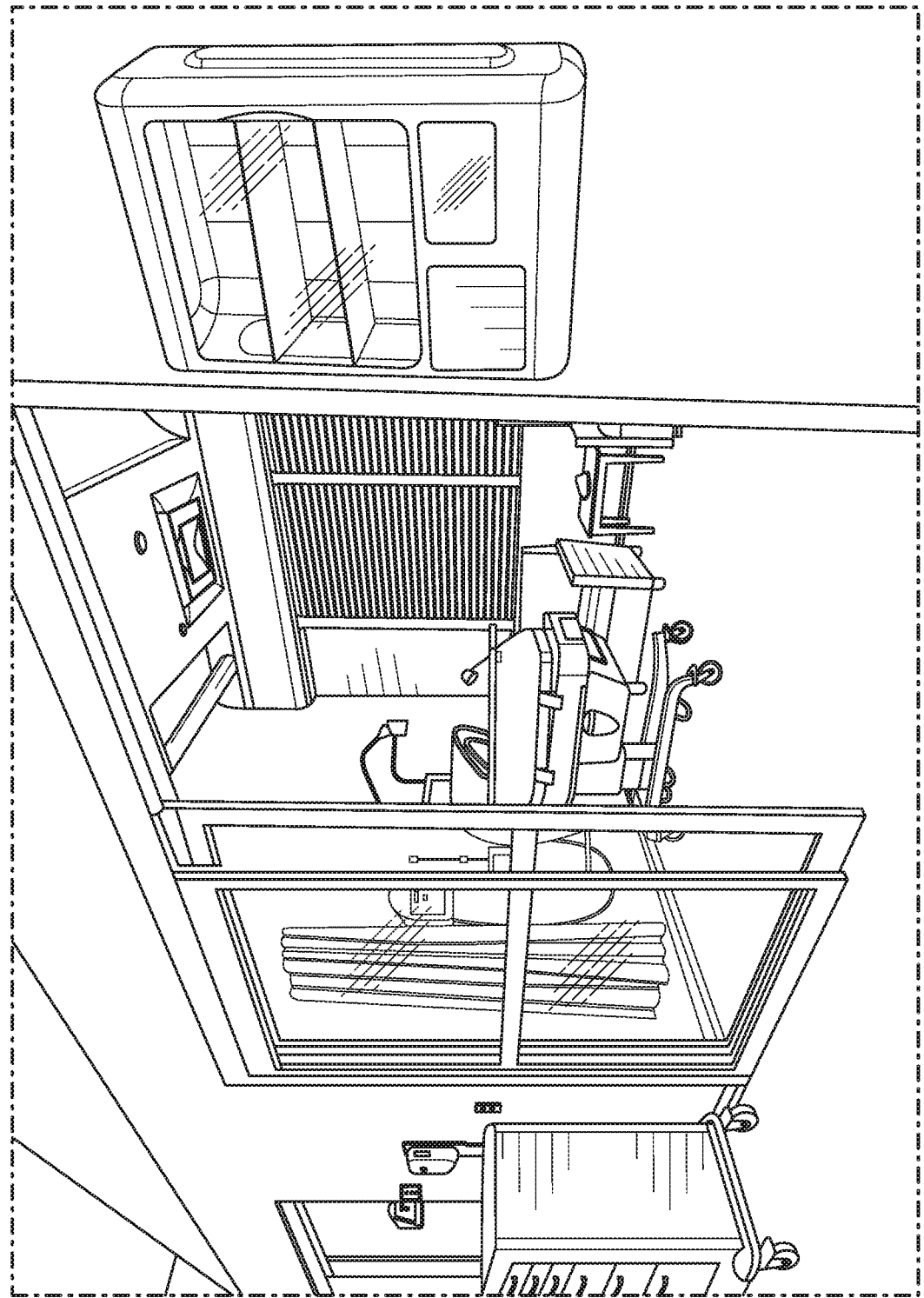
FIGS. 32F-32H show the embodiment of the wall mountable system for sterilization and/or disinfection illustrated in FIG. 32A in various environments.
Figure 32G:
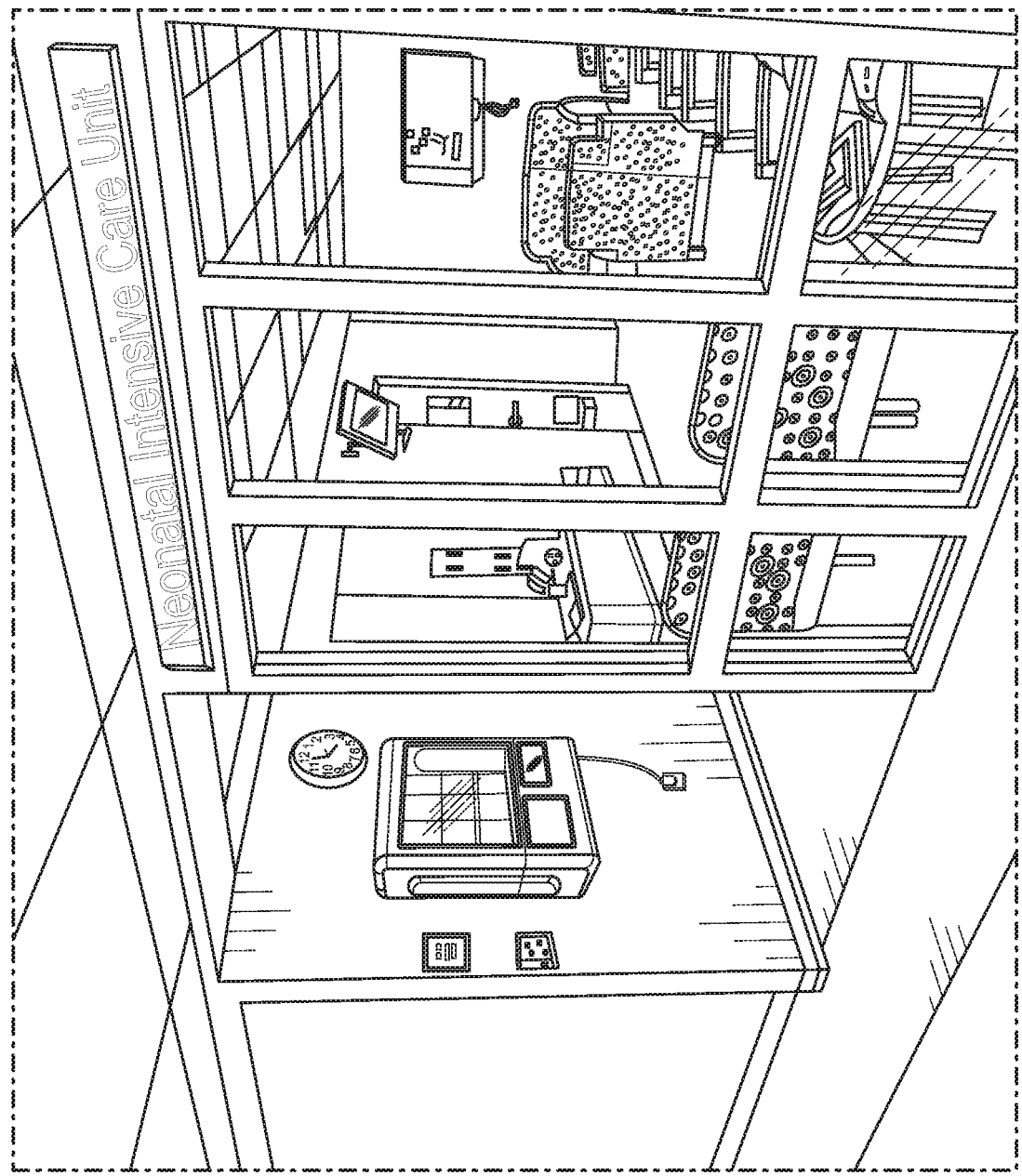
Figure 32H:
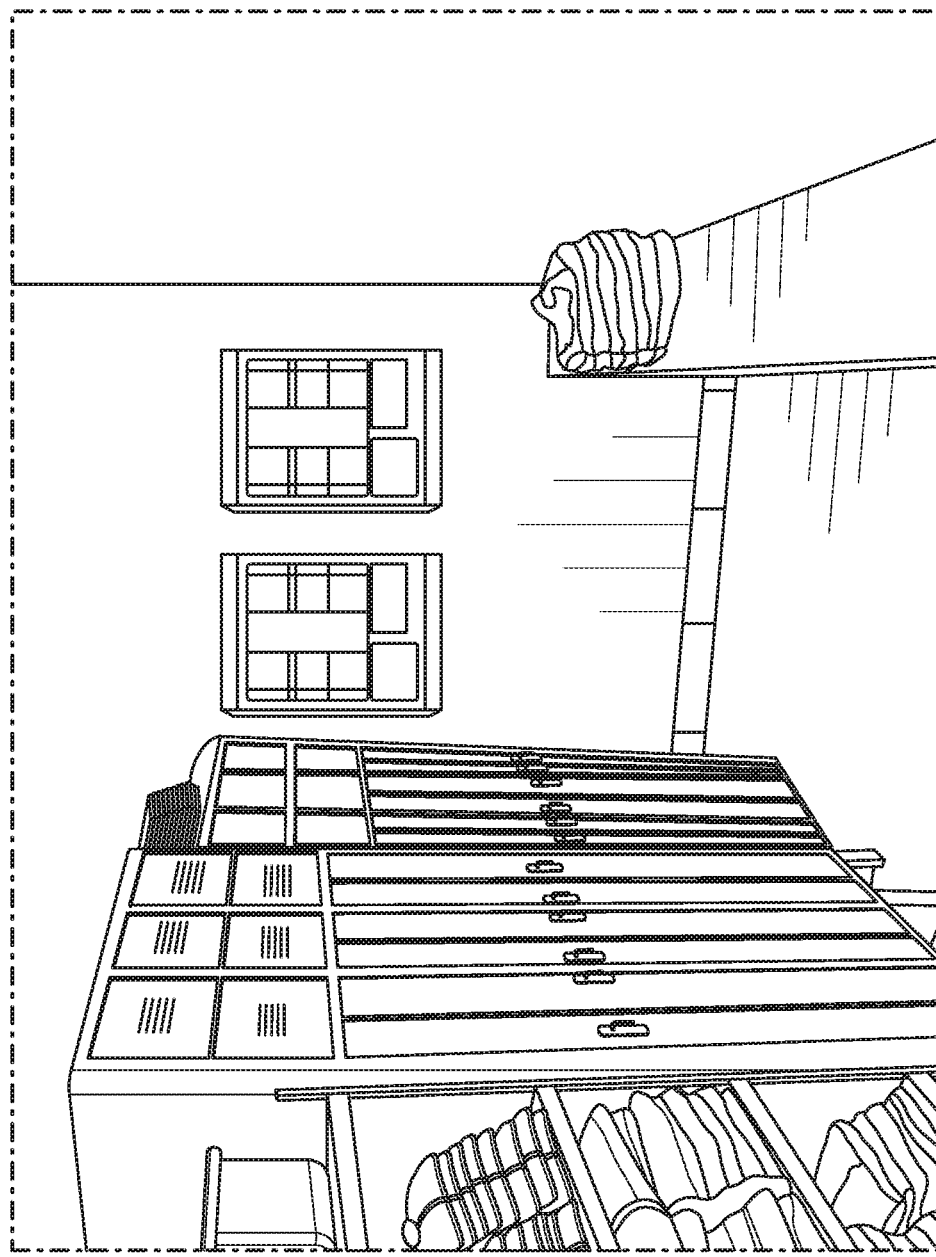

FIGS. 32A and 32C-32E illustrate a plurality of wall-mountable units for sterilization and disinfection. As discussed above, in some embodiments, the wall-mounted unit can provide enhanced space savings and retain workable benchtop space in a given environment. In other embodiments, the wall mounted unit can be a freestanding system that is dimensioned to fit next to an existing countertop or cabinet. FIGS. 32F-32H illustrate the wall mounted sterilization/disinfection unit mounted in a variety of settings such as a healthcare facility, locker room, or other facilities. The goal of a wall mounted unit is to provide for flexibility such that the system for sterilization and disinfection can be placed inside and outside a variety of environments (e.g., patient rooms, waiting rooms, cafeterias, locker rooms).

As illustrated in the embodiments of 32A and 32C-32E, the wall mounted unit can provide loading into the unit from the front, side, top, sash, or other. In some embodiments, the chamber size can vary and each of the wall mounted units can be configured to include a plurality of chambers. In some embodiments, the chamber provided by each of the wall mounted units can be customized to receive and sterilize or disinfect specific devices. This can include, for example, electronics (e.g., mobile communication devices, computers, tablets), items frequently seen in healthcare facilities (e.g., badges, stethoscopes, blood pressure cuffs), or other items carried by a personnel in the facility (e.g., pens, pencils, notebooks).

In some embodiments, the wall mounted unit can include a sterilant loading feature. This feature, while illustrated in FIG. 32B in relation to a wall mounted device, can be included with any of the aforementioned systems for sterilization and/or disinfection. As illustrated in FIG. 32B, the system can include an opening that allows a "cartridge" to be replaced. In some embodiments the cartridge can include hydrogen peroxide or any other sterilizing fluid. The feature of removing and replacing the sterilant cartridge illustrated in FIG. 32B can also be applied to other consumable features of the system (e.g., filters, drying medium).

Hand Sterilization/Disinfection Unit

Figure 33A:
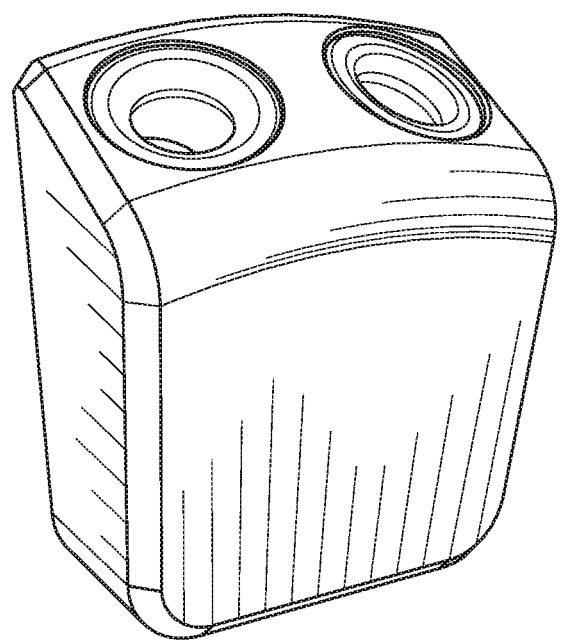
FIGS. 33A-33B show an embodiment of the system for sterilization and/or disinfection configured to sterilize/disinfect hands.
Figure 33B:
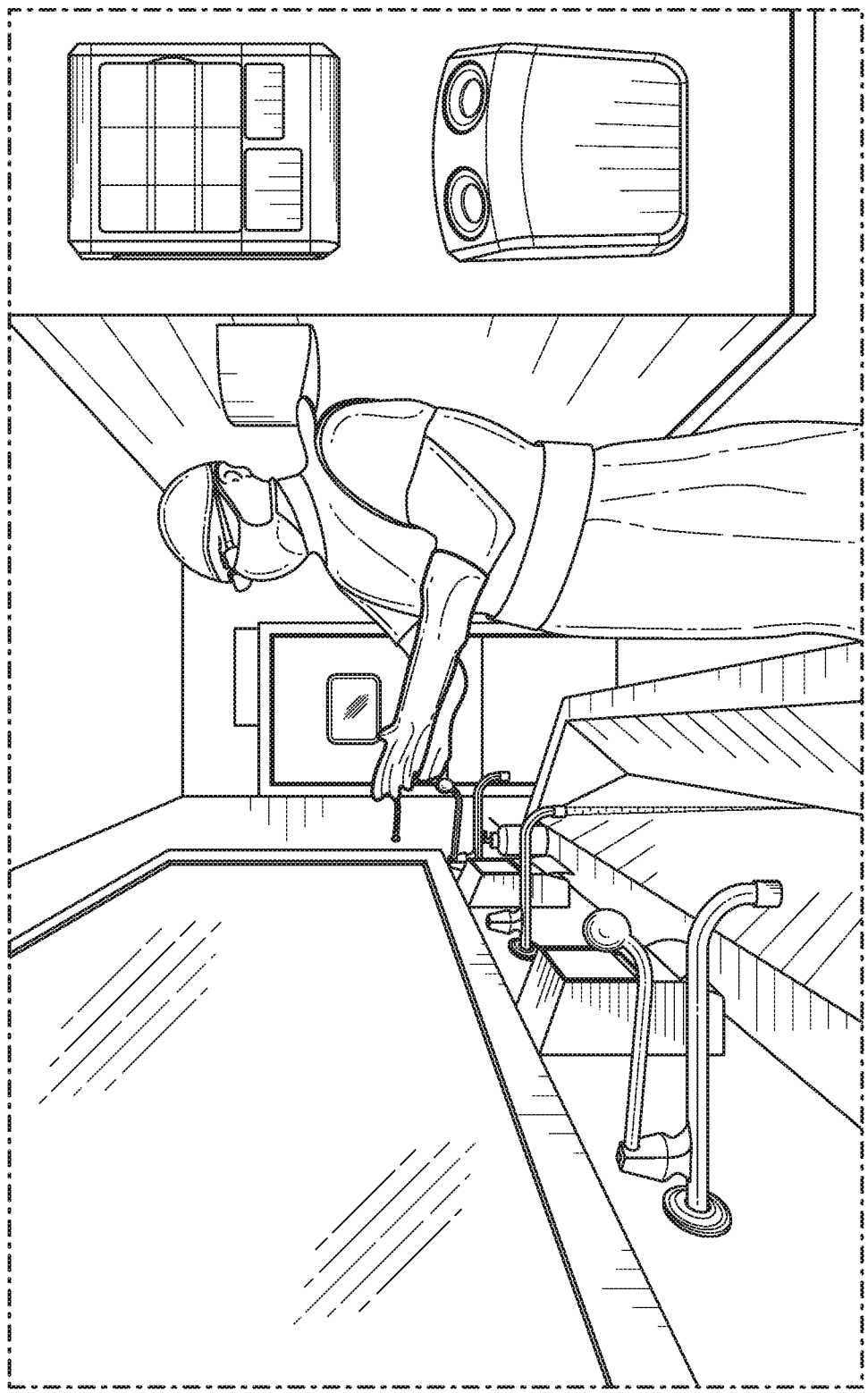

In some embodiments, the system for sterilization and disinfection can be incorporated into a hand drying system. FIG. 33A illustrates an embodiment of a hand sterilization/disinfection unit. In some embodiments, as illustrated in FIG. 33B, the hand sterilization/disinfection unit can be wall mounted, not unlike a wall mounted dryer.

The goal of the hand sterilization/disinfection unit would provide a "touch free" disinfection-post hand washing. It is well documented that hand washing is one of the most effective means for cleaning and disinfection. However, hand drying after hand washing has been shown to be a potential vector for pathogen transition. As well, in the context of acute-care settings, infection control personnel have identified variations in hand washing procedures (i.e., compliance with specific protocols) as an issue. For example, some surgeons may wash their hands for 2 minutes and others for only 1 minute. By providing an additional disinfecting drying step after hand washing can have the impact of "filling the infection control gap." That is to say, this can provide a second level of disinfection to further reduce the risk of pathogen transmission after hand washing. Furthermore, incorporating this step into a hand drier also has the advantage of avoiding adding an additional step into the process. As the disclosed system for sterilization/disinfection requires moisture (e.g., humidity) the water on the hands after hand washing can assist in the process of disinfection. While the obvious application of the disclosed hand sterilization/disinfection unit can be used for healthcare facilities, this system may also be utilized in clean room applications and other facilities where the potential for pathogen transmission may have high consequences.

In some embodiments, as illustrated in FIG. 33A, the hand sterilization/disinfection unit is configured to "collect" the atmosphere without exposing it to the air. This can be an important safety feature because the active chemical species, including the hydrogen peroxide, of the system for sterilization/disinfection unit can be harmful if inhaled. As shown in FIG. 33A, the hand sterilization/disinfection unit can be fully enclosed. In some embodiments, to ensure that the user's hands are sealed, the hand sterilization/disinfection unit can include an automatic enclosing mechanism around the wrists which can create a near air tight seal.

In some embodiments, once the hands are removed from the hand sanitation/disinfection unit, a different set of external doors can close over the openings which would allow a second sterilization/disinfection cycle to run and treat the part of the hand sanitation/disinfection unit that formed the wrist enclosing mechanism and was forming a seal. This can ensure that the wrist enclosing mechanism in contact with a user's skin does not itself become a vector for pathogens for a subsequent user. In some examples, the second sterilization/disinfection cycle can involve higher concentrations of hydrogen peroxide than that used in the first cycle which is intended to sterilize/disinfect hands.

In some embodiments, another option for the operation of the hand sterilization/disinfectant unit is to use a positive and negative pressure system. For example, the hand sterilization/disinfectant unit can blow out sterilant over the hands of the user at a lower pressure and pulls the sterilant back into the system at a higher pressure. In some embodiments, this can be accomplished with fans and/or pumps that work simultaneously to move the sterilant across the hands and then suck it back into a filtration system. In other embodiments, the hand sterilization/disinfection unit can include an engineered air curtain that flows across an opening to prevent the escape of sterilant during operation.

The disclosed system can be beneficial as it is a process that is safe and compatible with live tissue and is configured to avoid bleaching of the skin or hair. In some embodiments, the cycle times of sanitizing/disinfecting a user's hands can be compatible with a handwashing routine (e.g., 15-30 seconds) to provide a high level of pathogen reduction. In some embodiments, the cycle provided by the hand sanitizing/disinfecting cycle can be modified based on the desired outcome. For example, the hand sanitizing/disinfecting unit can be configured to only disinfect, only sanitize, or both disinfect and sanitize.

In some embodiments, the hand sanitization/disinfection unit can be configured to be implemented with or without hydrogen peroxide. In some examples, the hand sanitization/disinfection unit can be configured to be incorporated into multiple style units, wall mounted, or provided as a desktop unit. In some embodiments, the hand sanitizing/disinfecting unit can provide for hands-free operation. For example, the hand sanitizing/disinfecting unit can be provided with motion sensors to start the sterilization and disinfection process. This can help to remove another opportunity for the spreading of pathogens from one user to another. In some embodiments, the hand sanitizing/disinfecting unit can be incorporated into a hand dryer such that the sanitizing/disinfecting capability becomes part of the "hand drying step."

The hand sanitization/disinfection unit can be used in a variety of environments. For example, the hand sanitization/disinfection unit can be used in high risk areas for infection such as surgical suites and other healthcare facilities to reduce the threat of hospital acquired infections. In some embodiments, the hand sanitization/disinfection unit can be used in commercial food service and processing facilities (e.g., employee bathrooms and sinks) to provide a second line of defense to reduce the spread of infection through food service workers. The hand sanitization/disinfection unit can also be used in daycare and elder care facilities, such as employee bathrooms, to avoid the spread of infection diseases. Similarly, the hand sanitization/disinfection unit can be used in laboratory facilities (e.g., BSL 3 and other applicable facilities) where potential transmission of pathogens is an issue. The hand sanitization/disinfection unit can also be used in clean rooms where the production of high purity compounds (e.g., for use in the pharmaceutical and cosmetic industry) would require the maintenance of a sterile/infection-free environment.

Large Device Sterilization/Disinfection Unit

Figure 34A:
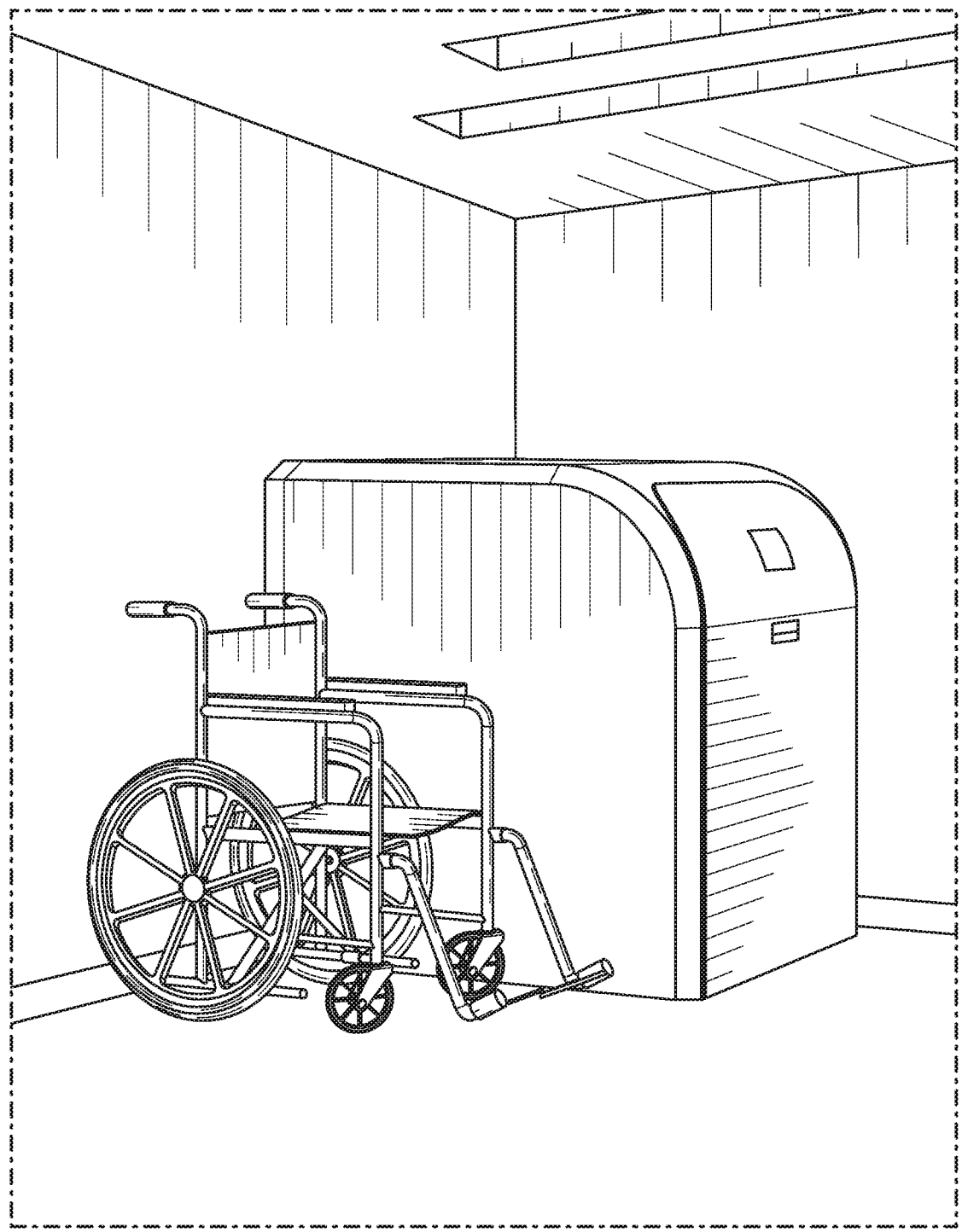
FIGS. 34A-34B show an embodiment of the system for sterilization and/or disinfection configured to sterilize or disinfect large devices.
Figure 34B:
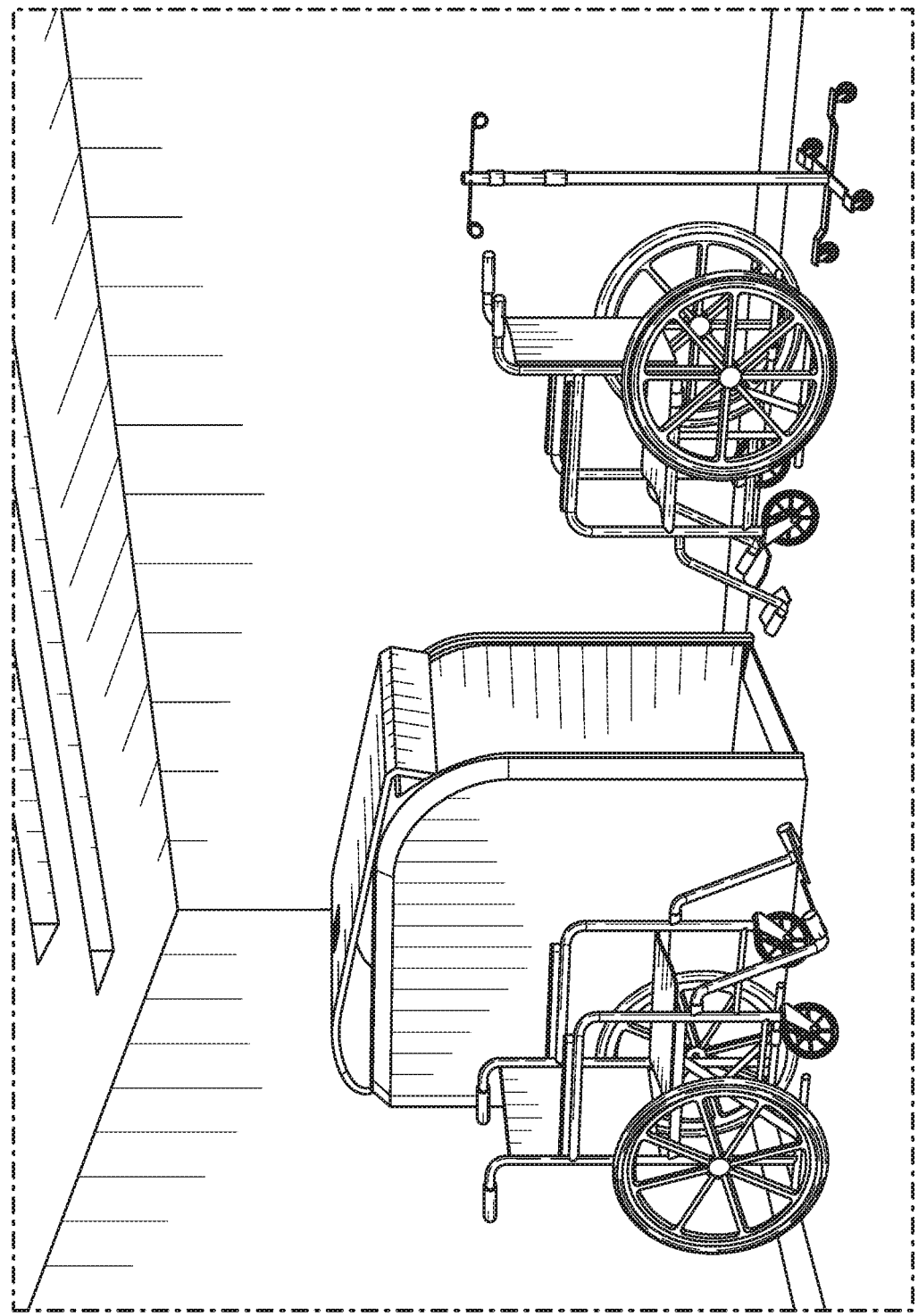

FIGS. 34A-34B illustrate an embodiment of a large device sterilization/disinfection unit. In some embodiments, the disclosed large device sterilization/disinfection unit is not limited to size and can be tailored to the application of use. In some embodiments, the large device sterilization/disinfection unit can include a chamber that is dimensioned to accommodate larger items. These items can include, for example, control modules for IV stands, power units for various equipment in surgical suites, end piece apparatuses used in an operating room (e.g., eyepieces for surgical scopes), or consumer-end healthcare products such as a wheelchair (as illustrated in FIGS. 34A-34B).

In some embodiments, as noted above, the goal of a large device sterilization/disinfection unit is to be configured to process larger items at a healthcare facility. In some examples, the large device sterilization/disinfection unit may be portable or stationary. In other embodiments, the large device sterilization/disinfection unit can be coupled with a pre-cleaning step to remove dirt and debris.

As illustrated in FIGS. 34A-34B, the chamber can be rectangular in shape, with a sliding door to allow for the easy accommodation of the device or item to be sterilized. However, the large device sterilization/disinfection unit can be configured to have a chamber of almost any shape and size. Similarly, the large device sterilization/disinfection unit can have any type of opening that allows a user to have easy access to the interior of the system for sterilization/disinfection. For example, the large device sterilization/disinfection unit can be top-loading, front loading, include a window sash, or open from either sides of the large device sterilization/disinfection unit.

Mobile Unit

Figure 35A:
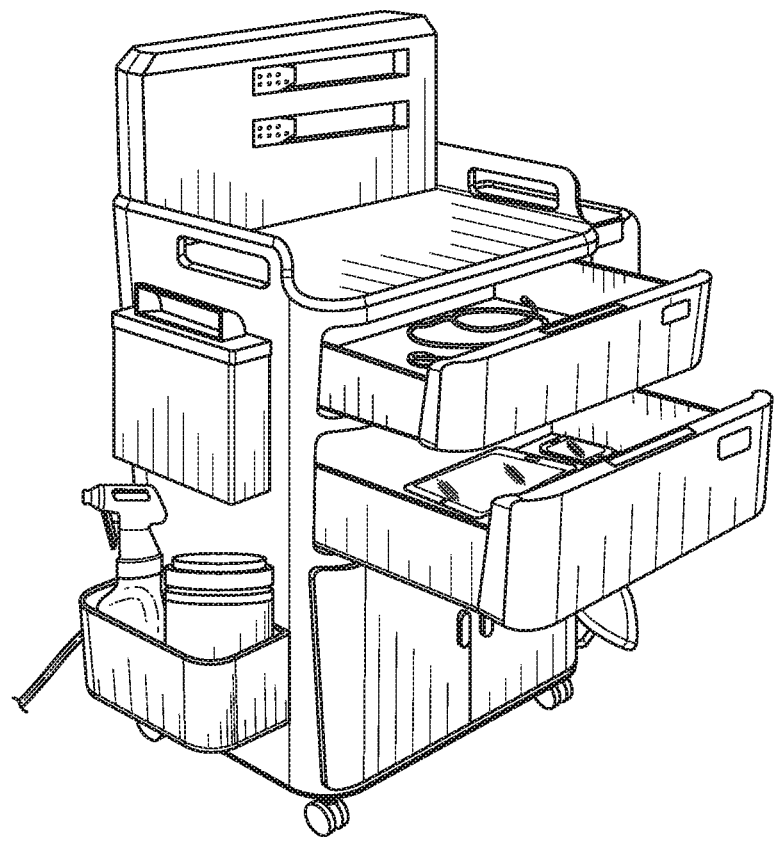
FIGS. 35A-35C show an embodiment of the system for sterilization and/or disinfection provided with a mobile unit.
Figure 35B:
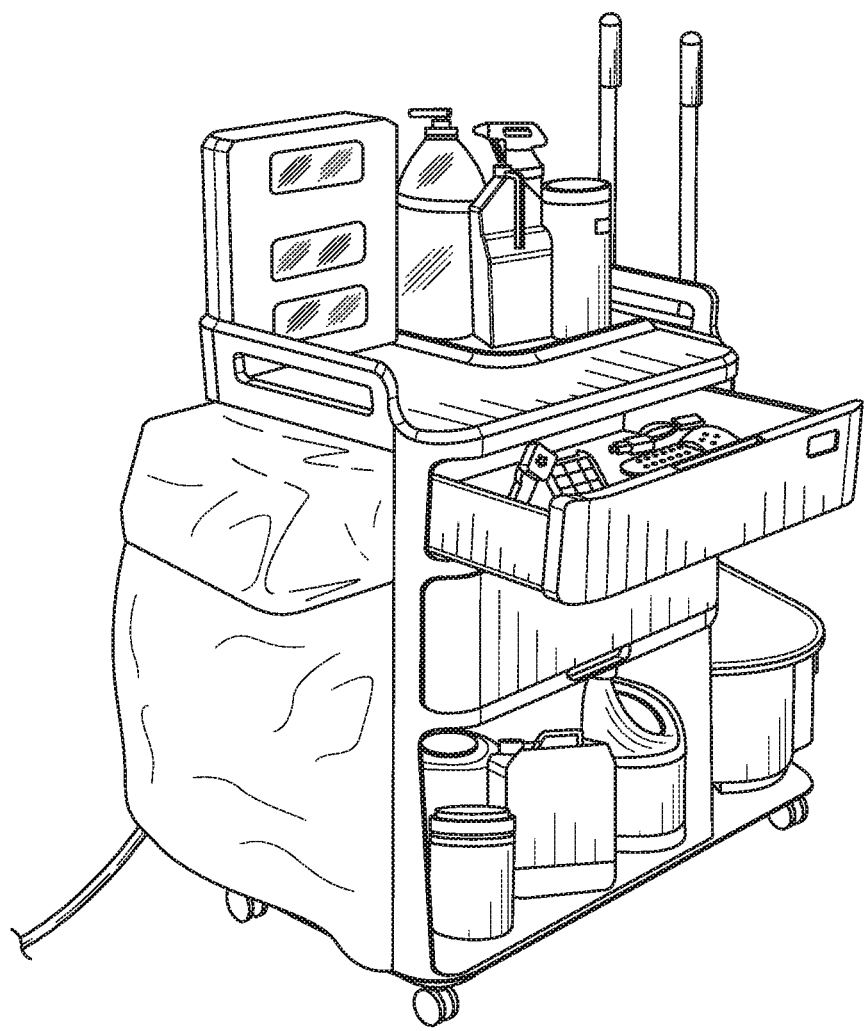
Figure 35C:
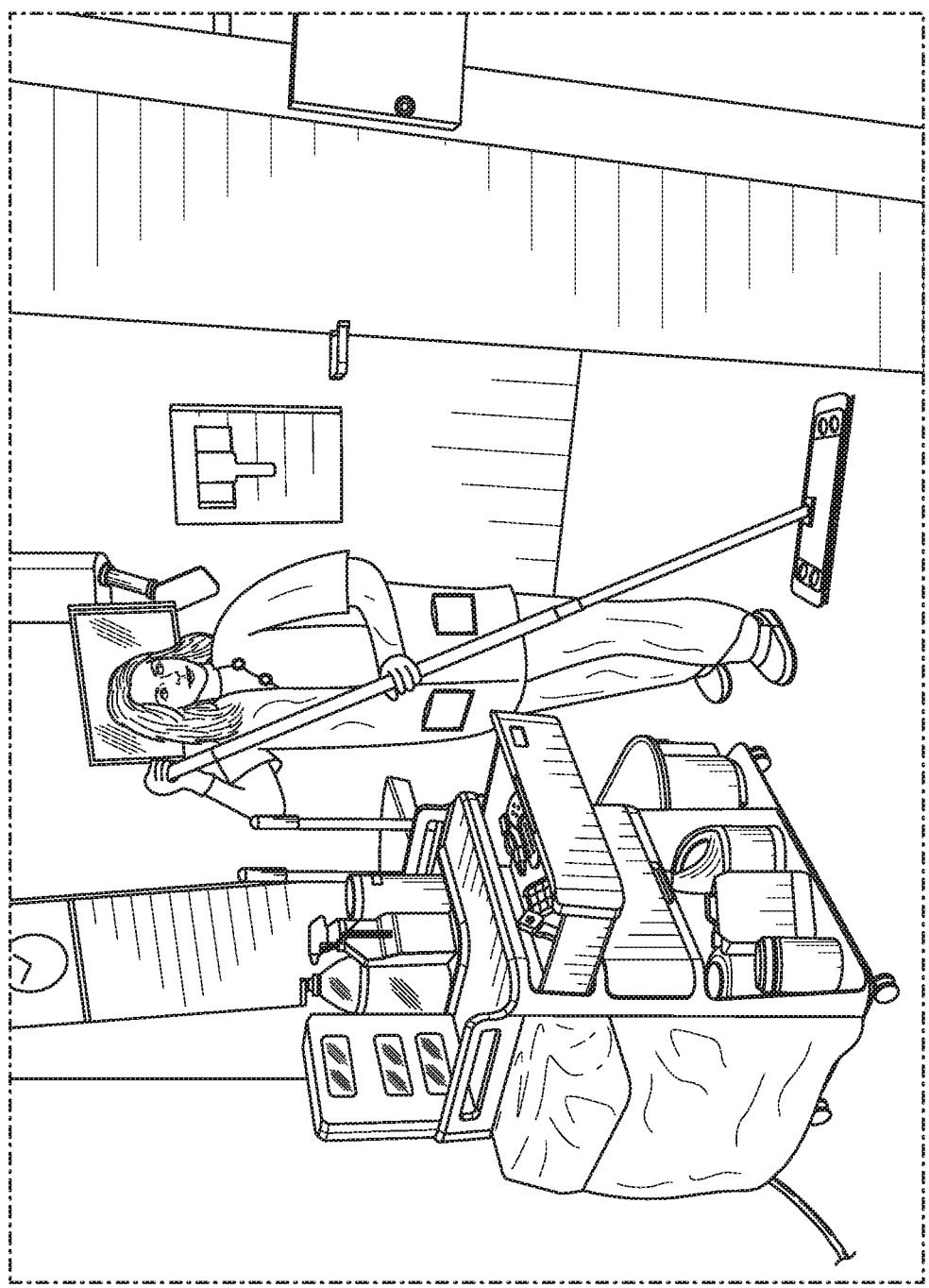
Figure 36A:
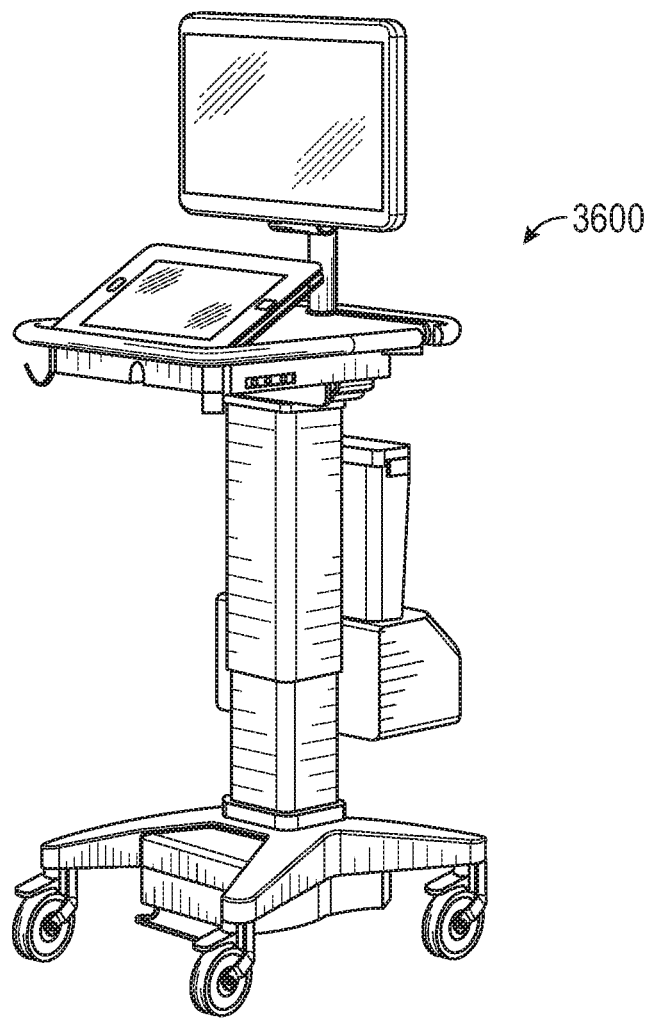
FIGS. 36A-36B show a plurality of examples of the system for sterilization and/or disinfection mounted on an embodiment of a portable medical treatment system (e.g. an ultrasound system).
Figure 36B:
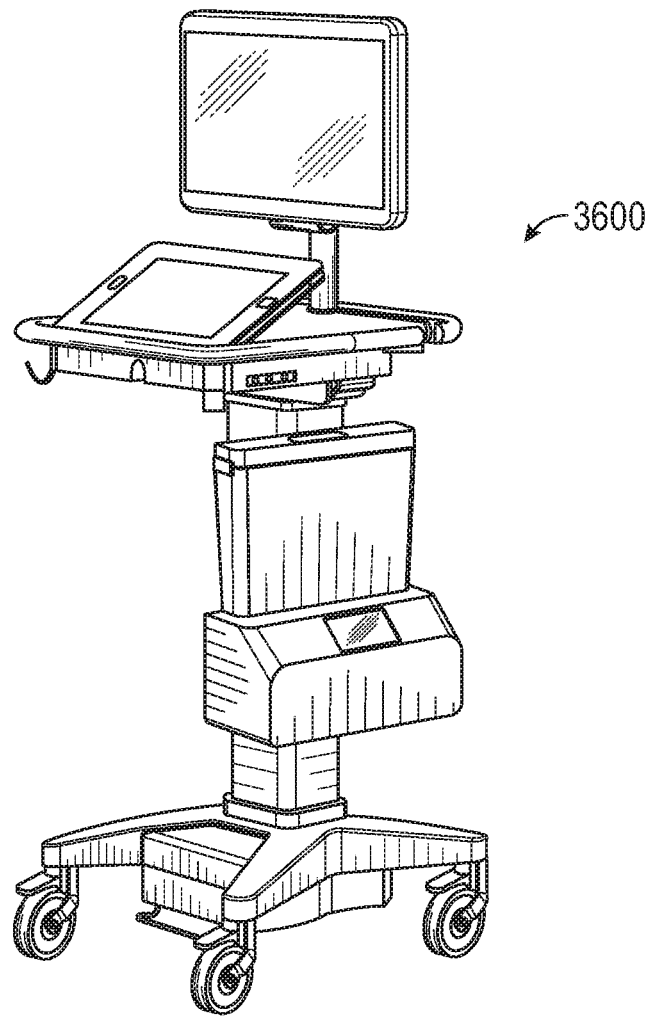
Figure 37A:
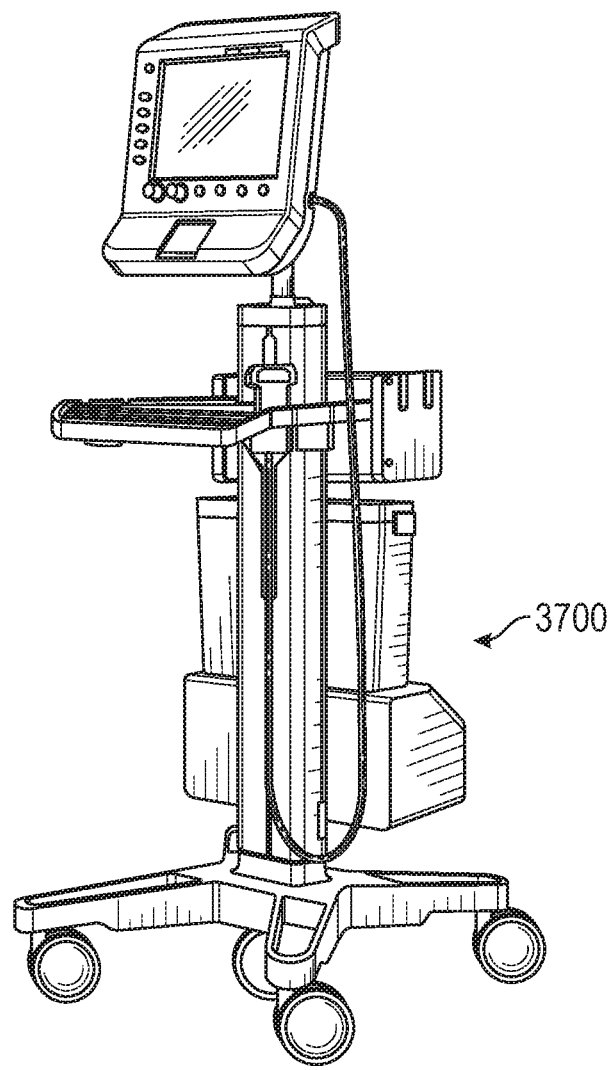
FIGS. 37A-37C show a plurality of examples of the system for sterilization and/or disinfection mounted on another embodiment of a portable medical treatment system (e.g. an ultrasound system).
Figure 37B:
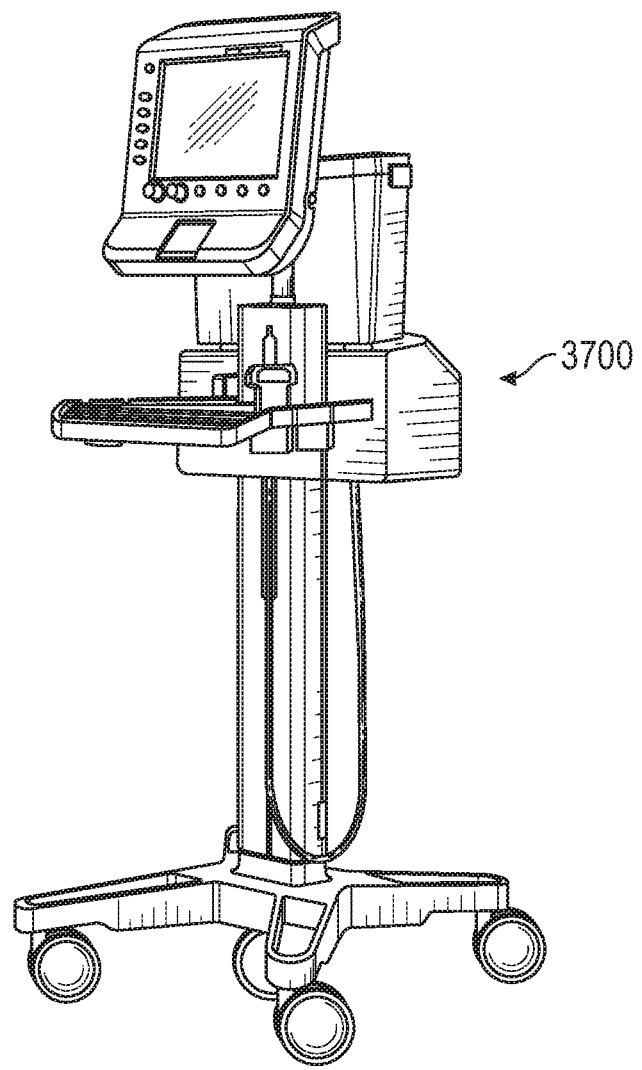
Figure 37C:
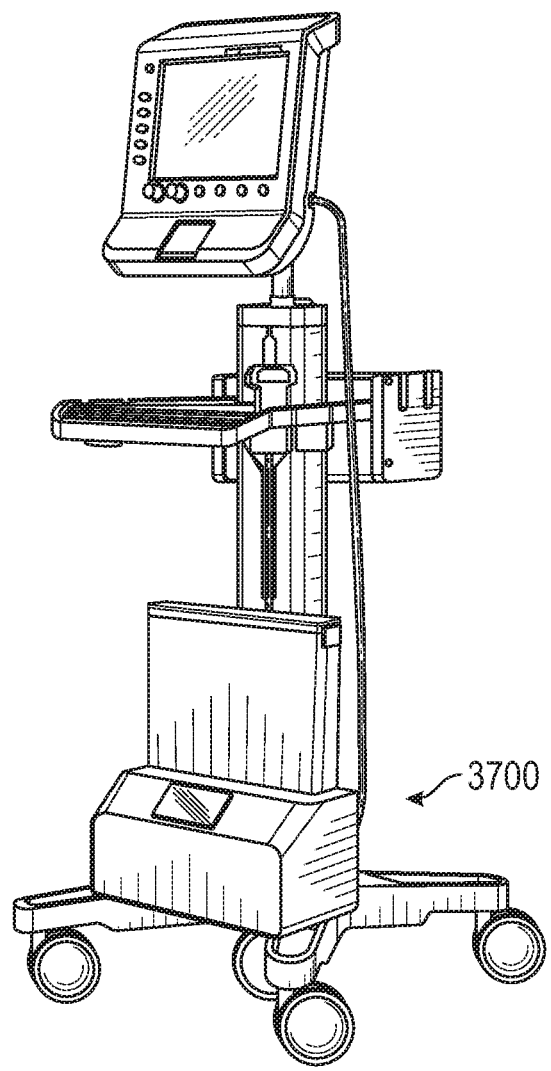

FIGS. 35A-35C illustrate an embodiment of a system for sterilization/disinfection that is configured to be portable. As discussed above, the disclosed mobile unit can be height adjustable and/or portable to be moved from one location to another. As shown, the mobile unit can include wheels or be provided with a rolling cart.

The mobile unit can be configured to have any type of opening that allows a user to have easy access to the interior of the system for sterilization/disinfection. For example, the mobile unit can have chambers that are top-loading, front loading, include a window sash, or open from either sides of the desktop unit. As illustrated in FIGS. 35A-35C, the mobile unit can include a plurality of pull-out drawers to provide for the loading of items for sterilization/disinfection. In some examples, the compartment for sterilization/disinfection can be fully integrated or mounted onto a mobile unit (e.g., a cart)

In some embodiments, as illustrated in FIG. 35A, the mobile sterilization/disinfection unit can be configured to be used with a crash cart. By including a system for sterilization/disinfection into a crash cart, the mobile unit can be placed outside a room with a patient infected with a highly contagious and/or drug resistant pathogen. As infected patients show up in different places in the hospital, by placing a sterilization/disinfection system on a moveable crash cart, it would provide hospital personnel with all the necessary personal protective gear, waste disposal resources, wipes/sprays/cleaners at any location. In some embodiments this unit can be plug-in, battery powered, or include a batter back-up power source.

In some embodiments, as illustrated in FIG. 35B, the mobile sterilization/disinfection unit can be configured to be used with a janitorial, cleaning, and/or environmental services cart. By including a system for sterilization/disinfection into a janitorial cart, this would provide for easy sterilization/disinfection when changing patient rooms and beds. In some embodiments, the janitorial and/or cleaning cart can be configured to include various wipes and surface disinfectants, garbage containers, mops, and/or buckets. In some embodiments this unit can be plug-in, battery powered, or include a batter back-up power source. In some embodiments, the sterilization/disinfection unit can optionally include a removable treatment chamber such that the sterilization/disinfection unit can be integrated into the any cart for providing environmental services. The cart can therefore be configured include a sterilization/disinfection system built inside the environmental services providing cart. In this way, the sterilization/disinfection system can be included and paired with a cart for providing services in a variety of settings (e.g. medical, industrial, etc.).

In some examples, as illustrated in FIGS. 36A-36B and 37A-37C, the sterilization/disinfection unit 3600, 3700 can be configured to be mounted on a mobile or portable medical treatment system. For example, the mobile or portable medical treatment system can be an ultrasound system. This can provide a low cost, lightweight technology for providing high level disinfection at the point of care. As shown in FIGS. 36A-36B and 37A-37C, the sterilization/disinfection unit 3600, 3700 can be mounted at various heights. Depending on the application, the sterilization/disinfection unit can be configured to be adjustable, removable, or permanently mounted on the mobile or portable medical treatment system. In some examples, the treatment chamber can double as a secure storage unit at the point of care. In some embodiments, the mobile sterilization/disinfection unit can include a power source that is either replaceable or rechargeable. In this way, the mobile or portable medical treatment system will not need to be proximate to a power outlet to operate the sterilization/disinfection unit.

Other Features

In some embodiments, in the non-limiting examples of embodiments disclosed above, in FIGS. 30A-30I, 31A-31C, 32A-32H, 33A-33B, 34A-34B, and 35A-35C, the device for the system for sterilization/disinfection can include a number of different features.

In some examples, the embodiments of the sterilization/disinfection unit described above can include a cover. The cover can be configured such that it does not fade or degrade when cleaned (e.g. by a wipe down with PDI or disinfecting wipes). The cover can be UL 94 V2 flammability rated. In some examples, the cover can be configured to withstand the impact of a 500 g stainless steel ball dropped from a height of 1 meter. In some embodiments, the cover is made of plastic. In some embodiments, the cover can have UV protection. In some examples, the cover can allow for exhaust heat venting.

In some embodiments, the sterilization/disinfection unit can include a sterilization chamber with a window. In some examples, the chamber window can be clear and/or incorporated into the sterilization/disinfection unit door such that the user can look inside the sterilization chamber to see the items inside. In some embodiments, the chamber window can have a double-pane—wherein a first pane is configured to be exposed to the effluent in the chamber and the second pane is resistant to the effluent. In some examples, an air gap exists between the double-pane windows. In some embodiments, the chamber window is comprised of a material that will not degrade when cleaned (e.g. with PDI or disinfecting wipe). In some examples, the chamber window is made of plastic. In some examples, the chamber window can include UV protection. In some embodiments, the chamber window can be thoroughly cleaned without using a tool to clean between cracks or crevices. In some examples, the chamber window and the unit door can have a gap that is no more than 0.5 mm±0.25 mm.

In some embodiments, the sterilization/disinfection unit can include a display. In some examples, the display is configured to allow the user to have access to information such as the number of sterilization/disinfection cycles remaining, time remaining before the disinfection/sterilization cycle completes, the status of the disinfection/sterilization cycle (e.g. dry, disinfect, or purge), etc. The display can be configured such that the user is able to see the user interface while either standing or sitting by the sterilization/disinfection unit. This can be accomplished, for example, by having the display screen positioned at an angle, according to the manufacturer, between about 0 degrees to about 15 degrees, including 0 degrees, 1, degree, 2 degrees, 3 degrees, 4 degrees, 5 degrees, 6 degrees, 7 degrees, 8 degrees, 9 degrees, 10 degrees, 11 degrees, 12 degrees, 13 degrees, 14 degrees or 15 degrees, and including the ranges between about 0 degrees and 5 degrees, about 5 degrees and 10 degrees, and about 10 degrees and 15 degrees. In some embodiments, the display can be easily seen in either a well-lit or dark room. The display can have, for example, a screen brightness that is adjustable from low to high.

As illustrated in FIGS. 30A-30I, 31A-31C, 32A-32H, 33A-33B, 34A-34B, and 35A-35C above, the sterilization/disinfection unit can have a chamber door. In some embodiments the chamber door can be configured to have a large radii to allow for easy cleaning by a user. In some examples, the chamber door is configured to be opened easily. The chamber door can be mechanical or electric and opened using a one-touch button. In some embodiments, the door is configured to be easily pushed closed and latched. The door can be configured to latch close, for example, with less than 3 lbs of horizontal force applied at the center edge of the door. In other embodiments, the chamber door can be automatically locked when latched shut. In some examples, the chamber door is configured to not harm the device if the chamber door is accidently slammed. This can be accomplished, for example, by having a chamber door that will close at an angular velocity over a set number of times (e.g. 100 times) without failure.

The chamber door can have a mechanical or an electronic lock. In some examples, the chamber door is configured to spring open when the lock is disengaged. In some embodiments, the chamber door is configured to be electronically unlocked by a multi-cap touch button push. In some examples, the chamber door can be configured to have a power-out manual override unlock to allow the user to be able to access items inside the sterilization chamber when and/or if electricity runs out. In other examples, the chamber door can be configured to automatically lock once the system is powered up after a power out and provide for a manual chamber door to be opened/closed. In some embodiments, the chamber door has an override button. In some examples, this override button can be obscured and recessed from the surface (e.g. a side surface) to prevent accidental use. In some embodiments, the user will not be able to open the chamber door during the disinfection/sterilization cycle. For example, the chamber door can remain closed and locked until it is safe for the user to open it under normal operation. In some examples, the chamber door manual override button will not function unless the system's user interface indicates that the system is purged.

As shown in FIGS. 30A-30I, 31A-31C, 32A-32H, 33A-33B, 34A-34B, and 35A-35C above, the sterilization/disinfection unit can have a consumable door. In some examples, the consumable door is configured to contain sterilant. The consumable door is configured to be opened only when the consumable (e.g. sterilant) is being replaced. In some embodiments, the consumable door can have an electronically controlled lock. The consumable door can be configured such that only the user with a proper access shall be able to open the consumable door. For example, the consumable can spring open when the lock is disengaged. In other examples, the consumable door will automatically lock when the latch is closed. In some embodiments, the user can have a tool to manually override the electronically controlled lock. For example, the consumable door can be electronically unlocked by a multi-cap touch button push.

In some embodiments, the sterilization/disinfection unit can include a service door. The service door can have a lock that requires a physical key to unlock. In some examples, the service door can have a manual lock. The service door manual lock can have a tool or a key that remains in the lock until the door is closed and relocked. In some embodiments, the manual lock for the service door is on a side that conceals the lock.

In some examples, the sterilization/disinfection unit is configured to allow the user to have open access into the chamber to insert or remove items. In some embodiments, the chamber can provide for 140 degrees in rotation. In other embodiments, the chamber can withstand a certain amount of force for overloading the door.

The sterilization/disinfection unit can include a wall bracket. The wall bracket can be configured to provide relief for airflow/vents for exhaust heat cooling. In some examples, the wall bracket can have four times the loading for all fasteners in a single stud. In other examples, the wall bracket can have 2 times the loading when removing one fastener from the wall bracket. In some embodiments, the wall bracket is configured to not corrode. In some examples, the wall bracket is configured such that a user can easily install the wall bracket in less than 5 minutes with the proper tools.

The exterior material of the sterilization/disinfection unit can be configured such that it does not fade or degrade when cleaned on a regular basis. In other embodiments, the exterior material is configured such that it is resistant to the chemicals in disinfecting wipes. This can include, for example, alcohol, ammonia, bleach, hydrogen peroxide, soap, etc.

In some embodiments the sterilization/disinfection unit can include a plurality of racks. In some embodiments, the sterilization/disinfection unit can include three removable racks. In some examples, the sterilization/disinfection unit includes a removable rack placed at the bottom of the chamber. This can enable a user to be able to clean out any debris that may collect at the bottom of the chamber. In some embodiments, the sterilization/disinfection unit is configure to fit a number of different devices for sterilization including, for example, cell phones, nurse communication devices, and other point of care hand-held devices in the chamber. In other embodiments, the sterilization/disinfection device is configured to hold up to 6 different point of care devices with room for adequate air flow between the devices. In some examples, each of the care devices is spaced apart by at least 15 mm.

The sterilization/disinfection unit can include lighting, for example LEDs, which enable a user to set the brightness. In some embodiments, the sterilization/disinfection unit is configured to include anti-slip feet that prevent the user from being able to slide the device on the smooth surface easily. In some examples, the sterilization/disinfection unit should weigh under about 25 lbs. to about 50 lbs. such that a user can be able to easily lift the disinfection/sterilization unit. In some embodiments, the sterilization/disinfection unit can be about 25 lbs., 26 lbs., 27 lbs., 28 lbs., 29 lbs., 30 lbs., 31 lbs., 32 lbs., 33 lbs., 34 lbs., 35 lbs., 36 lbs., 37 lbs., 38 lbs., 39 lbs., 40 lbs., 41 lbs., 42 lbs., 43 lbs., 44 lbs., 45 lbs., 46 lbs., 47 lbs., 48 lbs., 49 lbs., and 50 lbs. In some examples, the disinfection/sterilization unit can include a power cord that allows the user to be able to plug the device into a nearby outlet. In other examples, the device cord can have a grounded standard plug.

The sterilization/disinfection unit can include a user interface that can provide a number of different features. In some embodiments, the user interface is configured to allow a user to know when the device is powered (e.g. on or off). In some embodiments, the user interface is configured to allow a user to know when the device is on standby. In some examples, the user interface is configured to allow the user to open the door when it is safe to open the door. In some embodiments, the user can have a settings menu. In some examples, the user interface can notify the user that the door has been opened for an extended period of time. In some embodiments, the user interface is configured to receive "common language" if operational errors occur. In some examples, the user interface is configured to only allow users with proper credentials to access the user interface. For example, the users with proper credentials can have access to the service menu or the consumables menu.

In some embodiments, the sterilization/disinfection unit can include at least one bubble sensor. In some examples, the bubble sensor (or sensors) is placed in line with a peristaltic pump such that the system is configured to detect liquid sterilant or air in the tubing leading to the nebulizer. In some embodiments, if the bubble sensor determines that there has been sufficient air in the tubing leading to the nebulizer, the sterilization/disinfection system is configured to run the pump longer to compensate for the known gap in liquid sterilant so that the system is always configured to deliver the same volumetric amount of liquid sterilant to the nebulizer. This can enable a consistent delivery of vaporized sterilant during the disinfection/sterilization phase. In some examples the sterilization unit can include a plurality of bubble sensors.

In some examples, the sterilization/disinfection unit can include a mist catcher. As discussed above, the mist catcher is configured to collect unvaporized mist from the nebulizer so as to prevent mist deposition in the chamber and on the surface of the treated items. In some embodiments, the mist catcher is located downstream of the nebulizer.

System Operating Parameters

Non-limiting values for certain operating parameters for the presently disclosed systems for sterilization and/or disinfection are provided below. Any of the following parameters can be used with any of the embodiments disclosed above. As discussed, the sterilant/disinfectant used can be hydrogen peroxide vapor or microdroplets and/or ozone.

The ambient temperature for the operating environment for the disclosed system(s) can range between 15° C. to 50° C. (58° F. to 120° F.). In some embodiments, the ambient temperature can range between 15° C.-20° C., 20° C.-25° C., 25° C.-30° C., 30° C.-35° C., 35° C.-40° C., 40° C.-45° C., or 45° C.-50° C. and can be inclusive of 15° C., 16° C., 17° C., 18° C., 19° C., 20° C., 21° C., 22° C., 23° C., 24° C., 25° C., 26° C., 27° C., 28° C., 29° C., 30° C., 31° C., 32° C., 33° C., 34° C., 35° C., 36° C., 37° C., 38° C., 39° C., 40° C., 41° C., 42° C., 43° C., 44° C., 45° C., 46° C., 47° C., 48° C., 49° C., 50° C., and any ranges therebetween.

The relative humidity for the operating environment for the disclosed system(s) can range between 10% to 85% non-condensing. In some embodiments, the (non-condensing) relative humidity can range between 10%-15%, 15%-20%, 20%-25%, 25%-30%, 30%-35%, 35%-40%, 40%-45%, 45%-50%, 50%-55%, 55%-60%, 60%-65%, 65%-70%, 70%-75%, or 75%-80% and can be inclusive of 10%, 15%, 20%, 25%, 30%, 35%, 40%, 45%, 50%, 55%, 60%, 65%, 70%, 75%, 80%, 85%, and any ranges therebetween.

Each of the sterilization/disinfection cycles can include a number of steps. In some embodiments, the sterilization/disinfection cycle can include a conditioning (e.g. dry) phase. The conditioning phase can range between 0 to 180 seconds, 0-10 seconds, 10-20 seconds, 20-30 seconds, 30-40 seconds, 40-50 seconds, 50-60 seconds, 60-70 seconds, 70-80 seconds, 80-90 seconds, 90-100 seconds, 100-110 seconds, 110-120 seconds, 120-130 seconds, 130-140 seconds, 130-140 seconds, 140-150 seconds, 150-160 seconds, 160-170 seconds, or 170-180 seconds and can be inclusive of 0 seconds, 10 seconds, 20 seconds, 30 seconds, 40 seconds, 50 seconds, 60 seconds, 70 seconds, 80 seconds, 90 seconds, 100 seconds, 110 seconds, 120 seconds, 130 seconds, 140 seconds, 150 seconds, 160 seconds, 170 seconds, 180 seconds, and any ranges therebetween. In an embodiment, the conditioning phase can be eliminated (e.g., 0 seconds).

In some embodiments, the sterilization/disinfection cycle can include an exposure phase during which time the device/instrument to be sterilized/disinfected is exposed to a sterilant/disinfectant (e.g. hydrogen peroxide, ozone, UV, etc.). The exposure phase can be shorter when the goal of the system is to disinfect and longer when the goal of the system is to sterilize. To accomplish disinfection, the exposure phase can range between 30 seconds to 300 seconds, 30-60 seconds, 60-120 seconds, 120-180 seconds, 180-240 seconds, or 240-300 seconds and can be inclusive of 30 seconds, 40 seconds, 50 seconds, 60 seconds, 70 seconds, 80 seconds, 90 seconds, 100 seconds, 110 seconds, 120 seconds, 130 seconds, 140 seconds, 150 seconds, 160 seconds, 170 seconds, 180 seconds, 190 seconds, 200 seconds, 210 seconds, 220 seconds, 230 seconds, 240 seconds, 250 seconds, 260 seconds, 270 seconds, 280 seconds, 290 seconds, 300 seconds, and any ranges therebetween. In an embodiment, the exposure phase for disinfection can last between 2-3 minutes. To accomplish sterilization, the exposure phase can range between 5 minutes to 45 minutes, 5-10 minutes, 10-15 minutes 15-20 minutes, 20-25 minutes, 25-30 minutes, 30-35 minutes, 35-40 minutes, or 40-45 minutes, and can be inclusive of 5 minutes, 6 minutes, 7 minutes, 8 minutes, 9 minutes, 10 minutes, 11 minutes, 12 minutes, 13 minutes, 14 minutes, 15 minutes, 16 minutes, 17 minutes, 18 minutes, 19 minutes, 20 minutes, 21 minutes, 22 minutes, 23 minutes, 24 minutes, 25 minutes, 26 minutes, 27 minutes, 28 minutes, 29 minutes, 30 minutes, 31 minutes, 32 minutes, 33 minutes, 34 minutes, 35 minutes, 36 minutes, 37 minutes, 38 minutes, 39 minutes, 40 minutes, 41 minutes, 42 minutes, 43 minutes, 44 minutes, 45 minutes, and any ranges therebetween. In an embodiment, the exposure phase for sterilization can last approximately 30 minutes.

In some embodiments, the sterilization/disinfection cycle can include a purge (e.g., aeration) phase. The purge phase can range between 15 seconds to 240 seconds, 15-30 seconds, 30-45 seconds, 45-60 seconds, 60-75 seconds, 75-90 seconds, 90-105 seconds, 105-120 seconds, 120-135 seconds, 135-150 seconds, 150-165 seconds, 165-180 seconds, 180-195 seconds, 195-210 seconds, 210-225 seconds, or 225-240 seconds and can be inclusive of 15 seconds, 30 seconds, 45 seconds, 60 seconds, 75 seconds, 90 seconds, 105 seconds, 120 seconds, 135 seconds, 150 seconds, 165 seconds, 180 seconds, 195 seconds, 210 seconds, 225 seconds, 240 seconds, and any ranges therebetween. In an embodiment, the purge phase can last approximately 15 seconds.

In some examples, during operation of the system for sterilization and/or disinfection, the chamber temperature can range between 15° C. to 50° C. (58° F. to 120° F.). In some embodiments, the chamber temperature can range between 15° C.-20° C., 20° C.-25° C., 25° C.-30° C., 30° C.-35° C., 35° C.-40° C., 40° C.-45° C., or 45° C.-50° C. and can be inclusive of 15° C., 16° C., 17° C., 18° C., 19° C., 20° C., 21° C., 22° C., 23° C., 24° C., 25° C., 26° C., 27° C., 28° C., 29° C., 30° C., 31° C., 32° C., 33° C., 34° C., 35° C., 36° C., 37° C., 38° C., 39° C., 40° C., 41° C., 42° C., 43° C., 44° C., 45° C., 46° C., 47° C., 48° C., 49° C., 50° C., and any ranges therebetween.

In some embodiments, during operation of the system for sterilization and/or disinfection, the chamber relative humidity at the beginning of the exposure phase can be less than or equal to 20% relative humidity. In some embodiments, the chamber relative humidity during the exposure and purge phases can range between 10% to 85% non-condensing. In some embodiments, the (non-condensing) relative humidity can range between 10%-15%, 15%-20%, 20%-25%, 25%-30%, 30%-35%, 35%-40%, 40%-45%, 45%-50%, 50%-55%, 55%-60%, 60%-65%, 65%-70%, 70%-75%, or 75%-80% and can be inclusive of 10%, 15%, 20%, 25%, 30%, 35%, 40%, 45%, 50%, 55%, 60%, 65%, 70%, 75%, 80%, 85%, and any ranges therebetween.

In some embodiments, the electrical power required by the system for disinfection/sterilization can be 120V AC. In some embodiments the system can be powered by a rechargeable battery. In several embodiments, the system is capable of being configured to operate on 220V AC.

In some examples, the sterilization and/or disinfection cycle can have a duration ranging between about 1 minute to about 5 minutes or any ranges in between such as about 1 minute to about 1 minute 30 seconds, about 1 minute 30 seconds to about 2 minutes, about 2 minutes to about 2 minutes 30 seconds, about 2 minutes 30 seconds to about 3 minutes, about 3 minutes to about 3 minutes 30 seconds, about 3 minutes 30 seconds to about 4 minutes, about 4 minutes to about 4 minutes 30 seconds, about 4 minutes 30 seconds to about 5 minutes.

Figure 38A:
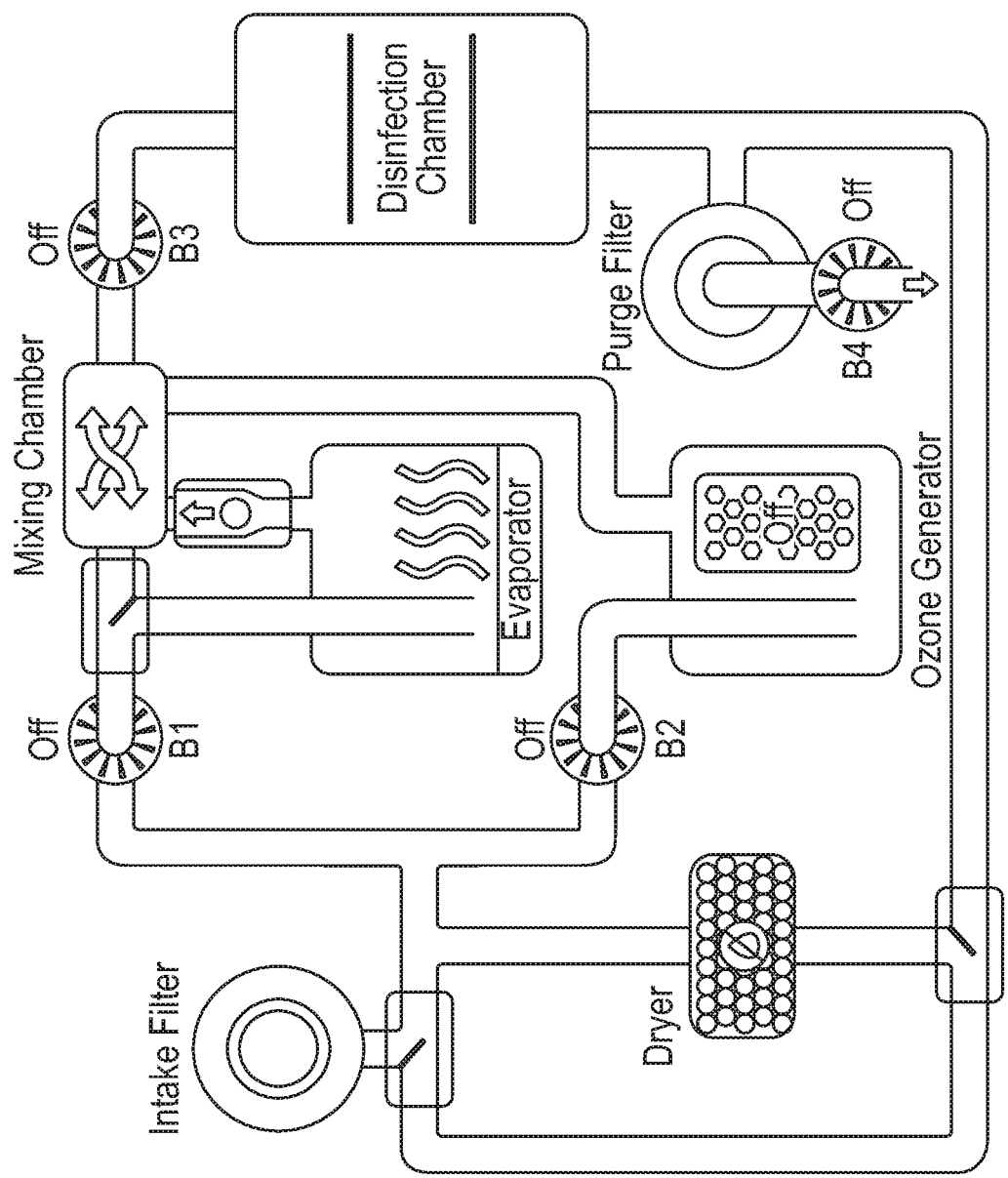
FIGS. 38A-38D show a plurality of schematic diagrams of non-limiting examples of the plumbing of a system for sterilizing and/or disinfecting.

FIGS. 38A-38D illustrate a non-limiting block diagram of a sterilization/disinfection system according to several embodiments described above. Turning first to FIG. 38A, illustrated is a block diagram of the plumbing for the system for sterilization and/or disinfection. In some embodiments, when the system is turned off, the valves are positioned to prevent any hydrogen peroxide gas vapor from filling the chamber (check valve) or escaping from the system.

Figure 38B:
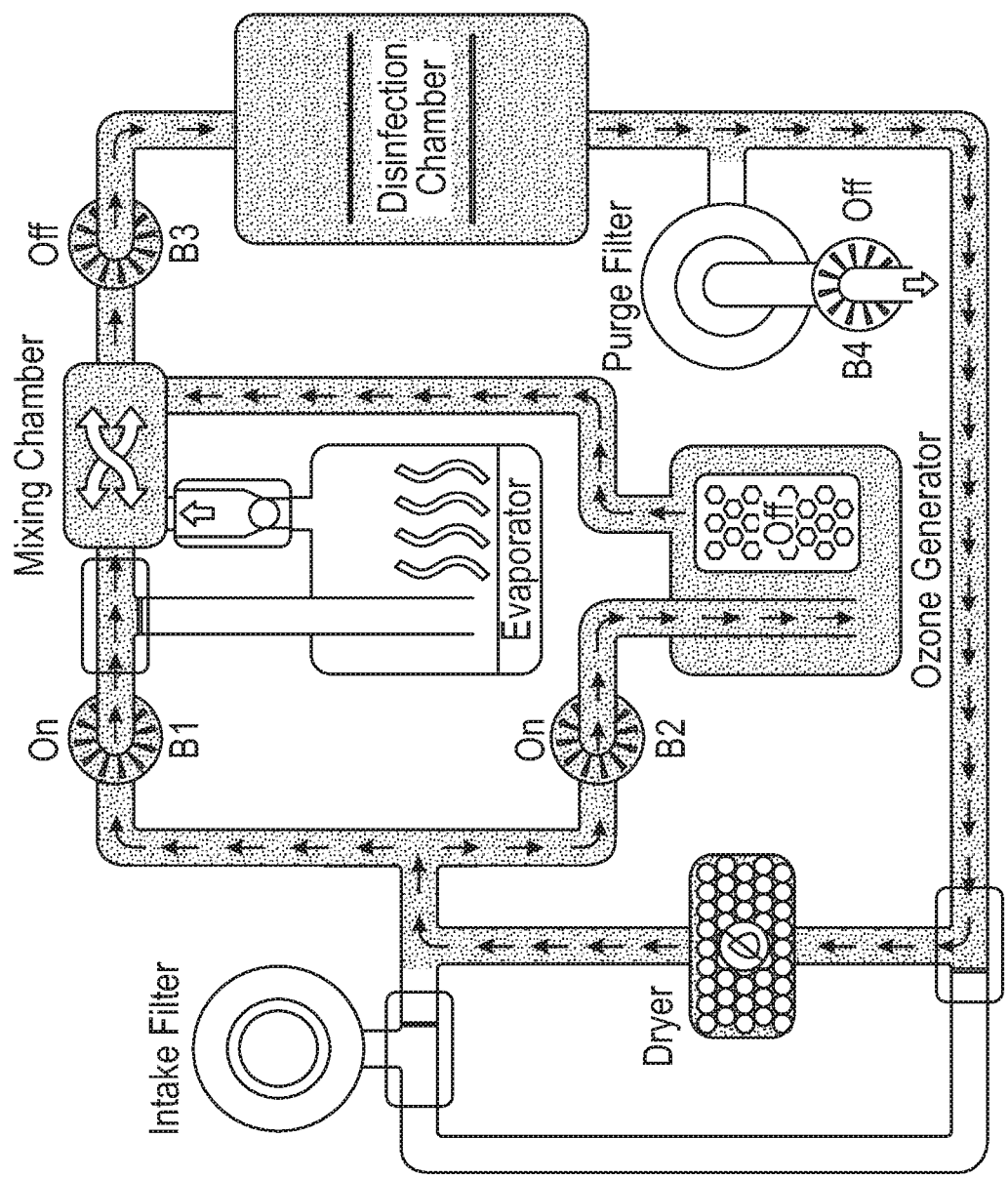

FIG. 38B illustrates a block diagram of the plumbing for the system for sterilization and/or disinfection during the conditioning phase (if the particular operating cycle is configured to include a conditioning phase). In some embodiments, the valves are first positioned to allow flow through the plumbing as shown, which bypasses the evaporator and ozone generator (which are turned off). As shown, during the conditioning phase Blower 1 (B1) and Blower 2 (B2) are turned on while Blower 3 (B3) and Blower 4 (B4) are off. In some examples, B4 can turn on intermittently to keep the pressure of the system below ambient pressure. As shown, the conditioning phase is a close loop operation which dries the air in the disinfection chamber and system plumbing. In some examples, the system operates in this conditioning phase until the pre-programmed percent of relative humidity (% RH) of the system is reached. Once the pre-determined % RH is reached, the system can proceed to the conditioning phase. In some embodiments, if the initial % RH of the system is more than 20% at the start of the conditioning phase, the target conditioning cycle can be greater than 10 seconds, including a range between 10 seconds to 60 seconds, between 10 seconds to 20 seconds, between 20 seconds to 30 seconds, between 30 seconds to 40 seconds, between 40 seconds 50 seconds, between 50 seconds to 60 seconds. In some embodiments, if the system has sufficient % RH (e.g. if the % RH is less than about 20%), the system does not proceed with the conditioning phase.

Figure 38C:
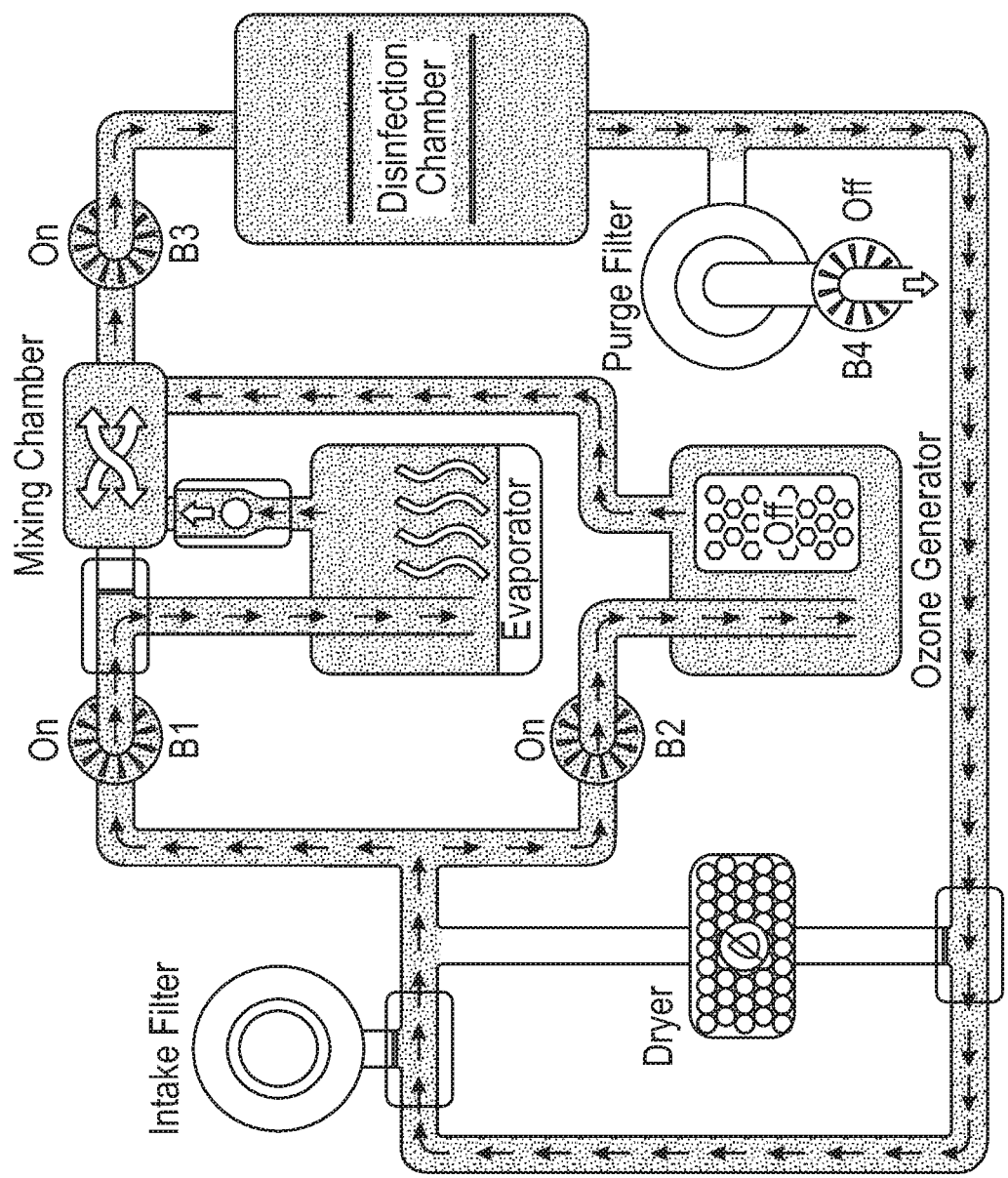

FIG. 38C illustrates a block diagram of the plumbing for the system for sterilization and/or disinfection during the exposure phase. As discussed above, during the exposure phase, the item/device to be sterilized/disinfection is exposed to a sterilant/disinfectant (e.g. hydrogen peroxide vapor or microdroplets, ozone, UV). As well, the exposure phase can last longer when sterilization is required rather than disinfection. In some embodiments, the valve positions can be changed to flow through the system as show. As illustrated in FIG. 38C, during the exposure phase, the dryer is bypassed. As shown, during the exposure phase, B1 and B2 can turn on, optional fan B3 can turn on, and the Ozone Generator can turn on. In some embodiments, B4 turns on intermittently to keep the pressure of the system below ambient pressure. During this phase, Ozone, hydrogen peroxide, and water vapor can fill the system and disinfection chamber. In some examples, the system can operate in this disinfection cycle for a pre-determined time according to the level of exposure to sterilant that is required (e.g. sterilization or disinfection).

Figure 38D:
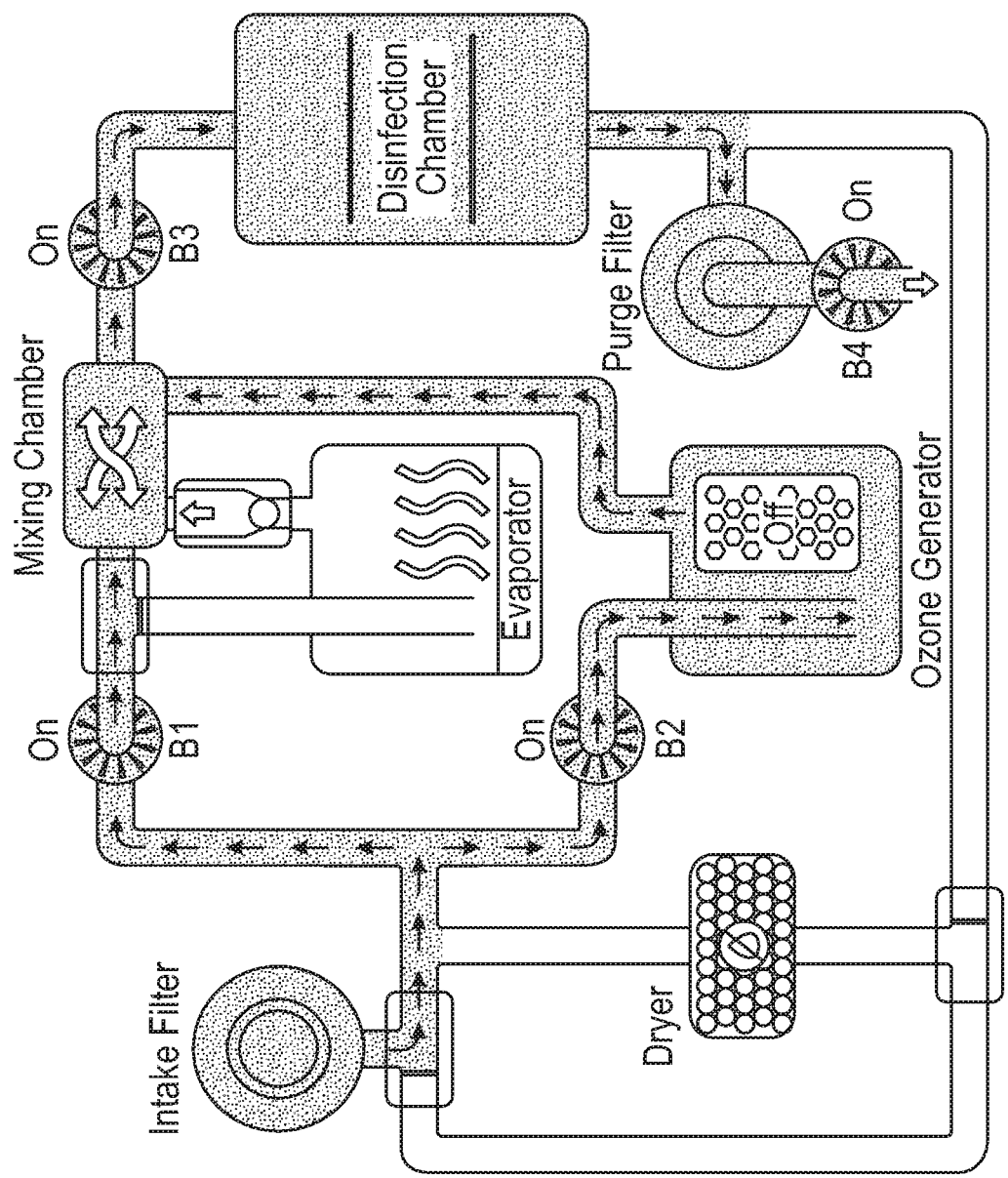

FIG. 38D illustrates a block diagram of the plumbing for the system for sterilization and/or disinfection during the purge (e.g., aeration) phase. As shown in FIG. 38D, the valve positions can change to flow through the system as shown. In some examples, the evaporator can be bypassed. During the purge phase, the ozone generator can be turned off, B1, B2 turned on, optional fan B3 turned on, and B4 is configured to turn on continuously. In some embodiments, fresh air can be configured to be pulled in through the intake filter. In some examples, effluent in the chamber and system can be forced to exit through the purge filter, where the ozone and hydrogen peroxide are converted into water vapor and oxygen before exhausting to atmosphere. As shown, the dryer is bypassed during this phase. In some examples, the system operates in this purge phase for a pre-determined time to clear the disinfection chamber from residual effluent.

Systems Employing Humidity Sensors

Figure 39:
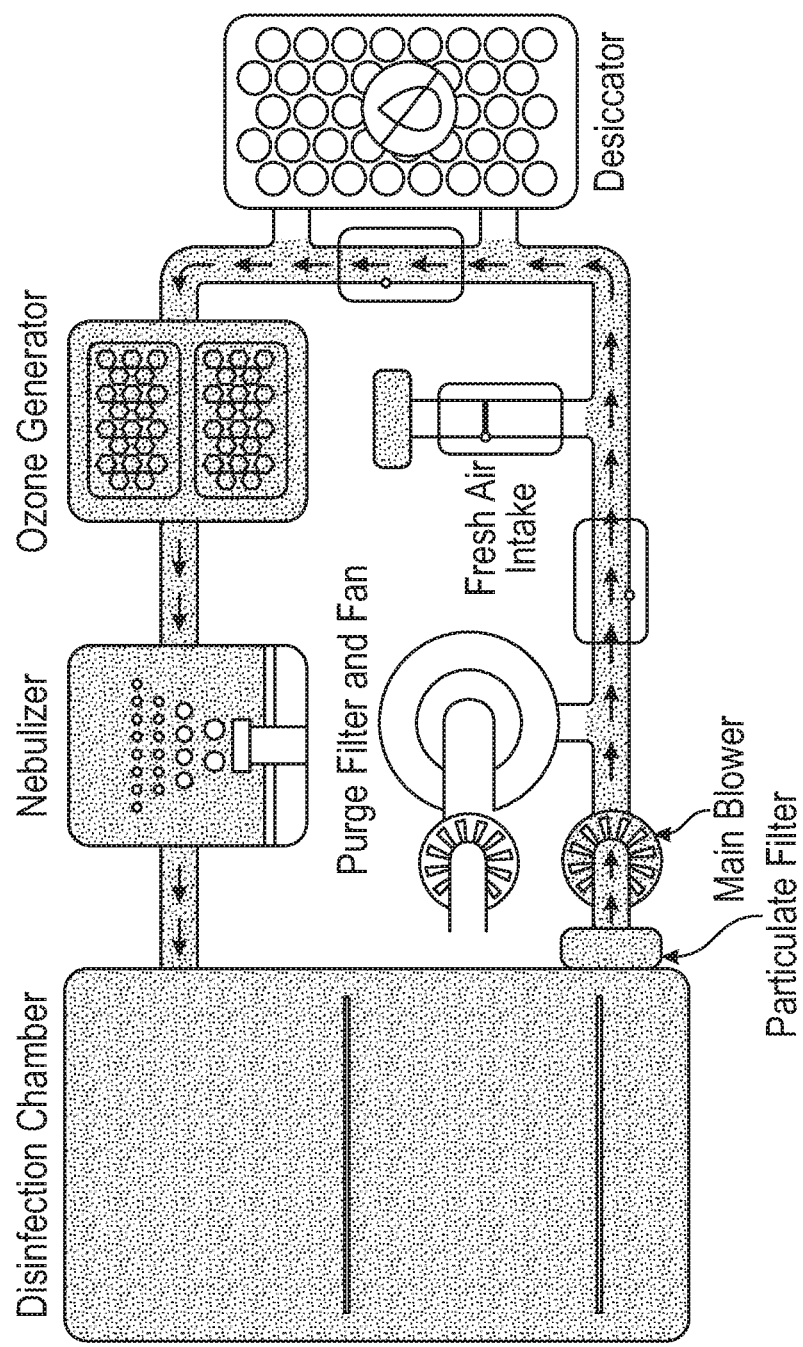
FIG. 39 shows an embodiment of a system for sterilization and/or disinfection including at least one humidity sensor and being configured prevent condensation within the disinfection chamber.

FIG. 39 illustrates an additional embodiment of a system for sterilization and/or disinfection including at least one humidity sensor and being configured to maintain the disinfection chamber below condensation levels to prevent condensation within the disinfection chamber. More specifically, the embodiment is configured to control the levels of hydrogen peroxide and water vapor in the disinfection chamber to dynamically prevent condensation while effectively disinfecting any object within the disinfection chamber.

The system of FIG. 39 may comprise one or more portions for delivering hydrogen peroxide vapor or microdroplets to the disinfection chamber at ambient pressure and temperature where it is mixed with non-thermal plasma effluent as disclosed herein. In several embodiments, the system is a closed loop system. For example, the evaporation of the hydrogen peroxide solution may be accomplished by air/gas flow through a nebulizer. Hydrogen peroxide solution may be delivered to the nebulizer by a pump (e.g., a precise pump, such as a peristaltic pump). The vapor and the plasma effluent may be mixed in a mixer prior to entering the sterilization or disinfection chamber.

In several embodiments, the disinfection chamber includes at least one humidity sensor. The level of vapor concentration can be determined by engaging such a sensor to measure the relative humidity level in the disinfection chamber, or other portion of the system. Controlling, e.g., precisely controlling, the amount of hydrogen peroxide solution delivered to the nebulizer may allow the system to regulate itself to maintain the chamber below the saturation level, and thereby advantageously prevent condensation within the system, e.g., within the disinfection chamber.

As shown in FIG. 39, the system may include one or more of a disinfection/sterilization chamber, a nebulizer, an ozone generator, a dryer (e.g., a desiccator), a dryer valve, a fresh air intake, aa purge filter and fan, a purge valve, a main blower and a particulate filter. The system may include one or more humidity sensors. In some embodiments, the system includes one humidity sensor. In other embodiments, the system includes more than one humidity sensor. For example, the system may include 2 sensors, 3 sensors, 4 sensors, 5 sensors, 6 sensors, 7 sensors, 8 sensors, 9 sensors, 10 sensors, or more sensors.

In some embodiments, all humidity sensors are located in the disinfection chamber. In some embodiments, the humidity sensors are located throughout the system. For example, one or more humidity sensors may be located near, at, or within one or more of the disinfection chamber, the nebulizer, a connecting tube between the disinfection chamber and the nebulizer, the ozone generator, a connecting tube between the ozone generator and the nebulizer, the dryer, the dryer valve, a connecting tube between the dryer and the ozone generator (or the nebulizer), a connecting tube between the dryer valve and the ozone generator (or the nebulizer), the fresh air intake, a connecting tube between the fresh air intake and the dryer (or the dryer valve), the purge valve, a connecting tube between the purge valve and the fresh air intake, a connecting tube between the purge valve and the dryer (or the dryer valve), the purge filter and fan, a connecting tube between the purge filter and fan and the purge valve (or the dryer valve), the main blower, a connecting tube between the main blower and the purge filter and fan (or the purge valve), the particulate filter, or any connecting tube within the system. In some embodiments, when more than one humidity sensor is included within the disinfection chamber, the various humidity sensors may provide localized humidity maps, which may be indicative of or correspond to areas of increased humidity, areas of increased risk for condensation, areas of decreased humidity, and/or improper mixing and/or turbulence within the disinfection chamber. In some embodiments, when a humidity sensor is included in a portion of the system other than or in addition to the disinfection chamber, the humidity sensor(s) may be used to provide relative or localized humidity maps. For example, it may be undesirable for condensation to occur in various components or connecting tubing (due to potential bacterial growth or other effect). Multiple humidity sensors may advantageously allow the system to regulate, e.g., to self-regulate the humidity in areas of the system in addition to the disinfection chamber.

Figure 40:
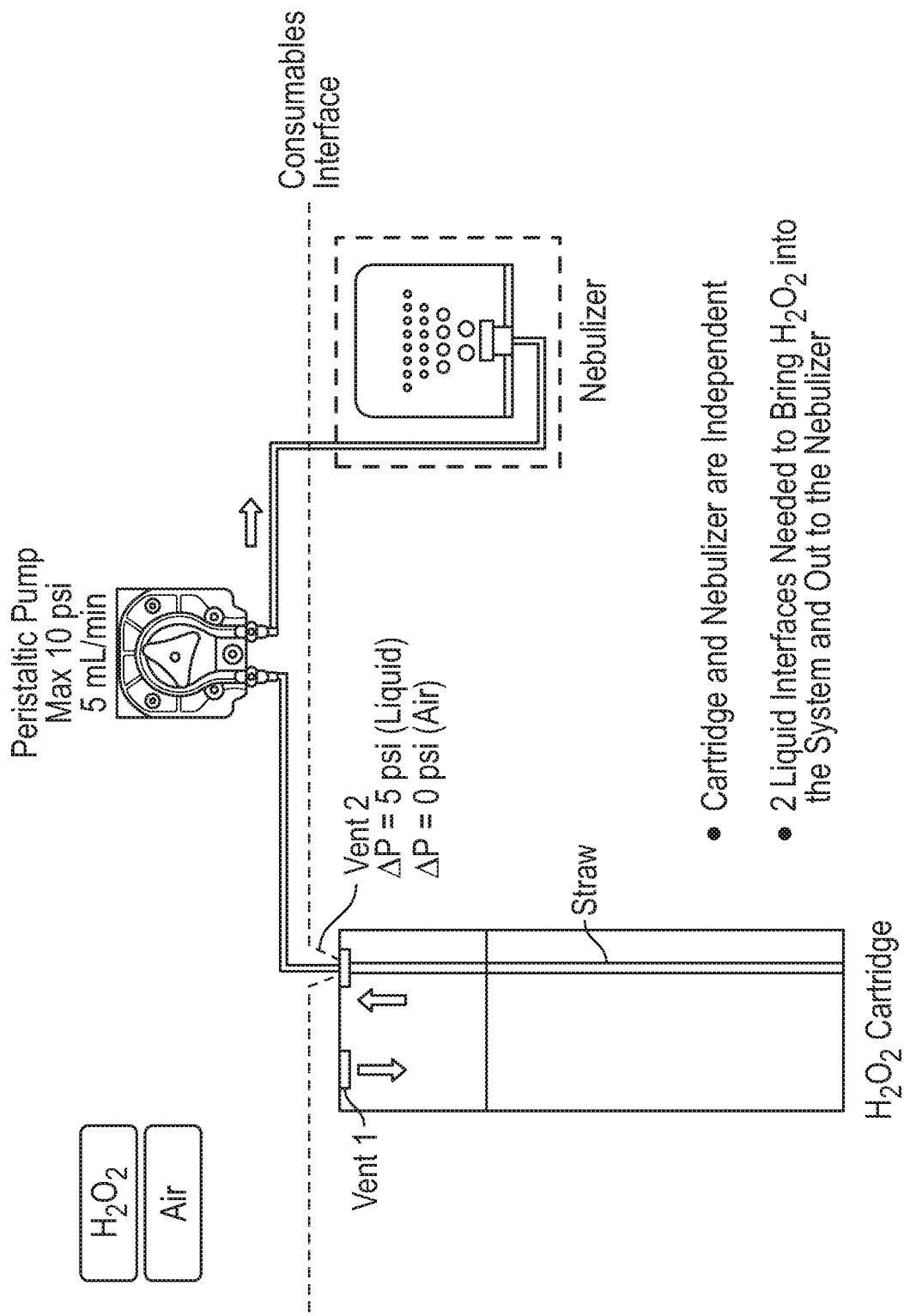
FIG. 40 shows an embodiment of a nebulizer with a peristaltic pump and hydrogen peroxide solution cartridge that may be used in connection with various systems disclosed herein.

FIG. 40 illustrates an embodiment of a nebulizer with a peristaltic pump and hydrogen peroxide solution cartridge that may be used in connection with various systems disclosed herein. The hydrogen peroxide cartridge may contain a quantity of hydrogen peroxide and a quantity of air. As the quantity of hydrogen peroxide decreases, due to use or evaporation, or other decreasing factor, air may enter the hydrogen peroxide cartridge through the vent.

The peristaltic pump may be connected to the hydrogen peroxide cartridge and pump hydrogen peroxide out of the hydrogen peroxide cartridge, e.g., pump hydrogen peroxide out of the hydrogen peroxide cartridge through a tube or a straw. In some embodiments, the peristaltic pump is configured to provide a pressure of about 10 psi. In some embodiments, the peristaltic pump is configured to provide a pressure of greater than about 10 psi. In other embodiments, the peristaltic pump is configured to provide a pressure of less than about 10 psi. For example, the peristaltic pump may be configured to provide a pressure of less than about 20 psi, less than about 19 psi, less than about 18 psi, less than about 17 psi, less than about 16 psi, less than about 15 psi, less than about 14 psi, less than about 13 psi, less than about 12 psi, less than about 11 psi, less than about 10 psi, less than about 9.5 psi, less than about 9 psi, less than about 8.5 psi, less than about 8 psi, less than about 7.5 psi, less than about 7 psi, less than about 6.5 psi, less than about 6 psi, less than about 5.5 psi, less than about 5 psi, less than about 4.5 psi, or less than about 4 psi. In several embodiments, the peristaltic pump is configured to provide a flow rate of about 5 ml/min. In several embodiments, the peristaltic pump is configured to provide a flow rate of greater than about 5 ml/min. In several embodiments, the peristaltic pump is configured to provide a flow rate of less than about 5 ml/min. For example, the peristaltic pump may be configured to provide a flow rate of less than about 25 ml/min, less than about 20 ml/min, less than about 15 ml/min, less than about 10 ml/min, less than about 9 ml/min, less than about 8 ml/min, less than about 7 ml/min, less than about 6 ml/min, less than about 5 ml/min, less than about 4.5 ml/min, less than about 4 ml/min, less than about 3.5 ml/min, less than about 3 ml/min, less than about 2.5 ml/min, less than about 2 ml/min, less than about 1.5 ml/min, or less than about 1 ml/min. The peristaltic pump may provide a flow of effluent, e.g., hydrogen peroxide, to the nebulizer where it is nebulized for provision to one or more parts, portions, or components of the system for disinfection or sterilization.

Several embodiments of the systems for disinfecting while minimizing condensation (e.g., managing humidity, pressure, temperature, etc.) include at least one temperature sensor and/or at least one pressure sensor.

Similar to the humidity sensor(s) disclosed herein, in some embodiments all temperature sensors are located in the disinfection chamber. In some embodiments, the temperature sensors are located throughout the system. For example, one or more temperature sensors may be located near, at, or within one or more of the disinfection chamber, the nebulizer, a connecting tube between the disinfection chamber and the nebulizer, the ozone generator, a connecting tube between the ozone generator and the nebulizer, the dryer, the dryer valve, a connecting tube between the dryer and the ozone generator (or the nebulizer), a connecting tube between the dryer valve and the ozone generator (or the nebulizer), the fresh air intake, a connecting tube between the fresh air intake and the dryer (or the dryer valve), the purge valve, a connecting tube between the purge valve and the fresh air intake, a connecting tube between the purge valve and the dryer (or the dryer valve), the purge filter and fan, a connecting tube between the purge filter and fan and the purge valve (or the dryer valve), the main blower, a connecting tube between the main blower and the purge filter and fan (or the purge valve), the particulate filter, or any connecting tube within the system. In some embodiments, when more than one temperature sensor is included within the disinfection chamber, the various temperature sensors may provide localized temperature maps, which may be indicative of or correspond to areas of increased temperature, areas of increased risk for condensation, areas of decreased temperature, and/or improper mixing and/or turbulence within the disinfection chamber. In some embodiments, when a temperature sensor is included in a portion of the system other than or in addition to the disinfection chamber, the temperature sensor(s) may be used to provide relative or localized temperature maps. For example, it may be undesirable for condensation to occur in various components or connecting tubing (due to potential bacterial growth or other effect). Multiple temperature sensors may advantageously allow the system to regulate, e.g., to self-regulate the temperature in areas of the system in addition to the disinfection chamber.

Similar to the humidity sensor(s) disclosed herein, in some embodiments all pressure sensors are located in the disinfection chamber. In some embodiments, the pressure sensors are located throughout the system. For example, one or more pressure sensors may be located near, at, or within one or more of the disinfection chamber, the nebulizer, a connecting tube between the disinfection chamber and the nebulizer, the ozone generator, a connecting tube between the ozone generator and the nebulizer, the dryer, the dryer valve, a connecting tube between the dryer and the ozone generator (or the nebulizer), a connecting tube between the dryer valve and the ozone generator (or the nebulizer), the fresh air intake, a connecting tube between the fresh air intake and the dryer (or the dryer valve), the purge valve, a connecting tube between the purge valve and the fresh air intake, a connecting tube between the purge valve and the dryer (or the dryer valve), the purge filter and fan, a connecting tube between the purge filter and fan and the purge valve (or the dryer valve), the main blower, a connecting tube between the main blower and the purge filter and fan (or the purge valve), the particulate filter, or any connecting tube within the system. In some embodiments, when more than one pressure sensor is included within the disinfection chamber, the various pressure sensors may provide localized pressure maps, which may be indicative of or correspond to areas of increased pressure, areas of increased risk for condensation, areas of decreased pressure, and/or improper mixing and/or turbulence within the disinfection chamber. In some embodiments, when a pressure sensor is included in a portion of the system other than or in addition to the disinfection chamber, the pressure sensor(s) may be used to provide relative or localized pressure maps. For example, it may be undesirable for condensation to occur in various components or connecting tubing (due to potential bacterial growth or other effect). Multiple pressure sensors may advantageously allow the system to regulate, e.g., to self-regulate the pressure in areas of the system in addition to the disinfection chamber.

In operation, the controller reads the door sensor position. For example, the controller will not begin a disinfecting cycle if the door sensor indicates that the door is open. If the door sensor indicates that the door is closed, the controller may determine whether the cartridge, e.g., the hydrogen peroxide sensor, is empty. If all criteria necessary for the controller to commence a disinfecting cycle have been met or are satisfied, the controller may turn on the main blower to begin circulating gases within the system.

In some embodiments, the disinfecting cycle comprises a single cycle portion. In some embodiments, the disinfecting cycle comprises a plurality of cycle portions, or sub-cycles. In some embodiments, the disinfecting cycle comprises three cycle portion or sub-cycles, e.g., three distinct sub-cycles. In some embodiments, the disinfecting cycle comprises a drying sub-cycle, a disinfection sub-cycle, and a purge sub-cycle.

To begin a drying sub-cycle, the drying valve may be closed so that the circulating air, e.g., the air being circulated by the main blower, is directed or driven into the dryer or desiccant, as disclosed herein. In some embodiments, the sterilization begins with a drying sub-cycle. As discussed, the air from the disinfection chamber (or the air from the disinfection circuit, comprising some, most, or all of the components of the system) is directed to the dryer by closing the dryer valve (shown in FIG. 39). Passing the air through the dryer removes some, most, or all of the water content from the air. In some embodiments, the air in the chamber or circuit is decreased in humidity by at least about 50%, at least about 55%, at least about 60%, at least about 65%, at least about 70%, at least about 75%, at least about 80%, at least about 85%, at least about 90%, or at least about 95%. In some embodiments, the air in the chamber or the circuit is dried during the drying sub-cycle until the air has a relative humidity of less than about 20%. In some embodiments, the air in the chamber or the circuit is dried during the drying sub-cycle until the air has a relative humidity of less than about 60%, less than about 55%, less than about 50%, less than about 45%, less than about 40%, less than about 35%, less than about 32.5%, less than about 30%, less than about 27.5%, less than about 25%, less than about 22.5%, less than about 20%, less than about 17.5%, less than about 15%, less than about 12.5%, less than about 10%, less than about 7.5%, less than about 5%, or less than about 2.5%. The humidity may be monitored using the at least one humidity sensor discussed herein. The drying sub-cycle may persist until the humidity level is lowered at least to the prescribed value. When the drying sub-cycle is complete, e.g., when the controller detects that the gases in the chamber or the circuit have sufficiently decreased, the drying valve may open and the effluent may flow into or to, e.g., directly into or to, the ozone generator (e.g., the fluid flow may substantially or entirely bypass the dryer).

In some embodiments, a disinfecting sub-cycle follows the drying sub-cycle. In some embodiments, the disinfection sub-cycle begins when the drying valve opens. In some embodiments, the disinfection sub-cycle begins when one or more of the ozone generator, the pump, and the nebulizer are turned on. In some embodiments, the disinfection sub-cycle beings when both the drying valve opens and at least one of the ozone generator, the pump, and the nebulizer is turned on. In some embodiments, the disinfection sub-cycle begins when both the drying valve opens and each of the ozone generator, the pump, and the nebulizer is turned on. The pump may be configured to deliver a prescribed initial amount of the disinfecting solution, e.g., the hydrogen peroxide solution, to the nebulizer. Following the initial delivery of disinfecting solution, the relatively humidity may be recorded. During the disinfecting sub-cycle, the at least one humidity sensor may monitor the relative humidity in the disinfecting chamber may be monitored, e.g., continuously monitored, periodically monitored, etc. If the relative humidity does not reach the minimum prescribed value, the pump may deliver more disinfecting solution to the nebulizer until the relative humidity is increased to the desired level, e.g., below saturation or below the condensation point. In some embodiments, once the desired level of relative humidity is reached, one or more of the ozone generator, pump, and nebulizer are cycled on and off to maintain the relative humidity. For example, one or more of the ozone generator, pump, and nebulizer may be cycled on and off to keep the relative humidity below a certain value (e.g., below the condensation point) and above a certain floor. In some embodiments, as soon as the desired humidity in the chamber is reached, the pump and the nebulizer are both turned off. In some embodiments, if the humidity level decreases below a set floor, the pump and the nebulizer are both turned back on until the humidity level reaches a set point, e.g., the desired humidity at which point the pump and nebulizer were originally turned off. Upon reaching that point again, the pump and the nebulizer may be turned off. Such cycling may continue until the prescribed sterilization time is complete.

The system may maintain the disinfecting sub-cycle for a pre-set time period. In some embodiments, the disinfecting sub-cycle is less than about 20 minutes, less than about 18 minutes, less than about 16 minutes, less than about 14 minutes, less than about 12 minutes, less than about 10 minutes, less than about 9 minutes, less than about 8 minutes, less than about 7 minutes, less than about 6 minutes, less than about 5 minutes, less than about 4 minutes, less than about 3 minutes, less than about 2 minutes or less than about 1 minute. In some embodiments, the disinfecting sub-cycle lasts for between about 1-60 minutes, between about 2-55 minutes, between about 3-50 minutes, between about 4-45 minutes, between about 5-40 minutes, between about 6-35 minutes, between about 7-30 minutes, between about 8-25 minutes, between about 9-20 minutes, or between about 10-15 minutes.

In some embodiments, the hydrogen peroxide reaches a minimum of 250 ppm from the start of the disinfection cycle. In some examples, the hydrogen peroxide is configured to reach a minimum of between about 200 ppm to about 500 ppm, including ranges in between such as about 200 ppm to about 250 ppm, about 250 ppm to about 300 ppm, about 300 ppm to about 350 ppm, about 350 ppm to about 400 ppm, about 400 ppm to about 450 ppm, and about 450 ppm to about 500 ppm. In some examples, the time for the disinfection cycle to reach the minimum ppm of hydrogen peroxide can range between about 0 seconds to about 1 minute or any ranges in between such as about 0 seconds to about 10 seconds, about 10 seconds to about 20 seconds, about 20 seconds to about 30 seconds, about 30 seconds to about 40 seconds, about 40 seconds to about 50 seconds, about 50 seconds to about 1 minute.

In some embodiments, the ozone reaches a minimum of 550 ppm from the start of the disinfection cycle. In some examples, the time for the disinfection cycle to reach the minimum ppm of ozone can range between about 0 seconds to about 1 minute or any ranges in between such as about 0 seconds to about 10 seconds, about 10 seconds to about 20 seconds, about 20 seconds to about 30 seconds, about 30 seconds to about 40 seconds, about 40 seconds to about 50 seconds, about 50 seconds to about 1 minute.

In some examples, after the disinfection sub-cycle reaches the minimum required sterilant ppm (e.g. hydrogen peroxide, ozone), the sterilant can be continuously sustained about the minimum ppm for a range between about 2 minutes to about 5 minutes or any ranges in between such as about 2 minutes to about 2 minutes 10 seconds, about 2 minutes 10 seconds to about 2 minutes 20 seconds, about 2 minutes 20 seconds to about 2 minutes 30 seconds, about 2 minutes 30 seconds to about 2 minutes 40 seconds, about 2 minutes 40 seconds to about 2 minutes 50 seconds, about 2 minutes 50 seconds to about 3 minutes, about 3 minutes to about 3 minutes 10 seconds, about 3 minutes 10 seconds to about 3 minutes 20 seconds, about 3 minutes 20 seconds to about 3 minutes 30 seconds, about 3 minutes 30 seconds to about 3 minutes 40 seconds, about 3 minutes 40 seconds to about 3 minutes 50 seconds, about 3 minutes 50 seconds to about 4 minutes, about 4 minutes to about 4 minutes 10 seconds, about 4 minutes 10 seconds to about 4 minutes 20 seconds, about 4 minutes 20 seconds to about 4 minutes 30 seconds, about 4 minutes 30 seconds to about 4 minutes 40 seconds, about 4 minutes 40 seconds to about 4 minutes 50 seconds, about 4 minutes 50 seconds to about 5 minutes. In some embodiments, after the disinfection sub-cycle reaches the minimum required sterilant ppm (e.g. hydrogen peroxide, ozone), the sterilant can be continuously sustained about the minimum ppm for a range between about 2 minutes to about 15 minutes, or any ranges in between such as about 2 minutes to 3 minutes, about 3 minutes to 4 minutes, about 4 minutes to about 5 minutes, about 5 minutes to about 6 minutes, about 6 minutes to about 7 minutes, about 7 minutes to about 8 minutes, about 8 minutes to about 9 minutes, about 9 minutes to about 10 minutes, about 10 minutes to about 11 minutes, about 11 minutes to about 12 minutes, about 12 minutes to about 13 minutes, about 13 minutes to about 14 minutes, and about 14 minutes to about 15 minutes.

In some embodiments, a purge sub-cycle follows the disinfecting sub-cycle. The purge sub-cycle may begin by turning off one or more of the ozone generator, the nebulizer, and the pump (e.g., turning off each of the ozone generator, the nebulizer, and the pump). In some embodiments, the purging sub-cycle includes closing the purging valve so that flow of gases/fluid is directed into the exhaust (e.g., the purge filter and fan) and fresh air is drawn into the system (e.g., the circuit) through the intake and the HEPA filter. In some embodiments, the filter is configured to convert effluent into water vapor and oxygen. The purging sub-cycle persists for a set amount of time. In some embodiments, the purging sub-cycle persists for less than about 15 minutes, less than about 14 minutes, less than about 13 minutes, less than about 12 minutes, less than about 11 minutes, less than about 10 minutes, less than about 9 minutes, less than about 8 minutes, less than about 7 minutes, less than about 6 minutes, less than about 5 minutes, less than about 4 minutes, less than about 3 minutes, less than about 2 minutes, or less than about 1 minute. In some embodiments, the purging sub-cycle continues until the concentration of disinfectant in the circulating air is less than about 650 ppm, less than about 600 ppm, less than about 550 ppm, less than about 500 ppm, less than about 450 ppm, less than about 400 ppm, less than about 350 ppm, less than about 300 ppm, less than about 250 ppm, less than about 200 ppm, less than about 190 ppm, less than about 180 ppm, less than about 170 ppm, less than about 160 ppm, less than about 150 ppm, less than about 140 ppm, less than about 130 ppm, less than about 120 ppm, less than about 110 ppm, less than about 100 ppm, less than about 90 ppm, less than about 80 ppm, less than about 70 ppm, less than about 60 ppm, less than about 50 ppm, less than about 40 ppm, less than about 30 ppm, less than about 20 ppm, or less than about 10 ppm. In some examples, the purge sub-cycle can have a duration ranging between 20 seconds to about 2 minutes such that safe levels of sterilant (e.g. hydrogen peroxide and ozone) are reached. In some embodiments, the range can include ranges in between about 20 seconds to about 30 seconds, about 30 seconds to about 40 seconds, about 40 seconds to about 50 seconds, about 50 seconds to about 1 minute, about 1 minute to about 1 minute 10 seconds, about 1 minute 10 seconds to about 1 minute 20 seconds, about 1 minute 20 seconds to about 1 minute 30 seconds, about 1 minute 30 seconds to about 1 minute 40 seconds, about 1 minute 40 seconds to about 1 minute 50 seconds, about 1 minute 50 seconds to about 2 minutes.

Figure 41:
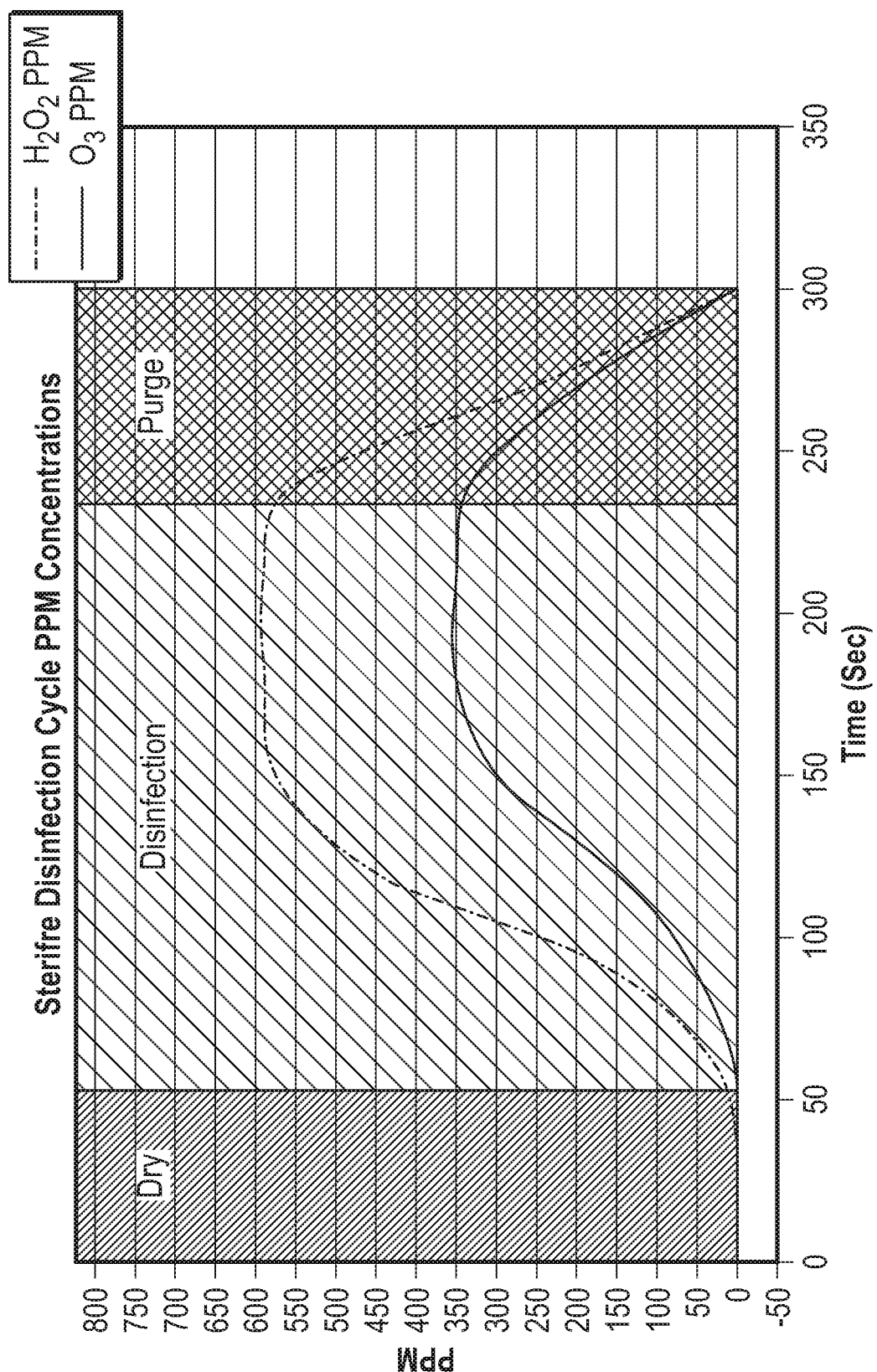
FIG. 41 shows a graph of exemplary hydrogen peroxide and ozone levels over time in a disinfectant chamber according to an embodiment of the systems and methods disclosed herein.

FIG. 41 illustrates a graph of exemplary hydrogen peroxide and ozone levels over time in a disinfectant chamber according to an embodiment of the systems and methods disclosed herein. As shown, the drying sub-cycle may see little if any humidity in the circuit, e.g., chamber. In the disinfection sub-cycle, the concentration of hydrogen peroxide in the chamber increases, and, thus, the relative humidity in the chamber also increases, until a set relative humidity value is reached. As shown the set relative humidity value corresponds to a hydrogen peroxide concentration of about 600 ppm. Once the set relative humidity value is reached, the various portions of the system injecting disinfectant into the system/circuit are cycled on and off to maintain the concentration of hydrogen peroxide at a level corresponding to the desired relative humidity. The desired relative humidity corresponds to a value lower than the saturation point and/or under the condensation point. In this way, the relative humidity in the chamber never becomes so high that condensation begins to form. After the prescribed time, e.g., when sterilization is complete, the disinfectant is purged from the chamber in the purge sub-cycle.

Implementation Mechanisms

According to some embodiments, the methods described herein can be implemented by one or more special-purpose computing devices. The special-purpose computing devices may be hard-wired to perform the techniques, or may include digital electronic devices such as one or more application-specific integrated circuits (ASICs) or field programmable gate arrays (FPGAs) that are persistently programmed to perform the techniques, or may include one or more general purpose hardware processors programmed to perform the techniques pursuant to program instructions in firmware, memory, other storage, or a combination. Such special-purpose computing devices may also combine custom hard-wired logic, ASICs, or FPGAs with custom programming to accomplish the techniques. The special-purpose computing devices may be desktop computer systems, server computer systems, portable computer systems, handheld devices, networking devices or any other device or combination of devices that incorporate hard-wired and/or program logic to implement the techniques.

Computing device(s) are generally controlled and coordinated by operating system software, such as iOS, Android, Chrome OS, Windows XP, Windows Vista, Windows 7, Windows 8, Windows Server, Windows CE, Unix, Linux, SunOS, Solaris, iOS, Blackberry OS, VxWorks, or other compatible operating systems. In other embodiments, the computing device may be controlled by a proprietary operating system. Conventional operating systems control and schedule computer processes for execution, perform memory management, provide file system, networking, I/O services, and provide a user interface functionality, such as a graphical user interface ("GUI"), among other things.

In some embodiments, the computer system includes a bus or other communication mechanism for communicating information, and a hardware processor, or multiple processors, coupled with the bus for processing information. Hardware processor(s) may be, for example, one or more general purpose microprocessors.

In some embodiments, the computer system may also include a main memory, such as a random access memory (RAM), cache and/or other dynamic storage devices, coupled to a bus for storing information and instructions to be executed by a processor. Main memory also may be used for storing temporary variables or other intermediate information during execution of instructions to be executed by the processor. Such instructions, when stored in storage media accessible to the processor, render the computer system into a special-purpose machine that is customized to perform the operations specified in the instructions.

In some embodiments, the computer system further includes a read only memory (ROM) or other static storage device coupled to bus for storing static information and instructions for the processor. A storage device, such as a magnetic disk, optical disk, or USB thumb drive (Flash drive), etc., may be provided and coupled to the bus for storing information and instructions.

In some embodiments, the computer system may be coupled via a bus to a display, such as a cathode ray tube (CRT) or LCD display (or touch screen), for displaying information to a computer user. An input device, including alphanumeric and other keys, is coupled to the bus for communicating information and command selections to the processor. Another type of user input device is cursor control, such as a mouse, a trackball, or cursor direction keys for communicating direction information and command selections to the processor and for controlling cursor movement on display. This input device typically has two degrees of freedom in two axes, a first axis (e.g., x) and a second axis (e.g., y), that allows the device to specify positions in a plane. In some embodiments, the same direction information and command selections as cursor control may be implemented via receiving touches on a touch screen without a cursor.

In some embodiments, the computing system may include a user interface module to implement a GUI that may be stored in a mass storage device as executable software codes that are executed by the computing device(s). This and other modules may include, by way of example, components, such as software components, object-oriented software components, class components and task components, processes, functions, attributes, procedures, subroutines, segments of program code, drivers, firmware, microcode, circuitry, data, databases, data structures, tables, arrays, and variables.

In general, the word "module," as used herein, refers to logic embodied in hardware or firmware, or to a collection of software instructions, possibly having entry and exit points, written in a programming language, such as, for example, Java, Lua, C or C++. A software module may be compiled and linked into an executable program, installed in a dynamic link library, or may be written in an interpreted programming language such as, for example, BASIC, Perl, or Python. It will be appreciated that software modules may be callable from other modules or from themselves, and/or may be invoked in response to detected events or interrupts. Software modules configured for execution on computing devices may be provided on a computer readable medium, such as a compact disc, digital video disc, flash drive, magnetic disc, or any other tangible medium, or as a digital download (and may be originally stored in a compressed or installable format that requires installation, decompression or decryption prior to execution). Such software code may be stored, partially or fully, on a memory device of the executing computing device, for execution by the computing device. Software instructions may be embedded in firmware, such as an EPROM. It will be further appreciated that hardware modules may be comprised of connected logic units, such as gates and flip-flops, and/or may be comprised of programmable units, such as programmable gate arrays or processors. The modules or computing device functionality described herein are preferably implemented as software modules, but may be represented in hardware or firmware. Generally, the modules described herein refer to logical modules that may be combined with other modules or divided into sub-modules despite their physical organization or storage In some embodiments, a computer system may implement the methods described herein using customized hard-wired logic, one or more ASICs or FPGAs, firmware and/or program logic which in combination with the computer system causes or programs the computer system to be a special-purpose machine. According to one embodiment, the methods herein are performed by the computer system in response to hardware processor(s) executing one or more sequences of one or more instructions contained in main memory. Such instructions may be read into main memory from another storage medium, such as a storage device. Execution of the sequences of instructions contained in main memory causes processor(s) to perform the process steps described herein. In alternative embodiments, hard-wired circuitry may be used in place of or in combination with software instructions.

The term "non-transitory media," and similar terms, as used herein refers to any media that store data and/or instructions that cause a machine to operate in a specific fashion. Such non-transitory media may comprise non-volatile media and/or volatile media. Non-volatile media includes, for example, optical or magnetic disks, or other types of storage devices. Volatile media includes dynamic memory, such as a main memory. Common forms of non-transitory media include, for example, a floppy disk, a flexible disk, hard disk, solid state drive, magnetic tape, or any other magnetic data storage medium, a CD-ROM, any other optical data storage medium, any physical medium with patterns of holes, a RAM, a PROM, and EPROM, a FLASH-EPROM, NVRAM, any other memory chip or cartridge, and networked versions of the same.

Non-transitory media is distinct from but may be used in conjunction with transmission media. Transmission media participates in transferring information between nontransitory media. For example, transmission media includes coaxial cables, copper wire and fiber optics, including the wires that comprise a bus. Transmission media can also take the form of acoustic or light waves, such as those generated during radio-wave and infra-red data communications.

Various forms of media may be involved in carrying one or more sequences of one or more instructions to a processor for execution. For example, the instructions may initially be carried on a magnetic disk or solid state drive of a remote computer. The remote computer can load the instructions into its dynamic memory and send the instructions over a telephone line using a modem or other network interface, such as a WAN or LAN interface. A modem local to a computer system can receive the data on the telephone line and use an infra-red transmitter to convert the data to an infra-red signal. An infra-red detector can receive the data carried in the infra-red signal and appropriate circuitry can place the data on a bus. The bus carries the data to the main memory, from which the processor retrieves and executes the instructions. The instructions received by the main memory may retrieve and execute the instructions. The instructions received by the main memory may optionally be stored on a storage device either before or after execution by the processor.

In some embodiments, the computer system may also include a communication interface coupled to a bus. The communication interface may provide a two-way data communication coupling to a network link that is connected to a local network. For example, a communication interface may be an integrated services digital network (ISDN) card, cable modem, satellite modem, or a modem to provide a data communication connection to a corresponding type of telephone line. As another example, a communication interface may be a local area network (LAN) card to provide a data communication connection to a compatible LAN (or WAN component to communicate with a WAN). Wireless links may also be implemented. In any such implementation, a communication interface sends and receives electrical, electromagnetic or optical signals that carry digital data streams representing various types of information.

A network link may typically provide data communication through one or more networks to other data devices. For example, a network link may provide a connection through a local network to a host computer or to data equipment operated by an Internet Service Provider (ISP). The ISP in turn provides data communication services through the world wide packet data communication network now commonly referred to as the "Internet." The local network and Internet both use electrical, electromagnetic or optical signals that carry digital data streams. The signals through the various networks and the signals on the network link and through a communication interface, which carry the digital data to and from the computer system, are example forms of transmission media.

In some embodiments, the computer system can send messages and receive data, including program code, through the network(s), the network link, and the communication interface. In the Internet example, a server might transmit a requested code for an application program through the Internet, ISP, local network, and communication interface.

The received code may be executed by a processor as it is received, and/or stored in a storage device, or other non-volatile storage for later execution.

Accordingly, it is to be understood that the embodiments of the invention herein described are merely illustrative of the application of the principles of the invention. Reference herein to details of the illustrated embodiments is not intended to limit the scope of the claims, which themselves recite those features regarded as essential to the invention. The drawings are for the purpose of illustrating embodiments of the invention only, and not for the purpose of limiting it.

It is contemplated that various combinations or subcombinations of the specific features and aspects of the embodiments disclosed above may be made and still fall within one or more of the inventions. Further, the disclosure herein of any particular feature, aspect, method, property, characteristic, quality, attribute, element, or the like in connection with an embodiment can be used in all other embodiments set forth herein. Accordingly, it should be understood that various features and aspects of the disclosed embodiments can be combined with or substituted for one another in order to form varying modes of the disclosed inventions. Thus, it is intended that the scope of the present inventions herein disclosed should not be limited by the particular disclosed embodiments described above. Moreover, while the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents, and alternatives falling within the spirit and scope of the various embodiments described and the appended claims. Any methods disclosed herein need not be performed in the order recited. The methods disclosed herein include certain actions taken by a practitioner; however, they can also include any third-party instruction of those actions, either expressly or by implication. For example, actions such as "deploying an instrument sterilized using the systems herein" include "instructing the deployment of an instrument sterilized using the systems herein." In addition, where features or aspects of the disclosure are described in terms of Markush groups, those skilled in the art will recognize that the disclosure is also thereby described in terms of any individual member or subgroup of members of the Markush group.

The ranges disclosed herein also encompass any and all overlap, sub-ranges, and combinations thereof. Language such as "up to," "at least," "greater than," "less than," "between," and the like includes the number recited. Numbers preceded by a term such as "about" or "approximately" include the recited numbers. For example, "about 10 nanometers" includes "10 nanometers."

What is claimed is:

1. A method for sterilizing or disinfecting at least one item, the method comprising:
   placing the at least one item into a chamber configured to contain the at least one item;
   activating a conditioning phase, the conditioning phase comprising activating a blower to circulate air in a closed loop to dry the chamber;
   activating a sterilization or disinfection phase, the sterilization or disinfection phase comprising:
      pumping sterilant with a peristaltic pump from a sterilant reservoir to a nebulizer;
      converting sterilant into a vapor with the nebulizer;

activating the blower to circulate air, including the vapor, in the closed loop between the nebulizer and the chamber;

activating an ozone generator to generate ozone;

activating the blower to circulate air, including the ozone, in the closed loop between the ozone generator and the chamber;

activating a purging phase, the purging phase comprising:

activating a valve to allow air to flow into the system through an inlet;

activating a valve to allow air to flow out of the system through an exhaust; and activating the blower to introduce the air through the inlet, into the chamber, and out the exhaust.

2. The method of claim 1, wherein the method is performed in 10 minutes, wherein the conditioning phase is 150 seconds in duration, wherein the sterilization or disinfection phase is 240 seconds to 270 seconds, and wherein the purging phase is 60 seconds.

3. The method of claim 1, wherein the pumping of the sterilant provides a flow rate of less than 1 ml/min of hydrogen peroxide.

4. The method of claim 1, wherein the purging phase further comprises opening a valve to allow air to flow through the inlet to the ozone generator.

5. The method of claim 1, wherein the inlet comprises a HEPA filter.

6. The method of claim 1, wherein the purging phase further comprises closing a valve to allow the blower to push air through the exhaust.

7. The method of claim 1, wherein the exhaust comprises an activated carbon filter and a high efficiency particulate air (HEPA) filter.

8. The method of claim 1, wherein the sterilant is hydrogen peroxide.

9. The method of claim 8, wherein the hydrogen peroxide is at a concentration of 30% to 60%.

10. The method of claim 1, wherein the sterilant reservoir is a replaceable cartridge.

11. The method of claim 1, further comprising performing the method at a temperature between 20° C. to 25° C. and the method at a relative humidity between 20% and 60%.

12. The method of claim 1, further comprising performing the method at an ambient pressure.

13. An automated method for sterilizing or disinfecting at least one item, the method comprising:

receiving at least one item to be sterilized or disinfected into an interior volume of a chamber for sterilization or disinfection, wherein the chamber is part of a system comprising:

an intake port, an exhaust port, an ozone generator, a sterilant generator, and a plurality of conduits configured to fluidly connect each of the intake, sterilant generator, ozone generator, and the chamber;

at least one blower, configured to provide gaseous flow through the system;

a controller; and a plurality of valves in respective conduits;

activating a conditioning phase by the controller, wherein the conditioning phase is configured to dry a surfaces of the at least one item in the chamber and internal flow conduits, wherein the controller activates the blower to move air, and wherein the valves are positioned by the controller to provide closed loop flow of air moved by the blower;

activating an exposure phase by the controller, wherein the exposure phase is configured to sterilize or disinfect the at least one item, wherein the controller causes the sterilant generator to begin generating sterilant, wherein the sterilant comprises a mist of hydrogen peroxide generated from a solution of hydrogen peroxide in the sterilant generator at a concentration of between about 30% to about 60%, wherein the valves are positioned by the controller to provide closed loop flow through the sterilant generator so that sterilant is delivered to the chamber for a pre-determined time to sterilize or disinfect the at least one item;

after the pre-determined time, introducing ozone generated by the ozone generator into the chamber containing residual hydrogen peroxide sterilant and generating gaseous water vapor and oxygen; and activating a purge phase by the controller, wherein the purge phase includes positioning the valves by the controller to allow open flow and to allow air to be pulled in through the intake port and force the gaseous water vapor and oxygen from the chamber and out the exhaust port, wherein each of the intake port and exhaust port comprise a respective filter.

14. The automated method of claim 13, wherein the controller activates the blower to move air through the ozone generator to produce ozone.

15. The automated method of claim 13, wherein the sterilant comprises a vapor of hydrogen peroxide.

16. The automated method of claim 13, wherein the method operates at a pre-programmed relative humidity between 10% to 85%, and wherein the method has a relative humidity before the exposure phase that is less than or equal to 20%.

17. The automated method of claim 13, wherein the method is performed in 10 minutes, wherein the conditioning phase is activated for 150 seconds, wherein the exposure phase is activated for a time between 240 seconds to 270 seconds to sterilize the at least one item, and wherein the purge phase is activated for a time between 45-60 seconds.

18. The automated method of claim 13, wherein the exposure phase is activated for a time between 5 and 45 minutes to sterilize the at least one item.

19. The automated method of claim 13, wherein the system is configured to receive a cartridge.

20. The automated method of claim 13, wherein the method operates between an ambient temperature between 20° C. to 25° C.

21. The automated method of claim 13, wherein the sterilant is delivered by a peristaltic pump.

22. The automated method of claim 13, wherein at least one of the filters of the intake port and exhaust port is a HEPA filter.

23. The automated method of claim 13, wherein at least one of the filters of the intake port and exhaust port is a charcoal filter.

* * * * *